(12) United States Patent
Chen et al.

(10) Patent No.: US 7,132,425 B2
(45) Date of Patent: Nov. 7, 2006

(54) 5-SUBSTITUTED-SIX-MEMBERED HETEROAROMATIC GLUCOKINASE ACTIVATORS

(75) Inventors: Shaoqing Chen, Bridgewater, NJ (US); Wendy Lea Corbett, Lebanon, NJ (US); Kevin Richard Guertin, Verona, NJ (US); Nancy-Ellen Haynes, Cranford, NJ (US); Robert Francis Kester, West Orange, NJ (US); Francis A. Mennona, Nutley, NJ (US); Steven Gregory Mischke, Florham Park, NJ (US); Yimin Qian, Wayne, NJ (US); Ramakanth Sarabu, Towaco, NJ (US); Nathan Robert Scott, Livingston, NJ (US); Kshitij Chhabilbhai Thakkar, Nutley, NJ (US)

(73) Assignee: Hoffmann-La Roche Inc., Nutley, NJ (US)

(*) Notice: Subject to any disclaimer, the term of this patent is extended or adjusted under 35 U.S.C. 154(b) by 309 days.

(21) Appl. No.: 10/732,838

(22) Filed: Dec. 10, 2003

(65) Prior Publication Data
US 2004/0147748 A1 Jul. 29, 2004

Related U.S. Application Data

(60) Provisional application No. 60/524,531, filed on Nov. 24, 2003, provisional application No. 60/432,806, filed on Dec. 12, 2002.

(51) Int. Cl.
*A61K 31/4965* (2006.01)
*A61K 31/44* (2006.01)
*A01N 43/40* (2006.01)
*C07D 401/00* (2006.01)
*C07D 241/02* (2006.01)

(52) U.S. Cl. .......................... 514/255.05; 514/255.06; 514/341; 514/342; 514/347; 514/349; 514/352; 544/405; 544/408; 546/268.7; 546/269.1; 546/269.7; 546/271.1; 546/272.7; 546/281.7; 546/294; 546/304; 546/307; 546/312

(58) Field of Classification Search .................... None
See application file for complete search history.

(56) References Cited

U.S. PATENT DOCUMENTS

| | | | |
|---|---|---|---|
| 3,431,301 | A | 3/1969 | Focella et al. |
| 3,776,917 | A | 12/1973 | Mann et al. |
| 5,113,013 | A | 5/1992 | Powell et al. |
| 5,169,951 | A | 12/1992 | Sutter et al. |
| 5,556,859 | A | 9/1996 | Johnson |
| 6,320,050 | B1 | 11/2001 | Bizzarro et al. |
| 6,353,111 | B1 | 3/2002 | Corbett et al. |
| 6,369,232 | B1 | 4/2002 | Sidduri |
| 6,384,220 | B1 | 5/2002 | Corbett et al. |
| 6,388,071 | B1 | 5/2002 | Mahaney |
| 6,388,088 | B1 | 5/2002 | Sidduri |
| 6,433,188 | B1 | 8/2002 | Corbett et al. |
| 6,441,180 | B1 | 8/2002 | Sidduri |
| 6,441,184 | B1 | 8/2002 | Corbett et al. |
| 6,448,399 | B1 | 9/2002 | Corbett et al. |
| 6,486,184 | B1 | 11/2002 | Kester et al. |
| 6,489,485 | B1 | 12/2002 | Bizzarro et al. |
| 6,528,543 | B1 | 3/2003 | Bizzarro et al. |
| 6,545,155 | B1 | 4/2003 | Corbett et al. |
| 6,610,846 | B1 | 8/2003 | Bizzarro et al. |

FOREIGN PATENT DOCUMENTS

| | | |
|---|---|---|
| DE | 249 241 | 7/1912 |
| EP | 566 138 | 10/1993 |
| GB | 1436502 | 5/1976 |
| WO | WO 00/26202 | 5/2000 |
| WO | WO 00/58293 | 10/2000 |
| WO | WO 02/08209 | 1/2002 |

OTHER PUBLICATIONS

Grimsby et al, "Allosteric Activators of Glucokinase: Potential Role in Diabetes Therapy" Science, vol. 301, pp. 370-373 (Jul. 18, 2003).*
Couzin, J., Comment on: Science. Jul. 18, 2003; vol. 301, pp. 370-373.*
Braunstein, S. "New Developments in Type 2 Diabetes Mellitus: Combination Therapy with a Thiazolidinone" Clinical Therapeutics, vol. 23(7), pp. 1895-1917 (2003).*
Colowick, S.P., The Enzymes, vol. 9 (P. Boyer, ed.) Academic Press, New York, NY, p. 1-48 (1973).

(Continued)

*Primary Examiner*—James O. Wilson
*Assistant Examiner*—Zachary C. Tucker
(74) *Attorney, Agent, or Firm*—George W. Johnston; Dennis P. Tramaloni; Samuel H. Megerditchian

(57) ABSTRACT

The present invention provides a compound according to formula I

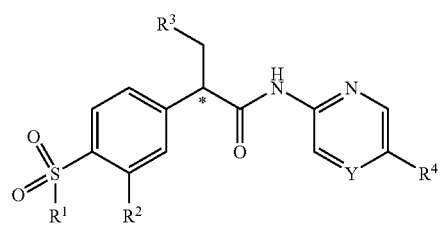

where the substituent designations are provided in the specification. Pharmaceutical compositions comprising a compound according to formula I are also provided.

93 Claims, No Drawings

OTHER PUBLICATIONS

Chipkin, et. al., in Joslin's Diabetes (C.R. Kahn and G.C. Wier, eds.), Lea and Febiger, Philadelphia, PA, p. 97-115 (1994).

Printz, et. al., Ann. Rev. Nutrition, vol. 13 (R.E. Olson, D.M. Bier, and D.B. McCormick, eds.) Annual Review Inc, Palo Alto, CA pp. 463-496 (1993).

Meglasson, et. al., Amer. J. Physiol., 246, E1-E13 (1984).

Grupe, et. al., Cell 83, 69-78, (1995).

Ferre, et al., Faseb J., 10, 1213-1218 (1996).

Liang, et al., Biochem. J. 309, 167-173 (1995).

Glaser, et. al. New England J. Med. 338, 226-230 (1998).

Rodier, et. al., Acta Crystallogr., C46 (1990) pp. 154-156.

Robert, J. M. H., et al., Eur J. Med. Chem. vol. 29, (1994), pp. 841-854.

Spickett, et. al., Eur. J. Med. Chem.-Chimica Therapeutica, vol. 11(1), (1976), pp. 7-12.

Bhat, A. R., et. al., J. Inst. Chemists (India), vol. 61, 1989, pp. 134-136.

Spielman, M.A., et. al., J. Am. Chem. Soc., 70 (1948), pp. 4189-4191.

* cited by examiner

5-SUBSTITUTED-SIX-MEMBERED HETEROAROMATIC GLUCOKINASE ACTIVATORS

PRIORITY TO RELATED APPLICATIONS

This application claims the benefit of Provisional Applications Ser. No. 60/524,531 filed Nov. 24, 2003, and Ser. No. 60/432,806 filed Dec. 12, 2002.

BACKGROUND OF THE INVENTION

Glucokinase (GK) is one of four hexokinases that are found in mammals [Colowick, S. P., in *The Enzymes*, Vol. 9 (P. Boyer, ed.) Academic Press, New York, N.Y., pages 1–48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97–115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10–15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463–496, 1993]. These findings contributed over a decade ago to the hypothesis that GK functions as a glucose sensor in β-cells and hepatocytes (Meglasson, M. D. and Matschinsky, F. M. *Amer. J. Physiol.* 246, E1–E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69–78, 1995; Ferrie, T., Riu, E., Bosch, F. et al., *FASEB J.*, 10, 1213–1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167–173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226–230, 1998). While mutations of the GK gene are not found in the majority of patients with type II diabetes, compounds that activate GK, and thereby increase the sensitivity of the GK sensor system, will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

This invention provides a compound, comprising an amide of the formula:

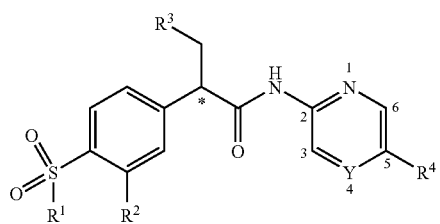

I wherein $R^1$ is a lower alkyl having from 1 to 5 carbon atoms;
$R^2$ is hydrogen, halo, nitro, cyano, methyl, trifluoromethyl, hydroxy, or methoxy;
$R^3$ is cycloalkyl having from 4 to 6 carbons;
Y is independently selected from the group of CH and N to form a pyridine or pyrazine ring, respectively;
$R^4$ is a substituent in position 5 of the pyridine or pyrazine ring selected from

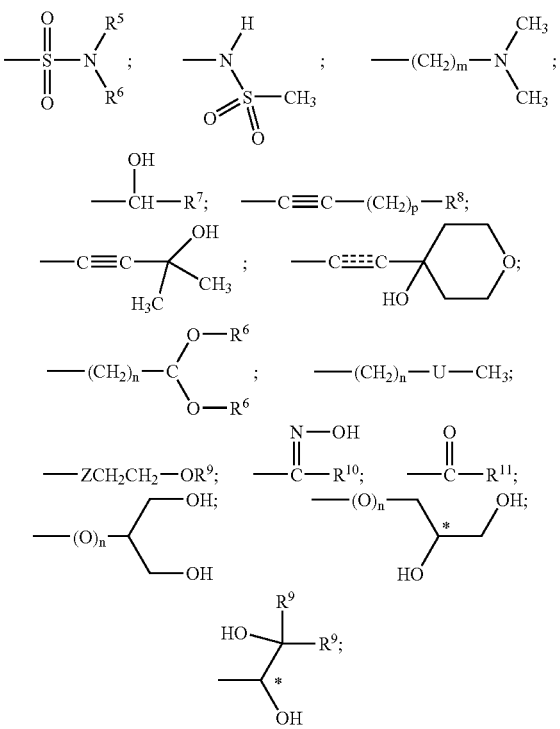

—$(CH_2)_n$-Q, wherein Q is a 5-membered saturated, substituted, heterocyclic ring connected by a ring carbon atom, said heterocyclic ring containing two heteroatoms selected from nitrogen, sulfur and oxygen, and substituted at each of two ring carbons with an oxo group, and optionally substituted at the connecting ring carbon with a substituent which is methyl or amino;

—(CH$_2$)$_n$—V, wherein V is an unsubstituted or mono-substituted five- or six-membered saturated or unsaturated heterocyclic ring connected by a ring carbon, which said heterocyclic ring containing from one to three hetero atoms selected from sulfur, oxygen or nitrogen; said mono-substituted heterocyclic ring being a heterocyclic ring which is mono-substituted with a substituent selected from the group consisting of cyano, halo, nitro, amino, methyl, methoxy and hydroxy;

a nine- or ten-membered bicyclic heterocyclic ring connected by a ring carbon atom, said bicyclic heterocyclic ring containing one hetero atom selected from the group consisting of oxygen, nitrogen or sulfur; and an unsubstituted or mono-substituted six-membered aryl ring connected by a ring carbon atom, said mono-substituted aryl ring being mono-substituted at a position on a ring carbon atom other than the connecting carbon atom with a substituent selected from the group consisting of cyano, halo, nitro, amino, methyl, methoxy, and hydroxy;

$R^5$ is hydrogen or lower alkyl;

$R^6$ is lower alkyl;

$R^7$ is lower alkyl, cyano, or —C(=O)NH$_2$;

$R^8$ is hydroxy, methoxy, or dimethylamine;

$R^9$ is hydrogen or methyl;

$R^{10}$ is lower alkyl, cyano, or —NH$_2$;

$R^{11}$ is hydrogen, lower alkyl, or NHOH;

m is 0, 1, 2, or 3;

n is 0 or 1;

p is 1 or 2;

U is S, SO, or SO$_2$;

Z is O, S, or NH;

----denotes an optional bond;

* denotes an asymmetric carbon atom;

or a pharmaceutically acceptable salt thereof.

Compounds of formula I have been found to activate glucokinase in vitro. Glucokinase activators are useful for increasing insulin secretion in the treatment of type II diabetes.

DETAILED DESCRIPTION OF THE INVENTION

This invention provides a compound, comprising an amide of the formula:

I wherein $R^1$ is a lower alkyl having from 1 to 5 carbon atoms;

$R^2$ is hydrogen, halo, nitro, cyano, methyl, trifluoromethyl, hydroxy, or methoxy;

$R^3$ is cycloalkyl having from 4 to 6 carbons;

Y is independently selected from the group of CH and N to form a pyridine or pyrazine ring, respectively;

$R^4$ is a substituent in position 5 of the pyridine or pyrazine ring (N being ring position 1 and Y being ring position 4) selected from the group consisting of —(CH$_2$)$_n$-Q, wherein Q is a 5-membered saturated, substituted, heterocyclic ring connected by a ring carbon atom, said heterocyclic ring containing two heteroatoms selected from nitrogen, sulfur and oxygen, and substituted at each of two ring carbons with an oxo group, and optionally substituted at the connecting ring carbon with a substituent which is methyl or amino;

—(CH$_2$)$_n$—V, wherein V is an unsubstituted or mono-substituted five- or six-membered saturated or unsaturated heterocyclic ring connected by a ring carbon, which said heterocyclic ring containing from one to three hetero atoms selected from sulfur, oxygen or nitrogen; said mono-substituted heterocyclic ring being a heterocyclic ring which is mono-substituted with a substituent selected from the group consisting of cyano, halo, nitro, amino, methyl, methoxy and hydroxy;

a nine- or ten-membered bicyclic heterocyclic ring connected by a ring carbon atom, said bicyclic heterocyclic ring containing one hetero atom selected from the group consisting of oxygen, nitrogen or sulfur; and an unsubstituted or mono-substituted six-membered aryl ring connected by a ring carbon atom, said mono-substituted aryl ring being mono-substituted at a position on a ring carbon atom other than the connecting carbon atom with a substituent selected from the group consisting of cyano, halo, nitro, amino, methyl, methoxy, and hydroxy;

$R^5$ is hydrogen or lower alkyl;

$R^6$ is lower alkyl;

$R^7$ is lower alkyl, cyano, or —C(=O)NH$_2$;

$R^8$ is hydroxy, methoxy, or dimethylamine;

$R^9$ is hydrogen or methyl;

$R^{10}$ is lower alkyl, cyano, or —NH$_2$;

$R^{11}$ is hydrogen, lower alkyl, or NHOH;

m is 0, 1, 2, or 3;
n is 0 or 1;
p is 1 or 2;
U is S, SO, or $SO_2$;
Z is O, S, or NH;
---- denotes an optional bond;
* denotes an asymmetric carbon atom;

or a pharmaceutically acceptable salt thereof.

In the compound of formula I, the "*" indicates an asymmetric carbon. The compound of formula I may be present either as a racemate or in the isolated "R" configuration at the asymmetric carbon upon which —$CH_2R^3$ is bound. The "R" enantiomers are at this carbon are preferred.

As used throughout this application, the term "lower alkyl" includes both straight chain and branched chain alkyl groups having from 1 to 7 carbon atoms, such as methyl, ethyl, propyl, isopropyl, preferably methyl and ethyl. As used herein, "perfluoro-lower alkyl" means any lower alkyl group wherein all of the hydrogens of the lower alkyl group are substituted or replaced by fluoro. Among the preferred perfluoro-lower alkyl groups are trifluoromethyl, pentafluoroethyl, heptafluoropropyl, etc.

As used herein, "cycloalkyl" means a saturated hydrocarbon ring having from 3 to 10 carbon atoms, preferably from 4 to 6 carbon atoms. A preferred cycloalkyl is cyclopentyl.

As used herein, the term "halogen" and the term "halo" unless otherwise stated, designates all four halogens, i.e. fluorine, chlorine, bromine, and iodine. A preferred halogen is chlorine.

The "heterocyclic" ring defined under $R^4$ can be a saturated or unsaturated five- or six-membered ring having from one to three heteroatoms selected from the group consisting of oxygen, nitrogen, or sulfur and connected by a ring carbon atom, optionally through a linking methyl group, to position 5 of the pyridine or pyrazine ring shown in formula I. Unsaturated heterocyclic rings may be partially saturated or aromatic. The heterocyclic rings include, for example, pyridinyl and furanyl. Substituted heterocyclic rings are heterocyclic rings that may be substituted on a ring carbon by oxo, lower alkyl, amino, cyano, halo, nitro, amino, methoxy and hydroxy, for example. The preferred lower alkyl substituent is methyl. Preferred halo substituents are chloro and bromo. For an aromatic heterocyclic ring, the ring carbon that is connected, optionally through a linking methyl group to the remainder of a formula I compound, cannot contain any substituent.

Bicyclic heterocyclic rings defined by $R^4$ may be a nine- or ten-membered bicyclic ring having one heteroatom selected from the group consisting of oxygen, nitrogen and sulfur and connected by a ring carbon atom, optionally through a linking methyl group, to position 5 of the pyridine or pyrazine ring. Such bicyclic heterocyclic rings include indole rings.

As used herein, the term "aryl" signifies aryl mononuclear aromatic hydrocarbon groups which are unsubstituted. Substituted aryl has ring substitution, unless otherwise indicated, on one or more positions with cyano halogen, nitro, amino lower alkyl, lower alkoxy or hydroxy substituents. The term "aryl" also signifies polynuclear aryl groups, such as naphthyl, anthryl, and phenanthryl, which can be unsubstituted or substituted with one or more of the aformentioned groups. Examples of aryl and substituted aryl include phenyl and tolyl. Preferred are phenyl groups. The term "arylalkyl" denotes an alkyl group, preferably lower alkyl, in which one of the hydrogen atoms can be replaced by an aryl group. Examples of arylalkyl groups are benzyl, 2-phenylethyl, 3-phenylpropyl, 4-chlorobenzyl, 4-methoxybenzyl and the like.

As used herein, the term "lower alkoxy" includes both straight chain and branched chain alkoxy groups having from 1 to 7 carbon atoms, such as methoxy, ethoxy, propoxy, isopropoxy, preferably methoxy and ethoxy.

As used herein, the term "lower alkanoic acid" denotes lower alkanoic acids containing from 2 to 7 carbon atoms such as propionic acid, acetic acid and the like. The term "lower alkanoyl" denotes monovalent alkanoyl groups having from 2 to 7 carbon atoms such as propionoyl, acetyl and the like. The term "aroic acids" denotes aryl alkanoic acids where aryl is as defined above and alkanoic contains from 1 to 6 carbon atoms. The term "aroyl" denotes aroic acids wherein aryl is as defined hereinbefore, with the hydroxy group of the COOH moiety removed. Among the preferred aroyl groups is benzoyl.

As used herein, "lower alkyl thio" means a lower alkyl group as defined above bound to a thio group which is bound to the rest of the molecule, for example, —$SCH_3$. As used herein, "lower alkyl sulfinyl" means a lower alkyl group as defined above bound to a sulfinyl group (sulfoxide) which is bound to the rest of the molecule. As used herein, "lower alkyl sulfonyl" means a lower alkyl group as defined above bound to a sulfonyl group which is bound to the rest of the molecule.

During the course of synthetic reactions, the various functional groups such as the free carboxylic acid or hydroxy groups may be protected via conventional hydrolyzable ester or ether protecting groups. As used herein, the term "hydrolyzable ester or ether protecting groups" designates any ester or ether conventionally used for protecting carboxylic acids or alcohols which can be hydrolyzed to yield the respective carboxy or hydroxy group. Exemplary ester groups useful for those purposes are those in which the acyl moieties are derived from a lower alkanoic, aryl lower alkanoic, or lower alkane dicarboxylic acid. Among the activated acids which can be utilized to form such groups are acid anhydrides, acid halides, preferably acid chlorides or acid bromides derived from aryl or lower alkanoic acids. Example of anhydrides are anhydrides derived from monocarboxylic acids such as acetic anhydride, benzoic acid anhydride, and lower alkane dicarboxylic acid anhydrides, e.g. succinic anhydride as well as chloro formates e.g. trichloromethyl chloroformate and ethyl chloroformate being preferred. A suitable ether protecting group for alcohols are, for example, the tetrahydropyranyl ethers such as 4-methoxy-5,6-dihydroxy-2H-pyranyl ethers. Others are aroylmethylethers such as benzyl, benzhydryl or trityl ethers or α-lower alkoxy lower alkyl ethers, for example, methoxymethyl or allylic ethers or alkyl silylethers such as trimethylsilylether.

The term "amino protecting group" designates any conventional amino protecting group which can be cleaved to yield the free amino group. The preferred protecting groups are the conventional amino protecting groups utilized in peptide synthesis. Especially preferred are those amino protecting groups which are cleavable under mildly acidic conditions from about pH=2 to 3. Particularly preferred amino protecting groups include t-butyl carbamate (BOC), benzyl carbamate (CBZ), and 9-flurorenylmethyl carbamate (FMOC).

The term "pharmaceutically acceptable salts" as used herein include any salt with both inorganic or organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, para-toluene sulfonic acid and the like. The term "pharmaceutically acceptable salts" also includes any pharmaceutically acceptable base salt such as amine salts, trialkyl amine salts and the like. Such salts can be formed quite readily by those skilled in the art using standard techniques.

Preferred compounds of formula I include those in which $R^1$ is methyl, those in which $R^2$ is hydrogen or halo such as chlorine, and those in which $R^3$ is cyclopentyl.

Preferred compounds of formula I include those in which $R^4$ is: —(CH$_2$)$_n$—U—CH$_3$ such as —SCH$_3$ and —SOCH$_3$; -ZCH$_2$CH$_2$—OR$^9$ such as —SCH$_2$CH$_2$OH; —(CH$_2$)$_m$—N(CH$_3$)CH$_3$; —C(=O)R$^{11}$; —(CH$_2$)$_n$—C(OR$^6$)OR$^6$ such as —(CH$_2$)$_n$—C(OCH$_3$)OCH$_3$; —C(OH)R$^7$; and —C≡C—C(CH$_3$)$_2$—OH.

Preferred compounds of formula I also include those in which $R^4$ is —CH$_2$)$_n$-Q, such as

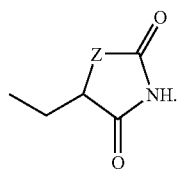

Preferably, Z is S or NH.

Further preferred compounds of formula I include those in which $R^4$ is —(CH$_2$)$_n$—V. Preferred compounds in which $R^4$ is —(CH$_2$)$_n$—V include those in which n (of —(CH$_2$)$_n$—V) is zero and V is an unsubstituted five- or six-membered heteroaromatic ring connected by a ring carbon atom to position 5 of the pyridine or pyrazine ring shown in formula I, with said five- or six-membered heteroaromatic ring containing one heteroatom selected from sulfur, oxygen or nitrogen.

Also preferred when $R^4$ is —(CH$_2$)$_n$—V are compounds wherein —(CH$_2$)$_n$—V is selected from the group consisting of:

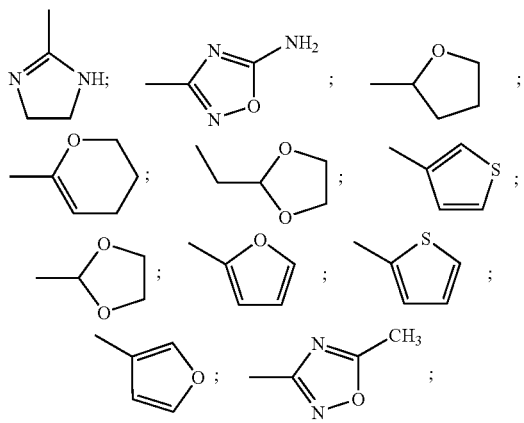

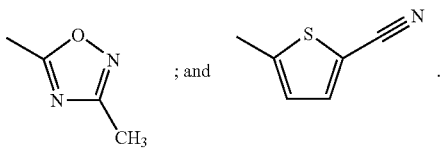

Of the above $R^4$ heterocyclic groups in which $R^4$ is —(CH$_2$)$_n$—V, a more preferred group is

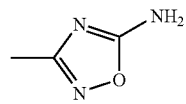

In an embodiment wherein $R^4$ is —(CH$_2$)$_n$—V, V is

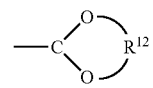

wherein $R^{12}$ is an unbranched alkyl chain of 2 or 3 carbon atoms wherein the chain, in combination with the oxygen atoms to which it is bonded, forms a five-or six-membered ring.

Further preferred compounds of formula I include those in which $R^4$ is an unsubstituted or mono-substituted six-membered aryl ring connected by a ring carbon atom to position 5 of the pyridine or pyrazine ring shown in formula I, said mono-substituted aryl ring being mono-substituted at a position on a ring carbon atom other than the connecting carbon atom with a substituent selected from the group consisting of chloro, bromo, nitro, amino, methyl, methoxy, and hydroxy. More preferable are compounds wherein $R^4$ is an unsubstituted or mono-substituted 6-membered aryl ring selected from the group consisting of unsubstituted aryl, aryl substituted with methoxy and aryl substituted with hydroxy.

The compound according to claim 50, wherein $R^4$ is a bicyclic heteroaromatic ring which is

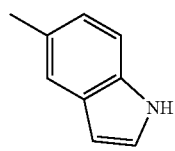

In an embodiment wherein $R^4$ is —(CH$_2$)$_m$—N(CH$_3$)(CH$_3$), m is preferably zero.

Further preferred compounds of formula I include those shown in formula II:

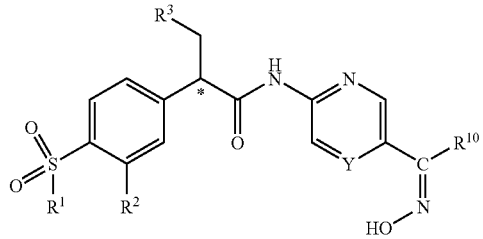

II wherein $R^{10}$ is as indicated above.

Preferred $R^{10}$ groups of formula II are methyl, ethyl, cyano or —$NH_2$. More preferred are methyl or —$NH_2$.

Further preferred compounds of formula I include those shown in formula III:

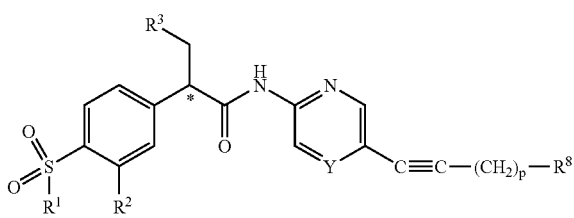

III wherein p and $R^8$ are as indicated above. In formula III, the preferred p value is 1. The preferred $R^8$ is hydroxy or dimethylamine.

Further preferred compounds of formula I include those in which $R^4$ is

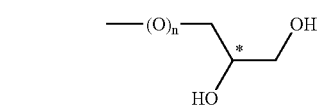

Further preferred compounds of formula I include those in which $R^4$ is

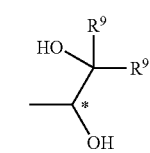

The compound may be a racemic mixture at the chiral carbon of $R^4$. Alternatively, the compound may be in a configuration wherein $R^4$ is

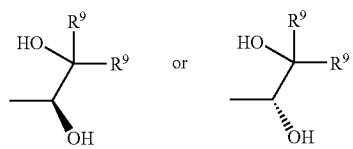

The S configuration is preferable.

In an embodiment of the present invention, $R^4$ is

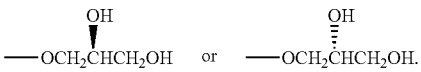

The compound may be a racemic mixture at the chiral carbon of $R^4$.

Alternatively, when n is 1, the compound may be in a configuration wherein $R^4$ is —OCH$_2$CHCH$_2$OH    or    —OCH$_2$CHCH$_2$OH.

The R configuration is preferable.

When n is zero, the compound may be in a configuration wherein $R^4$ is

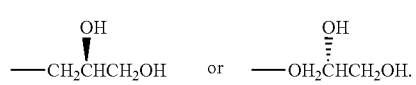

The R configuration is preferable.

With regard to the chiral carbon upon which —$CH_2R^3$ is a substituent as shown in formula I, in one embodiment, the compound of formula I is a racemic mixture at this carbon atom. In another embodiment, the compound is in the R or S configuration. Preferably, the compound of formula I is in the R configuration at the chiral carbon upon which —$CH_2R^3$ is a substituent.

In compounds containing a $R^6$ substituent within $R^4$, $R^6$ is preferably methyl or ethyl. More preferably, $R^6$ is methyl.

Compounds of formula I can be prepared starting from the compound of formula V by the following Reaction Scheme:

Reaction Scheme

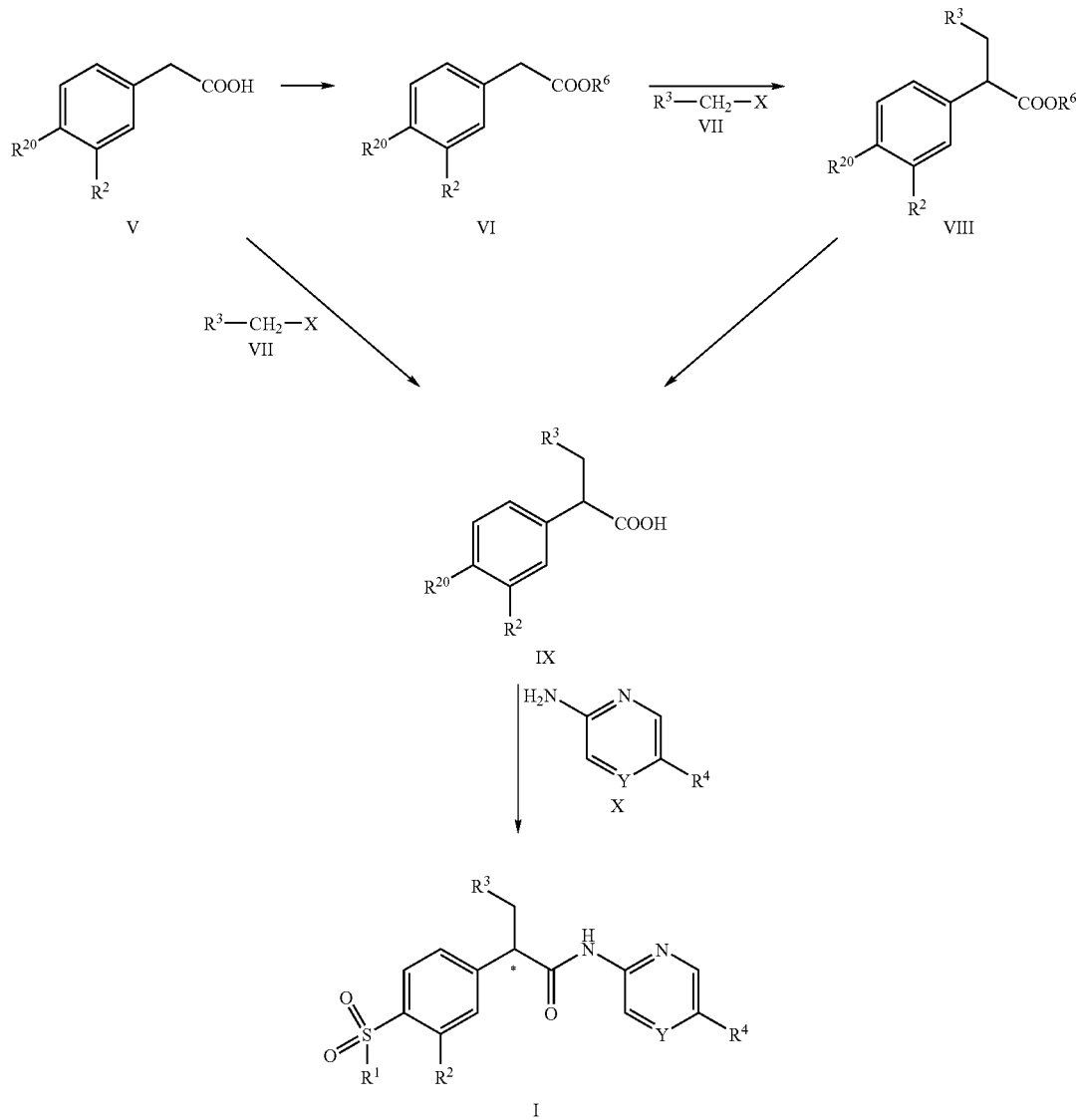

wherein $R^{20}$ is lower alkyl sulfonyl or a functional group that will be converted into a lower alkyl sulfone (such as the methylthio group or a halo group, preferably chloro or fluoro);

$R^1$, $R^2$, $R^3$, $R^4$, $R^6$, and Y are as above.

The carboxylic acids of formula V wherein $R^2$ is hydrogen and $R^{20}$ is mercapto [4-(mercapto)phenylacetic acid], methylthio [4-(methylthio)phenylacetic acid], or methylsulfonyl [4-(methylsulfonyl)phenylacetic acid] are commercially available. The carboxylic acid of formula V wherein $R^2$ is trifluoromethyl and $R^{20}$ is fluoro [4-fluoro-3-(trifluoromethyl)phenyl acetic acid], and the carboxylic acid of formula V wherein $R^2$ is nitro and $R^{20}$ is chloro [4-chloro-3-nitrophenyl acetic acid] are also commercially available. If necessary for further chemical modification to produce the desired substitutions at $R^{20}$ and $R^2$, the carboxylic acids can be converted to the corresponding esters of lower alkyl alcohols using any conventional esterification methods.

The reactions hereto forward are to be carried out on the lower alkyl esters of the carboxylic acids of formula VI or VIII or may be carried out on the carboxylic acids of formula V or IX themselves.

If it is desired to produce compounds of formula V where $R^2$ is hydrogen and $R^{20}$ is lower alkyl sulfonyl, the known 4-(mercapto)phenylacetic acid can be used as a starting material. The compound of formula V where $R^2$ is hydrogen and $R^{20}$ is mercapto can be alkylated by conventional methods (for example, with a lower alkyl halide) to the corresponding lower alkyl thio compounds of formula V. The lower alkyl thio compounds can then be converted to the corresponding lower alkyl sulfonyl compounds of formula V by oxidation. Any conventional method of oxidizing an alkyl thio substituent to the corresponding sulfone group can be utilized to effect this conversion.

If it is desired to produce compounds of formula V where $R^2$ is halo and $R^{20}$ is lower alkyl sulfonyl, the known 2-halothiophenols can be used as starting materials. In this reaction sequence, the mercapto group can be alkylated by conventional methods (for example, with a lower alkyl halide) to the corresponding 2-halo-1-lower alkyl thio benzenes. These compounds can then be converted to the corresponding 3-halo-4-(lower alkyl thio)-phenyl acetic acids. First, the 2-halo-1-lower alkyl thio benzenes can be acylated with a (lower alkyl)oxalyl chloride (such as methyloxalyl chloride or ethyloxalyl chloride) via a Friedel-Crafts acylation to produce the alpha-keto carboxylic ester in the position para to the lower alkyl thio functional group. The alpha-keto carboxylic ester can then be hydrolyzed by any conventional method for converting an alpha-keto carboxylic ester to an alpha-keto carboxylic acid. Wolff-Kishner reduction of the resulting alpha-keto carboxylic acid will produce the compounds of formula V where $R^2$ is halo and $R^{20}$ is lower alkyl thio (see for example, *J. Med. Chem.* 1972, 15, 1029–1032 for a similar reaction sequence). The lower alkyl thio compounds can then be converted to the corresponding lower alkyl sulfonyl compounds of formula V by oxidation. Any conventional method of oxidizing an alkyl thio substituent to the corresponding sulfone group can be utilized to effect this conversion.

On the other hand, if it is desired to produce the compounds of formula V where $R^2$ is bromo and $R^{20}$ is lower alkyl sulfonyl, the compounds wherein $R^2$ is hydrogen and $R^{20}$ is lower alkyl thio, compounds produced as described above, can also be used as starting materials. The phenyl acetic acid derivatives of formula V wherein $R^2$ is hydrogen and $R^{20}$ is lower alkyl thio can be brominated. Any conventional method of aromatic bromination can be utilized to effect this conversion (*J. Med. Chem.* 1989, 32, 2493–2500). Once the compounds of formula V where $R^2$ is bromo and $R^{20}$ is lower alkyl thio are available, they can be converted to the corresponding compounds of formula V where $R^2$ is bromo and $R^{20}$ is lower alkyl sulfonyl by oxidation. Any conventional method of oxidizing an alkyl thio substituent to the corresponding sulfone group can be utilized to effect this conversion.

If it is desired to produce the compounds of formula V where $R^2$ is cyano and $R^{20}$ is lower alkyl sulfonyl, these compounds can be prepared as described hereinbefore from compounds where $R^2$ is bromo and $R^{20}$ is lower alkyl sulfonyl. Any conventional method for the nucleophilic displacement of an aromatic bromo substituent with a cyano group transferring agent [such as copper(I) cyanide] can be utilized to effect this conversion.

If it is desired to produce the compounds of formula V wherein $R^2$ is nitro and $R^{20}$ is lower alkyl sulfonyl, the known 4-chloro-3-nitrophenyl acetic acid can be used as starting material. This compound can be converted to the compounds of formula V wherein $R^2$ is nitro and $R^{20}$ is lower alkyl thio. Any conventional method for the nucleophilic displacement of an aromatic chlorine group with a lower alkyl thiol can be utilized to effect this conversion (*Synthesis* 1983, 751–755). Once the compounds of formula V wherein $R^2$ is nitro and $R^{20}$ is lower alkyl thio are available, they can be converted to the corresponding compounds of formula V wherein $R^2$ is nitro and $R^{20}$ is lower alkyl sulfonyl by oxidation. Any conventional method of oxidizing an alkyl thio substituent to the corresponding sulfone group can be utilized to effect this conversion. On the other hand, if it is desired to directly produce the compounds of formula V wherein $R^2$ is nitro and $R^{20}$ is lower alkyl sulfonyl from the compound of formula V where $R^2$ is nitro and $R^{20}$ is chloro, any conventional method for the nucleophilic displacement of an aromatic chlorine group with a lower alkane sulfinate (such as sodium methane sulfinate) can be utilized to effect this conversion (*J. Org. Chem.*, 1989, 54, 4691–4692).

If it is desired to produce the compounds of formula V where $R^2$ is fluoro and $R^{20}$ is lower alkyl sulfonyl, these compounds can be alternatively prepared from the aforementioned compounds where $R^2$ is nitro and $R^{20}$ is lower alkyl sulfonyl. The aromatic nitro substituent is first converted to the aromatic amino group. Any conventional method for the reduction of a nitro group to an amino group can be utilized to effect this conversion. The amino group can then be converted to the fluorine group to produce the compounds of formula V where $R^2$ is fluoro and $R^{20}$ is lower alkyl sulfonyl. Any conventional method for converting an aromatic amino group to an aromatic fluorine can be utilized to effect this conversion (*Synthetic Commun.* 1992, 22, 73–82; *J. Fluorine Chem.* 1991, 51, 299–304).

On the other hand, if it is desired to produce the compounds of formula V where $R^2$ is trifluoromethyl and $R^{20}$ is lower alkyl sulfonyl, the known 4-fluoro-3-(trifluoromethyl) phenyl acetic acid can be used as a starting material. In this reaction, any conventional method for the nucleophilic displacement of an aromatic fluorine group with a lower alkyl thiol can be utilized to effect this conversion (*J. Org. Chem.* 1995, 60, 6592–6594; *J Org Chem.* 1982, 47, 4341–4344). Once the compounds of formula V where $R^2$ is trifluoromethyl and $R^{20}$ is lower alkyl thio are available, they can be converted to the corresponding compounds of formula V where $R^2$ is trifluoromethyl and $R^{20}$ is lower alkyl sulfonyl using conventional oxidation procedures.

If it is desired to produce compounds of formula V where $R^2$ is methyl and $R^{20}$ is lower alkyl sulfonyl, the commercially available 2-methylthiophenol can be used as starting material. In this reaction sequence, the mercapto group may be alkylated by conventional methods (for example, with a lower alkyl halide) to the corresponding 2-methyl-1-lower alkyl thio benzenes. These compounds can then be converted to the corresponding 3-methyl-4-(lower alkyl thio)-phenyl acetic acids. First, the 2-methyl-1-lower alkyl thio benzenes can be acylated with a (lower alkyl)oxalyl chloride (such as methyloxalyl chloride or ethyloxalyl chloride) via a Friedel-Crafts acylation to produce the alpha-keto carboxylic ester in the position para to the lower alkyl thio functional group. The alpha-keto carboxylic ester can then be hydrolyzed by any conventional method for converting an alpha-keto carboxylic ester to an alpha-keto carboxylic acid. Wolff-Kishner reduction of the resulting alpha-keto carboxylic acid will produce the compounds of formula V where $R^2$ is methyl and $R^{20}$ is lower alkyl thio. The lower alkyl thio compounds can then be converted to the corresponding lower alkyl sulfonyl compounds of formula V by oxidation. Any conventional method of oxidizing an alkyl thio substituent to the corresponding sulfone group can be utilized to effect this conversion.

If it is desired to produce the compounds of formula V wherein $R^2$ is methoxy and $R^{20}$ is lower alkyl sulfonyl, these compounds can also be prepared as described hereinbefore from compounds wherein $R^2$ is halo and $R^{20}$ is lower alkyl sulfonyl. In this reaction, any conventional method for the nucleophilic displacement of an aromatic halo group with sodium methoxide can be utilized to effect this conversion. Once the compounds of formula V wherein $R^2$ is methoxy and $R^{20}$ is lower alkyl sulfonyl are available, they can be converted to the corresponding compounds of formula V wherein $R^2$ is hydroxy and $R^{20}$ is lower alkyl sulfonyl. Any conventional method for the demethylation of an aromatic methoxy group to an aromatic hydroxy group can be utilized to effect this conversion. This compound of formula V wherein $R^2$ is hydroxy and $R^{20}$ is lower alkyl sulfonyl would have to be protected throughout the remaining reaction scheme. The aromatic hydroxy group may be protected via a conventional hydrolyzable ether protecting group. At the end of the reaction scheme, the ether protecting group can then be removed to produce the respective hydroxy group corresponding to the desired compound of formula I wherein $R^2$ is hydroxy. Alternatively, once the compound of formula I wherein $R^2$ is methoxy is made following the reaction scheme, this compound can be converted to the desired compound of formula I wherein $R^2$ is hydroxy. Any conventional method for the demethylation of an aromatic methoxy group to an aromatic hydroxy group can be utilized to effect this conversion For the alkylation reaction using the alkyl halide of formula VII, the carboxylic acids of formula V can be directly alkylated or first converted to the corresponding esters of lower alkyl alcohols of formula VI using any conventional esterification methods and then alkylated. In the alkylation step of the Reaction Scheme, the alkyl halide of formula VII is reacted with the dianion of formula V to produce the compound of formula IX or reacted with the anion of formula VI to produce the compound of formula VIII. The compounds of formula V and VI represent an organic acid and an organic acid derivative having an alpha carbon atom, and the compound of formula VII is an alkyl halide so that alkylation occurs at the alpha carbon atom of the carboxylic acid and the carboxylic acid ester. This reaction is carried out by any conventional means of alkylation of the alpha carbon atom of a carboxylic acid or a lower alkyl ester of a carboxylic acid. Generally, in these alkylation reactions, an alkyl halide is reacted with the dianion of the acetic acid or the anion generated from an acetic acid ester. The anion can be generated by using a strong organic base such as lithium diisopropylamide or n-butyl lithium as well as other organic lithium bases. In carrying out this reaction, low boiling ether solvents are utilized such as tetrahydrofuran at low temperatures, from $-80°$ C. to about $-10°$ C. being preferred. However, any temperature from $-80°$ C. to room temperature can be used. If necessary, the alkylation reactions may proceed using a triflate alkylation subunit instead of the halo alkylation subunit of compound VII. These triflate alkylation reactions can be performed according to procedures well-known in the art of synthetic organic chemistry.

The compound of formula VIII can be converted to the compound of formula IX by any conventional procedure for converting a carboxylic acid ester to a carboxylic acid. The compound of formula IX is then condensed with the compounds of formula X via conventional peptide coupling to produce the compounds of formula I. In carrying out this reaction, any conventional method of condensing a primary amine with a carboxylic acid can be utilized to effect this conversion.

The alkyl halides of formula VII wherein $R^3$ is cyclobutyl [cyclobutylmethyl bromide] or cyclohexyl [cyclohexylmethyl bromide] are commercially available. The alkyl halide of formula VII wherein $R^3$ is cyclopentyl [iodomethylcyclopentane] is known in the chemical literature, and a synthesis of this compound is described in the Examples.

The amino heteroaromatic compounds of formula X are known in the chemical literature or can be prepared from those skilled in the art by using adaptations of standard synthetic transformations reported in the chemical literature. To produce the compounds of formula I, the synthetic conversions described herein to produce the desired $R^4$ substituents can take place either before or after the compounds of formula X are converted to the compounds of formula I.

For example, if it is desired to produce the amino heteroaromatic compounds of formula X wherein $R^4$ is methylthio, the known amino heteroaromatic compounds of formula X wherein $R^4$ is bromo can be used as starting materials (if Y=CH, then the compound of formula X is the commercially available 2-amino-5-bromopyridine; if Y=N, then the compound of formula X is the known 2-amino-5-bromopyrazine which can be prepared according to *Tetrahedron* 1988, 44, 2977–2983). In this reaction sequence, the bromo substituent can be converted to the compounds of formula X wherein $R^4$ is a methylthio substituent. Any conventional method for the nucleophilic displacement of an aromatic bromo substituent with sodium thiomethoxide can be utilized to effect this conversion (*Tetrahedron* 2002, 58, 1125–1129). The resulting compounds of formula X wherein $R^4$ is methylthio can then be condensed with the compounds of formula IX via conventional peptide coupling to produce the desired compounds of formula I wherein $R^4$ is methylthio. In carrying out this reaction, any conventional method of condensing a primary amine with a carboxylic acid can be utilized to effect this conversion.

Once the compounds of formula I wherein $R^4$ is methylthio are available, they can be converted to the corresponding compounds of formula I wherein $R^4$ is methylsulfinyl. Any conventional method of oxidizing a methylthio substituent to a methylsulfinyl substituent (sulfoxide) can be utilized to effect this conversion. On the other hand, if it is desired to produce compounds of formula I wherein $R^4$ is methylsulfonyl, the compounds of formula I wherein $R^4$ is methylthio can also be used as starting materials. Any conventional method of oxidizing a methylthio substituent to a methylsulfone substituent can be utilized to effect this conversion.

If it is desired to produce the amino heteroaromatic compounds of formula X wherein $R^4$ is (methylthio)methyl, the following known heteroaromatic compounds can be used as starting materials: (1) In formula X, if Y=CH, then the known 5-methylpyridine-2-carboxylic acid, which can be prepared according to *J. Am. Chem. Soc.* 1956, 78, 1932–1934, can be used as starting material; and (2) In formula X, if Y=N then the commercially available 5-methylpyrazine-2-carboxylic acid can be used as starting material. The 5-(methyl)heteroaromatic-2-carboxylic acid can be converted to the corresponding acyl azide. Any conventional method for converting a carboxylic acid to an acyl azide can be utilized to effect this conversion. Curtius rearrangement involving pyrolysis of the resulting acyl azide in the presence of tert-butyl alcohol can provide the compounds of formula X wherein $R^4$ is methyl and wherein the amino group is protected as the tert-butyl carbamate. The 5-(methyl)heteroaromatic-2-carbamic acid tert-butyl ester can then be brominated to afford the 5-(bromomethyl)heteroaromatic-2-carbamic acid tert-butyl ester. Any conventional method of benzylic bromination can be utilized to effect this conversion. The resulting 5-(bromomethyl) substituent can then be converted to the corresponding 5-[(methylthio)methyl] substituent. In this reaction, any conventional method for the nucleophilic displacement of a benzylic bromide with sodium thiomethoxide can be utilized to effect this conversion. Deprotection of the tert-butyl carbamate under standard conditions can provide the desired amino heteroaromatic compounds of formula X wherein $R^4$ is (methylthio)methyl. The resulting compounds of formula X wherein $R^4$ is (methylthio)methyl can then be condensed with the compounds of formula IX via conventional peptide coupling to produce the desired compounds of formula I wherein $R^4$ is (methylthio)methyl. In carrying out this reaction, any conventional method of condensing a primary amine with a carboxylic acid can be utilized to effect this conversion.

Once the compounds of formula I wherein $R^4$ is (methylthio)methyl are available, they can be converted to the corresponding compounds of formula I wherein $R^4$ is (methylsulfinyl)methyl. Any conventional method of oxidizing a methylthio substituent to a methylsulfinyl substituent (sulfoxide) can be utilized to effect this conversion. On the other hand, if it is desired to produce compounds of formula I wherein $R^4$ is (methylsulfonyl)methyl, the compounds of formula I wherein $R^4$ is (methylthio)methyl can also be used as starting materials. Any conventional method of oxidizing a methylthio substituent to a methylsulfone substituent can be utilized to effect this conversion.

If it is desired to produce the compounds of formula I wherein $R^4$ is an N-(hydroxy)-carboximidamide substituent (an amidoxime substituent), the compounds of formula I wherein $R^4$ is bromo can be used as starting materials. In this reaction sequence, the aforementioned known compounds of formula X wherein $R^4$ is bromo can be condensed with the compounds of formula IX via conventional peptide coupling to produce the desired compounds of formula I wherein $R^4$ is bromo. In carrying out this reaction, any conventional method of condensing a primary amine with a carboxylic acid can be utilized to effect this conversion. Once the compounds of formula I wherein $R^4$ is bromo are available, the bromo substituent can then be converted to the compounds of formula I wherein $R^4$ is cyano. Any conventional method for the nucleophilic displacement of an aromatic bromo substituent with a cyano group transferring agent [such as copper(I) cyanide] can be utilized to effect this conversion. Finally, the resulting cyano substituent can then be converted to compounds of formula I wherein $R^4$ is an N-(hydroxy)-carboximidamide substituent (an amidoxime substituent). Any conventional method for converting a cyano substituent to an N-(hydroxy)-carboximidamide substituent (an amidoxime substituent) can be utilized to effect this conversion.

On the other hand, if it is desired to produce the compounds of formula I wherein $R^4$ is a 5-amino-[1,2,4]oxadiazole ring, the aforementioned compounds of formula I wherein $R^4$ is an N-(hydroxy)-carboximidamide substituent can be used as starting materials. The compounds of formula I wherein $R^4$ is an N-(hydroxy)-carboximidamide substituent can be treated with N-cyanopiperidine to afford the compounds of formula I wherein $R^4$ is a 5-amino-[1,2,4] oxadiazole ring (*Nippon Kagaku Kaishi* 1987, 10, 1807–1812).

If it is desired to produce the compounds of formula I wherein $R^4$ is a 5-methyl-[1,2,4]oxadiazole ring, the aforementioned compounds of formula I wherein $R^4$ is an N-(hydroxy)-carboximidamide substituent can also be used as starting materials. The compounds of formula I wherein $R^4$ is an N-(hydroxy)-carboximidamide substituent can be treated with acetic anhydride to afford the compounds of formula I wherein $R^4$ is a 5-methyl-[1,2,4]oxadiazole ring. (*J. Med. Chem.* 1991, 34, 2726–2735).

If it is desired to produce the compounds of formula I wherein $R^4$ is a (cyano-hydroxyimino-methyl) substituent, the aforementioned compounds of formula X wherein $R^4$ is methyl and wherein the amino group is protected as the tert-butyl carbamate can be used as starting materials. The 5-(methyl)heteroaromatic-2-carbamic acid acid tert-butyl ester can then be brominated to afford the 5-(bromomethyl) heteroaromatic-2-carbamic acid tert-butyl ester. Any conventional method of benzylic bromination can be utilized to effect this conversion. The resulting 5-(bromomethyl) substituent can then be converted to the corresponding 5-(cyanomethyl) substituent. In this reaction, any conventional method for the nucleophilic displacement of a benzylic bromide with a cyano group transferring agent can be utilized to effect this conversion. Deprotection of the tert-butyl carbamate under standard conditions can provide the desired amino heteroaromatic compounds of formula X wherein $R^4$ is cyanomethyl. The resulting compounds of formula X wherein $R^4$ is cyanomethyl can then be condensed with the compounds of formula IX via conventional peptide coupling to produce the desired compounds of formula I wherein $R^4$ cyanomethyl. In carrying out this reaction, any conventional method of condensing a primary amine with a carboxylic acid can be utilized to effect this conversion. Once the compounds of formula I wherein $R^4$ is cyanomethyl are available, the cyanomethyl substituent can then be converted to compounds of formula I wherein $R^4$ is a (cyano-hydroxyimino-methyl) substituent. Any conventional method for converting a cyanomethyl substituent to (cyano-hydroxyimino-methyl) substituent can be utilized to effect this conversion (U.S. Pat. No. 4,539,328).

If it is desired to produce the compounds of formula I wherein $R^4$ is a 2-hydroxyethyl thio substituent or a 2-methoxyethyl thio substituent the aforementioned compounds of formula I wherein $R^4$ is bromo can be used as starting materials. The bromo substituent in the compounds of formula I can be directly converted to the compounds of formula I wherein $R^4$ is a 2-hydroxyethyl thio substituent or a 2-methoxyethyl thio substituent. Any conventional method for the nucleophilic displacement of an aromatic bromo substituent with mercaptoethanol or 2-methoxyethanethiol can be utilized to effect this conversion.

If it is desired to produce the compounds of formula I wherein $R^4$ is a 3-substituted-1-propyne substituent or a 4-substituted-1-butyne substituent, $-C\equiv C-(CH_2)_p-R^8$, and $R^8$ is hydroxy, methoxy, or dimethylamine and p is 1 or 2, the aforementioned compounds of formula I wherein $R^4$ is bromo can be used as starting materials. The bromo substituent in the compounds of formula I can be directly converted to the compounds of formula I wherein $R^4$ is a 3-substituted-1-propyne substituent or a 4-substituted-1-butyne substituent, $-C\equiv C-(CH_2)_n-R^8$, and $R^8$ is hydroxy, methoxy, or dimethylamine and p is 1 or 2. Any conventional method for the catalytic substitution of an acetylenic hydrogen (for example, propargyl alcohol and 3-butyn-1-ol) with an aryl bromide, such as the Sonogashira reaction, can be utilized to effect this conversion (for a general review, see Campbell, I. B. *Organocopper Reagents* 1994, 217–235).

If it is desired to produce the compounds of formula I wherein $R^4$ is a 4-ethynyltetrahydropyran-4-ol substituent, the aforementioned compounds of formula I wherein $R^4$ is bromo can also be used as starting materials. In this reaction sequence, the commercially available tetrahydro-4H-pyran-4-one can be reacted with the commercially available ethynylmagnesium bromide to produce the desired compound with an acetylenic hydrogen, 4-ethynyltetrahydro-2H-pyran-4-ol. The compounds of formula I wherein $R^4$ is bromo can then be reacted with 4-ethynyltetrahydro-2H-pyran-4-ol to produce the compounds of formula I wherein $R^4$ is a 4-ethynyltetrahydropyran-4-ol substituent. Any conventional method for the catalytic substitution of an acetylenic hydrogen with an aryl bromide, such as the Sonogashira reaction, can be utilized to effect this conversion.

Once the compounds of formula I wherein $R^4$ is a 4-ethynyltetrahydropyran-4-ol substituent are available, they can be converted to the corresponding compounds of formula I wherein $R^4$ is a 4-ethyltetrahydropyran-4-ol substituent. The heteroaromatic 4-ethynyltetrahydropyran-4-ol substituent can be reduced to produce the corresponding heteroaromatic 4-ethyltetrahydropyran-4-ol substituent. Any conventional method for the reduction of an alkyne to a saturated hydrocarbon can be utilized to effect this conversion.

On the other hand, if it is desired to produce the compounds of formula I wherein $R^4$ is a —C≡C—C(CH$_3$)$_2$—OH substituent, the aforementioned compounds of formula I wherein $R^4$ is bromo can also be used as starting materials. The compounds of formula I wherein $R^4$ is bromo can be reacted with 2-methyl-3-butyn-2-ol to produce the compounds of formula I wherein $R^4$ is a —C≡C—C(CH$_3$)$_2$—OH substituent. Any conventional method for the catalytic substitution of an acetylenic hydrogen with an aryl bromide, such as the Sonogashira reaction, can be utilized to effect this conversion.

If it is desired to produce the compounds of formula I wherein $R^4$ is a N-methyl sulfonamide substituent or a N,N-dimethyl sulfonamide substituent, the aforementioned compounds of formula I wherein $R^4$ is methylsulfinyl (methyl sulfoxide) can be used as starting materials. The compounds of formula I wherein $R^4$ is methylsulfinyl can then be converted to the compounds of formula I wherein $R^4$ is thiol. A two-step procedure which involves a Pummerer methyl sulfoxide rearrangement using trifluoroacetic anhydride followed by hydrolysis of the Pummerer rearrangement intermediate with triethylamine and methanol can be utilized to effect this conversion. Once the compounds of formula I wherein $R^4$ is thiol are available, these compounds can be converted to the compounds of formula I wherein $R^4$ is sulfonyl chloride. Any conventional method of oxidizing a thiol substituent to a sulfonyl chloride substituent can be utilized to effect this conversion. Finally, the resulting compounds of formula I wherein $R^4$ is sulfonyl chloride can then be converted to the desired compounds of formula I wherein $R^4$ is a N-methyl sulfonamide substituent or a N,N-dimethyl sulfonamide substituent. Any conventional method of reacting a sulfonyl chloride substituent with methylamine to produce a N-methyl sulfonamide substituent or with dimethylamine to produce a N,N-dimethyl sulfonamide substituent can be utilized to effect this conversion.

If it is desired to produce the compounds of formula I wherein $R^4$ is dimethoxymethyl, the following known heteroaromatic compounds can be used as starting materials: (1) In formula I, if Y=CH, then the known 5-methylpyridine-2-carboxylic acid can be used as starting material; and (2) In formula I, if Y=N then the commercially available 5-methylpyrazine-2-carboxylic acid can be used as starting material. In this reaction sequence to produce the compounds of formula I wherein $R^4$ is dimethoxymethyl, the carboxylic acid can be esterified and the methyl group can be converted to the N,N-dimethyl-ethenamine concurrently using dimethylformamide dimethylacetal. The aromatic N,N-dimethyl-ethenamine functionality can then be oxidatively cleaved to produce the corresponding heteroaromatic aldehyde. Any conventional method of oxidatively cleaving a vinyl dimethyl amine to an aldehyde can be utilized to effect this conversion. The resulting heteroaromatic aldehyde can then be converted to the corresponding heteroaromatic dimethyl acetal. Any conventional method for converting an aldehyde to a dimethyl acetal can be utilized to effect this conversion. The resulting 5-(dimethoxymethyl) heteroaromatic-2-carboxylic acid methyl ester can then be converted to the corresponding carboxylic acid. Any conventional means of hydrolyzing a carboxylic acid ester to the carboxylic acid under basic conditions can be utilized to effect this conversion. Next, the 5-(dimethoxymethyl)heteroaromatic-2-carboxylic acid can be converted to the corresponding acyl azide. Any conventional method for converting a carboxylic acid to an acyl azide can be utilized to effect this conversion. Curtius rearrangement involving pyrolysis of the resulting acyl azide in the presence of benzyl alcohol can provide the compounds of formula X wherein $R^4$ is dimethoxymethyl and wherein the amino group is protected as the benzyl carbamate. Deprotection of the benzyl carbamate under standard hydrogenation conditions can provide the desired compounds of formula X wherein $R^4$ is dimethoxymethyl. The resulting compounds of formula X wherein $R^4$ is dimethoxymethyl can then be condensed with the compounds of formula IX via conventional peptide coupling to produce the desired compounds of formula I wherein $R^4$ is dimethoxymethyl. In carrying out this reaction, any conventional method of condensing a primary amine with a carboxylic acid can be utilized to effect this conversion.

If it is desired to produce the compounds of formula I wherein $R^4$ is 1,3-dioxolan-2-yl or wherein $R^4$ is 1,3-dioxan-2-yl, these compounds can be prepared according to the reaction sequence described above. To produce the desired cyclic acetals instead of the acyclic dimethyl acetal, at the reaction step wherein the heteroaromatic aldehyde is isolated after oxidative cleavage, the resulting aldehyde can be converted to the either the desired 1,3-dioxolane cyclic acetal or to the desired 1,3-dioxane cyclic acetal. Any conventional method of reacting an aldehyde with ethylene glycol to produce a 1,3-dioxolane cyclic acetal or reacting an aldehyde with 1,3-propanediol to produce a 1,3-dioxane cyclic acetal can be utilized to effect this conversion. Once the desired cyclic acetals are produced, the remaining sequence of reactions as described above are utilized to produce the compounds of formula I wherein $R^1$ is 1,3-dioxolan-2-yl or wherein $R^4$ is 1,3-dioxan-2-yl.

If it is desired to produce the compounds of formula I wherein $R^4$ is 2,2-(dimethoxy)ethyl, the following known heteroaromatic compounds can be used as starting materials: (1) In formula I, if Y=CH, then the known 5-methylpyridine-2-carboxylic acid can be used as starting material; and (2) In formula I, if Y=N then the commercially available 5-methylpyrazine-2-carboxylic acid can be used as starting material. In this reaction sequence to produce the compounds of formula I wherein $R^4$ is 2,2-(dimethoxy)ethyl, the carboxylic acid can be esterified and the methyl group can be converted to the N,N-dimethyl-ethenamine concurrently using dimethylformamide dimethylacetal. The N,N-dimethyl-ethenamine functionality can then be hydrolyzed to produce the corresponding aldehyde. Any conventional method of hydrolyzing an enamine to an aldehyde can be utilized to effect this conversion. The resulting heteroaromatic acetaldehyde can then be converted to the corresponding dimethyl acetal. Any conventional method for converting an aldehyde to a dimethyl acetal can be utilized to effect this conversion. The resulting 5-[2,2-(dimethoxy)ethyl]heteroaromatic-2-carboxylic acid methyl ester can then be converted to the corresponding carboxylic acid. Any conventional means of hydrolyzing a carboxylic acid ester to the carboxylic acid under basic conditions can be utilized to effect this conversion. Next, the 5-[2,2-(dimethoxy)ethyl] heteroaromatic-2-carboxylic acid can be converted to the corresponding acyl azide. Any conventional method for converting a carboxylic acid to an acyl azide can be utilized to effect this conversion. Curtius rearrangement involving pyrolysis of the resulting acyl azide in the presence of benzyl alcohol can provide the compounds of formula X wherein $R^4$ is 2,2-(dimethoxy)ethyl and wherein the amino group is protected as the benzyl carbamate. Deprotection of the benzyl carbamate under standard hydrogenation conditions can provide the desired compounds of formula X wherein $R^4$ is 2,2-(dimethoxy)ethyl. The resulting compounds of formula X wherein $R^4$ is 2,2-(dimethoxy)ethyl can then be condensed with the compounds of formula IX via conventional peptide coupling to produce the desired compounds of formula I wherein $R^4$ is 2,2-(dimethoxy)ethyl. In carrying out this reaction, any conventional method of condensing a primary amine with a carboxylic acid can be utilized to effect this conversion.

If it is desired to produce the compounds of formula I wherein $R^4$ is (1,3-dioxolan-2-yl)methyl or wherein $R^4$ is (1,3-dioxan-2-yl)methyl, these compounds can be prepared according to the reaction sequence described above. To produce the desired cyclic acetals instead of the acyclic dimethyl acetal, at the reaction step wherein the heteroaromatic acetaldehyde is isolated after hydrolysis, the resulting acetaldehyde can be converted to the either the desired 1,3-dioxolane cyclic acetal or to the desired 1,3-dioxane cyclic acetal. Any conventional method of reacting an aldehyde with ethylene glycol to produce a 1,3-dioxolane cyclic acetal or reacting an aldehyde with 1,3-propanediol to produce a 1,3-dioxane cyclic acetal can be utilized to effect this conversion. Once the desired cyclic acetals are produced, the remaining sequence of reactions as described above are utilized to produce the compounds of formula I wherein $R^4$ is (1,3-dioxolan-2-yl)methyl or wherein $R^4$ is (1,3-dioxan-2-yl)methyl.

If it is desired to produce the compounds of formula I wherein $R^4$ is a (2,3-dihydroxy-propoxyl) substituent, the following known heteroaromatic compounds can be used as starting materials: (1) In formula I, if Y=CH, then the known 5-chloro-pyridine-2-carboxylic acid methyl ester, which can be prepared according to Tetrahedron Lett. 1999, 40, 3719–3722, can be used as starting material; and (2) In formula I, if Y=N then the commercially available methyl 5-chloropyrazine-2-carboxylate can be used as starting material. In this reaction sequence, the 5-chloro substituent can be displaced to produce a 5-allyloxy substituent, and the 2-carboxylic acid methyl ester substituent can be hydrolyzed to produce to the 2-carboxylic acid concurrently using allyl alcohol and potassium hydroxide under heating conditions, preferably from 90° C. to 100° C. Next, the 5-[allyloxy] heteroaromatic-2-carboxylic acid can be converted to the corresponding acyl azide. Any conventional method for converting a carboxylic acid to an acyl azide can be utilized to effect this conversion. Curtius rearrangement involving pyrolysis of the resulting acyl azide in the presence of tert-butyl alcohol can provide the compounds of formula X wherein $R^4$ is an allyloxy substituent and wherein the amino group is protected as the tert-butyl carbamate. Deprotection of the tert-butyl carbamate under standard acidic conditions can provide the desired compounds of formula X wherein $R^1$ is an allyloxy substituent. The resulting compounds of formula X wherein $R^4$ is an allyloxy substituent can then be condensed with the compounds of formula IX via conventional peptide coupling to produce the desired compounds of formula I wherein $R^1$ is an allyloxy substituent. In carrying out this reaction, any conventional method of condensing a primary amine with a carboxylic acid can be utilized to effect this conversion. Once the compounds of formula I wherein $R^4$ is allyloxy are available, they can be converted to the desired compounds of formula I wherein $R^4$ is a [2(S),3-dihydroxy-propoxyl] substituent, a [2(R),3-dihydroxy-propoxyl] substituent, or a (2,3-dihydroxy-propoxyl) substituent. The allyloxy substituent can be subjected to Sharpless asymmetric dihydroxylation conditions to produce the desired chiral diols (Chem. Rev. 1994, 94, 2483–2547; J. Chem. Soc., Perkin Trans. 1, 1999, 3015–3018). The compounds of formula I wherein $R^4$ is allyloxy can be subjected to conventional Sharpless asymmetric dihydroxylation conditions using $(DHQD)_2PHAL$ [hydroquinidine 1,4-phthalazinediyl diether] to produce the desired compounds of formula I wherein $R^4$ is a [2(S),3-dihydroxy-propoxyl] substituent. On the other hand, the compounds of formula I wherein $R^4$ is allyloxy can be subjected to conventional Sharpless asymmetric dihydroxylation conditions using $(DHQ)_2PHAL$ [hydroquinine 1,4-phthalazinediyl diether] to produce the desired compounds of formula I wherein $R^4$ is a [2(R),3-dihydroxy-propoxyl] substituent. If the compounds of formula I wherein $R^4$ is allyloxy are subjected to conventional non-asymmetric dihydroxylation conditions, the racemic diols of formula I wherein $R^4$ is a (2,3-dihydroxy-propoxyl) substituent can be produced. In accordance with this invention, the preferred stereoconfiguration at the chiral center with the hydroxyl functional group is "R."

If it is desired to produce the compounds of formula I wherein $R^4$ is a (2,3-dihydroxy-propyl) substituent, the known amino heteroaromatic compounds of formula X wherein $R^4$ is bromo can be used as starting materials. In this reaction sequence, the bromo substituent can be directly converted to the compounds of formula X wherein $R^4$ is an allyl substituent. The palladium-mediated Stille coupling reaction of the heteroaromatic bromo substituent with the commercially available allyltri-n-butyltin can be utilized to effect this conversion. The resulting compounds of formula X wherein $R^4$ is an allyl substituent can then be condensed with the compounds of formula IX via conventional peptide coupling to produce the desired compounds of formula I wherein $R^4$ is an allyl substituent. In carrying out this reaction, any conventional method of condensing a primary amine with a carboxylic acid can be utilized to effect this conversion. Once the compounds of formula I wherein $R^4$ is allyl are available, they can be converted to the desired compounds of formula I wherein $R^4$ is a [2(R),3-dihydroxy-propyl] substituent, a [2(S),3-dihydroxy-propyl] substituent, or a (2,3-dihydroxy-propyl) substituent. The allyl substituent can be subjected to Sharpless asymmetric dihydroxylation conditions to produce the desired chiral diols. The compounds of formula I wherein $R^4$ is allyl can be subjected to conventional Sharpless asymmetric dihydroxylation conditions using $(DHQD)_2PHAL$ to produce the desired compounds of formula I wherein $R^4$ is a [2(R),3-dihydroxy-propyl] substituent. On the other hand, the compounds of formula I wherein $R^4$ is allyl can be subjected to conventional Sharpless asymmetric dihydroxylation conditions using $(DHQ)_2PHAL$ to produce the desired compounds of formula I wherein $R^4$ is a [2(S),3-dihydroxy-propyl] substituent. If the compounds of formula I wherein $R^4$ is allyl are subjected to conventional non-asymmetric dihydroxylation conditions, the racemic diols of formula I wherein $R^4$ is a (2,3-dihydroxy-propyl) substituent can be produced. In accordance with this invention, the preferred stereoconfiguration at the chiral center with the hydroxyl functional group is "R."

If it is desired to produce the compounds of formula I wherein $R^4$ is a (1,2-dihydroxy-ethyl) substituent, the known amino heteroaromatic compounds of formula X wherein $R^4$ is bromo can also be used as starting materials. In this reaction sequence, the bromo substituent can be directly converted to the compounds of formula X wherein $R^4$ is a vinyl substituent. The palladium-mediated Stille coupling reaction of the heteroaromatic bromo substituent with the commercially available vinyltri-n-butyltin can be utilized to effect this conversion. The resulting compounds of formula X wherein $R^4$ is a vinyl substituent can then be condensed with the compounds of formula IX via conventional peptide coupling to produce the desired compounds of formula I wherein $R^4$ is a vinyl substituent. In carrying out this reaction, any conventional method of condensing a primary amine with a carboxylic acid can be utilized to effect this conversion. Once the compounds of formula I wherein $R^4$ is vinyl are available, they can be converted to the desired compounds of formula I wherein $R^4$ is a [1(R),2-dihydroxy-ethyl] substituent, a [1(S),2-dihydroxy-ethyl] substituent, or a (1,2-dihydroxy-ethyl) substituent. The vinyl substituent can be subjected to Sharpless asymmetric dihydroxylation conditions to produce the desired chiral diols. The compounds of formula I wherein $R^4$ is vinyl can be subjected to conventional Sharpless asymmetric dihydroxylation conditions using (DHQD)$_2$PHAL to produce the desired compounds of formula I wherein $R^4$ is a [1(R),2-dihydroxy-ethyl] substituent. On the other hand, the compounds of formula I wherein $R^4$ is vinyl can be subjected to conventional Sharpless asymmetric dihydroxylation conditions using (DHQ)$_2$PHAL to produce the desired compounds of formula I wherein $R^4$ is a [1(S),2-dihydroxy-ethyl] substituent. If the compounds of formula I wherein $R^4$ is vinyl are subjected to conventional non-asymmetric dihydroxylation conditions, the racemic diols of formula I wherein $R^4$ is a (1,2-dihydroxy-ethyl) substituent can be produced. In accordance with this invention, the preferred stereoconfiguration at the chiral center with the hydroxyl functional group is "S."

If it is desired to produce the compounds of formula I wherein $R^4$ is a (1,2-dihydroxy-2-methyl-propyl) substituent, the known amino heteroaromatic compounds of formula X wherein $R^4$ is bromo can also be used as starting materials. In this reaction sequence, the bromo substituent can be directly converted to the compounds of formula X wherein $R^4$ is an isobutenyl substituent. The palladium-mediated Stille coupling reaction of the heteroaromatic bromo substituent with the known isobutenyltri-n-butyltin can be utilized to effect this conversion. The resulting compounds of formula X wherein $R^4$ is an isobutenyl substituent can then be condensed with the compounds of formula IX via conventional peptide coupling to produce the desired compounds of formula I wherein $R^4$ is an isobutenyl substituent. In carrying out this reaction, any conventional method of condensing a primary amine with a carboxylic acid can be utilized to effect this conversion. Once the compounds of formula I wherein $R^4$ is isobutenyl are available, they can be converted to the desired compounds of formula I wherein $R^4$ is a [1(R),2-dihydroxy-2-methyl-propyl] substituent, a [1(S),2-dihydroxy-2-methyl-propyl] substituent, or a (1,2-dihydroxy-2-methyl-propyl) substituent. The isobutenyl substituent can be subjected to Sharpless asymmetric dihydroxylation conditions to produce the desired chiral diols. The compounds of formula I wherein $R^4$ is isobutenyl can be subjected to conventional Sharpless asymmetric dihydroxylation conditions using (DHQD)$_2$PHAL to produce the desired compounds of formula I wherein $R^4$ is a [1(R),2-dihydroxy-2-methyl-propyl] substituent. On the other hand, the compounds of formula I wherein $R^4$ is isobutenyl can be subjected to conventional Sharpless asymmetric dihydroxy-lation conditions using (DHQ)$_2$PHAL to produce the desired compounds of formula I wherein $R^4$ is a [1(S),2-dihydroxy-2-methyl-propyl] substituent. If the compounds of formula I wherein $R^4$ is isobutenyl are subjected to conventional non-asymmetric dihydroxylation conditions, the racemic diols of formula I wherein $R^4$ is a (1,2-dihydroxy-2-methyl-propyl) substituent can be produced. In accordance with this invention, the preferred stereoconfiguration at the chiral center with the hydroxyl functional group is "S."

If it is desired to produce the amino heteroaromatic compounds of formula X wherein $R^4$ is a —NHCH$_2$CH$_2$OCH$_3$ (2-methoxy-ethylamino) substituent or wherein $R^4$ is a —OCH$_2$CH$_2$OCH$_3$ (2-methoxy-ethoxy) substituent, the following known heteroaromatic compounds can be used as starting materials: (1) In formula X, if Y=CH, then the commercially available 5-bromo-2-nitropyridine can be used as starting material; and (2) In formula X, if Y=N then the known 2-bromo-5-nitropyrazine, which can be prepared according to Tetrahedron 1988, 44, 2977–2983, can be used as starting material. In this reaction sequence, the bromo substituent can be directly converted to the compounds of formula X wherein $R^4$ is a (2-methoxy-ethylamino) substituent or wherein $R^4$ is a (2-methoxy-ethoxy) substituent. Any conventional method for the nucleophilic displacement of an aromatic bromo substituent with 2-methoxyethylamine or 2-methoxyethanol, respectively, can be utilized to effect this conversion. Once the resulting 5-[2-methoxy-ethylamino]-2-nitro-heteroaromatic compounds and the resulting 5-[2-methoxy-ethoxy]-2-nitro-heteroaromatic compounds are available, the nitro substituent can be converted to the amino heteroaromatic compounds of formula X wherein $R^4$ is the desired (2-methoxy-ethylamino) substituent or the desired (2-methoxy-ethoxy) substituent. Any conventional method for the reduction of a nitro substituent to an amino substituent can be utilized to effect this conversion. These compounds of formula X wherein $R^4$ is a —NHCH$_2$CH$_2$OCH$_3$ substituent or wherein $R^4$ is a —OCH$_2$CH$_2$OCH$_3$ substituent can then be condensed with the compounds of formula IX via conventional peptide coupling to produce the desired compounds of formula I wherein $R^4$ is a —NHCH$_2$CH$_2$OCH$_3$ substituent or wherein $R^4$ is a —OCH$_2$CH$_2$OCH$_3$ substituent, respectively. In carrying out this reaction, any conventional method of condensing a primary amine with a carboxylic acid can be utilized to effect this conversion.

If it is desired to produce the compounds of formula I wherein $R^4$ is a —NHCH$_2$CH$_2$OH (2-hydroxy-ethylamino) substituent or wherein $R^4$ is a —OCH$_2$CH$_2$OH (2-hydroxy-ethoxy) substituent, the following known heteroaromatic compounds can be used as starting materials: (1) In formula X, if Y=CH, then the commercially available 5-bromo-2-nitropyridine can be used as starting material; and (2) In formula X, if Y=N then the known 2-bromo-5-nitropyrazine can be used as starting material. In this reaction sequence, the bromo substituent can be directly converted to the compounds of formula X wherein $R^4$ is a [2-(tetrahydropyran-2-yloxy)-ethylamino] substituent or wherein $R^4$ is a [2-(tetrahydropyran-2-yloxy)-ethoxy] substituent. Any conventional method for the nucleophilic displacement of an aromatic bromo substituent with the known 2-tetrahydropyran-2-yloxy-ethylamine (*J. Med. Chem.* 1999, 42, 1587–1603) or the commercially available 2-(2-hydroxy-ethoxy)tetrahydropyran, respectively, can be utilized to effect this conversion. Once the resulting 5-[2-(tetrahydropyran-2-yloxy)-ethylamino]-2-nitro-heteroaromatic compounds and the resulting 5-[2-(tetrahydropyran-2-yloxy)- ethoxy]-2-nitro-heteroaromatic compounds are available, the nitro substituent can be converted to the amino heteroaromatic compounds of formula X wherein $R^4$ is the [2-(tetrahydropyran-2-yloxy)-ethylamino] substituent or the [2-(tetrahydropyran-2-yloxy)-ethoxy] substituent. Any conventional method for the reduction of a nitro substituent to an amino substituent can be utilized to effect this conversion. These compounds of formula X wherein $R^4$ is the [2-(tetrahydropyran-2-yloxy)-ethylamino] substituent or the [2-(tetrahydropyran-2-yloxy)-ethoxy] substituent can then be condensed with the compounds of formula IX via conventional peptide coupling to produce the desired compounds of formula I wherein $R^4$ is the [2-(tetrahydropyran-2-yloxy)-ethylamino] substituent or the [2-(tetrahydropyran-2-yloxy)-ethoxy] substituent, respectively. In carrying out this reaction, any conventional method of condensing a primary amine with a carboxylic acid can be utilized to effect this conversion. Once the compounds of formula I wherein $R^4$ is the [2-(tetrahydropyran-2-yloxy)-ethylamino] substituent or the [2-(tetrahydropyran-2-yloxy)-ethoxy] substituent are available, they can then be converted to the desired compounds of formula I wherein $R^4$ is a —NHCH$_2$CH$_2$OH (2-hydroxy-ethylamino) substituent or wherein $R^4$ is a —OCH$_2$CH$_2$OH (2-hydroxy-ethoxy) substituent. Any conventional method for the deprotection of a tetrahydropyranyl ether to the produce the hydroxy group can be utilized to effect this conversion If it is desired to produce the amino heteroaromatic compounds of formula X wherein $R^4$ is a methanesulfonylamino substituent, the following known heteroaromatic compounds can be used as starting materials: (1) In formula X, if Y=CH, then the commercially available 5-bromo-2-nitropyridine can be used as starting material; and (2) In formula X, if Y=N then the known 2-bromo-5-nitropyrazine can be used as starting material. In this reaction sequence, the bromo substituent can be directly converted to the compounds of formula X wherein $R^4$ is a methanesulfonylamino substituent. Any conventional method for the displacement of an aromatic bromo substituent with methanesulfonamide can be utilized to effect this conversion. Once the resulting 5-[methansulfonylamino]-2-nitro-heteroaromatic compounds are available, the nitro substituent can be converted to the amino heteroaromatic compounds of formula X wherein $R^4$ is the desired methanesulfonylamino substituent. Any conventional method for the reduction of a nitro substituent to an amino substituent can be utilized to effect this conversion. These compounds of formula X wherein $R^4$ is methanesulfonylamino can then be condensed with the compounds of formula IX via conventional peptide coupling to produce the desired compounds of formula I wherein $R^4$ is a methanesulfonylamino substituent. In carrying out this reaction, any conventional method of condensing a primary amine with a carboxylic acid can be utilized to effect this conversion.

If it is desired to produce the amino heteroaromatic compounds of formula X wherein $R^4$ is dimethylamino, the following known heteroaromatic compounds can be used as starting materials: (1) In formula X, if Y=CH, then the commercially available 5-bromo-2-nitropyridine can be used as starting material; and (2) In formula X, if Y=N then the known 2-bromo-5-nitropyrazine can be used as starting material. In this reaction sequence, the bromo substituent can be directly converted to the compounds of formula X wherein $R^4$ is dimethylamino. Any conventional method for the nucleophilic displacement of an aromatic bromo substituent with dimethylamine can be utilized to effect this conversion. Once the resulting 5-[dimethylamino]-2-nitro-heteroaromatic compounds are available, the nitro substituent can be converted to the heteroaromatic amines of formula X wherein $R^4$ is dimethylamino. Any conventional method for the reduction of a nitro substituent to an amino substituent can be utilized to effect this conversion. These compounds of formula X wherein $R^4$ is dimethylamino can then be condensed with the compounds of formula IX via conventional peptide coupling to produce the desired compounds of formula I wherein $R^4$ is dimethylamino. In carrying out this reaction, any conventional method of condensing a primary amine with a carboxylic acid can be utilized to effect this conversion.

If it is desired to produce the amino heteroaromatic compounds of formula X wherein $R^4$ is (dimethylamino)methyl, the following known heteroaromatic compounds can be used as starting materials: (1) In formula X, if Y=CH, then the known 5-methylpyridine-2-carboxylic acid can be used as starting material; and (2) In formula X, if Y=N then the commercially available 5-methylpyrazine-2-carboxylic acid can be used as starting material. In the reaction sequence to produce the compounds of formula X wherein $R^4$ is (dimethylamino)methyl, the carboxylic acid can be converted to the corresponding methyl ester. Any conventional esterification method for converting a carboxylic acid to a carboxylic acid methyl ester can be utilized to effect this conversion. The 5-(methyl)heteroaromatic-2-carboxylic acid methyl ester can then be brominated to afford the 5-(bromomethyl)heteroaromatic-2-carboxylic acid methyl ester. Any conventional method of benzylic bromination can be utilized to effect this conversion. The resulting bromomethyl substituent can then be converted to the corresponding (dimethylamino)methyl substituent. In this reaction, any conventional method for the nucleophilic displacement of a benzylic bromide with dimethylamine can be utilized to effect this conversion. The resulting 5-[(dimethylamino)methyl]heteroaromatic-2-carboxylic acid methyl ester can then be converted to the corresponding carboxylic acid. Any conventional means of hydrolyzing a carboxylic acid ester to the carboxylic acid can be utilized to effect this conversion. Next, the 5-[(dimethylamino)methyl]heteroaromatic-2-carboxylic acid can be converted to the corresponding acyl azide. Any conventional method for converting a carboxylic acid to an acyl azide can be utilized to effect this conversion. Curtius rearrangement involving pyrolysis of the resulting acyl azide in the presence of benzyl alcohol can provide the compounds of formula X wherein $R^4$ is (dimethylamino)methyl and wherein the amino group is protected as the benzyl carbamate. Deprotection of the benzyl carbamate under standard hydrogenation conditions can provide the desired amino heteroaromatic compounds of formula X wherein $R^4$ is (dimethylamino)methyl. The resulting compounds of formula X wherein $R^4$ is (dimethylamino)methyl can then be condensed with the compounds of formula IX via conventional peptide coupling to produce the desired compounds of formula I wherein $R^4$ is (dimethylamino)methyl. In carrying out this reaction, any conventional method of condensing a primary amine with a carboxylic acid can be utilized to effect this conversion.

If it is desired to produce the amino heteroaromatic compounds of formula X wherein $R^4$ is 2-(dimethylamino) ethyl, the following known heteroaromatic compounds can be used as starting materials: (1) In formula X, if Y=CH, then the known 5-methylpyridine-2-carboxylic acid can be used as starting material; and (2) In formula X, if Y=N then the commercially available 5-methylpyrazine-2-carboxylic acid can be used as starting material. In this reaction sequence to produce the compounds of formula X wherein $R^4$ is 2-(dimethylamino)ethyl, the carboxylic acid can be esterified and the methyl group can be converted to the N,N-dimethyl-ethenamine concurrently using dimethylformamide dimethylacetal. The heteroaromatic N,N-dimethyl-ethenamine substituent can then be reduced to produce the corresponding heteroaromatic 2-(dimethylamino)ethyl substituent. Any conventional method for the reduction of a carbon-carbon double bond to a saturated hydrocarbon can be utilized to effect this conversion. The resulting 5-[2-(dimethylamino)ethyl]heteroaromatic-2-carboxylic acid methyl ester can then be converted to the corresponding carboxylic acid. Any conventional means of hydrolyzing a carboxylic acid ester to the carboxylic acid can be utilized to effect this conversion. Next, the 5-[2-(dimethylamino)ethyl] heteroaromatic-2-carboxylic acid can be converted to the corresponding acyl azide. Any conventional method for converting a carboxylic acid to an acyl azide can be utilized to effect this conversion. Curtius rearrangement involving pyrolysis of the resulting acyl azide in the presence of benzyl alcohol can provide the compounds of formula X wherein $R^4$ is 2-(dimethylamino)ethyl and wherein the amino group is protected as the benzyl carbamate. Deprotection of the benzyl carbamate under standard hydrogenation conditions can provide the desired amino heteroaromatic compounds of formula X wherein $R^4$ is 2-(dimethylamino)ethyl. The resulting compounds of formula X wherein $R^4$ is 2-(dimethylamino)ethyl can then be condensed with the compounds of formula IX via conventional peptide coupling to produce the desired compounds of formula I wherein $R^4$ is 2-(dimethylamino)ethyl. In carrying out this reaction, any conventional method of condensing a primary amine with a carboxylic acid can be utilized to effect this conversion.

If it is desired to produce the compounds of formula I wherein $R^4$ is 3-(dimethylamino)propyl, the compounds of formula I wherein $R^4$ is bromo can be used as starting materials. In this reaction sequence, the aforementioned known compounds of formula X wherein $R^4$ is bromo can be condensed with the compounds of formula IX via conventional peptide coupling to produce the desired compounds of formula I wherein $R^4$ is bromo. In carrying out this reaction, any conventional method of condensing a primary amine with a carboxylic acid can be utilized to effect this conversion. Once the compounds of formula I wherein $R^4$ is bromo are available, the bromo substituent can then be converted to compounds of formula I wherein $R^4$ is a 3-(dimethylamino)-1-propyne substituent. Any conventional method for the catalytic substitution of the acetylenic hydrogen of 1-dimethylamino-2-propyne with an aryl bromide, such as the Sonogashira reaction, can be utilized to effect this conversion. Once the compounds of formula I wherein $R^4$ is 3-(dimethylamino)-1-propyne are available, they can be converted to the desired compounds of formula I wherein $R^4$ is 3-(dimethylamino)propyl. The heteroaromatic 3-(dimethylamino)-1-propyne substituent can be reduced to produce the corresponding heteroaromatic 3-(dimethylamino) propyl substituent. Any conventional method for the reduction of an alkyne to a saturated hydrocarbon can be utilized to effect this conversion.

If it is desired to produce the compounds of formula I wherein $R^4$ is a formyl substituent, the aforementioned compounds of formula I wherein $R^4$ is bromo can be used as starting materials. Once the compounds of formula I wherein $R^4$ is bromo are available, the bromo substituent can then be converted to compounds of formula I wherein $R^4$ is a formyl substituent. Any conventional method for the carbonylation of an aryl bromide can be utilized to effect this conversion.

If it is desired to produce the compounds of formula I wherein $R^4$ is a secondary alcohol substituent corresponding to —CH(OH)—$R^7$ and $R^7$ is lower alkyl, the aforementioned compounds of formula I wherein $R^4$ is a formyl substituent can be used as starting materials. In this reaction sequence, the formyl substituent can be directly converted to the compounds of formula I wherein $R^4$ is a secondary alcohol substituent corresponding to —CH(OH)—$R^7$ and $R^7$ is lower alkyl. Any conventional method for converting an aldehyde to a secondary alcohol, such as the Grignard reaction, can be utilized to effect this conversion.

Once the compounds of formula I wherein $R^4$ is —CH(OH)—$R^7$ and $R^7$ is lower alkyl are available, the secondary alcohol substituent can then be converted to the desired compounds of formula I wherein $R^4$ is —C(=O)—$R^{11}$ and $R^{11}$ is lower alkyl. Any conventional method of oxidizing an alcohol substituent to a ketone substituent can be utilized to effect this conversion.

Once the compounds of formula I wherein $R^4$ is —C(=O)—$R^{11}$ and $R^{11}$ is lower alkyl are available, the ketone substituent can then be converted to the desired compounds of formula I wherein $R^4$ is —C(=NOH)—$R^{10}$ and $R^{10}$ is lower alkyl. Any conventional method of transforming a ketone substituent into an oxime substituent can be utilized to effect this conversion.

On the other hand, if it is desired to produce the compounds of formula I wherein $R^4$ is a cyanohydrin substituent corresponding to —CH(OH)—$R^7$ and $R^7$ is cyano, the aforementioned compounds of formula I wherein $R^4$ is a formyl substituent can also be used as starting materials. In this reaction sequence, the formyl substituent can be directly converted to the compounds of formula I wherein $R^4$ is a cyanohydrin substituent corresponding to —CH(OH)—$R^7$ and $R^7$ is cyano. Any conventional method for converting an aldehyde substituent to a cyanohydrin substituent can be utilized to effect this conversion. Once the compounds of formula I wherein $R^4$ is cyanohydrin are available, the cyano substituent can then be converted to compounds of formula I wherein $R^4$ is —CH(OH)—$R^7$ and $R^7$ is —C(=O)NH$_2$. Any conventional method for the hydrolysis of a nitrile to an amide can be utilized to effect this conversion.

If it is desired to produce the compounds of formula I wherein $R^4$ is a (2,4-dioxo-thiazolidin-5-ylmethyl) substituent, the aforementioned compounds of formula I wherein $R^4$ is a formyl substituent can be used as starting materials. In this reaction sequence, the formyl substituent can be reacted with 2,4-thiazolidinedione to afford the corresponding compounds of formula I wherein $R^4$ is a (2,4-dioxo-thiazolidin-5-ylidenemethyl) substituent (*J. Med. Chem.* 1998, 41, 1619–1630; PCT Intl. Appl. 9743283, 20 Nov. 1997). The compounds of formula I wherein $R^4$ is a (2,4-dioxo-thiazolidin-5-ylidenemethyl) substituent can then be converted into the desired compounds of formula I wherein $R^4$ is a (2,4-dioxo-thiazolidin-5-ylmethyl) substituent by reduction of the carbon-carbon double bond using 2,6-dimethyl-1,4-dihydro-pyridine-3,5-dicarboxylic acid diethyl ester and silica gel in toluene.

If it is desired to produce the compounds of formula I wherein $R^4$ is a (2,5-dioxo-imidazolidin-4-ylmethyl) substituent, the aforementioned compounds of formula I wherein $R^4$ is a formyl substituent can also be used as starting materials. In this reaction sequence, the formyl substituent can be reacted with hydantoin to afford the corresponding compounds of formula I wherein $R^4$ is a (2,5-dioxo-imidazolidin-4-ylidenemethyl) substituent (*Egyptian Journal of Chemistry* 1987, 30, 281–294). The compounds of formula I wherein $R^4$ is a (2,5-dioxo-imidazolidin-4-ylidenemethyl) substituent can then be converted into the desired compounds of formula I wherein $R^4$ is a (2,5-dioxo-imidazolidin-4-ylmethyl) substituent by catalytic hydrogenation of the carbon-carbon double bond.

If it is desired to produce the compounds of formula I wherein $R^4$ is a methylhydantoin substituent, the known amino heteroaromatic compounds of formula X wherein $R^4$ is bromo can be used as starting materials (if Y=CH, then the compound of formula X is the commercially available 2-amino-5-bromopyridine; if Y=N, then the compound of formula X is the known 2-amino-5-bromopyrazine. In this reaction sequence, the amino group can be protected using any conventional amino protecting group which can be cleaved to yield the free amino group, the preferred group being the trimethylacetyl amino protecting group. Once the amino group is protected, the bromo substituent can be directly converted to the compounds of formula X wherein $R^4$ is an acetyl substituent and wherein the amino group is protected as the trimethylacetyl amide. The palladium-mediated Stille coupling reaction of the heteroaromatic bromo substituent with the commercially available 1-ethoxyvinyl-tri-n-butyltin followed by acid hydrolysis of the intermediate ethyl enol ether can be utilized to effect this conversion (*Synthesis* 1997, 1446–1450). Next, the compounds of formula X wherein $R^4$ is an acetyl substituent and wherein the amino group is protected as the trimethylacetyl amide can be converted to the compounds of formula X wherein $R^4$ is a methylhydantoin substituent and wherein the amino group is protected as the trimethylacetyl amide using the Bucherer-Bergs reaction conditions (*Bioorg. Med. Chem, Lett.* 2001, 11(6), 777–780). Deprotection of the trimethylacetyl amide under standard basic conditions can provide the desired amino heteroaromatic compounds of formula X wherein $R^4$ is methylhydantoin. The resulting compounds of formula X wherein $R^4$ is methylhydantoin can then be condensed with the compounds of formula IX via conventional peptide coupling to produce the desired compounds of formula I wherein $R^4$ is a methylhydantoin substituent. In carrying out this reaction, any conventional method of condensing a primary amine with a carboxylic acid can be utilized to effect this conversion.

If it is desired to produce the amino heteroaromatic compounds of formula X wherein $R^4$ is an unsubstituted or mono-substituted five- or six-membered heteroaromatic ring connected by a ring carbon atom to position 5 of the pyridine or pyrazine ring, with said five- or six-membered heteroaromatic ring containing one heteroatom selected from sulfur, oxygen or nitrogen; said mono-substituted heteroaromatic ring being mono-substituted at a position on a ring carbon atom other than the said connecting carbon atom with a substituent selected from the group consisting of cyano, chloro, bromo, nitro, amino, methyl, methoxy or hydroxy, the known amino heteroaromatic compounds of formula X wherein $R^4$ is bromo can be used as starting materials (if Y=CH, then the compound of formula X is the commercially available 2-amino-5-bromopyridine; if Y=N, then the compound of formula X is the known 2-amino-5-bromopyrazine). In this reaction sequence, the bromo substituent can be directly converted to the compounds of formula X wherein $R^4$ is the aforementioned unsubstituted or mono-substituted five- or six-membered heteroaromatic rings. Any conventional method for the palladium-mediated coupling of an aromatic bromo substituent with a heteroaromatic boronic acid (such as the Suzuki coupling reaction) or with a heteroaromatic stannyl reagent (such as the Stille coupling reaction) can be utilized to effect this conversion. The resulting compounds of formula X wherein $R^4$ is the desired unsubstituted or mono-substituted five- or six-membered heteroaromatic ring can then be condensed with the compounds of formula IX via conventional peptide coupling to produce the desired compounds of formula I wherein $R^4$ is the desired unsubstituted or mono-substituted five- or six-membered heteroaromatic ring connected by a ring carbon atom to position 5 of the pyridine or pyrazine ring, with said five- or six-membered heteroaromatic ring containing one heteroatom selected from sulfur, oxygen or nitrogen; said mono-substituted heteroaromatic ring being mono-substituted at a position on a ring carbon atom other than the said connecting carbon atom with a substituent selected from the group consisting of cyano, chloro, bromo, nitro, amino, methyl, methoxy or hydroxy. In carrying out this reaction, any conventional method of condensing a primary amine with a carboxylic acid can be utilized to effect this conversion. On the other hand, if it is desired to produce the compounds of formula I wherein $R^4$ is a nine- or ten-membered bicyclic heteroaromatic ring having one heteroatom selected from the group consisting of oxygen, nitrogen, or sulfur and connected by a ring carbon atom, these compounds can be prepared according to the reaction sequence described above using the desired fused heteroaromatic boronic acid or fused heteroaromatic stannyl reagents.

If it is desired to produce the amino heteroaromatic compounds of formula X wherein $R^4$ is an unsubstituted or mono-substituted aryl ring connected by a ring carbon atom to position 5 of the pyridine or pyrazine ring, with said aryl ring containing six carbon atoms; said mono-substituted aryl ring being mono-substituted at a position on a ring carbon atom other than the said connecting carbon atom with a substituent selected from the group consisting of cyano, chloro, bromo, nitro, amino, methyl, methoxy or hydroxy, the aforementioned known amino heteroaromatic compounds of formula X wherein $R^4$ is bromo can also be used as starting materials. In this reaction sequence, the bromo substituent can be directly converted to the compounds of formula X wherein $R^4$ is the aforementioned unsubstituted or mono-substituted aryl ring. Any conventional method for the palladium-mediated coupling of an aromatic bromo substituent with a heteroaromatic boronic acid, such as the Suzuki coupling reaction, can be utilized to effect this conversion. The resulting compounds of formula X wherein $R^4$ is the desired unsubstituted or mono-substituted aryl ring can then be condensed with the compounds of formula IX via conventional peptide coupling to produce the desired compounds of formula I wherein $R^4$ is the unsubstituted or mono-substituted aryl ring, In carrying out this reaction, any conventional method of condensing a primary amine with a carboxylic acid can be utilized to effect this conversion. Once the compounds of formula I wherein $R^4$ is a mono-substituted aryl ring connected by a ring carbon atom to position 5 of the pyridine or pyrazine ring, with said aryl ring containing six carbon atoms; said mono-substituted aryl ring being mono-substituted at a position on a ring carbon atom other than the said connecting carbon atom with a nitro substituent, these compounds with the nitro substituent can then be converted to the corresponding amino substituent. Any conventional method for the reduction of a nitro group to an amino group can be utilized to effect this conversion. On the other hand, once the compounds of formula I wherein $R^4$ is a mono-substituted aryl ring connected by a ring carbon atom to position 5 of the pyridine or pyrazine ring, with said aryl ring containing six carbon atoms; said mono-substituted aryl ring being mono-substituted at a position on a ring carbon atom other than the said connecting carbon atom with a methoxy substituent, these compounds with the methoxy substituent can then be converted to the corresponding hydroxy substituent. Any conventional method for the demethylation of an aromatic methoxy group to an aromatic hydroxy group can be utilized to effect this conversion.

If it is desired to produce the amino heteroaromatic compounds of formula X wherein $R^4$ is a (tetrahydro-furan-2-yl) substituent, the aforementioned known amino heteroaromatic compounds of formula X wherein $R^4$ is bromo can also be used as starting materials. In this reaction sequence, the bromo substituent can be directly converted to the compounds of formula X wherein $R^4$ is a (4,5-dihydro-furan-2-yl) substituent. The palladium-mediated Stille coupling reaction of the heteroaromatic bromo substituent (*Syn. Lett.* 1995, 1227–1228). with the known tributyl(4,5-dihydro-2-furanyl)stannane (WO 01/62233) can be utilized to effect this conversion. The resulting amino heteroaromatic compounds of formula X wherein $R^4$ is a (4,5-dihydro-furan-2-yl) substituent can then be converted to the amino heteroaromatic compounds of formula X wherein $R^4$ is a (tetrahydro-furan-2-yl) substituent. Any conventional method for the reduction of a carbon-carbon double bond to a saturated hydrocarbon can be utilized to effect this conversion. Once the amino heteroaromatic compounds of formula X wherein $R^4$ is a (tetrahydro-furan-2-yl) substituent are available, they can then be condensed with the compounds of formula IX via conventional peptide coupling to produce the desired compounds of formula I wherein $R^4$ is a (tetrahydro-furan-2-yl) substituent. In carrying out this reaction, any conventional method of condensing a primary amine with a carboxylic acid can be utilized to effect this conversion.

If it is desired to produce the amino heteroaromatic compounds of formula X wherein $R^4$ is a (5,6-dihydro-4H-pyran-2-yl) substituent, the aforementioned known amino heteroaromatic compounds of formula X wherein $R^4$ is bromo can also be used as starting materials. In this reaction sequence, the bromo substituent can be directly converted to the compounds of formula X wherein $R^4$ is a (5,6-dihydro-4H-pyran-2-yl) substituent. The palladium-mediated Stille coupling reaction of the heteroaromatic bromo substituent with the commercially available 5,6-dihydro-2-(tributylstannyl)-4H-pyran can be utilized to effect this conversion. The resulting compounds of formula X wherein $R^4$ is a (5,6-dihydro-4H-pyran-2-yl) substituent can then be condensed with the compounds of formula IX via conventional peptide coupling to produce the desired compounds of formula I wherein $R^4$ is a (5,6-dihydro-4H-pyran-2-yl) substituent. In carrying out this reaction, any conventional method of condensing a primary amine with a carboxylic acid can be utilized to effect this conversion.

If it is desired to produce the compounds of formula I wherein $R^4$ is an imidazoline substituent, the following known heteroaromatic compounds can be used as starting materials: (1) In formula X, if Y=CH, then the commercially available 2-amino-5-cyanopyridine can be used as starting material; and (2) In formula X, if Y=N then the known 2-amino-5-cyanopyrazine, which can be prepared according to *J. Heterocyclic Chem.* 1987, 24(5), 1371–1372, can be used as starting material. In this reaction sequence, the cyano substituent can be directly converted to the compounds of formula X wherein $R^4$ is an imidazoline substituent. Any conventional method for the nucleophilic addition of ethylenediamine to an aromatic cyano group can be utilized to effect this conversion (*Bioorg. Med. Chem.* 2001, 9(3), 585–592). The compounds of formula X wherein $R^4$ is an imidazoline substituent can then be condensed with the compounds of formula IX via conventional peptide coupling to produce the desired compounds of formula I wherein $R^4$ is an imidazoline substituent. In carrying out this reaction, any conventional method of condensing a primary amine with a carboxylic acid can be utilized to effect this conversion.

If it is desired to produce the compounds of formula I wherein $R^4$ is a substituent corresponding to —C(=O)NH—OH, the following known heteroaromatic compounds can be used as starting materials: (1) In formula I, if Y=CH, then the known 5-chloro-pyridine-2-carboxylic acid methyl ester can be used as starting material; and (2) In formula I, if Y=N then the commercially available methyl 5-chloro-pyrazine-2-carboxylate can be used as starting material. In this reaction sequence, the known 5-[chloro]heteroaromatic-2-carboxylic acid methyl ester can be converted to the corresponding carboxylic acid. Hydrolysis of the carboxylic acid methyl ester to the carboxylic acid without displacement of the chloro substituent can be accomplished using potassium carbonate in water/tetrahydrofuran (*Chem. Pharm. Bull.* 1980, 28, 3057–3063). The resulting 5-[chloro]heteroaromatic-2-carboxylic acid can then be converted to the corresponding tert-butyl ester. Any conventional esterification method for converting a carboxylic acid to a carboxylic acid tert-butyl ester can be utilized to effect this conversion (*Tetrahedron* 1990, 46, 3019–3028). The 5-[chloro]heteroaromatic-2-carboxylic acid tert-butyl ester can then be converted to the corresponding 5-[fluoro]heteroaromatic-2-carboxylic acid tert-butyl ester using silver(I) fluoride in acetonitrile (*J. Med. Chem.* 1995, 38, 3902–3907). Next, the 5-[fluoro]heteroaromatic-2-carboxylic acid tert-butyl ester can then be converted to the compounds of formula X wherein $R^4$ is a tert-butyl carboxylate substituent. Any conventional method for the nucleophilic displacement of an aromatic fluoro group with ammonia to afford an aromatic amino group can be utilized to effect this conversion. The resulting compounds of formula X wherein $R^4$ is a tert-butyl carboxylate substituent can then be condensed with the compounds of formula IX via conventional peptide coupling to produce the desired compounds of formula I wherein $R^4$ is a tert-butyl carboxylate substituent. In carrying out this reaction, any conventional method of condensing a primary amine with a carboxylic acid can be utilized to effect this conversion. Once the compounds of formula I wherein $R^4$ is a tert-butyl carboxylate substituent are available, they can be converted to the compounds of formula I wherein $R^4$ is carboxy. Any conventional method for the acidic hydrolysis of a tert-butyl ester to a carboxylic acid can be utilized to effect this conversion. Once the compounds of formula I wherein $R^4$ is carboxy are available, they can be converted to the desired compounds of formula I wherein $R^4$ is a substituent corresponding to —C(=O)NH—OH (the carboxylic acid hydroxy amide substituent). In this reaction sequence, any conventional method for reacting a carboxylic acid with the commercially available O-(tert-butyl)hydroxylamine hydrochloride to from the corresponding carboxylic acid tert-butoxy amide analog can be utilized to effect this conversion. The resulting carboxylic acid tert-butoxy amide analog can then be deprotected under acidic conditions to afford the desired compounds of formula I wherein $R^4$ is a substituent corresponding to —C(=O)NH—OH (the carboxylic acid hydroxy amide substituent).

On the other hand, if it is desired to produce the compounds of formula I wherein $R^4$ is a 3-methyl-[1,2,4]oxadiazole ring, the aforementioned compounds of formula I wherein $R^4$ is a carboxy substituent can be used as starting materials. In this sequence of reactions, the compounds of formula I wherein $R^4$ is a carboxy substituent can be converted to the corresponding acyl chloride. Any conventional method for converting a carboxylic acid to an acyl chloride can be utilized to effect this conversion. Next, the acyl chloride can be treated with acetamide oxime to afford the intermediate compounds of formula I wherein $R^4$ is an acetamide oxime ester substituent. Finally, the compounds of formula I wherein $R^4$ is the acetamide oxime ester substituent can be dehydrated under thermal conditions to afford the desired compounds of formula I wherein $R^4$ is a 3-methyl-[1,2,4]oxadiazole ring (*J. Med. Chem.* 1991, 34, 2726–2735).

If it is desired to produce the compounds of formula I wherein $R^4$ is a (bis-hydroxymethyl)methyl substituent, the following known heteroaromatic compounds can be used as starting materials: (1) In formula X, if Y=CH, then the commercially available 5-bromo-2-nitropyridine can be used as starting material; and (2) In formula X, if Y=N then the known 2-bromo-5-nitropyrazine can be used as starting material. In this reaction sequence, the bromo substituent can be directly converted to the compounds of formula X wherein $R^4$ is a (malonic acid dialkyl ester) substituent. Any conventional method for the displacement of an aromatic bromo substituent with a dialkyl malonate can be utilized to effect this conversion. Once the resulting 5-(malonic acid dialkyl ester)-2-nitro-heteroaromatic compounds are available, the nitro substituent can be converted to the amino heteroaromatic compounds of formula X wherein $R^4$ is the desired (malonic acid dialkyl ester) substituent. Any conventional method for the reduction of a nitro substituent to an amino substituent can be utilized to effect this conversion. These compounds of formula X wherein $R^4$ is a (malonic acid dialkyl ester) substituent can then be condensed with the compounds of formula IX via conventional peptide coupling to produce the desired compounds of formula I wherein $R^4$ is a (malonic acid dialkyl ester) substituent. In carrying out this reaction, any conventional method of condensing a primary amine with a carboxylic acid can be utilized to effect this conversion. Once the compounds of formula I wherein $R^4$ is a (malonic acid dialkyl ester) substituent are available, the (malonic acid dialkyl ester) substituent can then be converted to the compounds of formula I wherein $R^4$ is a (bis-hydroxymethyl)methyl substituent. Any conventional method for the reduction of an ester to an alcohol can be utilized to effect this conversion.

If it is desired to produce the compounds of formula I wherein $R^4$ is a (bis-hydroxymethyl)methoxy substituent, the following known heteroaromatic compounds can be used as starting materials: (1) In formula I, if Y=CH, then the known 5-chloro-pyridine-2-carboxylic acid methyl ester can be used as starting material; and (2) In formula I, if Y=N then the commercially available methyl 5-chloropyrazine-2-carboxylate can be used as starting material. In this reaction sequence, the known 5-[chloro]heteroaromatic-2-carboxylic acid methyl ester can be converted to the corresponding carboxylic acid. Hydrolysis of the carboxylic acid methyl ester to the carboxylic acid without displacement of the chloro substituent can be accomplished using potassium carbonate in water/tetrahydrofuran (*Chem. Pharm. Bull.* 1980, 28, 3057–3063). The 5-[chloro]heteroaromatic-2-carboxylic acid can then be converted to the corresponding (bis-benzyloxymethyl)methyl ester. Any conventional esterification method for converting a carboxylic acid to a carboxylic ester can be utilized to effect this conversion. Next, the chloro substituent on the resulting 5-[chloro] heteroaromatic-2-carboxylic acid (bis-benzyloxymethyl) methyl ester can be directly displaced with 1,3-dibenzyloxy-2-propanol to produce the corresponding 5-[(bis-benzyloxymethyl)methoxy]heteroaromatic-2-carboxylic acid (bis-benzyloxymethyl)methyl ester Any conventional method for the nucleophilic displacement of an aromatic chloro substituent with a secondary alcohol can be utilized to effect this conversion. Once the fully protected 5-[(bis-benzyloxymethyl)methoxy]heteroaromatic-2-carboxylic acid (bis-benzyloxymethyl)methyl ester compounds are available, they can be converted to the corresponding carboxylic acid. Any conventional method for the hydrolysis of an ester to a carboxylic acid can be utilized to effect this conversion. The 5-[(bis-benzyloxymethyl)methoxy]heteroaromatic-2-carboxylic acid can then be converted to the corresponding acyl azide. Any conventional method for converting a carboxylic acid to an acyl azide can be utilized to effect this conversion. Curtius rearrangement involving pyrolysis of the resulting acyl azide in the presence of tert-butyl alcohol can provide the compounds of formula X wherein $R^4$ is (bis-benzyloxymethyl)methoxy and wherein the amino group is protected as the tert-butyl carbamate. Deprotection of the tert-butyl carbamate under standard conditions can provide the desired amino heteroaromatic compounds of formula X wherein $R^4$ is (bis-benzyloxymethyl)methoxy. The resulting compounds of formula X wherein $R^4$ is (bis-benzyloxymethyl)methoxy can then be condensed with the compounds of formula IX via conventional peptide coupling to produce the desired compounds of formula I wherein $R^4$ is (bis-benzyloxymethyl)methoxy. In carrying out this reaction, any conventional method of condensing a primary amine with a carboxylic acid can be utilized to effect this conversion. Deprotection of the benzyl ethers under standard hydrogenation conditions can provide the desired compounds of formula I wherein $R^4$ is a (bis-hydroxymethyl)methoxy substituent.

The compounds of formula I have an asymmetric carbon atom through which the group —$CH_2R^3$ and the amide substituents are connected. In accordance with this invention, the preferred stereoconfiguration at this carbon is "R."

If it is desired to produce the R isomer or the S isomer of the compounds of formula I, these compounds can be isolated as the desired isomer by conventional chemical means. The preferred chemical mean is the use of pseudoephedrine as a chiral auxiliary for the asymmetric alkylation of the phenylacetic acids of formula V (*J. Am. Chem. Soc.* 1997, 119, 6496–6511). To form the desired R acids of formula IX, the compounds of formula V where $R^{20}$ is lower alkyl thio and $R^2$ is as described above are first converted to the pseudoephedrine amides using 1R,2R-(–)-pseudoephedrine as the desired enantiomer of pseudoephedrine. Any conventional method for converting a carboxylic acid to a carboxamide can be utilized to effect this conversion. The pseudoephedrine amides can undergo highly diastereoselective alkylations with alkyl halides to afford the α-substituted amide products corresponding to formula IX. These highly diastereomerically enriched amides can be converted to the highly enantiomerically enriched R carboxylic acids of formula IX where $R^{20}$ is lower alkyl thio and $R^2$ is as described above by conventional acidic hydrolysis methods for converting a carboxamide to a carboxylic acid. These R carboxylic acids of formula IX where $R^{20}$ is lower alkyl thio and $R^2$ is as described above can be converted to the R isomers of formula I where $R^{20}$ is lower alkyl thio and $R^2$ is as described above. In carrying out this reaction, any conventional method of condensing a primary amine with a carboxylic acid, without racemization, can be utilized to effect this conversion. Once the compounds of formula I where $R^{20}$ is lower alkyl thio and $R^2$ is as described above are available, they can be converted to the corresponding R compounds of formula I where $R^{20}$ is lower alkyl sulfonyl and $R^2$ is as described above by oxidation. Any conventional method of oxidizing an alkyl thio substituent to the corresponding sulfone group can be utilized to effect this conversion.

On the other hand, the R carboxylic acids of formula IX where $R^{20}$ is lower alkyl thio and $R^2$ is as described above can first be oxidized to the R compounds of formula IX where $R^{20}$ is lower alkyl sulfonyl and $R^2$ is as described above. Any conventional method of oxidizing an alkyl thio substituent to the corresponding sulfone group can be utilized to effect this conversion. These compounds can be then converted to the corresponding R compounds of formula I where $R^{20}$ is lower alkyl sulfonyl and $R^2$ is as described above. In carrying out this reaction, any conventional method of condensing a primary amine with a carboxylic acid, without racemization, can be utilized to effect this conversion.

Another chemical means to produce the R or S isomer of the compounds of formula I is to react the compound of formula IX with an optically active base. Any conventional optically active base can be utilized to carry out this resolution. Among the preferred optically active bases are the optically active amine bases such as alpha-methylbenzylamine, quinine, dehydroabietylamine, and alpha-methylnaphthylamine. Any of the conventional techniques utilized in resolving organic acids with optically active organic amine bases can be utilized in carrying out this reaction. In the resolution step, the compound of formula IX is reacted with the optically active base in an inert organic solvent medium to produce salts of the optically active amine with both the R and S isomers of the compound of formula IX. In the formation of these salts, temperatures and pressure are not critical and the salt formation can take place at room temperature and atmospheric pressure. The R and S salts can be separated by any conventional method such as fractional crystallization. After crystallization, each of the salts can be converted to the respective compounds of formula IX in the R and S configuration by hydrolysis with an acid. Among the preferred acids are dilute aqueous acids, i.e., from about 0.001N to 2N aqueous acids, such as aqueous sulfuric or aqueous hydrochloric acid. The configuration of formula IX which is produced by this method of resolution is carried out throughout the entire reaction scheme to produce the desired R or S isomers of formula I.

The resolution of racemates of the compounds of the formula IX can also be achieved via the formation of corresponding diastereomeric esters or amides. These diastereomeric esters or amides can be prepared by coupling the carboxylic acids of the formula IX with a chiral alcohol or a chiral amine. This reaction can be carried out using any conventional method of coupling a carboxylic acid with an alcohol or an amine. The corresponding diastereomers of compounds of the formula IX can then be separated using any conventional separation methods. The resulting pure diastereomeric esters or amides can then be hydrolyzed to yield the corresponding pure R or S isomers. The hydrolysis reaction can be carried out using conventional known methods to hydrolyze an ester or an amide without racemization. Finally, the separation of R and S isomers can also be achieved using an enzymatic ester hydrolysis of any lower alkyl esters corresponding to the compound of the formula VIII (*Tetrahedron Lett.* 1989, 30, 7053–7056), which results in the formation of corresponding chiral acid and chiral ester. The ester and the acid can be separated by any conventional method of separating an acid from an ester. The configuration of formula VIII which is produced by this method of resolution is carried out throughout the entire reaction scheme to produce the desired R or S isomers of formula I.

The resolution of racemates of the compounds of the formula IX can also be achieved via the formation of corresponding diastereomeric esters or amides. These diastereomeric esters or amides can be prepared by coupling the carboxylic acids of the formula IX with a chiral alcohol or a chiral amine. This reaction can be carried out using any conventional method of coupling a carboxylic acid with an alcohol or an amine. The corresponding diastereomers of compounds of the formula IX can then be separated using any conventional separation methods. The resulting pure diastereomeric esters or amides can then be hydrolyzed to yield the corresponding pure R or S isomers. The hydrolysis reaction can be carried out using conventional known methods to hydrolyze an ester of an amide without racemization. Finally, the separation of R and S isomers can also be achieved using an enzymatic ester hydrolysis of any lower alkyl esters corresponding to the compound of the formula VIII (*Tetrahedron Lett.* 1989, 30, 7053–7056), which results in the formation of corresponding chiral acid and chiral ester. The ester and the acid can be separated by any conventional method of separating an acid from an ester. The configuration of formula VIII which is produced by this method of resolution is carried out throughout the entire reaction scheme to produce the desired R or S isomers of formula I.

U.S. Pat. No. 6,320,050 is directed to 2,3-di-substituted N-heteroaromatic propionamides as glucokinase activators. U.S. Pat. No. 6,320,050 is incorporated by reference herein. Substituent designations for functional groups of formula I of the present invention are as provided herein.

All of the compounds of the present invention set forth in the Examples herein activated glucokinase in vitro by the procedure of Example A. In this manner, they increase the flux of glucose metabolism, which causes increased insulin secretion. Therefore, the compounds of formula I are glucokinase activators useful for increasing insulin secretion.

The following compounds, when administered orally in accordance with the assay described in Example B, were found to exhibit a statistically significant ($p \leq 0.05$) decrease in blood glucose compared to vehicle for two consecutive assay time points.

2(R)-(3-Chloro-4-methanesulfonyl-phenyl)-3-cyclopentyl-N-[5-(N-hydroxycarbamimidoyl)-pyrazin-2-yl]-propionamide;

3-Cyclopentyl-2(R)-N-[5-(N-hydroxycarbamimidoyl)-pyrazin-2-yl]-2-(4-methanesulfonyl-phenyl)-propionamide;

2(R)-(3-Chloro-4-methanesulfonyl-phenyl)-3-cyclopentyl-N-(5-methylsulfanyl-pyrazin-2-yl)-propionamide;

2(R)-(3-Chloro-4-methanesulfonyl-phenyl)-3-cyclopentyl-N-[5-(2-hydroxy-ethylsulfanyl)-pyrazin-2-yl]-propionamide;

2(R)-(3-Chloro-4-methanesulfonyl-phenyl)-3-cyclopentyl-N-(5-methanesulfinyl-pyrazin-2-yl)-propionamide;

2(R)-(3-Chloro-4-methanesulfonyl-phenyl)-3-cyclopentyl-N-[5-(3-hydroxy-prop-1-ynyl)-pyrazin-2-yl]-propionamide;

2(R)-(3-Chloro-4-methanesulfonyl-phenyl)-3-cyclopentyl-N-[5-(3-dimethylamino-prop-1-ynyl)-pyrazin-2-yl]-propionamide;

2(R)-(3-Chloro-4-methanesulfonyl-phenyl)-3-cyclopentyl-N-(5-methanesulfonylamino-pyridin-2-yl)-propionamide;

2(R)-(3-Chloro-4-methanesulfonyl-phenyl)-3-cyclopentyl-N-(5-dimethylamino-pyridin-2-yl)-propionamide;

2(R)-(3-Chloro-4-methanesulfonyl-phenyl)-3-cyclopentyl-N-(5-dimethylamino-pyrazin-2-yl)-propionamide;

2(R)-(3-Chloro-4-methanesulfonyl-phenyl)-3-cyclopentyl-N-[5-(3-dimethylamino-propyl)-pyrazin-2-yl]-propionamide;

N-[5-(5-Amino-[1,2,4]oxadiazol-3-yl)-pyrazin-2-yl]-2(R)-(3-chloro-4-methanesulfonyl-phenyl)-3-cyclopentyl-propionamide;

2-(3-Chloro-4-methanesulfonyl-phenyl)-3-cyclopentyl-N-(5-formyl-pyrazin-2-yl)-propionamide;

2-(3-Chloro-4-methanesulfonyl-phenyl)-3-cyclopentyl-N-[5-(2,4-dioxo-thiazolidin-5-ylmethyl)-pyrazin-2-yl]-propionamide;

2(R)-(3-Chloro-4-methanesulfonyl-phenyl)-3-cyclopentyl-N-(5-dimethoxymethyl-pyrazin-2-yl)-propionamide;

N-(5-Acetyl-pyrazin-2-yl)-2-(3-chloro-4-methanesulfonyl-phenyl)-3-cyclopentyl-propionamide;

2(R)-(3-Chloro-4-methanesulfonyl-phenyl)-N-[5-(cyano-hydroxy-methyl)-pyrazin-2-yl]-3-cyclopentyl-propionamide;

2(R)-(3-Chloro-4-methanesulfonyl-phenyl)-3-cyclopentyl-N-[5-(1-(Z)-hydroxyimino-ethyl)-pyrazin-2-yl]-propionamide;

5-[2(R)-(3-Chloro-4-methanesulfonyl-phenyl)-3-cyclopentyl-propionylamino]-pyrazine-2-carboxylic acid hydroxyamide;

2(R)-(3-Chloro-4-methanesulfonyl-phenyl)-3-cyclopentyl-N-(5-methanesulfonylmethyl-pyrazin-2-yl)-propionamide;

3-Cyclopentyl-N-[5-(1-hydroxyimino-ethyl)-pyrazin-2-yl]-2(R)-(4-methanesulfonyl-phenyl)-propionamide;

2(R)-(3-Chloro-4-methanesulfonyl-phenyl)-3-cyclopentyl-N-(5-[1,3]dioxolan-2-yl-pyrazin-2-yl)-propionamide;

2(R)-(3-Chloro-4-methanesulfonyl-phenyl)-3-cyclopentyl-N-5-(2-methoxyethoxy-pyrazin-2-yl)-propionamide;

2(R)-(3-Chloro-4-methanesulfonyl-phenyl)-3-cyclopentyl-N-[5-2(R),3-dihydroxy-propoxy)-pyrazin-2-yl]-propionamide;

3-Cyclopentyl-N-5-[(4-hydroxy-tetrahydropyran-4-yl-ethynyl)pyrazin-2-yl]-2(R)-(4-methanesulfonyl-phenyl)-propionamide;

2(R)-(3-Chloro-4-methanesulfonyl-phenyl)-3-cyclopentyl-N-[5-(3-methoxy-prop-1-ynyl)-pyrazin-2-yl]-propionamide;

2(R)-(3-Chloro-4-methanesulfonyl-phenyl)-3-cyclopentyl-N-[5-(2(S),3-dihydroxy-propoxy)-pyrazin-2-yl]-propionamide;

2(R)-(3-Chloro-4-methanesulfonyl-phenyl)-3-cyclopentyl-N-[5-(4-hydroxy-tetrahydropyran-4-yl-ethynyl)-pyrazin-2-yl]-propionamide;

2(R)-(3-Chloro-4-methanesulfonyl-phenyl)-3-cyclopentyl-N-[5-(4-hydroxy-tetrahydropyran-4-yl-ethyl)-pyrazin-2-yl]-propionamide;

2(R)-(3-Chloro-4-methanesulfonyl-phenyl)-3-cyclopentyl-N-[5-(3-hydroxy-3-methyl-but-1-ynyl)-pyrazin-2-yl]-propionamide;

2(R)-(3-Chloro-4-methanesulfonyl-phenyl)-3-cyclopentyl-N-[5-(4-hydroxy-but-1-ynyl)-pyrazin-2-yl]-propionamide;

2(R)-(3-Chloro-4-methanesulfonyl-phenyl)-3-cyclopentyl-N-[5-(1(S),2-dihydroxy-ethyl)-pyrazin-2-yl]-propionamide;

2(R)-(3-Chloro-4-methanesulfonyl-phenyl)-3-cyclopentyl-N-[5-1(R),2-dihydroxy-ethyl)-pyrazin-2-yl]-propionamide;

3-Cyclopentyl-N-[5-(3-hydroxy-3-methyl-but-1-ynyl)-pyrazin-2-yl]-2(R)-(4-methanesulfonyl-3-methyl-phenyl)-propionamide;

3-Cyclopentyl-N-[5-1(S),2-dihydroxy-ethyl]-2(R)-(4-methanesulfonyl-3-methyl)-propionamide;

3-Cyclopentyl-N-[5-(4-hydroxy-tetrahydro-pyran-4-yl-ethynyl)-pyrazin-2-yl]-2(R)-(4-methanesulfonyl-3-methyl-phenyl)-propionamide;

3-Cyclopentyl-2(R)-(4-methanesulfonyl-phenyl)-N-[5-(3-hydroxy-3-methyl-but-1-ynyl)-pyrazin-2-yl]-propionamide;

2(R)-(3-Chloro-4-methanesulfonyl-phenyl)-3-cyclopentyl-N-[5-(2-hydroxy-ethoxy)-pyrazin-2-yl]-propionamide;

2(R)-(3-Chloro-4-methanesulfonyl-phenyl)-3-cyclopentyl-N-[5-(1(S),2-dihydroxy-2-methyl-propyl)-pyrazin-2-yl]-propionamide;

2(R)-(3-Chloro-4-methanesulfonyl-phenyl)-3-cyclopentyl-N-[5-(tetrahydro-furan-2-yl)-pyridin-2-yl]-propionamide;

2(R)-(3-Chloro-4-methanesulfonyl-phenyl)-3-cyclopentyl-N-(5-furan-2-yl-pyrazin-2-yl)-propionamide;

2(R)-(3-Chloro-4-methanesulfonyl-phenyl)-3-cyclopentyl-N-[5-(2-hydroxy-ethylamino)-pyrazin-2-yl]-propionamide;

2(R)-(3-Chloro-4-methanesulfonyl-phenyl)-3-cyclopentyl-N-[5-(5,6-dihydro-4H-pyran-2-yl)-pyrazin-2-yl]-propionamide;

2(R)-(3-Chloro-4-methanesulfonyl-phenyl)-3-cyclopentyl-N-(5-thiophen-2-yl-pyrazin-2-yl)-propionamide; and 2(R)-(3-Chloro-4-methanesulfonyl-phenyl)-3-cyclopentyl-N-(5-furan-3-yl-pyrazin-2-yl)-propionamide.

The present invention encompasses pharmaceutical compositions comprising a compound of formula I or a pharmaceutically acceptable salt thereof, and a pharmaceutically acceptable carrier. Preferred pharmaceutical compositions of the present invention comprise a compound listed above as having preferred glucokinase activator in vivo activity, or a pharmaceutically acceptable salt thereof.

The pharmaceutical compositions of the present invention can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, and/or the salts thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. In such cases, a pharmaceutically acceptable carriers are considered to include soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

A therapeutically effective amount of a compound in accordance with this invention means an amount of compound that is effective to treat obesity and/or type II diabetes. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 100 mg to about 1,000 mg should be appropriate. The daily dosage can be administered as a single dose or in divided doses, or for parenteral administration, it may be given as continuous infusion.

The present invention will be better understood from the following examples, which are for purposes of illustration and are not intended to limit the invention defined in the claims, which follow thereafter.

EXAMPLE 1

2(R)-(3-Chloro-4-methanesulfonyl-phenyl)-3-cyclopentyl-N-[5-(N-hydroxycarbamimidoyl)-pyrazin-2-yl]-propionamide

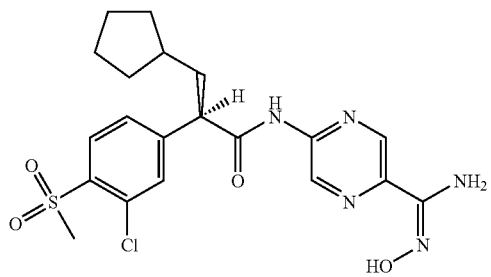

A solution of triphenylphosphine (28.80 g, 109.8 mmol) and imidazole (14.9 g, 219.6 mmol) in methylene chloride (160 mL) was cooled to 0° C. and then slowly treated with iodine (27.87 g, 109.8 mmol). The reaction mixture was then treated dropwise with a solution of cyclopentylmethanol (10.00 g, 99.8 mmol) in methylene chloride (10 mL). The resulting reaction mixture was allowed to warm to 25° C. where it was stirred for 4 h. The reaction mixture was then diluted with water (50 mL), and the reaction mixture was further extracted with methylene chloride (3×20 mL). The combined organic layers were dried over sodium sulfate, filtered, and concentrated in vacuo at 25° C. The resulting solid was washed with pentane (4×50 mL) and filtered through a silica gel plug. The filtrate was concentrated in vacuo at 25° C. to afford iodomethylcyclopentane (18.48 g, 88%) as a clear colorless liquid: EI-HRMS m/e calcd for $C_6H_{11}I$ ($M^+$) 209.9906, found 209.9911.

A solution of aluminum trichloride (54.9 g, 412 mmol) in chloroform (180 mL) under argon was cooled to 0° C. and then treated dropwise with a solution of methyl chlorooxoacetate (24.3 mL, 264 mmol) in chloroform (180 mL). The reaction mixture was stirred at 0° C. for 30 min and then was treated dropwise with a solution of 2-chlorothioanisole (39.4 g, 247 mmol) in chloroform (180 mL). The reaction mixture turned red in color. The resulting reaction mixture was allowed to warm to 25° C. where it was stirred for 4 h. The reaction mixture was then slowly poured onto ice (700 mL). The resulting yellow mixture was stirred for 15 min and then was filtered through celite to remove the aluminum salts. The filtrate was then extracted with methylene chloride (3×50 mL). The combined organic layers were washed with a saturated aqueous sodium bicarbonate solution (1×50 mL). The organic layer was then dried over magnesium sulfate, filtered, and concentrated in vacuo to afford (3-chloro-4-methylsulfanyl-phenyl)-oxo-acetic acid methyl ester (36.4 g, 60%) as a light yellow oil: EI-HRMS m/e calcd for $C_{10}H_9ClO_3S$ ($M^+$) 243.9961, found 243.9958.

A solution of (3-chloro-4-methylsulfanyl-phenyl)-oxo-acetic acid methyl ester (61.7 g, 252 mmol) in toluene (120 mL) was heated at 50° C. This heated solution was then treated dropwise with a 3M aqueous sodium hydroxide solution (105 mL, 315 mmol) via a dropping funnel, taking care to keep the temperature below 60° C. After the addition was complete, the reaction mixture was stirred at 50° C. for another 1.5 h, during which time, a yellow precipitate began to form. After this time, the heat was removed, and the warm solution was treated dropwise with concentrated hydrochloric acid (10.6 mL, 290 mmol). The resulting reaction mixture was allowed to cool to 25° C. and then was stirred at 25° C. for 16 h. The solid was filtered and then washed with water (50 mL) and toluene (50 mL). The solid was dried by suction for 1 h and then dried in a high vacuum desiccator to afford (3-chloro-4-methylsulfanyl-phenyl)-oxo-acetic acid (57.22 g, 98%) as a white solid: mp 166° C. (dec); FAB-HRMS m/e calcd for $C_9H_7ClO_3S$ $(M+Na)^+$ 252.9702, found 252.9700.

A reaction flask equipped with mechanical stirrer was charged with hydrazine hydrate (8.5 mL, 273 mmol). The hydrazine hydrate was cooled to −50° C. and then treated with (3-chloro-4-methylsulfanyl-phenyl)-oxo-acetic acid (12.6 g, 54.6 mmol) in one portion. An exotherm ensued that raised the temperature. The resulting white milky mixture was then heated to 80° C. After reaching 80° C., the heating element was removed, and the reaction mixture was then treated with potassium hydroxide (2.09 g, 31.7 mmol) in one portion. An exotherm was observed. The reaction was then stirred at 25° C. until the reaction temperature cooled back to 80° C. At this time, another portion of potassium hydroxide (2.09 g, 31.7 mmol) was added. Again, an exotherm was observed, and the resulting reaction mixture was allowed to cool back to 80° C. Once at 80° C., a third portion of potassium hydroxide (2.09 g, 31.7 mmol) was added to the reaction mixture. Another exotherm was observed, and after cooling back to 80° C., the fourth and final portion of potassium hydroxide (2.09 g, 31.7 mmol) was added. At this point, the heating element was added, and the reaction mixture was heated at 100° C. for 16 h. The resulting homogenous reaction mixture was cooled to 25° C. and then diluted with water (12 mL). The reaction mixture was then transferred to a separatory funnel, rinsing with additional water (12 mL) and diethyl ether (40 mL). The layers were separated, and the aqueous layer was transferred to a flask. The organic layer was extracted with water (2×15 mL). The aqueous layers were combined and treated with heptane (20 mL), and the resulting reaction mixture was vigorously stirred. This stirred solution was then treated dropwise with concentrated hydrochloric acid (26 mL) over 30 min while the temperature was kept under 50° C. with an ice bath. A cloudy suspension formed, and this suspension was stirred at 25° C. for 3 h. The solid that formed was collected by filtration and then washed sequentially with a 1N aqueous hydrochloric acid solution (2×6 mL), heptane (1×12 mL), and a solution of heptane/diethyl ether (15 mL, 4:1). The resulting solid was dried under high vacuum to afford (3-chloro-4-methylsulfanyl-phenyl)-acetic acid (10.48 g, 89%) as an off-white solid: mp 105.6–108.4° C.; EI-HRMS m/e calcd for $C_9H_9ClO_2S$ $(M^+)$ 216.0012, found 216.0022.

A mixture of (3-chloro-4-methylsulfanyl-phenyl)-acetic acid (10.48 g, 48.4 mmol) and potassium carbonate (20.1 g, 145.1 mmol) in acetone (65 mL) was cooled to −10° C. The pale yellow slurry was then treated dropwise with trimethylacetyl chloride (6.25 mL, 50.8 mmol) while maintaining the temperature below −10° C. The resulting reaction mixture was stirred at −10° C. for 15 min and then allowed to warm to 0° C. where it was stirred for 10 min. The reaction mixture was re-cooled to −10° C. and then treated with (1R, 2R)-(−)-pseudoephedrine (11.99 g, 72.5 mmol), resulting in an exotherm. The reaction mixture was stirred at −10° C. for 10 min and then warmed to 25° C. where it was stirred for 1 h. After such time, thin layer chromatography analysis indicated that the reaction was complete. The reaction mixture was then quenched with water (50 mL) and then extracted with ethyl acetate (1×100 mL). The organic layer was washed with water (2×40 mL). The aqueous layers were combined and back-extracted with ethyl acetate (2×50 mL). The combined organic layers were dried over magnesium sulfate, filtered, and concentrated in vacuo. The crude material was recrystallized from ethyl acetate (45 mL) and hexanes (80 mL) to afford 2-(3-chloro-4-methylsulfanyl-phenyl)-N-[2(R)-hydroxy-1(R)-methyl-2(R)-phenyl-ethyl]-N-methyl-acetamide (13.75 g, 78%) as a light yellow solid: mp 111.5–112.9° C.; FAB-HRMS m/e calcd for $C_{19}H_{22}ClNO_2S$ $(M+H)^+$ 364.1138, found 364.1142.

A solution of 1,1,1,3,3,3-hexamethyldisilazane (17.9 mL, 85 mmol) in tetrahydrofuran (90 mL) was cooled to −78° C. and then treated with a 2.34M solution of n-butyllithium in hexanes (33.9 mL, 79.3 mmol). The reaction mixture was stirred at −78° C. for 15 min and then slowly treated with a solution of 2-(3-chloro-4-methylsulfanyl-phenyl)-N-[2(R)-hydroxy-1(R)-methyl-2(R)-phenyl-ethyl]-N-methyl-acetamide (13.75 g, 37.8 mmol) in tetrahydrofuran (90 mL) while maintaining the temperature below −65° C. The resulting yellow-orange reaction mixture was stirred at −78° C. for 15 min and then allowed to warm to 0° C. where it was stirred for 20 min. The reaction mixture was then re-cooled to −78° C. and then treated with a solution of iodomethylcyclopentane (11.9 g, 56.7 mmol) in 1,3-dimethyl-3,4,5,6-tetrahydro-2(1H)-pyrimidinone (9.6 mL, 79.3 mmol). The resulting reaction mixture was stirred at −78° C. for 30 min and then allowed to warm to 25° C. where it was stirred for 16 h. The reaction mixture was diluted with ethyl acetate (200 mL) and then washed with a saturated aqueous ammonium chloride solution (1×100 mL). The aqueous layer was then extracted with ethyl acetate (2×50 mL). The combined organic layers were washed with a saturated aqueous sodium chloride solution (1×50 mL), dried over sodium sulfate, filtered, and concentrated in vacuo. The resulting material was then re-dissolved in ethyl acetate. This organic phase was washed with a 10% aqueous sulfuric acid solution (2×100 mL) and a 10% aqueous sodium bicarbonate solution (2×100 mL), dried over magnesium sulfate, filtered, and concentrated in vacuo. The crude material was recrystallized from ethyl acetate/hexanes to afford 2(R)-(3-chloro-4-methylsulfanyl-phenyl)-3-cyclopentyl-N-[2(R)-hydroxy-1(R)-methyl-2(R)-phenyl-ethyl]-N-methyl-propionamide (11.36 g, 67%) as a light yellow solid: mp 113.8–117.6° C.; FAB-HRMS m/e calcd for $C_{25}H_{32}ClNO_2S$ $(M-H)^+$ 444.1764, found 444.1765.

A solution of 2(R)-(3-chloro-4-methylsulfanyl-phenyl)-3-cyclopentyl-N-[2(R)-hydroxy-1(R)-methyl-2(R)-phenyl-ethyl]-N-methyl-propionamide (11.36 g, 25.5 mmol) in dioxane (45 mL) was treated with a 9N aqueous sulfuric acid solution (28 mL). The resulting reaction mixture was then heated at 105° C. for 16 h. The reaction mixture was then cooled to 0° C. with an ice bath, and the product was precipitated by adding water (200 mL). The suspension was stirred at 0° C. until the supernatant, which was initially turbid, became clear and light yellow in color. The solid was filtered off and dried by suction. The solid material was dissolved in hot glacial acetic acid (15 mL), and the hot solution was treated with water (10 mL) to initiate crystallization. The mixture was allowed to cool to 25° C. and then treated with an additional amount of water (20 mL). After stirring at 25° C. for 1 h, the solid was collected by filtration. The solid was dried in a high vacuum desiccator with phosphorous pentoxide to afford 2(R)-(3-chloro-4-methylsulfanyl-phenyl)-3-cyclopentyl-propionic acid (7.46 g, 98%) as a white solid: mp 116.9–119.2° C.; EI-HRMS m/e calcd for $C_{15}H_{19}ClO_2S$ $(M)^+$ 298.0794, found 298.0804.

A slurry of 2(R)-(3-chloro-4-methylsulfanyl-phenyl)-3-cyclopentyl-propionic acid (15.68 g, 52.5 mmol) in formic acid (10 mL) was cooled to 0° C. and then treated with a 30% aqueous hydrogen peroxide solution (30 mL). The resulting solution was allowed to warm to 25° C. where it was stirred for 16 h. The product was precipitated by the addition of water (120 mL). The solid was filtered off, washed with water, and dried by suction. Flash chromatography (Merck Silica gel 60, 230–400 mesh, 1/1 hexanes/ethyl acetate plus 1% acetic acid) afforded 2(R)-(3-chloro-4-methanesulfonyl-phenyl)-3-cyclopentyl-propionic acid (13.93 g, 80%) as a white solid: mp 123.9–126.2° C.; FAB-HRMS m/e calcd for $C_{15}H_{19}ClO_4S$ $(M+H)^+$ 331.0771, found 331.0776.

A solution of 2-amino-5-cyanopyrazine (500.0 mg, 4.162 mmol) in 1,4-dioxane (8.3 mL) was treated with 4-(dimethylamino)pyridine (305.1 mg, 2.497 mmol), N,N,N',N'-tetramethylethylenediamine (241.8 mg, 2.081 mmol), and di-tert-butyl dicarbonate (2.9 mL, 12.49 mmol). The reaction stirred at 25° C. for 20 h and then was concentrated in vacuo. Biotage chromatography (FLASH 40M, Silica, 1/9 ethyl acetate/hexanes) afforded 5-[[bis[(1,1-dimethylethoxy)carbonyl]]amino]-2-pyrazinecarbonitrile as a white solid: mp 67–68° C.; (ES)⁺-HRMS m/e calcd for $C_{15}H_{20}N_4O_4$ $(M+Na)^+$ 343.1377, found 343.1379.

A solution of 5-[[bis[(1,1-dimethylethoxy)carbonyl]] amino]-2-pyrazinecarbonitrile (305.7 mg, 0.954 mmol) in dimethyl sulfoxide (5.8 mL) was treated with hydroxylamine hydrochloride (333.8 mg, 4.804 mmol) and piperidine (0.50 mL, 5.050 mmol). The reaction was stirred at 25° C. for 50 min and then was partitioned between ethyl acetate (100 mL) and water (50 mL). The organic layer was washed with water (50 mL) and a saturated aqueous sodium chloride solution (50 mL), dried over sodium sulfate, filtered, and concentrated in vacuo. Biotage chromatography (FLASH 40L, Silica, 1/3 ethyl acetate/hexanes) afforded the 5-[[bis[(1,1-dimethylethoxy)carbonyl]]amino]-N-hydroxy-2-pyrazinecarboximidamide as a white solid (186.2 mg, 55%): mp 185–186° C.; (ES)$^+$-HRMS m/e calcd for $C_{15}H_{23}N_5O_5$ (M+H)$^+$ 354.1772, found 354.1775.

A solution of the 5-[[bis[(1,1-dimethylethoxy)carbonyl]]amino]-N-hydroxy-2-pyrazinecarboximidamide (77.0 mg, 0.218 mmol) in pyridine (2 mL) at 25° C. was treated with 9-fluorenylmethyl chloroformate (68.0 mg, 0.263 mmol). The reaction mixture was stirred at 25° C. for 45 min. The reaction mixture was then diluted with ethyl acetate, water, and a saturated aqueous sodium chloride solution. The mixture was shaken and separated. The aqueous layer was extracted with ethyl acetate. The combined organic layers were dried over anhydrous sodium sulfate, filtered, and concentrated in vacuo. Biotage chromatography (FLASH 40S, Silica, 1/9 to 1/1 ethyl acetate/hexanes) afforded the desired 5-[[bis[(1,1-dimethylethoxy)carbonyl]]amino]-N-[[[(9H-fluoren-9-yl)methoxy]carbonyl]oxy]-2-pyrazine carboximidamide. This material was dissolved in methylene chloride (0.5 mL). The solution was cooled to 0° C. and then was treated with trifluoroacetic acid (0.16 mL, 2.077 mmol). The reaction mixture was stirred at 0° C. for 30 min and at 25° C. for 30 min. The reaction mixture was then treated with additional trifluoroacetic acid (1.0 mL, 12.99 mmol) and stirred at 25° C. for 2 h. The reaction mixture was further treated with trifluoroacetic acid (1.0 mL, 12.99 mmol) and stirred at 25° C. for 2 h. The reaction mixture was then diluted with methylene chloride, washed three times with a saturated aqueous sodium bicarbonate solution, dried over anhydrous sodium sulfate, filtered, concentrated in vacuo, and then dried under high vacuum to afford 5-amino-N-[[[(9H-fluoren-9-yl)methoxy]carbonyl]oxy]-2-pyrazinecarboximidamide (36.7 mg, 44.9%) as a white solid: LRMS for $C_{20}H_{17}N_5O_3$ (M+H)$^+$ at m/z=376

A solution of 2(R)-(3-chloro-4-methanesulfonyl-phenyl)-3-cyclopentyl-propionic acid (140.0 mg, 0.423 mmol) in methylene chloride (2 mL) was cooled to 0° C. and then treated with N,N-dimethylformamide (1 drop) followed by oxalyl chloride (0.08 mL, 0.917 mmol). The reaction mixture was stirred at 0° C. for 30 min and then stirred at 25° C. for 2 h. The reaction mixture was concentrated in vacuo to afford an oil. A solution of this oil in methylene chloride (2 mL) was cooled to 0° C. and then treated with a slurry of the 5-amino-N-[[[(9H-fluoren-9-yl)methoxy]carbonyl]oxy]-2-pyrazinecarboximidamide (210 mg, assume 0.45 mmol) and pyridine (0.04 mL, 0.495 mmol) in tetrahydrofuran (2 mL) followed by a tetrahydrofuran (1 mL) rinse of the slurry into the reaction mixture. The resulting orange reaction mixture was treated with pyridine (0.04 mL, 0.495 mmol) and then stirred at 0° C. for 30 min and then at 25° C. for 22 h. The reaction mixture was diluted with ethyl acetate, washed with a saturated aqueous sodium bicarbonate solution, dried over anhydrous sodium sulfate, filtered, and concentrated in vacuo. Biotage chromatography (FLASH 40S, Silica, 1/4 to 1/1 ethyl acetate/hexanes) afforded the (R)-3-chloro-α-(cyclopentylmethyl)-N-[2-[[[[[(9H-fluoren-9-yl)methoxy]carbonyl]oxy]-amino]iminoethyl]-5-pyrazinyl]-4-(methylsulfonyl)benzeneacetamide (151.9 mg, 52.2%) as an off-white foam: LRMS for $C_{35}H_{34}ClN_5O_6S$ (M+H)$^+$ at m/z=688.

A solution of (R)-3-chloro-α-(cyclopentylmethyl)-N-[2-[[[[[(9H-fluoren-9-yl)methoxy]carbonyl]oxy]amino]iminoethyl]-5-pyrazinyl]-4-(methylsulfonyl)benzeneacetamide (130.0 mg, 0.189 mmol) in pyridine (2 mL) was treated with triethylamine (0.26 mL, 1.865 mmol) and stirred at 25° C. for 2 h. The reaction mixture was concentrated in vacuo. The residue was diluted with ethyl acetate. The organic layer was washed with a 0.1N aqueous hydrochloric acid solution followed by an aqueous copper(II) sulfate solution, dried over anhydrous sodium sulfate, filtered, and concentrated in vacuo. Biotage chromatography (FLASH 40S, Silica 2/1 ethyl acetate/hexanes) afforded 2(R)-(3-chloro-4-methanesulfonyl-phenyl)-3-cyclopentyl-N-[5-(N-hydroxycarbamimidoyl)-pyrazin-2-yl]-propionamide (42.1 mg, 47.8%) as a white solid: mp 117–121° C.; (ES)$^+$-HRMS m/e calcd for $C_{20}H_{24}ClN_5O_4S$ (M+H)$^+$ 466.1311, found 466.1302.

EXAMPLE 2

2(R)-(3-Chloro-4-methanesulfonyl-phenyl)-3-cyclopentyl-N-[5-(N-hydroxycarbamimidoyl)-pyridin-2-yl]-propionamide

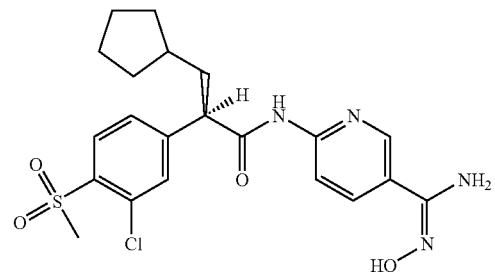

A solution of 2(R)-(3-chloro-4-methanesulfonyl-phenyl)-3-cyclopentyl-propionic acid (prepared as in Example 1, 300 mg, 0.91 mmol) in methylene chloride (10 mL) and N,N-dimethylformamide (1 drop) cooled to 0° C. was treated with a 2.0M solution of oxalyl chloride in methylene chloride (0.52 mL, 1.04 mmol). The reaction was stirred at 0° C. for 30 min. At this time, the reaction was concentrated in vacuo to give a light yellow oil. The residue was then treated with a solution of 2-amino-5-cyanopyridine (216 mg, 1.80 mmol) in tetrahydrofuran (5 mL) and pyridine (0.37 mL, 4.5 mmol). The reaction was then stirred at 25° C. for 16 h. At this time, the reaction was diluted with water (15 mL) and extracted with methylene chloride (3×25 mL). The combined organic layers were dried over sodium sulfate, filtered, and concentrated in vacuo. Biotage chromatography (FLASH 12M, Silica, 7/3 hexanes/ethyl acetate) afforded 2(R)-(3-chloro-4-methanesulfonyl-phenyl)-N-(5-cyano-pyridin-2-yl)-3-cyclopentyl-propionamide (53 mg, 86%) as a colorless oil: (ES)$^+$-HRMS m/e calcd for $C_{21}H_{22}ClN_3O_3S$ (M+H)$^+$ 432.1143, found 432.1147.

A solution of 2(R)-(3-chloro-4-methanesulfonyl-phenyl)-N-(5-cyano-pyridin-2-yl)-3-cyclopentyl-propionamide (74 mg, 0.17 mmol) in ethanol (1 mL) and water (0.5 mL) was treated with hydroxylamine hydrochloride (14 mg, 0.21 mmol) and sodium carbonate (9 mg, 0.08 mmol). This solution was then heated at 70° C. for 1.5 h, after which time, the product precipitated out of solution. The resulting solid was collected by filtration, washed with water, and dried under vacuum to afford 2(R)-(3-chloro-4-methanesulfonyl-phenyl)-3-cyclopentyl-N-[5-(N-hydroxycarbamimidoyl)-pyridin-2-yl]-propionamide (27 mg, 34%) as a white solid: (ES)$^+$-HRMS m/e calcd for $C_{21}H_{25}ClN_4O_4S$ (M+H)$^+$ 465.1358, found 465.1362.

EXAMPLE 3

3-Cyclopentyl-2(R)-N-[5-(N-hydroxycarbamimidoyl)-pyrazin-2-yl]-2-(4-methanesulfonyl-phenyl)-propionamide

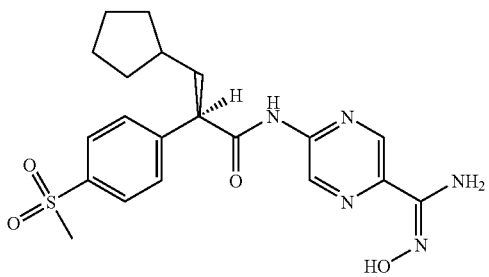

A mixture of 4-(methylthio)phenylacetic acid (50 g, 272 mmol) in tetrahydrofuran (250 mL) was treated with freshly powdered potassium carbonate (93.8 g, 679 mmol). A very mild exotherm ensued, and the resulting white suspension was stirred at 25–26° C. for 30 min. The reaction mixture was then cooled to –10° C. and treated with trimethylacetyl chloride (35.5 mL, 285 mmol) over 30 min. After completion of the addition, the reaction mixture was then stirred at –10° C. to –5° C. for 30 min and then treated with (1R,2R)-(–)-pseudoephedrine (59.5 g, 353 mmol) in portions over 15 min while maintaining the temperature of the reaction mixture between –10° C. and –4° C. The reaction mixture was then stirred at –7° C. to 0° C. for 3 h. The reaction mixture was then quenched at 0° C. by the addition of water (150 mL). After vigorously stirring for 10 min, toluene (150 mL) was added, and the reaction mixture was stirred for 5 min. The organic layer was separated and washed with water (2×100 mL). The combined aqueous layers were back-extracted with toluene (1×50 mL). The combined organic layers were washed sequentially with a 1N aqueous sulfuric acid solution (1×200 mL), a saturated aqueous sodium bicarbonate solution (1×200 mL), and a solution of water/saturated aqueous sodium chloride solution (1:1, 1×50 mL). The resulting organic layer was then concentrated in vacuo to afford a white solid. This white solid was dried overnight under high vacuum (0.4 mmHg) to afford crude N-[2(R)-hydroxy-1(R)-methyl-2(R)-phenyl-ethyl]-N-methyl-2-(4-methylsulfanyl-phenyl)-acetamide (82.8 g, 92.6% pure by high-performance liquid chromatography analysis). This material was dissolved in toluene (225 mL) at reflux. After standing in a refrigerator over the weekend, the resulting crystalline material was collected by filtration, washed with cold toluene (3×35 mL), and dried under high vacuum to afford N-[2(R)-hydroxy-1(R)-methyl-2(R)-phenyl-ethyl]-N-methyl-2-(4-methylsulfanyl-phenyl)-acetamide (66.1 g, 73.1%) as white crystals: mp 112–113° C.; 99.6% pure by high-performance liquid chromatography analysis. The high-performance liquid chromatography conditions are as follows:

| | |
|---|---|
| Column: | ES Si, 3μ, 5 × 150 mm |
| Mobile Phase: | 30% tetrahydrofuran in heptane at 1 mL/min |
| Detection: | UV, 259 nm |
| Retention Time: | 20 min |

A solution of 1,1,1,3,3,3-hexamethyldisilazane (98.4 mL, 457 mmol) in tetrahydrofuran (400 mL) was cooled to –20° C. and then treated with a 2.29M solution of n-butyllithium in hexanes (182 mL, 417 mmol) over 35 min while maintaining the temperature between –20° C. and –15° C. The reaction mixture was stirred at –20° C. for 30 min and then was treated with a solution of N-[2(R)-hydroxy-1(R)-methyl-2(R)-phenyl-ethyl]-N-methyl-2-(4-methylsulfanyl-phenyl)-acetamide (66.1 g, 201 mmol) in tetrahydrofuran (500 mL) over 50 min while maintaining the temperature between –20° C. and –15° C. The resulting yellow solution was stirred at 0° C. for 30 min and then treated with a pre-mixed solution of 1,3-dimethyl-3,4,5,6-tetrahydro-2(1H)-pyrimidinone (51 mL, 418 mmol) and iodomethylcyclopentane (prepared as in Example 1, 50.6 g, 239 mmol) over 30 min. The resulting reaction mixture was stirred at 0° C. for 4 h. At this time, the reaction mixture was poured into toluene (400 mL). The organic phase was washed sequentially with a solution of water/saturated aqueous sodium chloride solution (1:1, 1×1000 mL), a solution of water/saturated aqueous sodium chloride solution (1:2, 1×1000 mL), a 1M aqueous sulfuric acid solution (1×800 mL), water (1×200 mL), and a saturated aqueous sodium bicarbonate solution (1×1000 mL). The resulting organic layer was concentrated in vacuo to afford crude 3-cyclopentyl-N-[2(R)-hydroxy-1(R)-methyl-2(R)-phenyl-ethyl]-N-methyl-2(R)-(4-methylsulfanyl-phenyl)-propionamide as an oily yellow residue (98.5% de by high-performance liquid chromatography analysis). This material was dissolved in ethyl acetate (70 mL) and subsequently treated with hexanes (200 mL). The solution was stored in a freezer over the weekend. The resulting solid was collected by filtration, washed with cold hexanes (ca. –10° C., 3×30 mL), and then dried under high vacuum to afford 3-cyclopentyl-N-[2(R)-hydroxy-[(R)-methyl-2(R)-phenyl-ethyl]-N-methyl-2(R)-(4-methylsulfanyl-phenyl)-propionamide (48.8 g, 59%) as a white solid: mp 82–84° C.; 100% de by high-performance liquid chromatography analysis. The combined filtrates and washes were concentrated in vacuo, and the residue (34.4 g) was placed on top of a plug of thin layer chromatography grade silica gel (2–25μ, 70 g). The silica gel plug was then washed with a solution of hexanes/ethyl acetate (4:1, 1.5 L), and the combined organics were concentrated in vacuo. The resulting pale-yellow oil was dissolved in ethyl acetate (35 mL) and subsequently treated with hexanes (100 mL). The solution was stored in a refrigerator overnight. The resulting solid was collected by filtration, washed with cold hexanes (ca. –10° C., 3×25 mL), and dried under high vacuum to afford 3-cyclopentyl-N-[2(R)-hydroxy-1(R)-methyl-2(R)-phenyl-ethyl]-N-methyl-2(R)-(4-methylsulfanyl-phenyl)-propionamide (17.3 g, 20.9%) as a white solid: mp 83–85° C.; 99.6% de by high-performance liquid chromatography analysis. These two crops were combined to afford the desired diastereomer, 3-cyclopentyl-N-[2(R)-hydroxy-1(R)-methyl-2(R)-phenyl-ethyl]-N-methyl-2(R)-(4-methylsulfanyl-phenyl)-propionamide (66.1 g, 79.9%), as a white solid. The high-performance liquid chromatography conditions are as follows:

| | |
|---|---|
| Column: | ES Si, 3μ, 5 × 150 mm |
| Mobile Phase: | 20% tetrahydrofuran in heptane at 1 mL/min |
| Detection: | UV, 259 nm |
| Retention Time: | 9.2 min (undesired diastereomer) and 14.4 min (desired diastereomer) |

A solution of 3-cyclopentyl-N-[2(R)-hydroxy-1(R)-methyl-2(R)-phenyl-ethyl]-N-methyl-2(R)-(4-methylsulfanyl-phenyl)-propionamide (4.00 g, 9.72 mmol) in dioxane (8 mL) was treated with a 9N aqueous sulfuric acid solution (7.7 mL). The two-phase mixture was heated under reflux, resulting in a homogeneous colorless solution. After heating under reflux for 16 h, the reaction mixture was cooled to 5° C. with an ice-water bath and then treated dropwise with water (20 mL) to precipitate the product. After the resulting suspension was stirred for 1 h with ice-water cooling, the solid was collected by filtration, washed with water (4×10 mL), and dried by suction to afford crude 3-cyclopentyl-2(R)-(4-methylsulfanyl-phenyl)-propionic (2.57 g, 96.6%, 96.3% ee by chiral high-performance liquid chromatography analysis) as a light tan solid. This material was dissolved in glacial acetic acid (5 mL) at reflux and then was treated with water (1 mL) to initiate crystallization. The heating bath was removed, and then water (4 mL) was added dropwise to the suspension to complete the crystallization. The mixture was allowed to cool to ambient temperature. After stirring for 1 h, the solid was collected by filtration. The solid was washed with a solution of acetic acid/water (1:1, 10 mL) and water (4×10 mL), and then dried to afford 3-cyclopentyl-2(R)-(4-methylsulfanyl-phenyl)-propionic (2.24 g, 87.2%) as a white solid: mp 75–76° C.; 96.4% ee by chiral high-performance liquid chromatography analysis. The chiral high-performance liquid chromatography conditions are as follows:

| | |
|---|---|
| Column: | Chiralpak AS, 5μ, 5 × 250 mm |
| Mobile Phase: | 6% isopropanol in hexane + 0.1% TFA at 0.5 mL/min |
| Detection: | UV, 259 nm |
| Retention Time: | 13.2 min (desired R-isomer) and 17.1 min (S-isomer) |

A solution of 3-cyclopentyl-2(R)-(4-methylsulfanyl-phenyl)-propionic acid (50.03 g, 189.21 mmol) in formic acid (189 mL) was cooled to 0° C. and then slowly treated with a 30% aqueous hydrogen peroxide solution (58 mL, 567.64 mmol). The resulting reaction mixture was allowed to stir at 0° C. for 1 h and then allowed to warm to 25° C. where it was stirred for 3 h. The reaction mixture was re-cooled to 0° C. and then slowly quenched with a saturated aqueous sodium bisulfite solution (500 mL). A precipitate formed. The resulting suspension was stirred at 0° C. for 1 h and then the solid was filtered. The solid was washed with cold water (4×700 mL) and dried by suction to afford 3-cyclopentyl-2(R)-(4-methanesulfonylphenyl)-propionic acid as a cream solid: mp 138–140° C.; EI-HRMS m/e calcd for $C_{15}H_{20}O_4S$ $(M^+)$ 296.1082, found 296.1080.

A solution of triphenylphosphine (5.75 g, 21.7 mmol) in anhydrous methylene chloride (35 mL) under argon at 0° C. was treated with N-bromosuccinimide (3.86 g, 21.7 mmol). The mixture was allowed to stir for 15 min at 0° C. and then was treated with 3-cyclopentyl-2(R)-(4-methanesulfonylphenyl)-propionic acid (4.95 g, 16.7 mmol). The resulting mixture was then allowed to warm to 25° C. for 10 min. At this time, 2-amino-5-bromopyrazine (5.81 g, 33.4 mmol) was added, followed by the slow addition of pyridine (5.5 mL, 68.0 mmol). This mixture was allowed to stir for 3 h at 25° C., at which time, the reaction was concentrated in vacuo. The residue was dissolved in ethyl acetate and washed sequentially with a 1N aqueous hydrochloric acid solution (150 mL), a 10% aqueous potassium carbonate solution (100 mL), and a saturated aqueous sodium chloride solution (250 mL). The organic layer was dried over sodium sulfate, filtered, and concentrated in vacuo. Biotage chromatography (FLASH 75S, Silica, 2.5% to 5% gradient ethyl acetate/methylene chloride) afforded 2(R)-(4-methanesulfonyl-phenyl)-3-cyclopentyl-5-bromo-pyrazin-2-yl-propionamide (6.12 g, 81%) as a light yellow solid.

A solution of 2(R)-(4-methanesulfonyl-phenyl)-3-cyclopentyl-5-bromo-pyrazin-2-yl-propionamide (6.11 g, 13.5 mmol), potassium cyanide (2.27 g, 33.8 mmol), copper(I) iodide (6.43 g, 33.8 mmol), tetrakis(triphenylphosphine)palladium(0) (320 mg, 0.27 mmol), and 18-crown-6 (365 mg, 1.37 mmol) in anhydrous N,N-dimethylformamide (30 mL) was heated at 150° C. under argon. After 4 h, the mixture was allowed to cool to 25° C. The mixture was concentrated to about one-half volume and then chloroform (700 mL) was added to precipitate the copper salts. The mixture was filtered through a pad of celite, and the salts were washed with warm chloroform (2×100 mL). The filtrate was then concentrated in vacuo. Biotage chromatography (FLASH 75S, Silica, 0% to 35% gradient ethyl acetate/hexanes) afforded 2(R)-(4-methanesulfonyl-phenyl)-3-cyclopentyl-5-cyano-pyrazin-2-yl-propionamide (4.49 g, 83%) as a light yellow solid: mp 229–231° C.; $(ES)^+$-HRMS m/e calcd for $C_{20}H_{23}N_4O_3S_2$ $(M+H)^+$ 399.1486, found 399.1488.

A mixture 2(R)-(4-methanesulfonyl-phenyl)-3-cyclopentyl-5-cyano-pyrazin-2-yl-propionamide (1.00 g, 2.51 mmol) and hydroxylamine hydrochloride (219 mg, 3.15 mmol) in pH=7 buffer/ethanol (40 mL) was heated at 70° C. After 17 h, the mixture was allowed to cool to 25° C. and then was concentrated in vacuo. The mixture was extracted with ethyl acetate (3×50 mL). The combined organic layers were washed with a saturated aqueous sodium chloride solution, dried over sodium sulfate, filtered, and concentrated in vacuo. The crude product was purified by reverse phase high-performance liquid chromatography (C-18, acetonitrile/water, 0.1% trifluoroacetic acid, 40% to 80% acetonitrile gradient), and the fractions containing product were concentrated in vacuo and lyophilized to afford 3-cyclopentyl-2(R)-N-[5-(N-hydroxycarbamimidoyl)-pyrazin-2-yl]-2-(4-methanesulfonyl-phenyl)-propionamide (740 mg, 68%) as an off-white solid: mp 223° C. (dec.); $(ES)^+$-HRMS m/e calcd for $C_{20}H_{26}N_5O_4S$ $(M+H)^+$ 432.1700, found 432.1706.

EXAMPLE 4

2(R)-(3-Chloro-4-methanesulfonyl-phenyl)-3-cyclopentyl-N-(5-methylsulfanyl-pyrazin-2-yl)-propionamide

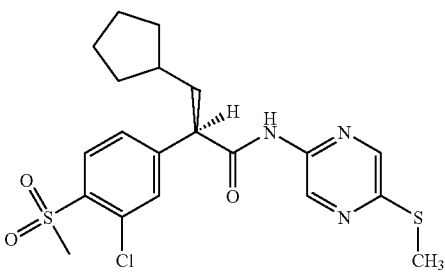

A mixture of tetrakis(triphenylphosphine)palladium(0) (3.32 g, 2.87 mmol) and 2-amino-5-bromopyrazine (5.00 g, 28.73 mmol) in N,N-dimethylformamide (144 mL) was treated with 95% sodium thiomethoxide (4.24 g, 57.47 mmol). The resulting reaction mixture was heated at 60° C.

for 10 h. The reaction mixture was allowed to cool to 25° C. and then was poured into a saturated aqueous sodium bicarbonate solution (500 mL). The product was extracted with ethyl acetate (5×200 mL). The combined organic layers were washed with a saturated aqueous sodium chloride solution (1×200 mL), dried over sodium sulfate, filtered, and concentrated in vacuo. Flash chromatography (Merck Silica gel 60, 230–400 mesh, 3/7 ethyl acetate/hexanes) afforded 5-methylsulfanyl-pyrazin-2-ylamine (1.66 g, 40.9%) as an orange solid: mp 65–67° C.; EI-HRMS m/e calcd for $C_5H_7N_3S$ (M$^+$) 141.0361, found 141.0357.

A solution of 2(R)-(3-chloro-4-methanesulfonyl-phenyl)-3-cyclopentyl-propionic acid (prepared as in Example 1, 2.34 g, 7.08 mmol) and N,N-dimethylformamide (5 drops) in methylene chloride (15 mL) was cooled to 0° C. The reaction mixture was then treated with oxalyl chloride (1.24 mL, 14.16 mmol). The reaction mixture was stirred at 0° C. for 15 min and then at 25° C. for 2 h. The solution was then concentrated in vacuo, and the yellow semi-solid was dissolved in methylene chloride (8 mL). The resulting solution was added dropwise via an addition funnel at 0° C. to a solution of 5-methylsulfanyl-pyrazin-2-ylamine (1.0 g, 7.08 mmol) in methylene chloride (5 mL) and pyridine (0.86 mL, 10.6 mmol). The reaction mixture was stirred at 0° C. for 2 h and then at 25° C. overnight. The reaction mixture was quenched with a 1N aqueous citric acid solution (10 mL) and was stirred for 10 min. The reaction was then diluted with water (50 mL), methylene chloride (100 mL), and a 1N aqueous citric acid solution (25 mL). The layers were separated, and the organic layer was then washed with a saturated aqueous sodium bicarbonate solution (50 mL) and a saturated aqueous sodium chloride solution (50 mL), dried over magnesium sulfate, filtered, and concentrated in vacuo. Biotage chromatography (FLASH 40M, Silica, 1/3 ethyl acetate/hexanes) afforded impure product. Re-purification by Biotage chromatography (FLASH 40M, Silica, 1/1 ethyl acetate/hexanes) afforded 2(R)-(3-chloro-4-methanesulfonyl-phenyl)-3-cyclopentyl-N-(5-methylsulfanyl-pyrazin-2-yl)-propionamide (1.75 g, 54%) as a white foam: mp 65–70° C. (foam to gel); (ES)$^+$-HRMS m/e calcd for $C_{20}H_{24}ClN_3O_3S_2$ (M+H)$^+$ 454.1021, found 454.1026.

EXAMPLE 5

3-Cyclopentyl-2(R)-(4-methanesulfonyl-phenyl)-N-(5-methylsulfanyl-pyrazin-2-yl)-propionamide

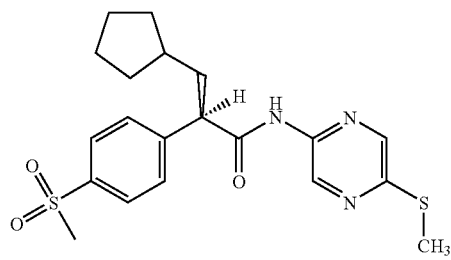

A solution of 3-cyclopentyl-2(R)-(4-methanesulfonylphenyl)-propionic acid (prepared as in Example 3, 1.21 g, 4.07 mmol) and N,N-dimethylformamide (5 drops) in methylene chloride (10 mL) was cooled to 0° C. The reaction mixture was then treated with oxalyl chloride (0.53 mL, 6.10 mmol), and the resulting reaction mixture was stirred at 0° C. for 1 h. The solution was then concentrated in vacuo, and the orange-brown gel was dissolved in methylene chloride. The resulting solution was added dropwise via an addition funnel at 0° C. to a solution of 5-methylsulfanyl-pyrazin-2-ylamine (prepared as in Example 4, 0.58 g, 4.07 mmol) in methylene chloride (10 mL) and pyridine (0.36 mL, 4.48 mmol). The reaction mixture was stirred at 0° C. for 30 min and then was allowed to warm to 25° C. where it was stirred for 3 h. The reaction mixture was quenched with a 1N aqueous citric acid solution (10 mL) and was stirred for 15 min. The reaction was then diluted with ethyl acetate (75 mL) and a 1N aqueous citric acid solution (50 mL). The layers were separated, and the organic layer was then washed with a saturated aqueous sodium bicarbonate solution (50 mL), water (50 mL), and a saturated aqueous sodium chloride solution (50 mL), dried over magnesium sulfate, filtered, and concentrated in vacuo. Biotage chromatography (FLASH 40M, Silica, 1/1 ethyl acetate/hexanes) afforded 3-cyclopentyl-2(R)-(4-methanesulfonyl-phenyl)-N-(5-methylsulfanyl-pyrazin-2-yl)-propionamide (0.864 g, 51%) as a white foam: mp 71–77° C. (foam to gel); (ES)$^+$-HRMS m/e calcd for $C_{20}H_{25}N_3O_3S_2$ (M+H)$^+$ 420.1410, found 420.1415.

EXAMPLE 6

2(R)-(3-Chloro-4-methanesulfonyl-phenyl)-3-cyclopentyl-N-[5-(2-hydroxy-ethylsulfanyl)-pyrazin-2-yl]-propionamide

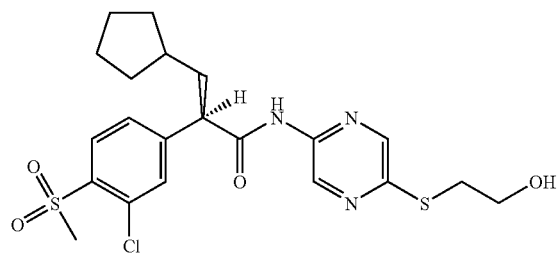

A stirred solution of triphenylphosphine (8.57 g, 32.6 mmol) in anhydrous methylene chloride (110 mL) under nitrogen at 0° C. was treated with N-bromosuccinimide (5.80 g, 32.6 mmol). After 15 min, 2(R)-(3-chloro-4-methanesulfonyl-phenyl)-3-cyclopentyl-propionic acid (prepared as in Example 1, 9.00 g, 27.2 mmol) was added to the reaction. The mixture was allowed to warm to 25° C. After stirring at 25° C. for 10 min, the reaction was treated with 2-amino-5-bromopyrazine (7.92 g, 45.6 mmol) followed by pyridine (8.79 mL, 108.8 mmol). The mixture was allowed to stir at 25° C. for 1.5 h. At this time, the reaction was diluted with methylene chloride and then was washed with a 1N aqueous hydrochloric acid solution (200 mL) followed by a 10% aqueous potassium carbonate solution (100 mL). The organic layer was dried over sodium sulfate, filtered, and concentrated in vacuo. Flash chromatography (Merck Silica gel 60, 70–230 mesh, 3/7 ethyl acetate/hexanes) afforded N-(5-bromo-pyrazin-2-yl)-2(R)-(3-chloro-4-methanesulfonyl-phenyl)-3-cyclopentyl-propionamide (10.02 g, 76%) as a white foam: mp 77–82° C. (foam to gel); (ES)$^+$-HRMS m/e calcd for $C_{19}H_{21}BrClN_3O_3S$ (M+H)$^+$ 486.0249, found 486.0255.

A mixture of the N-(5-bromo-pyrazin-2-yl)-2(R)-(3-chloro-4-methanesulfonyl-phenyl)-3-cyclopentyl-propionamide (94 mg, 0.19 mmol), mercaptoethanol (0.031 mL, 0.44 mmol), and tetrakis(triphenylphosphine)palladium(0) (111 mg, 0.097 mmol) in anhydrous N,N-dimethylformamide (0.5 mL) was heated at 120° C. in a sealed tube. After 3 h, the mixture was allowed to cool to 25° C., diluted with water, and then extracted with diethyl ether. The organic layer was dried over sodium sulfate, filtered, and concentrated in vacuo. Flash chromatography (Merck silica gel 60, 230–400 mesh, 55% ethyl acetate/hexanes) afforded 2(R)-(3-chloro-4-methanesulfonyl-phenyl)-3-cyclopentyl-N-[5-(2-hydroxy-ethylsulfanyl)-pyrazin-2-yl]-propionamide (58 mg, 62%) as a light brown foam: mp=78–81° C.; (ES)$^+$-HRMS m/e calcd for $C_{21}H_{27}ClN_3O_4S_2$ (M+H)$^+$ 484.1126, found 484.1131.

EXAMPLE 7

2(R)-(3-Chloro-4-methanesulfonyl-phenyl)-3-cyclopentyl-N-(5-methanesulfinyl-pyrazin-2-yl)-propionamide

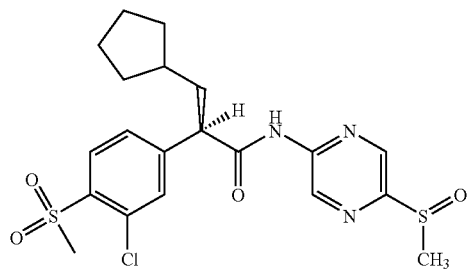

A solution of 2(R)-(3-chloro-4-methanesulfonyl-phenyl)-3-cyclopentyl-N-(5-methylsulfanyl-pyrazin-2-yl)-propionamide (prepared as in Example 4, 0.20 g, 0.441 mmol) in tetrahydrofuran (3 mL) was added dropwise to a solution of sodium-meta-periodate (0.189 g, 0.882 mmol) in water (1.5 mL). The resulting reaction mixture was stirred at 25° C. for 72 h. The reaction mixture was then concentrated in vacuo, and the residue was then diluted with chloroform (25 mL). The organic layer was washed with water (25 mL), dried over magnesium sulfate, filtered, and concentrated in vacuo. Biotage chromatography (FLASH 40S, Silica, 2/1 ethyl acetate/hexanes) afforded 2(R)-(3-chloro-4-methanesulfonyl-phenyl)-3-cyclopentyl-N-(5-methane-sulfinyl-pyrazin-2-yl)-propionamide (96 mg, 46%) as a white foam: mp 88–95° C. (foam to gel); (ES)$^+$-HRMS m/e calcd for $C_{20}H_{24}ClN_3O_4S_2$ (M+H)$^+$ 470.0970 found 470.0976.

EXAMPLE 8

2(R)-(3-Chloro-4-methanesulfonyl-phenyl)-3-cyclopentyl-N-(5-methylsulfamoyl-pyrazin-2-yl)-propionamide

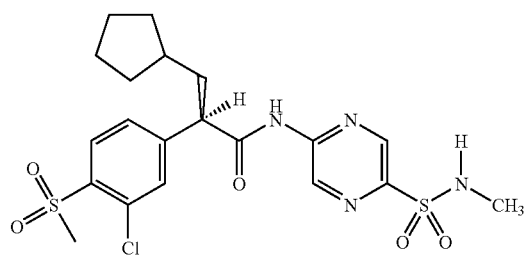

A solution of 2(R)-(3-chloro-4-methanesulfonyl-phenyl)-3-cyclopentyl-N-(5-methanesulfinyl-pyrazin-2-yl)-propionamide (prepared as in Example 7, 0.30 g, 0.65 mmol) in methylene chloride (5.6 mL) was treated with trifluoroacetic anhydride (0.40 mL, 2.83 mmol). The resulting reaction mixture was heated under reflux for 90 min. The reaction was allowed to cool to 25° C. and then was concentrated in vacuo to afford trifluoro-acetic acid 5-[2(R)-(3-chloro-4-methanesulfonyl-phenyl)-3-cyclopentyl-propionylamino]-pyrazin-2-yl-sulfanyl methyl ester which was used without further purification.

A solution of crude trifluoro-acetic acid 5-[2(R)-(3-chloro-4-methanesulfonyl-phenyl)-3-cyclopentyl-propionylamino]-pyrazin-2-yl-sulfanyl methyl ester (0.37 g, based on 0.65 mmol of crude material) in methanol (2.5 mL) and triethylamine (2.5 mL, 17.9 mmol) was stirred at 25° C. for 2 h, and then the reaction mixture was then concentrated in vacuo. The resulting orange oil was dissolved in methylene chloride (10 mL) and was then washed with a 0.5M aqueous hydrochloric acid solution (10 mL). The aqueous layer was extracted with methylene chloride (3×3 mL). The combined organic layers were dried over sodium sulfate, filtered, and concentrated in vacuo to afford 2(R)-(3-chloro-4-methanesulfonyl-phenyl)-3-cyclopentyl-N-(5-mercapto-pyrazin-2-yl)-propionamide as an orange solid which was used without further purification.

A solution of crude 2(R)-(3-chloro-4-methanesulfonyl-phenyl)-3-cyclopentyl-N-(5-mercapto-pyrazin-2-yl)-propionamide (0.29 g, based on 0.65 mmol of crude material) in acetonitrile (6.5 mL) was treated with powdered potassium nitrate (0.192 g, 1.90 mmol) and then sulfuryl chloride (0.150 mL, 1.87 mmol). The resulting solution was stirred at 25° C. for 15 min, at which time, low resolution mass spectrometry indicated the presence of the desired crude product, 5-[2(R)-(3-chloro-4-methanesulfonyl-phenyl)-3-cyclopentyl-propionylamino]-pyrazine-2-sulfonyl chloride, in the solution. One-half of the volume of this solution was charged with a 2.0M solution of methylamine in tetrahydrofuran (0.65 mL, 1.30 mmol) and was stirred at 25° C. for 5 min, at which point, a precipitate had formed. The resulting reaction mixture was diluted with methylene chloride (15 mL), and the organic layer was washed with a saturated aqueous sodium bicarbonate solution (10 mL) and a 1N aqueous citric acid solution (10 mL). The combined aqueous layers were back-extracted with methylene chloride (2×5 mL). The combined organic layers were then concentrated in vacuo. Flash chromatography (Merck Silica gel 60, 75% ethyl acetate/hexanes) provided impure product. The impure product was re-purified by reverse phase high-performance liquid chromatography (C-18, acetonitrile/water, 0.1% trifluoroacetic acid, 50% to 100% acetonitrile gradient). The fractions containing product were concentrated in vacuo and lyophilized to afford 2(R)-(3-chloro-4-methanesulfonyl-phenyl)-3-cyclopentyl-N-(5-methylsulfamoyl-pyrazin-2-yl)-propionamide (15 mg, ~9% overall yield) as a yellow gum: (ES)$^+$-HRMS m/e calcd for $C_{20}H_{25}ClN_4O_5S_2$ (M+Na)$^+$ 523.0847 found 523.0854.

EXAMPLE 9

2(R)-(3-Chloro-4-methanesulfonyl-phenyl)-3-cyclopentyl-N-(5-dimethylsulfamoyl-pyrazin-2-yl)-propionamide

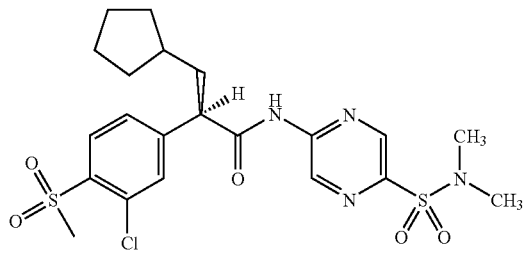

A solution of 2(R)-(3-chloro-4-methanesulfonyl-phenyl)-3-cyclopentyl-N-(5-methanesulfinyl-pyrazin-2-yl)-propionamide (prepared as in Example 7, 199.9 mg, 0.42 mmol) in methylene chloride (3.6 mL) was treated with trifluoroacetic anhydride (0.25 mL, 1.77 mmol). The resulting reaction mixture was heated under reflux for 90 min. The reaction mixture was allowed to cool to 25° C. and then was concentrated in vacuo to afford trifluoro-acetic acid 5-[2(R)-(3-chloro-4-methanesulfonyl-phenyl)-3-cyclopentyl-propionylamino]-pyrazin-2-yl-sulfanyl methyl ester as a crude yellow foam (291.3 mg, 121%). This material was used without further purification.

A solution of crude trifluoro-acetic acid 5-[2(R)-(3-chloro-4-methanesulfonyl-phenyl)-3-cyclopentyl-propionylamino]-pyrazin-2-yl-sulfanyl methyl ester (240.7 mg, based on 0.42 mmol of crude material) in methanol (1.7 mL) and triethylamine (1.6 mL, 11.48 mmol) was stirred at 25° C. for 3 h, and the reaction mixture was then concentrated in vacuo. The resulting orange oil was dissolved in methylene chloride (11 mL) and was then washed with a 0.5M aqueous hydrochloric acid solution (10 mL). The aqueous layer was back-extracted with methylene chloride (3×3 mL). The combined organic layers were then dried over sodium sulfate, filtered, and concentrated in vacuo to afford the 2(R)-(3-chloro-4-methanesulfonyl-phenyl)-3-cyclopentyl-N-(5-mercapto-pyrazin-2-yl)-propionamide as a crude red-orange solid (289.1 mg, 155%). This material was used without further purification.

A solution of crude 2(R)-(3-chloro-4-methanesulfonyl-phenyl)-3-cyclopentyl-N-(5-mercapto-pyrazin-2-yl)-propionamide (187.1 mg, based on 0.42 mmol of crude material) in acetonitrile (4.4 mL) was treated with powdered potassium nitrate (125.1 mg, 1.24 mmol) and then sulfuryl chloride (0.100 mL, 1.24 mmol). The resulting solution was stirred at 25° C. for 30 min, at which time, low resolution mass spectrometry indicated the presence of the desired crude product, 5-[2(R)-(3-chloro-4-methanesulfonyl-phenyl)-3-cyclopentyl-propionylamino]-pyrazine-2-sulfonyl chloride, in the solution. This solution was charged with a 2.0M solution of dimethylamine in tetrahydrofuran (0.85 mL, 1.70 mmol). The reaction mixture was stirred at 25° C. overnight and then was charged with an additional aliquot of a 2.0M solution of dimethylamine in tetrahydrofuran (0.21 mL, 0.42 mmol). The resulting reaction mixture was stirred at 25° C. for 5–6 h and then was treated with a final aliquot of a 2.0M solution of dimethylamine in tetrahydrofuran (0.21, 0.42 mmol). The reaction mixture was stirred at 25° C. overnight, monitoring by low resolution mass spectrometry. The resulting reaction mixture was diluted with ethyl acetate (10 mL) and then was washed with a saturated aqueous sodium bicarbonate solution (10 mL). The aqueous layer was back-extracted with ethyl acetate (10 mL). The combined organic layers were washed with a 1N aqueous citric acid solution (10 mL), dried over sodium sulfate, filtered, and concentrated in vacuo onto silica gel (Merck Silica gel 60, 230–400 mesh). Biotage chromatography (FLASH 40S, Silica, 40% ethyl acetate/hexanes) provided impure product. The impure product was re-purified by reverse phase high-performance liquid chromatography (C-18, acetonitrile/water, 0.1% trifluoroacetic acid, 50% to 100% acetonitrile gradient). The fractions containing product were concentrated in vacuo and lyophilized to afford 2(R)-(3-chloro-4-methanesulfonyl-phenyl)-3-cyclopentyl-N-(5-dimethylsulfamoyl-pyrazin-2-yl)-propionamide (44.6 mg, 20% overall yield) as a light yellow solid: mp 100.2° C.; (ES)$^+$-HRMS m/e calcd for $C_{21}H_{27}ClN_4O_5S_2$ (M+H)$^+$ 515.1184, found 515.1189.

EXAMPLE 10

2(R)-(3-Chloro-4-methanesulfonyl-phenyl)-3-cyclopentyl-N-[5-(3-hydroxy-prop-1-ynyl)-pyrazin-2-yl]-propionamide

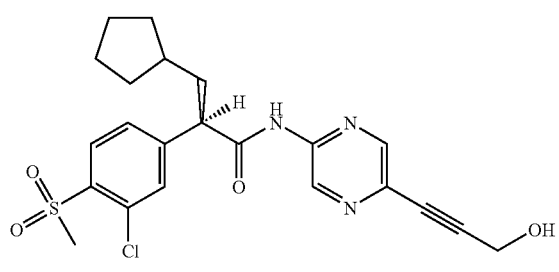

A solution of N-(5-bromo-pyrazin-2-yl)-2(R)-(3-chloro-4-methanesulfonyl-phenyl)-3-cyclopentyl-propionamide (prepared as in Example 6, 486 mg, 1 mmol) and propargyl alcohol (84 mg, 1.5 mmol) in toluene (6 mL) was treated with copper(I) iodide (19.2 mg, 0.10 mmol), dichlorobis(triphenylphosphine)palladium(II) (36 mg, 0.05 mmol), and N,N-diisopropylethylamine (2 ml). The resulting mixture was stirred at 25° C. for 1 h and was then heated to 60° C. for 1 h. At this time, the reaction was concentrated in vacuo. The residue was extracted into ethyl acetate from a 1N aqueous hydrochloric acid solution. The combined organic layers were washed with a saturated aqueous sodium chloride solution, dried, and concentrated in vacuo. Flash chromatography (Merck Silica gel 60, 230–400 mesh, 1/1 ethyl acetate/hexanes) afforded 2(R)-(3-chloro-4-methanesulfonyl-phenyl)-3-cyclopentyl-N-[5-(3-hydroxy-prop-1-ynyl)- pyrazin-2-yl]-propionamide (275 mg, 57%) as a pale yellow solid: (ES)⁺-HRMS m/e calcd for $C_{22}H_{24}ClN_3O_4S$ (M+H)⁺ 462.1249, found 462.1252.

EXAMPLE 11

2(R)-(3-Chloro-4-methanesulfonyl-phenyl)-3-cyclopentyl-N-[5-(3-dimethylamino-prop-1-ynyl)-pyrazin-2-yl]-propionamide

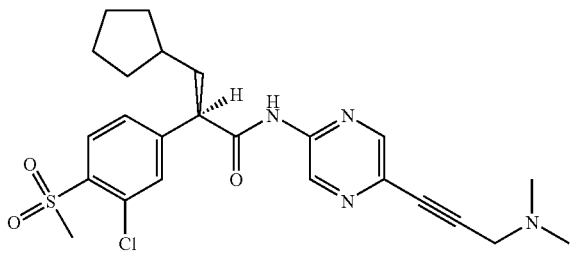

A solution of N-(5-bromo-pyrazin-2-yl)-2(R)-(3-chloro-4-methanesulfonyl-phenyl)-3-cyclopentyl-propionamide (prepared as in Example 6, 486 mg, 1.0 mmol) and 1-dimethylamino-2-propyne (830 mg, 10.0 mmol) in toluene (6 ml) was treated with N,N-diisopropylethylamine (1.5 ml), copper(I) iodide (19.2 mg, 0.10 mmol), and dichlorobis (triphenylphosphine)palladium(II) (36.0 mg, 0.05 mmol). The resulting reaction mixture was stirred at 25° C. for 24 h. At this time, the reaction mixture was concentrated in vacuo. The residue was extracted into methylene chloride from water. The combined organic layers were dried and concentrated in vacuo. Flash chromatography (Merck Silica gel 60, 230–400 mesh, 4/1 ethyl acetate/methanol) afforded 2(R)-(3-chloro-4-methanesulfonyl-phenyl)-3-cyclopentyl-N-[5-(3-dimethylamino-prop-1-ynyl)-pyrazin-2-yl]-propionamide (360 mg, 74%) as a pale brown solid: (ES)⁺-HRMS m/e calcd for $C_{24}H_{29}ClN_4O_3S$ (M+H)⁺ 489.1722, found 489.1725.

EXAMPLE 12

2(R)-(3-Chloro-4-methanesulfonyl-phenyl)-3-cyclopentyl-N-(5-methanesulfonylamino-pyridin-2-yl)-propionamide

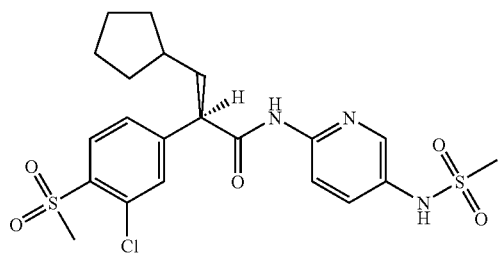

A solution of molten acetamide (2.36 g, 40.0 mmol) heated to 90° C. was treated with a mixture of 5-bromo-2-nitropyridine (2.0 g, 9.85 mmol), methanesulfonamide (2.81 g, 29.55 mmol), and potassium carbonate (3.43 g, 24.8 mmol). The resulting mixture was quickly brought to 145° C. The resulting solution was stirred at 145° C. for 30 min. At this time, the reaction was cooled to 25° C. and then was treated with water (8 mL). This solution was cooled to 0° C. and then was treated with a 1N aqueous hydrochloric acid solution until the pH of the solution was adjusted to pH=8. The precipitate which resulted was removed by filtration. The filtrate was adjusted to pH=4 by the addition of a 1N aqueous hydrochloric acid solution. The resulting precipitate was collected and dried in vacuo to afford N-(6-nitro-pyridin-3-yl)-methanesulfonamide (1.46 g, 68%) as a white solid: mp 187–189° C.; (ES)⁻-HRMS m/e calcd for $C_6H_7N_3O_4S$ (M–H)⁻ 216.0084, found 216.0085.

A solution of N-(6-nitro-pyridin-3-yl)-methanesulfonamide (298 mg, 1.37 mmol) in methanol (8.3 mL) was treated with a solution of ammonium chloride (154 mg, 2.88 mmol) in water (1 mL). This solution was stirred at 25° C. for 5 min. At this time, zinc dust (879 mg, 13.44 mmol) was added to the reaction. The resulting reaction mixture was then heated under reflux for 3 h. At this time, the reaction was cooled to 25° C. and then was filtered through a pad of celite (9/1 methylene chloride/methanol wash). The filtrate was concentrated in vacuo. Flash chromatography (Merck Silica gel 60, 230–400 mesh, 9/1 methylene chloride/methanol) afforded N-(6-amino-pyridin-3-yl)-methanesulfonamide (196.3 mg, 76.4%) as a reddish-brown oil: EI-HRMS m/e calcd for $C_6H_9N_3O_2S$ (M⁺) 184.0415, found 184.0415.

A solution of 2(R)-(3-chloro-4-methanesulfonyl-phenyl)-3-cyclopentyl-propionic acid (prepared as in Example 1, 224 mg, 0.67 mmol) in methylene chloride was cooled to 0° C. and then was treated with a 2.0M solution of oxalyl chloride in methylene chloride (0.37 mL, 0.74 mmol) and a few drops of N,N-dimethylformamide. The reaction mixture was stirred at 0° C. for 10 min and at 25° C. for 20 min. The reaction mixture was then treated with a solution of N-(6-amino-pyridin-3-yl)-methanesulfonamide (190 mg, 1.01 mmol) and pyridine (0.08 mL, 1.01 mmol) in tetrahydrofuran (3.38 mL). This solution was stirred at 25° C. for 18 h. At this time, the reaction was concentrated in vacuo. The residue was dissolved in methylene chloride (50 mL), and the organic layer was washed consecutively with a 1N aqueous hydrochloric acid solution (1×100 mL) and a saturated aqueous sodium bicarbonate solution (1×100 mL). The organic layer was then dried over sodium sulfate, filtered, and concentrated in vacuo. Flash chromatography (Merck Silica gel 60, 230–400 mesh, 3/1 ethyl acetate/hexanes) afforded 2(R)-(3-chloro-4-methanesulfonyl-phenyl)-3-cyclopentyl-N-(5-methanesulfonylamino-pyridin-2-yl)-propionamide (34.4 mg, 10.2%) as a light tan solid: mp 146–150° C.; EI-HRMS m/e calcd for $C_{21}H_{26}ClN_3O_5S_2$ (M+H)⁺ 500.1075, found 500.1081.

EXAMPLE 13

2(R)-(3-Chloro-4-methanesulfonyl-phenyl)-3-cyclopentyl-N-(5-methanesulfonylamino-pyrazin-2-yl)-propionamide

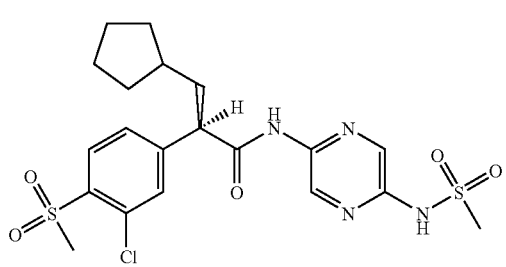

A solution of molten acetamide (1.58 g, 26.7 mmol) heated to 90° C. was treated with a mixture of 2-bromo-5-nitropyrazine (1.34 g, 6.58 mmol), methanesulfonamide (1.88 g, 19.7 mmol), and potassium carbonate (2.30 g, 16.6 mmol). The resulting mixture was quickly brought to 145° C. The resulting solution was stirred at 145° C. for 30 min. At this time, the reaction was cooled to 25° C. and then was treated with water (4 mL). This solution was cooled to 0° C. and then was treated with a 1N aqueous hydrochloric acid solution until the pH of the solution was adjusted to pH=8. This solution was treated with charcoal and was filtered through a pad of celite (9/1 methylene chloride/methanol wash). The filtrate was partitioned, and the aqueous layer was extracted with a solution of 9/1 methylene chloride/methanol. The combined organic layers were dried over sodium sulfate, filtered, and concentrated in vacuo. Flash chromatography (Merck Silica gel 60, 230–400 mesh, ethyl acetate) afforded N-(5-nitro-pyrazin-2-yl)-methanesulfonamide (583.9 mg, 40.6%) as a yellow solid: mp 204–207° C.; EI-HRMS m/e calcd for $C_5H_6N_4O_4S$ (M+H)$^+$ 219.0183, found 219.0185.

A solution of N-(5-nitro-pyrazin-2-yl)-methanesulfonamide (583.9 mg, 2.67 mmol) in methanol (26.8 mL) was treated with a solution of ammonium chloride (300.6 mg, 5.62 mmol) in water (2 mL). This solution was stirred at 25° C. for 5 min. At this time, the reaction was treated with zinc dust (1.71 g, 26.2 mmol). The resulting mixture was heated under reflux for 2 h. At this time, the reaction was cooled to 25° C. and was filtered through a pad of silica gel (9/1 methylene chloride/methanol wash). The filtrate was concentrated in vacuo to afford N-(5-amino-pyrazin-2-yl)-methanesulfonamide (548.8 mg, 100%) as a dark-brown gum: EI-HRMS m/e calcd for $C_5H_8N_4O_2S$ (M+H)$^+$ 189.0441, found 189.0442.

A solution of 2(R)-(3-chloro-4-methanesulfonyl-phenyl)-3-cyclopentyl-propionic acid (prepared as in Example 1, 482 mg, 1.45 mmol) in methylene chloride (14.6 mL) cooled to 0° C. was treated with a 2.0M solution of oxalyl chloride in methylene chloride (0.80 mL, 1.60 mmol) and a few drops of N,N-dimethylformamide. The reaction mixture was stirred at 0° C. for 10 min and at 25° C. for 30 min. The reaction mixture was then treated with a solution of N-(5-amino-pyrazin-2-yl)-methanesulfonamide (548.8 mg, 2.91 mmol) and pyridine (0.24 mL, 2.91 mmol) in tetrahydrofuran (7.29 mL). This solution was stirred at 25° C. for 18 h. At this time, the reaction was concentrated in vacuo. The residue was dissolved in methylene chloride (50 mL) and was washed consecutively with a 1N aqueous hydrochloric acid solution (1×100 mL) and a saturated aqueous sodium bicarbonate solution (1×100 mL). The organic layer was dried over sodium sulfate, filtered, and concentrated in vacuo. Flash chromatography (Merck Silica gel 60, 230–400 mesh, 95/5 methylene chloride/methanol) afforded 2(R)-(3-chloro-4-methanesulfonyl-phenyl)-3-cyclo-pentyl-N-(5-methanesulfonylamino-pyrazin-2-yl)-propionamide (43.0 mg, 5.9%) as an off-white solid: mp 108–110° C.; EI-HRMS m/e calcd for $C_{20}H_{25}ClN_4O_5S_2$ (M+H)$^+$ 501.1028, found 501.1031.

EXAMPLE 14

2(R)-(3-Chloro-4-methanesulfonyl-phenyl)-3-cyclopentyl-N-(5-dimethylamino-pyridin-2-yl)-propionamide

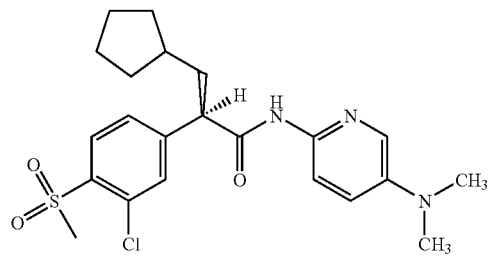

A sealed tube apparatus was charged with 2-bromo-5-nitropyridine (1.02 g, 5.02 mmol) and a 5.6M solution of dimethylamine in ethanol (5.0 mL, 28.0 mmol). The resulting solution was heated at 90° C. for 3 d, allowed to cool to 0° C., and then diluted with acetone and ethyl acetate. A white solid was removed via filtration, and the filtrate was absorbed onto silica gel (Merck Silica gel 60, 230–400 mesh). Biotage chromatography (FLASH 40S, Silica, 1/2 to 3/1 ethyl acetate/hexanes) afforded dimethyl-(6-nitro-pyridin-3-yl)-amine (0.64 g, 76%) as an intensely yellow solid: mp 199.8–200.5° C.; EI-HRMS m/e calcd for $C_7H_9N_3O_2$ (M$^+$) 167.0695, found 167.0697.

A solution of dimethyl-(6-nitro-pyridin-3-yl)-amine (0.64 g, 3.83 mmol) in ethanol (45 mL) was treated with 10% palladium on activated carbon (203 mg). The reaction mixture was stirred under a positive pressure of hydrogen gas (balloon) at 25° C. and atmospheric pressure overnight. The catalyst was then filtered off through a pad of celite, and the celite pad was washed well with ethanol. The filtrate was concentrated in vacuo to afford $N^5,N^5$-dimethyl-pyridine-2,5-diamine (493.6 mg, 94%) as a dark red-purple oil: EI-HRMS m/e calcd for $C_7H_{11}N_3$ (M$^+$) 137.0953, found 137.0957.

A solution of 2(R)-(3-chloro-4-methanesulfonyl-phenyl)-3-cyclopentyl-propionic acid (prepared as in Example 1, 701 mg, 2.12 mmol) in methylene chloride (5.0 mL) was cooled to 0° C. The reaction mixture was then treated with oxalyl chloride (0.43 mL, 4.93 mmol) and N,N-dimethylformamide (4 drops). The reaction mixture was stirred at 0° C. and then allowed to slowly warm to 25° C. over 5 h. The solution was then concentrated in vacuo, and the yellow slurry was dissolved in methylene chloride (3 mL). The resulting solution was added dropwise via an addition funnel at 0° C. to a solution of $N^5,N^5$-dimethyl-pyridine-2,5-diamine (287 mg, 2.09 mmol) in methylene chloride (5 mL) and pyridine (0.3 mL). The reaction mixture was stirred at 0° C. and then was allowed to warm to 25° C. overnight. The reaction mixture was then concentrated in vacuo and treated with ethyl acetate (75 mL) and a 1N aqueous citric acid solution (75 mL). The layers were separated. The aqueous layer was extracted with ethyl acetate (2×50 mL). The combined organic layers were washed with a saturated aqueous sodium bicarbonate solution (75 mL). The combined aqueous layers were back-extracted with ethyl acetate (50 mL). The combined organic layers were washed with a saturated aqueous sodium chloride solution (75 mL), dried over sodium sulfate, filtered, and concentrated in vacuo. Biotage chromatography (FLASH 40M, Silica, 1/2 to 1/1 ethyl acetate/ hexanes) afforded the 2(R)-(3-chloromethanesulfonyl-phenyl)-3-cyclopentyl-N-(5-dimethylamino-pyridin-2-yl)-propionamide (0.67 g, 70%) as a white foam: mp 166.2° C. (foam to gel); (ES)$^+$-HRMS m/e calcd for $C_{22}H_{28}ClN_3O_3S$ (M+H)$^+$ 450.1613, found 450.1618.

EXAMPLE 15

2(R)-(3-Chloro-4-methylsulfonyl-phenyl)-3-cyclopentyl-N-(5-dimethylamino-pyrazin-2-yl)-propionamide

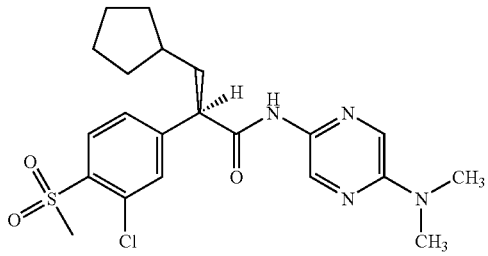

A sealed tube apparatus was charged with 2-bromo-5-nitropyridine (1.89 g, 9.27 mmol), water (6.5 mL), and a 40% solution of dimethylamine in water (2.2 mL, 17.5 mmol). The resulting solution was heated at 110° C. overnight. The solution was then cooled to 0° C., and a precipitate formed. The precipitate was isolated via filtration to afford dimethyl-(6-nitro-pyrazin-3-yl)-amine (1.28 g, 82%) as tan-yellow powder: mp 221.4–222.7° C.; EI-HRMS m/e calcd for $C_6H_8N_4O_2$ (M$^+$) 168.0647, found 168.0648.

A solution of dimethyl-(6-nitro-pyrazin-3-yl)-amine (1.27 g, 7.55 mmol) in ethanol (90 mL) was treated with 10% palladium on activated carbon (0.40 g). The reaction mixture was stirred under a positive pressure of hydrogen gas (balloon) at 25° C. and atmospheric pressure overnight. The catalyst was then filtered off through a pad of celite, and the celite pad was washed well with ethanol. The filtrate was concentrated in vacuo, and the resulting black-orange solid was triturated with petroleum ether to afford $N^5,N^5$-dimethyl-pyrazine-2,5-diamine (0.78 g, 75%) as a black solid: mp 71.5–74.2° C.; EI-HRMS m/e calcd for $C_6H_{10}N_4$ (M$^+$) 138.0905, found 138.0903.

A solution of 2(R)-(3-chloro-4-methanesulfonyl-phenyl)-3-cyclopentyl-propionic acid (prepared as in Example 1, 276.1 mg, 0.83 mmol) in methylene chloride (6 mL) was cooled to 0° C. The reaction mixture was then treated with oxalyl chloride (0.37 mL, 4.15 mmol) and N,N-dimethylformamide (2 drops). The reaction mixture was stirred at 0° C. and then slowly allowed to warm to 25° C. over 2 h. The solution was then concentrated in vacuo, and the yellow slurry was dissolved in methylene chloride (4 mL) and pyridine (0.5 mL). This solution was then treated dropwise, via an addition funnel at 0° C., with a solution of $N^5,N^5$-dimethyl-pyrazine-2,5-diamine (114.9 mg, 0.83 mmol) in methylene chloride (2 mL), followed by quick rinses with methylene chloride (2×0.5 mL). The reaction mixture was stirred at 0° C. and then was allowed to warm to 25° C. over 2.5 h. The reaction mixture was then quenched with water (1 mL) and diluted with ethyl acetate (250 mL). The organic layer was washed with a saturated aqueous sodium bicarbonate solution (210 mL), water (210 mL), and a saturated aqueous sodium chloride solution (210 mL), dried over sodium sulfate and decolorizing carbon, filtered through a pad of celite, and concentrated in vacuo onto a pad of celite. Biotage chromatography (FLASH 40S, Silica, 1/2 ethyl acetate/hexanes) afforded 2(R)-(3-chloromethanesulfonyl-phenyl)-3-cyclopentyl-N-(5-dimethylamino-pyrazin-2-yl)-propionamide (0.189 g, 50%) as a light yellow foam: mp 93.3–97.7° C. (foam to gel); (ES)$^+$-HRMS m/e calcd for $C_{21}H_{27}ClN_4O_3S$ (M+H)$^+$ 451.1565, found 451.1567.

EXAMPLE 16

2(R)-(3-Chloro-4-methanesulfonyl-phenyl)-3-cyclopentyl-N-[5-(3-dimethylamino-propyl)-pyrazin-2-yl]-propionamide

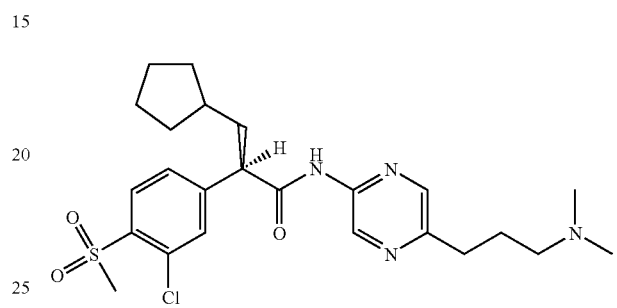

A solution of 2(R)-(3-chloro-4-methanesulfonyl-phenyl)-3-cyclopentyl-N-[5-(3-dimethylamino-prop-1-ynyl)-pyrazin-2-yl]-propionamide (prepared as in Example 11, 190 mg, 0.389 mmol) in methanol (20 ml) was treated with 10% palladium on activated carbon (65 mg). The resulting reaction mixture was stirred under a positive pressure of hydrogen gas (balloon) overnight. At this time, the catalyst was removed by filtration through a pad of celite, and the filtrate was concentrated in vacuo. Flash chromatography (Merck Silica gel 60, 230–400 mesh, 1/1 methylene chloride/methanol) afforded the 2(R)-(3-chloro-4-methanesulfonyl-phenyl)-3-cyclopentyl-N-[5-(3-dimethylamino-propyl)-pyrazin-2-yl]-propionamide (120 mg, 63%) as a solid: (ES)$^+$-HRMS m/e calcd for $C_{24}H_{33}ClN_4O_3S$ (M+H)$^+$ 493.2035, found 493.2041.

EXAMPLE 17

N-[5-(5-Amino-[1,2,4]oxadiazol-3-yl)-pyrazin-2-yl]-2(R)-(3-chloro-4-methanesulfonyl-phenyl)-3-cyclopentyl-propionamide

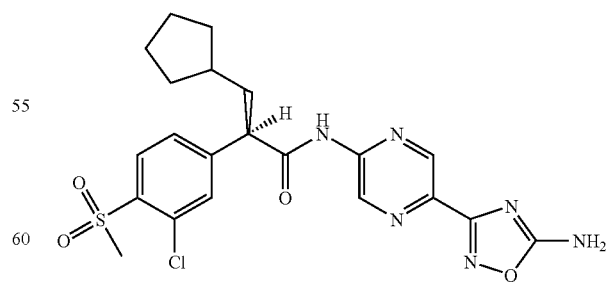

A mixture of 2(R)-(3-chloro-4-methanesulfonyl-phenyl)-3-cyclopentyl-N-[5-(N-hydroxycarbamimidoyl)-pyrazin-2-yl]-propionamide (prepared as in Example 1, 7.00 g, 15.02 mmol) in N-cyanopiperidine (25 mL) was heated at 130° C.

in a sealed tube for 1.5 h. The mixture was allowed to cool to 25° C. and then concentrated under a stream of anhydrous nitrogen overnight. Flash chromatography (Merck Silica gel 60, 230–400 mesh, 3/2 ethyl acetate/hexanes) afforded the N-[5-(5-amino-[1,2,4]oxadiazol-3-yl)-pyrazin-2-yl]-2(R)-(3-chloro-4-methanesulfonyl-phenyl)-3-cyclopentyl-propionamide (2.74 g, 37%) as an off-white solid: mp 262–264° C.; (ES)$^+$-HRMS m/e calcd for $C_{21}H_{23}ClN_6O_4S_2$ (M+Na)$^+$ 513.1082, found 513.1088.

EXAMPLE 18

2-(3-Chloro-4-methanesulfonyl-phenyl)-3-cyclopentyl-N-(5-formyl-pyrazin-2-yl)-propionamide

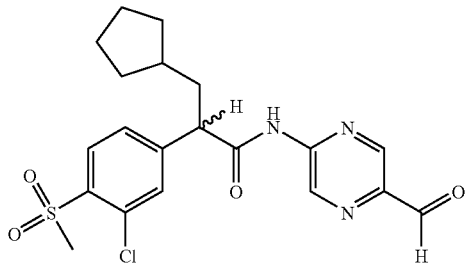

A mixture of N-(5-bromo-pyrazin-2-yl)-2(R)-(3-chloro-4-methanesulfonyl-phenyl)-3-cyclopentyl-propionamide (prepared as in Example 6, 5.73 g, 11.8 mmol), potassium iodide (2.2 g, 13.0 mmol), 18-crown-6 (0.62 g, 2.4 mmol), triethylamine (4.2 mL, 29.5 mmol), diphenylpropylphosphine (81 μL, 0.35 mmol), and palladium(II) acetate (80 mg, 0.35 mmol) in anhydrous N,N-dimethylformamide (95 mL) in a pressure tube was stirred under carbon monoxide at 65 psi at 25° C. for 30 min. At this time, the reaction was treated with trihexylsilane (8.42 mL, 23.6 mmol) and was stirred under carbon monoxide at 65 psi at 110° C. for 4 h. The reaction was then allowed to cool to 25° C. and was extracted with ethyl acetate (2×200 mL). The combined organic layers were successively washed with a saturated aqueous sodium bicarbonate solution (3×50 mL) and water (3×50 mL), dried over sodium sulfate, filtered, and concentrated in vacuo. Flash chromatography (Merck Silica gel 60, 70–230 mesh, 1/9 to 7/3 ethyl acetate/hexanes) afforded racemized 2-(3-chloro-4-methanesulfonyl-phenyl)-3-cyclopentyl-N-(5-formyl-pyrazin-2-yl)-propionamide (1.53 g, 30%) as a white solid.

EXAMPLE 19

2-(3-Chloro-4-methanesulfonyl-phenyl)-3-cyclopentyl-N-[5-(2,4-dioxo-thiazolidin-5-ylmethyl)-pyrazin-2-yl]-propionamide

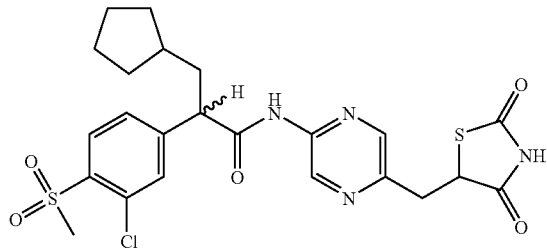

A solution of 2-(3-chloro-4-methanesulfonyl-phenyl)-3-cyclopentyl-N-(5-formyl-pyrazin-2-yl)-propionamide (prepared as in Example 18, 44 mg, 0.1 mmol), 2,4-thiazolidinedione (18 mg, 0.15 mmol), piperidine (2 μL, 0.02 mmol), and benzoic acid (1.2 mg, 0.01 mmol) in anhydrous ethanol (5 mL) was heated under reflux overnight. The reaction mixture was allowed to cool to 25° C. and then was concentrated in vacuo. Flash chromatography (Merck Silica gel 60, 230–400 mesh, 0%–60% ethyl acetate/hexanes) afforded 2-(3-chloro-4-methanesulfonyl-phenyl)-3-cyclopentyl-N-[5-(2,4-dioxo-thiazolidin-5-ylidenemethyl)-pyrazin-2-yl]-propionamide (40 mg, 75%) as a white solid: LC-MS m/e 535 (MH$^+$).

A suspension of 2-(3-chloro-4-methanesulfonyl-phenyl)-3-cyclopentyl-N-[5-(2,4-dioxo-thiazolidin-5-ylidenemethyl)-pyrazin-2-yl]-propionamide (150 mg, 0.28 mmol), 2,6-dimethyl-1,4-dihydro-pyridine-3,5-dicarboxylic acid diethyl ester (92.5 mg, 0.37 mmol), and silica gel (450 mg) in anhydrous toluene (12 mL) was heated at 90° C. for 12 h. The reaction mixture was then allowed to cool to 25° C. and then was acidified to pH=2 with acetic acid. The silica gel was removed by filtration and washed with a small amount of methanol. The product was then extracted with ethyl acetate. The organic layer was washed with water, dried over sodium sulfate, filtered, and concentrated in vacuo. Flash chromatography (Merck Silica gel 60, 230–400 mesh, 1/9 to 7/3 ethyl acetate/hexanes) afforded the 2-(3-chloro-4-methanesulfonyl-phenyl)-3-cyclopentyl-N-[5-(2,4-dioxo-thiazolidin-5-ylmethyl)-pyrazin-2-yl]-propionamide (86.5 mg, 57%) as a white solid: LC-MS m/e 537 (MH$^+$).

EXAMPLE 20

2-(3-Chloro-4-methanesulfonyl-phenyl)-3-cyclopentyl-N-[5-(2,5-dioxo-imidazolidin-4-ylmethyl)-pyrazin-2-yl]-propionamide

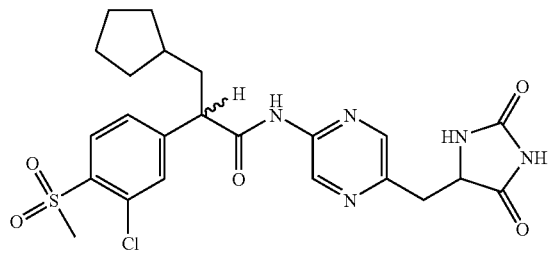

A solution of 2-(3-chloro-4-methanesulfonyl-phenyl)-3-cyclopentyl-N-(5-formyl-pyrazin-2-yl)-propionamide (prepared as in Example 18, 217 mg, 0.5 mmol), hydantoin (75 mg, 0.75 mmol), piperidine (10 μL, 0.10 mmol), and benzoic acid (6.1 mg, 0.05 mmol) in anhydrous ethanol (30 mL) was heated under reflux for 2 d. The reaction mixture was allowed to cool to 25° C. and then was concentrated in vacuo. Flash chromatography (Merck Silica gel 60, 230–400 mesh, 10%–65% ethyl acetate/hexanes) afforded the 2-(3-chloro-4-methanesulfonyl-phenyl)-3-cyclopentyl-N-[5-(2,5-dioxo-imidazolidin-4-ylidenemethyl)-pyrazin-2-yl]-propionamide (84 mg, 33%) as a white solid: LC-MS m/e 518 (MH$^+$).

A solution of 2-(3-chloro-4-methanesulfonyl-phenyl)-3-cyclopentyl-N-[5-(2,5-dioxo-imidazolidin-4-ylidenemethyl)-pyrazin-2-yl]-propionamide (130 mg, 0.25 mmol) in ethanol (5 mL) was treated with 10% palladium on activated carbon (260 mg). The reaction mixture was stirred under hydrogen (65 psi) at 25° C. for 2 d. The catalyst was then filtered off through a pad of celite, and the celite pad was washed well with ethanol. The filtrate was concentrated in vacuo. Flash chromatography (Merck Silica gel 60, 230–400 mesh, 80%–100% ethyl acetate/hexanes) afforded 2-(3-chloro-4-methanesulfonyl-phenyl)-3-cyclopentyl-N-[5-(2,5-dioxo-imidazolidin-4-ylmethyl)-pyrazin-2-yl]-propionamide (20 mg, 15%) as a white solid: LC-MS m/e 520 (MH$^+$).

EXAMPLE 21

2(R)-(3-Chloro-4-methanesulfonyl-phenyl)-3-cyclopentyl-N-(5-dimethoxymethyl-pyrazin-2-yl)-propionamide

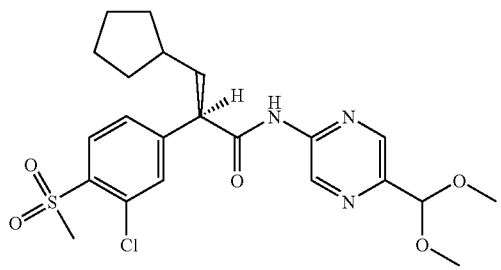

A solution of 5-methylpyrazine-2-carboxylic acid (1.38 g, 10 mmol) in anhydrous N,N-dimethylformamide (5 mL) was treated with dimethylformamide dimethylacetal (5 mL). The resulting mixture was heated at 90° C. for 1 h and then at 125° C. for 2 h. The mixture was cooled to 25° C. and then was poured into water (100 mL). This solution was extracted with ethyl acetate (3×50 mL). The combined organic layers were washed with water (1×50 mL) and a saturated aqueous sodium chloride solution (1×50 mL), dried over anhydrous magnesium sulfate, filtered, and concentrated in vacuo. The resulting dark oil was triturated with diethyl ether/hexanes (5/1) to afford 5-(2-dimethylamino-vinyl)-pyrazine-2-carboxylic acid methyl ester (1.3 g, 63%) as an orange solid which was used without further purification.

A mixture of 5-(2-dimethylamino-vinyl)-pyrazine-2-carboxylic acid methyl ester (3.00 g, 14.5 mmol) and sodium periodate (9.09 g, 43.5 mmol) in methanol (40 mL) at 0° C. was treated dropwise with water (80 mL). The mixture was stirred at 0° C. for 30 min and then at 25° C. for 30 min. The mixture was partitioned between a saturated aqueous sodium bicarbonate solution (50 mL) and ethyl acetate (50 mL). The aqueous later was separated and saturated with sodium chloride. The aqueous layer was then extracted with ethyl acetate (4×50 mL). The combined organic extracts were dried over anhydrous magnesium sulfate, filtered, and concentrated in vacuo to afford a red solid. The resulting solid was combined with trimethylorthoformate (15 mL) and methanol (40 mL) and then was treated with p-toluenesulfonic acid monohydrate (191 mg, 1 mmol). The reaction mixture was heated under reflux for 1.5 h and then cooled to 25° C. The reaction was diluted with ethyl acetate (100 mL) and washed with a saturated aqueous sodium bicarbonate solution (50 mL). The organic layer was separated, and the aqueous layer was extracted with ethyl acetate (3×25 mL). The combined organic layers were dried over anhydrous sodium sulfate, filtered, and concentrated in vacuo to afford 5-dimethoxymethyl-pyrazine-2-carboxylic acid methyl ester (2.26 g, 73%) as a yellow oil which was used without further purification.

A mixture of 5-dimethoxymethyl-pyrazine-2-carboxylic acid methyl ester (690 mg, 3.26 mmol) in methanol/tetrahydrofuran/water (3:3:1, 5 mL) was treated with potassium hydroxide (365 mg, 6.52 mmol). The mixture was stirred at 25° C. for 2 h. At this time, the reaction was concentrated in vacuo. The residue was concentrated from methanol (3×5 mL) and then was suspended in N,N-dimethylformamide (30 mL). This suspension was treated with diphenylphosphoryl azide (0.92 mL, 4.24 mmol) and was stirred at 25° C. for 5 h. The resulting homogeneous solution was poured into water (100 mL) and was extracted with ethyl acetate (3×30 mL). The combined organic layers were washed with water (3×30 mL) and a saturated aqueous sodium chloride solution (1×30 mL), dried over anhydrous magnesium sulfate, filtered, and concentrated in vacuo. The resulting residue was dissolved in benzyl alcohol (0.66 mL, 6.54 mmol) and heated at 93° C. for 20 min. The mixture was cooled to 25° C. and then triturated with diethyl ether/hexanes (2:1) to afford (5-dimethoxymethylpyrazin-2-yl)-carbamic acid phenyl ester (552 mg, 56%) as a tan solid which was used without further purification.

A solution of (5-dimethoxymethylpyrazin-2-yl)-carbamic acid phenyl ester (500 mg, 2.2 mmol) in ethanol (30 mL) was treated with 10% palladium on activated carbon (212 mg). The reaction vessel was flushed with hydrogen, and the mixture was stirred at 25° C. for 1 h under hydrogen (1 atm). The excess hydrogen was evacuated from the reaction vessel, and the mixture was filtered through a pad of celite. The filtrate was concentrated in vacuo to afford 5-dimethoxypyrazin-2-ylamine (183 mg, 76%) as a tan solid which was used without further purification.

A solution of 2(R)-(3-chloro-4-methanesulfonyl-phenyl)-3-cyclopentyl-propionic acid (prepared as in Example 1, 883 mg, 2.67 mmol) and oxalyl chloride (677 mg, 5.34 mmol) in methylene chloride/toluene (1:1, 5 mL) was treated with N,N-dimethylformamide (2 drops) at 25° C. The reaction mixture was stirred at 25° C. for 2 h. The solution was concentrated in vacuo, and the residue was concentrated three times from toluene (5 mL). The residue was suspended in tetrahydrofuran (5 mL) at 0° C. and then treated with a mixture of 5-dimethoxymethyl-pyrazin-2-ylamine (451 mg, 2.67 mmol) and pyridine (0.216 mL, 2.67 mmol) in tetrahydrofuran (5 mL) over 5 min. At this time, the reaction was allowed to warm to 25° C. where it stirred for 18 h. The resulting mixture was partitioned between ethyl acetate (50 mL) and a dilute aqueous ammonium chloride solution (50 mL). The aqueous layer was separated. The organic layer was sequentially washed with water (1×25 mL), a saturated aqueous sodium bicarbonate solution (1×25 mL), water (1×25 mL), an aqueous copper(II) sulfate solution (1×25 mL), and a saturated aqueous sodium chloride solution (1×25 mL). The organic layer was then dried over anhydrous magnesium sulfate, filtered, and concentrated in vacuo. Flash chromatography (Merck Silica gel 60, 230–400 mesh, 2/3 ethyl acetate/hexanes) afforded the 2-(R)-(3-chloro-4-methanesulfonylphenyl)-3-cyclopentyl-N-(5-dimethoxymethylpyrazin-2-yl)-propionamide (890 mg, 69%) as a pale yellow foam: (ES)$^+$-HRMS m/e calcd for $C_{22}H_{28}ClN_3O_5S$ (M+H)$^+$ 424.0729, found 424.0733.

EXAMPLE 22

2-(3-Chloro-4-methanesulfonyl-phenyl)-3-cyclopentyl-N-[5-(1-hydroxy-ethyl)-pyrazin-2-yl]-propionamide

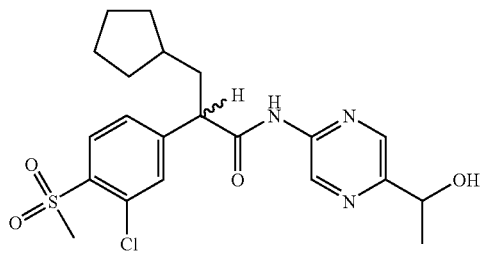

A solution of 2-(3-chloro-4-methanesulfonyl-phenyl)-3-cyclopentyl-N-(5-formyl-pyrazin-2-yl)-propionamide (prepared as in Example 18, 218 mg, 0.5 mmol) in diethyl ether (15 mL) at 0° C. was slowly treated with 3.0M solution of methylmagnesium chloride in diethyl ether (0.35 mL, 1.05 mmol). After complete addition, the reaction mixture was stirred at 0° C. for 1 h. The reaction was then quenched by the dropwise addition of a 1N aqueous hydrochloric acid solution. The reaction was then diluted with water (25 mL) and extracted with ethyl acetate (2×50 mL). The combined organic layers were washed with a saturated aqueous sodium chloride solution (2×20 mL), dried over sodium sulfate, filtered, and concentrated in vacuo. Flash chromatography (Merck Silica gel 60, 230–400 mesh, 3/7 to 7/3 ethyl acetate/hexanes) afforded 2-(3-chloro-4-methanesulfonyl-phenyl)-3-cyclopentyl-N-[5-(1-hydroxy-ethyl)-pyrazin-2-yl]-propionamide (140 mg, 62%) as a white solid: LC-MS m/e 451 (MH+).

EXAMPLE 23

N-(5-Acetyl-pyrazin-2-yl)-2-(3-chloro-4-methanesulfonyl-phenyl)-3-cyclopentyl-propionamide

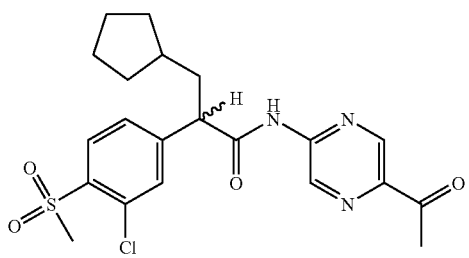

A solution of 2-(3-chloro-4-methanesulfonyl-phenyl)-3-cyclopentyl-N-(1-hydroxy-ethyl-pyrazin-2-yl)-propionamide (prepared as in Example 22, 100 mg, 0.22 mmol) in chloroform (20 mL) was treated with manganese dioxide (200 mg, 2.2 mmol). The reaction mixture was heated under reflux for 12 h. At this time, the resulting solids were removed by filtration. The filtrate was concentrated in vacuo. Flash chromatography (Merck Silica gel 60, 230–400 mesh, 1/9 to 3/7 ethyl acetate/hexanes) afforded N-(5-acetyl-pyrazin-2-yl)-2-(3-chloro-4-methanesulfonyl-phenyl)-3-cyclopentyl-propionamide (90 mg, 90%) as a white solid: LC-MS m/e 450 (MH+).

EXAMPLE 24

2-(3-Chloro-4-methanesulfonyl-phenyl)-3-cyclopentyl-N-[5-(1-hydroxy-2-methyl-propyl)-pyrazin-2-yl]-propionamide

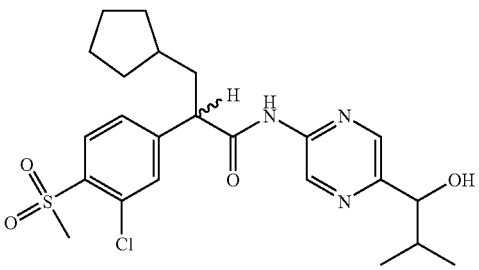

A solution of 2-(3-chloro-4-methanesulfonyl-phenyl)-3-cyclopentyl-N-(5-formyl-pyrazin-2-yl)-propionamide (prepared as in Example 18, 218 mg, 0.5 mmol) in diethyl ether (15 mL) was slowly treated with a 2.0M solution of isopropylmagnesium chloride in diethyl ether (1.5 mL, 3.0 mmol) at −20° C. After complete addition, the reaction mixture was stirred at −20° C. for 30 min. The reaction was then diluted with water (25 mL) and extracted with ethyl acetate (2×50 mL). The combined organic layers were washed with a saturated aqueous sodium chloride solution (2×20 mL), dried over sodium sulfate, filtered, and concentrated in vacuo. Flash chromatography (Merck Silica gel 60, 230–400 mesh, 1/4 to 1/1 ethyl acetate/hexanes) afforded 2-(3-chloro-4-methanesulfonyl-phenyl)-3-cyclopentyl-N-[5-(1-hydroxy-2-methyl-propyl-pyrazin-2-yl)]-propionamide (110 mg, 46%) as a white solid: LC-MS m/e 479 (MH+).

EXAMPLE 25

2-(3-Chloro-4-methanesulfonyl-phenyl)-3-cyclopentyl-N-(5-isobutyryl-pyrazin-2-yl)-propionamide

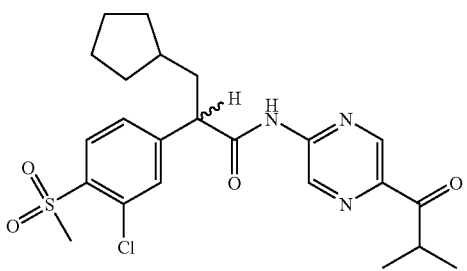

A solution of 2-(3-chloro-4-methanesulfonyl-phenyl)-3-cyclopentyl-N-[5-(1-hydroxy-2-methyl-propyl-pyrazin-2-yl)]-propionamide (prepared as in Example 24, 100 mg, 0.21 mmol) in chloroform (20 mL) was treated with manganese dioxide (300 mg, 3.3 mmol). The reaction mixture was heated under reflux for 12 h. At this time, the resulting solids were removed by filtration. The filtrate was concentrated in vacuo. Flash chromatography (Merck Silica gel 60, 230–400 mesh, 1/9 to 2/3 ethyl acetate/hexanes) afforded 2-(3-chloro-4-methanesulfonyl-phenyl)-3-cyclopentyl-N-(5-isobutyryl-pyrazin-2-yl)-propionamide (22 mg, 22%) as a white solid: LC-MS m/e 478 (MH+).

EXAMPLE 26

2(R)-(3-Chloro-4-methanesulfonyl-phenyl)-N-[5-(cyano-hydroxy-methyl)-pyrazin-2-yl]-3-cyclopentyl-propionamide

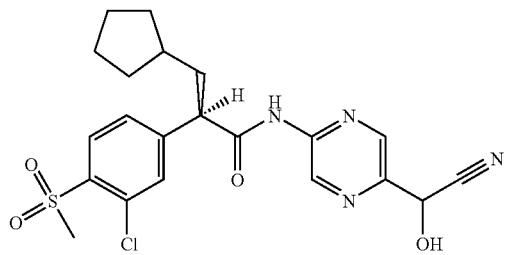

A solution of 2-(R)-(3-chloro-4-methanesulfonylphenyl)-3-cyclopentyl-N-(5-dimethoxymethylpyrazin-2-yl)-propionamide (prepared as in Example 21, 740 mg, 1.53 mmol) and p-toluenesulfonic acid monohydrate (80 mg, 0.41 mmol) in acetone/water (20 mL, 9:1) was heated at 60° C. for 30 min. The mixture was cooled and then diluted with ethyl acetate (100 mL). The organic layer was washed sequentially with a saturated aqueous sodium bicarbonate solution (1×30 mL), water (1×30 mL), and a saturated aqueous sodium chloride solution (1×30 mL). The organic layer was then dried over anhydrous magnesium sulfate, filtered, and concentrated in vacuo to afford a pale yellow foam. The resulting material was dissolved in a mixture of ethyl acetate/water (1:1, 10 mL), cooled to 0° C., and then treated with sodium bisulfite (69 mg, 1.5 mmol). The resulting reaction mixture was stirred at 0° C. for 15 min. At this time, the reaction was treated with sodium cyanide (73 mg, 1.5 mmol), and the reaction was stirred at 0° C. for 30 min. At this time, the mixture was partitioned between a saturated aqueous sodium chloride solution (50 mL) and ethyl acetate (50 mL). The organic layer was separated, and the aqueous layer was extracted with ethyl acetate (3×25 mL). The combined organic layers were washed with a saturated ammonium chloride solution (1×30 mL), a saturated aqueous sodium bicarbonate solution (1×30 mL), and a saturated aqueous sodium chloride solution (1×30 mL). The organic layer was then dried over anhydrous magnesium sulfate, filtered, and concentrated in vacuo. Flash chromatography (Merck Silica gel 60, 230–400 mesh, 1/1 ethyl acetate/hexanes) afforded 2(R)-(3-chloro-4-methanesulfonyl-phenyl)-N-[5-(cyano-hydroxy-methyl)-pyrazin-2-yl]-3-cyclopentyl-propionamide (230 mg, 32%) as a yellow foam: (ES)$^+$-HRMS m/e calcd for $C_{21}H_{23}ClN_4O_4S$ (M+H)$^+$ 463.1208, found 463.1202.

EXAMPLE 27

N-[5-(Carbamoyl-hydroxy-methyl)-pyrazin-2-yl]-2(R)-(3-chloro-4-methanesulfonyl-phenyl)-3-cyclopentyl-propionamide

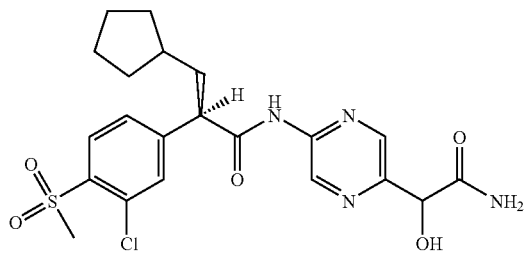

A mixture of 2(R)-(3-chloro-4-methanesulfonyl-phenyl)-N-[5-(cyano-hydroxy-methyl)-pyrazin-2-yl]-3-cyclopentyl-propionamide (prepared as in Example 26, 100 mg, 0.22 mmol) and potassium carbonate (400 mg, 2.9 mmol) in dimethyl sulfoxide (6 mL) was cooled to 0° C. and then was treated dropwise with a 30% aqueous hydrogen peroxide solution (2 mL). The reaction was stirred at 0° C. for 1 h. The resulting mixture was partitioned between ethyl acetate (50 mL) and water (50 mL). The organic layer was separated, and the aqueous layer was extracted with ethyl acetate (3×25 mL). The combined organic layers were washed with water (3×30 mL) and a saturated aqueous sodium chloride solution (1×30 mL), dried over anhydrous magnesium sulfate, filtered, and concentrated in vacuo. Flash chromatography (Merck Silica gel 60, 230–400 mesh, ethyl acetate) afforded N-[5-(carbamoyl-hydroxy-methyl)-pyrazin-2-yl]-2(R)-(3-chloro-4-methanesulfonyl-phenyl)-3-cyclopentyl-propionamide (30 mg, 28%) as a white solid: (ES)$^+$-HRMS m/e calcd for $C_{21}H_{25}ClN_4O_5S$ (M+H)$^+$ 481.1314, found 481.1307.

EXAMPLE 28

2(R)-(3-Chloro-4-methanesulfonyl-phenyl)-3-cyclopentyl-N-[5-(1-(Z)-hydroxyimino-ethyl)-pyrazin-2-yl]-propionamide

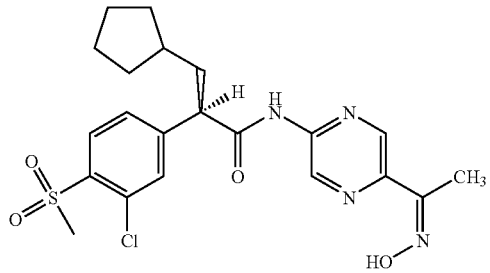

A solution of 2-amino-5-bromopyrazine (10.00 g, 57.47 mmol) and pyridine (5.6 mL, 68.96 mmol) in methylene chloride (144 mL) was cooled to 0° C. and then was treated slowly with trimethylacetyl chloride (8.6 mL, 68.96 mmol). The resulting reaction mixture was stirred at 0° C. for 30 min and then was allowed to warm to 25° C. where it was stirred for 18 h. At this time, the reaction mixture still contained the starting material 2-amino-5-bromopyrazine. The reaction mixture was treated with an additional amount of trimethylacetyl chloride (4.3 mL, 34.48 mmol) and then stirred at 25° C. for 4 h. The reaction mixture was then concentrated in vacuo to remove methylene chloride. The resulting residue was diluted with ethyl acetate (700 mL). The organic layer was washed with a 1N aqueous hydrochloric acid solution (2×200 mL) and a saturated aqueous sodium chloride solution (1×200 mL), dried over sodium sulfate, filtered, and concentrated in vacuo. Biotage chromatography (FLASH 65M, Silica, 1/9 ethyl acetate/hexanes) afforded N-(5-bromo-pyrazin-2-yl)-2,2-dimethyl-propionamide (12.19 g, 82%) as a white solid: mp 122–124° C.; (ES)$^+$-HRMS m/e calcd for $C_9H_{12}BrN_3O$ (M+H)$^+$ 258.0237, found 258.0240.

A slurry of N-(5-bromo-pyrazin-2-yl)-2,2-dimethyl-propionamide (1.30 g, 5.04 mmol) and dichlorobis(triphenylphosphine)palladium(II) (35.3 mg, 0.05 mmol) in toluene (10 mL) was treated with tributyl(1-ethoxyvinyl)tin (2.00 g, 5.54 mmol). The reaction slurry was then heated under reflux, resulting in a homogeneous yellow solution.

After heating under reflux for 15 h, the resulting black reaction mixture was allowed to cool to 25° C. and then was cooled to 0° C. with an ice-water bath. The cooled reaction mixture was treated slowly with a 5% aqueous hydrochloric acid solution (8.4 mL). The reaction mixture was stirred at 0° C. for 30 min and then allowed to warm to 25° C. where it was stirred for 24 h. The resulting two layers were separated, and the organic layer was further diluted with ethyl acetate (100 mL). The organic layer was then diluted with a 10% aqueous ammonium fluoride solution (100 mL), and the resulting mixture was stirred at 25° C. for 5 h. The solids were then filtered, and the filtrate layers were separated. The organic layer was washed with a saturated aqueous sodium chloride solution (1×100 mL), dried over sodium sulfate, filtered, and concentrated in vacuo. Biotage chromatography (FLASH 40M, Silica, 15% ethyl acetate/hexanes) afforded N-(5-acetyl-pyrazin-2-yl)-2,2-dimethyl-propionamide (1.07 g, 96%) as a white solid: mp 173–174° C.; (ES)$^+$-HRMS m/e calcd for $C_{11}H_{15}N_3O_2$ (M+H)$^+$ 222.1237, found 222.1240.

A solution of N-(5-acetyl-pyrazin-2-yl)-2,2-dimethyl-propionamide (800.0 mg, 3.62 mmol) in methanol (9 mL) and pyridine (9 mL) was treated with O-(tert-butyl)hydroxylamine hydrochloride (681.1 mg, 5.42 mmol). The resulting reaction mixture was heated under reflux for 30 min. The reaction mixture was allowed to cool to 25° C. and then was concentrated in vacuo. The resulting residue was diluted with ethyl acetate (50 mL). The organic layer was washed with a 1N aqueous hydrochloric acid solution (1×50 mL), dried over sodium sulfate, filtered, and concentrated in vacuo. Biotage chromatography (FLASH 40M, Silica, 1/9 ethyl acetate/hexanes) afforded N-[5-(1-tert-butoxyimino-ethyl)-pyrazin-2-yl]-2,2-dimethyl-propionamide (1.04 g, 98%) as a white solid: mp 123–124° C.; EI-HRMS m/e calcd for $C_{15}H_{24}N_4O_2$ (M$^+$) 292.1899, found 292.1901.

A solution of N-[5-(1-tert-butoxyimino-ethyl)-pyrazin-2-yl]-2,2-dimethyl-propionamide (563.4 mg, 1.93 mmol) in dioxane (5.8 mL) and hydrazine monohydrate (9.6 mL) was heated under reflux for 48 h. The reaction mixture was allowed to cool to 25° C. and then was diluted with ethyl acetate (100 mL). The organic layer was washed with a saturated aqueous sodium chloride solution (1×100 mL), dried over sodium sulfate, filtered, and concentrated in vacuo. Biotage chromatography (FLASH 40L, Silica, 3/7 ethyl acetate/hexanes) afforded 1-(5-amino-pyrazin-2-yl)-ethanone O-tert-butyl-oxime (408.4 g, quant.) as a light yellow solid: mp 113–115° C.; EI-HRMS m/e calcd for $C_{10}H_{16}N_4O$ (M$^+$) 208.1324, found 208.1325.

A solution of 2(R)-(3-chloro-4-methanesulfonyl-phenyl)-3-cyclopentyl-propionic acid (prepared as in Example 1, 262.9 mg, 0.79 mmol) in methylene chloride (4 mL) was cooled to 0° C. The reaction mixture was then treated with oxalyl chloride (275 μL, 3.15 mmol) and N,N-dimethylformamide (2 drops). The reaction mixture was stirred at 0° C. for 30 min and then slowly allowed to warm to 25° C. where it was stirred for 2.5 h. The solution was then concentrated in vacuo to remove solvents. The resulting residue was dissolved in methylene chloride (3 mL) and then cooled to 0° C. This cooled solution was then treated dropwise with a solution of 1-(5-amino-pyrazin-2-yl)-ethanone O-tert-butyl-oxime (150.2 mg, 0.72 mmol) and 2,6-lutidine (100 μL) in tetrahydrofuran (4 mL), followed by quick rinse with methylene chloride (1 mL). The reaction mixture was stirred at 0° C. for 30 min and then was allowed to warm to 25° C. where it was stirred overnight. The reaction mixture was then quenched with water and stirred at 25° C. for 30 min. The reaction mixture was then diluted with ethyl acetate (300 mL) and a 1N aqueous citric acid solution (300 mL), and the layers were shaken and separated. The organic layer was washed with a saturated aqueous sodium bicarbonate solution (1×300 mL), water (1×300 mL), and a saturated aqueous sodium chloride solution (1×300 mL). The organic layer was then dried over sodium sulfate, filtered, and concentrated in vacuo. Biotage chromatography (FLASH 40L, Silica, 1/3 ethyl acetate/hexanes) afforded the N-[5-(1-tert-butoxyimino-ethyl)-pyrazin-2-yl]-2(R)-(3-chloro-4-methanesulfonyl-phenyl)-3-cyclopentyl-propionamide (216.5 mg, 58%) as a white foam: mp 95.7–99.9° C. (foam to gel); (ES)$^+$-HRMS m/e calcd for $C_{25}H_{33}ClN_4O_4S$ (M+H)$^+$ 521.1984, found 521.1994.

A solution of N-[5-(1-tert-butoxyimino-ethyl)-pyrazin-2-yl]-2(R)-(3-chloro-4-methanesulfonyl-phenyl)-3-cyclopentyl-propionamide (195.5 mg, 0.38 mmol) in methylene chloride (1.4 mL) was treated with trifluoroacetic acid (2.8 mL). The resulting reaction mixture was stirred at 25° C. for 2 h, at which time, thin layer chromatography still indicated the presence of starting material. The reaction was then heated at 40° C. where it was stirred overnight. At this time, thin layer chromatography again still indicated the presence of starting material. The reaction mixture was then heated at 60° C. where it was stirred for a second night. The reaction mixture was then allowed cool to 25° C. The reaction mixture was diluted with ethyl acetate (50 mL), and the organic layer was washed with a saturated aqueous sodium bicarbonate solution (2×50 mL) and a saturated aqueous sodium chloride solution (1×50 mL), dried over sodium sulfate, filtered, and concentrated in vacuo. Biotage chromatography (FLASH 40L, Silica, 1/2 ethyl acetate/hexanes) afforded the 2(R)-(3-chloro-4-methanesulfonyl-phenyl)-3-cyclopentyl-N-[5-(1(Z)-hydroxyimino-ethyl)-pyrazin-2-yl]-propionamide (110.0 mg, 63%) as an off-white powdery solid: mp 94.2–102.5° C. (foam to gel); (ES)$^+$-HRMS m/e calcd for $C_{21}H_{25}ClN_4O_4S$ (M+H)$^+$ 465.1358, found 465.1363.

EXAMPLE 29

5-[2(R)-(3-Chloro-4-methanesulfonyl-phenyl)-3-cyclopentyl-propionylamino]-pyrazine-2-carboxylic acid hydroxyamide

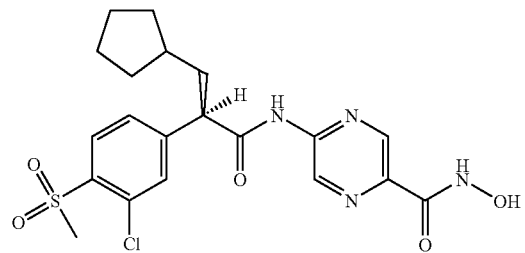

A solution of methyl 5-chloropyrazine-2-carboxylate (30.00 g, 0.17 mol) in tetrahydrofuran (87 mL) was treated with a solution of potassium carbonate (72.08 g, 0.52 mol) in water (261 mL). The resulting reaction mixture stirred at 25° C. for 42 h. The reaction mixture was then acidified to a pH=2 with concentrated hydrochloric acid, diluted with a saturated aqueous sodium chloride solution (300 mL), and was continuously extracted with ethyl acetate (4 L total) until no product was present in the aqueous layer. The combined organic layers were dried over sodium sulfate, filtered, and concentrated in vacuo to afford 5-chloro-pyrazine-2-carboxylic acid (26.54 g, 96%) as an off-white solid: mp 150–151° C.; EI-HRMS m/e calcd for $C_5H_3ClN_2O_2$ ($M^+$) 157.9883, found 157.9877.

A solution of 5-chloro-pyrazine-2-carboxylic acid (10.00 g, 63.07 mmol) in tetrahydrofuran (126 mL) was treated with a solution of tert-butyl 2,2,2-trichloroacetimidate (23 mL, 126.14 mmol) in cyclohexane (126 mL). The reaction was stirred at 25° C. for 5 min and then was treated with boron trifluoride dimethyl etherate (3.2 mL, 25.23 mmol). The resulting reaction mixture was stirred at 25° C. for 16 h and then was diluted with ethyl acetate (200 mL), washed with a saturated aqueous sodium bicarbonate solution (200 mL) and water (200 mL), dried over sodium sulfate, filtered, and concentrated in vacuo. Biotage chromatography (FLASH 65M, Silica, 1/9 ethyl acetate/hexanes) afforded 5-chloro-pyrazine-2-carboxylic acid tert-butyl ester (12.73 g, 94%) as a colorless oil: EI-HRMS m/e calcd for $C_9H_{11}ClN_2O_2$ ($M^+$) 214.0502, found 214.0510.

A solution of 5-chloro-pyrazine-2-carboxylic acid tert-butyl ester (12.6 g, 58.7 mmol) in acetonitrile (150 mL) was treated with a new bottle of silver(I) fluoride (11.26 g, 87.86 mmol). The reaction setup was covered with aluminum foil, and the reaction mixture was heated under reflux overnight. The mixture was swirled with decolorizing carbon, filtered through a pad of celite, and the pad of celite was rinsed with acetonitrile. The filtrate was then concentrated in vacuo and absorbed onto silica gel (Merck Silica gel 60, 230–400 mesh). Biotage chromatography (FLASH 65M, Silica, 1/9 to 1/4 diethyl ether/petroluem ether) afforded 5-fluoro-pyrazine-2-carboxylic acid tert-butyl ester (9.19 g, 79%) as a white crystalline solid upon cooling to 0° C. An analytical sample was obtained by trituration with petroleum ether to afford 5-fluoro-pyrazine-2-carboxylic acid tert-butyl ester as a white crystalline solid: mp 26.5–28.1° C., EI-HRMS m/e calcd for $C_9H_{11}FN_2O_2$ ($M^+$) 198.0799, found 198.0804.

A solution of 5-fluoro-pyrazine-2-carboxylic acid tert-butyl ester (7.99 g, 40.31 mmol) in tetrahydrofuran (20 mL) was prepared in a large sealed tube reaction vessel. The reaction solution was cooled to 0° C. and then was saturated with ammonia gas over 35 min. The tube was tightly sealed, and the reaction was stirred. As the reaction warmed to 25° C. overnight, a precipitate formed. The precipitate was isolated via filtration and rinsed with petroleum ether to afford 5-amino-pyrazine-2-carboxylic acid tert-butyl ester (5.63 g, 71%) as a white powder: mp 190–193° C.; EI-HRMS m/e calcd for $C_9H_{13}N_3O_2$ ($M^+$) 195.1008, found 195.1009.

A solution of 2(R)-(3-chloro-4-methanesulfonyl-phenyl)-3-cyclopentyl-propionic acid (prepared as in Example 1, 1.00 g, 3.02 mmol) in methylene chloride (15 mL) was cooled to 0° C. The reaction mixture was then treated with oxalyl chloride (1.10 mL, 12.61 mmol) and N,N-dimethyl-formamide (2 drops). The reaction mixture was stirred at 0° C. for 30 min and then slowly warmed to 25° C. over 45 min. The solution was then concentrated in vacuo. The yellow slurry was dissolved in methylene chloride (15 mL) and then cooled to 0° C. To this solution was added a solution of 5-amino-pyrazine-2-carboxylic acid tert-butyl ester (0.71 g, 3.64 mmol) and pyridine (295 μL, 3.65 mmol) in tetrahydrofuran (15 mL). The reaction mixture was stirred at 0° C. and was slowly warmed to 25° C. overnight. The reaction was then quenched with a 1N aqueous citric acid solution (10 mL), stirred at 25° C. for 3 min, and was concentrated in vacuo. The reaction material was partitioned between ethyl acetate (400 mL) and a 1N aqueous citric acid solution (200 mL), and the layers were seperated. The organic layer was washed with a saturated aqueous sodium bicarbonate solution (200 mL), water (200 mL), and a saturated aqueous sodium chloride solution (200 mL), dried over sodium sulfate, filtered, and concentrated in vacuo onto silica gel (Merck Silica gel 60, 230–400 mesh). Biotage chromatography (FLASH 40L, Silica, 1/2 ethyl acetate/hexanes) afforded 5-[2(R)-(3-chloro-4-methanesulfonyl-phenyl)-3-cyclopentyl-propionylamino]-pyrazine-2-carboxylic acid tert-butyl ester (0.80 g, 52%) as a white foam: mp 107–111° C. (foam to gel); $(ES)^+$-HRMS m/e calcd for $C_{24}H_{30}ClN_3O_5S$ $(M+H)^+$ 508.1668, found 508.1666.

A solution of 5-[2(R)-(3-chloro-4-methanesulfonyl-phenyl)-3-cyclopentyl-propionylamino]-pyrazine-2-carboxylic acid tert-butyl ester (3.29 g, 6.48 mmol) in methylene chloride (30 mL) was treated with trifluoroacetic acid (60 mL) and stirred at 25° C. for 65 min. The reaction solution was then concentrated in vacuo The resulting oil was diluted with ethyl acetate (500 mL), washed with water (2×250 mL) and a saturated sodium chloride solution (5×250 mL), dried over sodium sulfate, treated with decolorizing carbon, filtered through a pad of celite, and concentrated in vacuo to afford the 5-[2(R)-(3-chloro-4-methanesulfonyl-phenyl)-3-cyclopentyl-propionylamino]-pyrazine-2-carboxylic acid (2.89 g, 99%) as a light yellow foam: mp 121–127° C.; $(ES)^+$-HRMS m/e calcd for $C_{20}H_{22}ClN_3O_5S$ $(M+H)^+$ 452.1042, found 452.1046. This material was used without further purification.

A solution of 5-[2(R)-(3-chloro-4-methanesulfonyl-phenyl)-3-cyclopentyl-propionylamino]-pyrazine-2-carboxylic acid (401.6 mg, 0.889 mmol) in methylene chloride (4.4 mL) was cooled to 0° C. The reaction mixture was then treated with oxalyl chloride (310 μL, 3.554 mmol) and N,N-dimethylformamide (2 drops). The reaction mixture was stirred at 0° C. for 45 min and then slowly warmed to 25° C. over 1 h 45 min. The solution was then concentrated in vacuo. The residue was dissolved in methylene chloride (3.4 mL) and cooled to 0° C. The resulting solution was then treated with a mixture of O-(tert-butoxyl)hydroxylamine hydrochloride (133.3 mg, 1.061 mmol) and pyridine (180 μL, 2.226 mmol) in tetrahydrofuran (4.4 mL), followed by a methylene chloride rinse (1 mL). The reaction mixture was stirred at 0° C. for 45 min and then stirred at 25° C. for 2 h 15 min. The reaction was then quenched with water (5 mL) and stirred at 25° C. for 30–45 min. The reaction was partitioned between ethyl acetate (300 mL) and a 1N aqueous citric acid solution (250 mL), and the layers were seperated. The organic layer was washed with a saturated aqueous sodium bicarbonate solution (250 mL), water (250 mL), and a saturated aqueous sodium chloride solution (250 mL), dried over sodium sulfate, filtered, and concentrated in vacuo. Biotage chromatography (FLASH 40L, Silica, 2/3 to 1/1 ethyl acetate/hexanes) afforded 5-[2(R)-(3-chloro-4-methanesulfonyl-phenyl)-3-cyclopentyl-propionylamino]-pyrazine-2-carboxylic acid tert-butoxy-amide (338.8 mg, 73%) as an off-white foam: mp 128–131° C. (foam to gel); $(ES)^+$-HRMS m/e calcd for $C_{24}H_{31}ClN_4O_5S$ $(M+H)^+$ 523.1777, found 523.1782.

A solution of 5-[2(R)-(3-chloro-4-methanesulfonyl-phenyl)-3-cyclopentyl-propionylamino]-pyrazine-2-carboxylic acid tert-butoxy-amide (318.3 mg, 0.609 mol) in methylene chloride (2.3 mL) was treated with trifluoroacetic acid (4.6 mL) and stirred at 25° C. overnight, then at 40° C. for 10–11 h, followed by stirring again at 25° C. overnight. The reaction solution was then concentrated in vacuo. Reverse phase high-performance liquid chromatography (Rainin Dynamax system, 60 Å C-18 column, l=214 nm, 50 mL/min of 50–100% acetonitrile with 0.1% trifluoroacetic acid/water with 0.1% trifluoroacetic acid over 55 min) afforded 5-[2(R)-(3-chloro-4-methanesulfonyl-phenyl)-3-cyclopentyl-propionylamino]-pyrazine-2-carboxylic acid hydroxyamide (90.0 mg, 32%) as a pink foam: mp 134–139° C. (foam to gel); (ES)⁺-HRMS m/e calcd for $C_{20}H_{23}ClN_4O_5S$ (M+H)⁺ 467.1151, found 467.1155.

EXAMPLE 30

2-(3-Chloro-4-methanesulfonyl-phenyl)-3-cyclopentyl-N-(5-methylsulfanylmethyl-pyrazin-2-yl)-propionamide

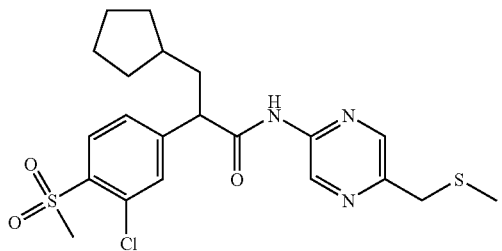

A solution of methyl 5-chloropyrazine-2-carboxylate (5.00 g, 28.97 mmol) in acetonitrile (290 mL) was treated with a new bottle of silver(I) fluoride (11.00 g, 86.70 mmol). The reaction setup was covered with aluminum foil, and the reaction mixture was heated at reflux overnight. The mixture was filtered through a pad of celite, and the pad of celite was rinsed with acetonitrile. The filtrate was then concentrated in vacuo. Biotage chromatography (FLASH 40M, Silica, 1/3 ethyl acetate/hexanes) afforded 5-fluoro-pyrazine-2-carboxylic acid methyl ester (2.98 g, 66%) an off-white solid upon cooling to 0° C. An analytical sample was obtained by trituration with petroleum ether to afford 5-fluoro-pyrazine-2-carboxylic acid methyl ester as a white crystalline solid: mp 55.6–56.7° C., EI-HRMS m/e calcd for $C_6H_5FN_2O_2$ (M⁺) 156.0335, found 156.0331.

A large steel reaction vessel was charged with a solution of 5-fluoro-pyrazine-2-carboxylic acid methyl ester (17.45 g, 111.78 mmol) in tetrahydrofuran (200 mL). The reaction solution was cooled to 0° C. and was saturated with ammonia gas over 2–3 h. The vessel was then tightly sealed. The reaction was then mechanically agitated and allowed to warm to 25° C. overnight. The vessel was then cooled to −78° C. for 15–20 min, the vessel was carefully vented, and the contents of the vessel were diluted with diethyl ether (100 mL). The resulting precipitate was isolated via filtration, rinsed with petroleum ether (2×100 mL), and air-dried to afford 5-amino-pyrazine-2-carboxylic acid methyl ester (16.97 g, 99%) as an off-white solid: mp 229–231° C.; EI-HRMS m/e calcd for $C_6H_7N_3O_2$ (M⁺) 153.0538, found 153.0537.

A solution of 2(R)-(3-chloro-4-methanesulfonyl-phenyl)-3-cyclopentyl-propionic acid (prepared as in Example 1, 196.4 mg, 0.59 mmol) in methylene chloride (3 mL) was cooled to 0° C. The reaction mixture was then treated with N,N-dimethylformamide (1 drop) and oxalyl chloride (109 μL, 1.25 mmol). The reaction mixture was stirred at 0° C. for 15 min and then at 25° C. for 2 h. The solution was then concentrated in vacuo. The yellow slurry was dissolved in methylene chloride (1 mL) and cooled to 0° C. To this solution was added a suspension of 5-amino-pyrazine-2-carboxylic acid methyl ester (100.0 mg, 0.65 mmol) and pyridine (53 μL, 0.6529 mmol) in warm methylene chloride (2 mL). The reaction mixture was stirred at 0° C. for 30 min and then at 25° C. for 3 h. The reaction mixture was then concentrated in vacuo. The reaction material was diluted with ethyl acetate (50 mL) and washed with a saturated aqueous sodium bicarbonate solution (100 mL), a saturated aqueous sodium chloride solution (100 mL), a 1N aqueous hydrochloric acid solution (100 mL), and a saturated aqueous sodium chloride solution (100 mL), dried over sodium sulfate, filtered, and concentrated in vacuo. Biotage chromatography (FLASH 40S, Silica, 1/1 ethyl acetate/hexanes) afforded 5-[2(R)-(3-chloro-4-methanesulfonyl-phenyl)-3-cyclopentyl-propionylamino]-pyrazine-2-carboxylic acid methyl ester (225.9 mg, 82%) as a white foam: mp 94–97° C. (foam to gel); (ES)⁺-HRMS m/e calcd for $C_{21}H_{24}ClN_3O_5S$ (M+H)⁺466.1198, found 466.1204.

A suspension of 5-[2(R)-(3-chloro-4-methanesulfonyl-phenyl)-3-cyclopentyl-propionylamino]-pyrazine-2-carboxylic acid methyl ester (200 mg, 0.43 mmol) in methanol (2 mL) was cooled to 0° C. and then was treated with sodium borohydride (49.2 mg, 1.29 mmol). The reaction mixture was stirred at 0° C. for 5 min and then at 25° C. for 1.5 h. The reaction was cooled to 0° C. and then quenched with water. The reaction mixture was then diluted with ethyl acetate (75 mL), washed with a 1N aqueous hydrochloric acid solution (3×75 mL) and a saturated aqueous sodium chloride solution (75 mL), dried over sodium sulfate, filtered, and concentrated in vacuo. Biotage chromatography (FLASH 40S, Silica, 3/2 ethyl acetate/hexanes) afforded 2(R)-(3-chloro-4-methanesulfonyl-phenyl)-3-cyclopentyl-N-(5-hydroxymethyl-pyrazin-2-yl)-propionamide (110.4 mg, 59%) as a white foam: mp 78–81° C. (foam to gel); (ES)⁺-HRMS m/e calcd for $C_{20}H_{24}ClN_3O_4S$ (M+H)⁺ 438.1249, found 438.1252.

A solution of 2(R)-(3-chloro-4-methanesulfonyl-phenyl)-3-cyclopentyl-N-(5-hydroxymethyl-pyrazin-2-yl)-propionamide (457.1 mg, 1.04 mmol) in tetrahydrofuran (10 mL) was treated with triphenylphosphine (573.5 mg, 2.19 mmol) and carbon tetrabromide (726.2 mg, 2.19 mmol). The reaction solution was stirred at 25° C. for 6 h and then was concentrated in vacuo. Biotage chromatography (FLASH 40L, Silica, 1/2 ethyl acetate/hexanes) afforded N-(5-bromomethyl-pyrazin-2-yl)-2(R)-(3-chloro-4-methanesulfonyl-phenyl)-3-cyclopentyl-propionamide (337.2 mg, 65%) as a purple foam: mp 98–103° C. (foam to gel); (ES)⁺-HRMS m/e calcd for $C_{20}H_{23}BrClN_3O_3S$ (M+H)⁺ 500.0405, found 500.0410.

A solution of N-(5-bromomethyl-pyrazin-2-yl)-2(R)-(3-chloro-4-methanesulfonyl-phenyl)-3-cyclopentyl-propionamide (95.1 mg, 0.19 mmol) in acetone (1 mL) was cooled to 0° C. and then treated with sodium thiomethoxide (12.9 mg, 0.18 mmol). The reaction stirred at 0° C. for 1.5 h and then was treated with a second aliquot of sodium thiomethoxide (3.6 mg, 0.051 mmol). The reaction was stirred at 0° C. and then slowly warmed to 25° C. over 1.5 h. A third aliquot of sodium thiomethoxide (3–4 mg, 0.042–0.057 mmol) was added, and the reaction mixture was stirred at 25° C. for 1.5 h, at which point, APCI-LRMS indicated the reaction had gone to completion. The reaction was then diluted with ethyl acetate (50 mL), washed with water (2×25 mL) and a saturated aqueous sodium chloride solution (25 mL), dried over sodium sulfate, filtered, and concentrated in vacuo. Biotage chromatography (FLASH 40S, Silica, 1/2 ethyl acetate/hexanes) afforded racemized 2-(3-chloro-4-methanesulfonyl-phenyl)-3-cyclopentyl-N-(5-methylsulfanylmethyl-pyrazin-2-yl)-propionamide (51.9 mg, 58%) as a white foam: mp 70–75° C. (foam to gel); (ES)⁺-HRMS m/e calcd for $C_{21}H_{26}ClN_3O_3S_2$ (M+H)⁺ 468.1177, found 468.1179.

EXAMPLE 31

2(R)-(3-Chloro-4-methanesulfonyl-phenyl)-3-cyclopentyl-N-(5-methanesulfonylmethyl-pyrazin-2-yl)-propionamide

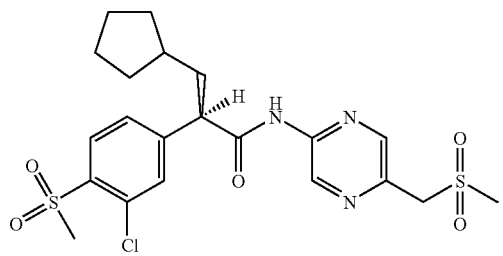

A solution of N-(5-bromomethyl-pyrazin-2-yl)-2(R)-(3-chloro-4-methanesulfonyl-phenyl)-3-cyclopentyl-propionamide (prepared as in Example 30, 102.2 mg, 0.20 mmol) in acetone (1 mL) was cooled to 0° C. and then treated with the sodium salt of methanesulfinic acid (31.8 mg, 0.30 mmol). The reaction stirred at 0° C. for 1 h and then at 25° C. for 4 h 20 min. A second aliquot of the sodium salt of methanesulfinic acid (24.0 mg, 0.24 mmol) was added, and the reaction was stirred at 25° C. overnight. The reaction was then concentrated in vacuo. The residue was diluted with ethyl acetate (50 mL), washed with water (2×25 mL) and a saturated aqueous sodium chloride solution (25 mL), dried over sodium sulfate, filtered, and concentrated in vacuo. Biotage chromatography (FLASH 40S, Silica, 1/1 ethyl acetate/hexanes) afforded 2(R)-(3-chloro-4-methanesulfonyl-phenyl)-3-cyclopentyl-N-(5-methanesulfonylmethyl-pyrazin-2-yl)-propionamide (74.9 mg, 73%) as a white foam: mp 91–95° C. (foam to gel); (ES)⁺-HRMS m/e calcd for $C_{21}H_{26}ClN_3O_5S_2$ (M+H)⁺ 500.1075, found 500.1080.

EXAMPLE 32

2(R)-(3-Chloro-4-methanesulfonyl-phenyl)-3-cyclopentyl-N-(5-dimethylaminomethyl-pyrazin-2-yl)-propionamide

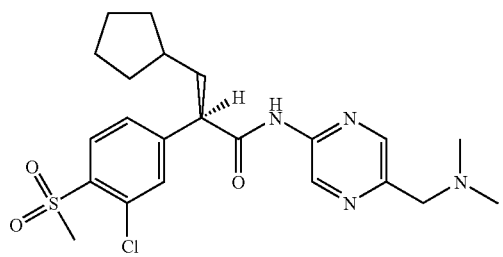

A solution of N-(5-bromomethyl-pyrazin-2-yl)-2(R)-(3-chloro-4-methanesulfonyl-phenyl)-3-cyclopentyl-propionamide (prepared as in Example 30, 138.5 mg, 0.28 mmol) in tetrahydrofuran (2.6 mL) was cooled to 0° C. and then was treated with a 2.0M solution of dimethylamine in tetrahydrofuran (275 μL, 0.55 mmol). The reaction was stirred at 0° C. for 30 min and then at 25° C. for 1 h. A second aliquot of a 2.0M solution of dimethylamine in tetrahydrofuran (275 μL, 0.55 mmol) was added, and the reaction was stirred at 25° C. for 1 h. A third aliquot of a 2.0M solution of dimethylamine in tetrahydrofuran (138 μL, 0.28 mmol) was added, and the reaction was stirred at 25° C. for 1.5 h, at which point, APCI-LRMS indicated the reaction had gone to completion. The reaction was concentrated in vacuo and then was diluted with ethyl acetate (50 mL), washed with water (25 mL), dried over sodium sulfate, filtered, and concentrated in vacuo. Biotage chromatography (FLASH 40S, Silica, 100% methanol) afforded impure 2(R)-(3-chloro-4-methanesulfonyl-phenyl)-3-cyclopentyl-N-(5-dimethylaminomethyl-pyrazin-2-yl)-propionamide as an orange oil. This impure product was re-purified by reverse phase high-performance liquid chromatography (Waters symmetry packing, acetonitrile/water with 0.05% trifluoroacetic acid, 2% to 45% acetonitrile gradient). The fractions containing product were concentrated in vacuo to afford 2(R)-(3-chloro-4-methanesulfonyl-phenyl)-3-cyclopentyl-N-(5-dimethylaminomethyl-pyrazin-2-yl)-propionamide (50.4 mg, 39%) as a light yellow foam: mp 88.0–91.5° C. (foam to gel); (ES)⁺-HRMS m/e calcd for $C_{22}H_{29}ClN_4O_3S$ (M+H)⁺ 465.1722, found 465.1726.

EXAMPLE 33

2-(3-Chloro-4-methanesulfonyl-phenyl)-3-cyclopentyl-N-[5-(5-methyl-[1,2,4]oxadiazyl-3-yl)-pyrazin-2-yl]-propionamide

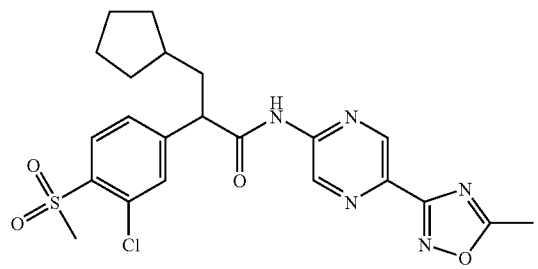

A solution of (3-chloro-4-methylsulfanyl-phenyl)-acetic acid (prepared as in Example 1, 8.00 g, 36.92 mmol) in methanol (200 mL) was treated slowly with concentrated sulfuric acid (1 mL). The resulting reaction mixture was heated under reflux overnight. The reaction mixture was allowed to cool to 25° C. and then was concentrated in vacuo to remove methanol. The resulting residue was dissolved with ethyl acetate (50 mL). The organic layer was washed with water (1×50 mL). The water layer was further extracted with ethyl acetate (3×20 mL). The combined organic layers were washed with a saturated aqueous sodium bicarbonate solution (1×25 mL). The organic layer was then dried over sodium sulfate, filtered, and concentrated in vacuo to afford (3-chloro-4-methylsulfanyl-phenyl)-acetic acid methyl ester (7.28 g, 85.5%) as a yellow oil which was used without further purification: EI-HRMS m/e calcd for $C_{10}H_{11}ClO_2S$ (M⁺) 230.0168, found 230.0166.

A solution of diisopropylamine (4.86 mL, 34.70 mmol) in dry tetrahydrofuran (212.3 mL) was cooled to −78° C. and then treated with a 2.5M solution of n-butyllithium in hexanes (13.88 mL, 34.70 mmol). The resulting reaction mixture was stirred at −78° C. for 15 min and then slowly treated with a solution of (3-chloro-4-methylsulfanyl-phenyl)-acetic acid methyl ester (7.28 g, 31.55 mmol) in dry tetrahydrofuran (23.6 mL) and 1,3-dimethyl-3,4,5,6-tetrahydro-2(1H)-pyrimidinone (9.43 mL). The resulting bright yellow solution was allowed to stir at −78° C. for 1 h, at which time, a solution of iodomethylcyclopentane (prepared as in Example 1, 7.95 g, 37.86 mmol) in 1,3-dimethyl-3,4,5,6-tetrahydro-2(1H)-pyrimidinone (7.08 mL) was slowly added. The reaction mixture was allowed to warm to 25° C. where it was stirred overnight. The reaction mixture was then quenched with a saturated aqueous ammonium chloride solution (20 mL), and the layers were separated. The aqueous layer was extracted with ethyl acetate (3×20 mL). The combined organic layers were dried over sodium sulfate, filtered, and concentrated in vacuo. Flash chromatography (Merck Silica gel 60, 230–400 mesh, 19/1 hexanes/ethyl acetate) afforded 2-(3-chloro-4-methylsulfanyl-phenyl)-3-cyclopentyl-propionic acid methyl ester (5.74 g, 58.1%) as a colorless oil.

A solution of 2-(3-chloro-4-methylsulfanyl-phenyl)-3-cyclopentyl-propionic acid methyl ester (4.85 g, 15.50 mmol) in ethanol (108 mL) was treated with a solution of potassium hydroxide (4.35 g, 77.50 mmol) in water (25.2 mL). The reaction mixture was stirred at 25° C. for 3 h. The reaction mixture was then concentrated in vacuo to remove ethanol. The resulting aqueous residue was acidified to pH=2 with a 1N aqueous hydrochloric acid solution and then extracted with methylene chloride (3×15 mL). The combined organic layers were then dried over sodium sulfate, filtered, and concentrated in vacuo to afford 2-(3-chloro-4-methylsulfanyl-phenyl)-3-cyclopentyl-propionic acid (4.14 g, 89.4%) as a white solid which was used without further purification.

A mixture of 2-(3-chloro-4-methylsulfanyl-phenyl)-3-cyclopentyl-propionic acid (4.14 g, 13.85 mmol) in formic acid (7.08 mL) was cooled to 0° C. and then treated with a 30% aqueous hydrogen peroxide solution (7.85 µL). Tetrahydrofuran (4 mL) was added to help solubilize the starting material. The resulting reaction mixture was allowed to warm to 25° C. where it was stirred overnight. The reaction mixture was then cooled to 0° C. and slowly treated with a saturated aqueous sodium sulfite solution. The product was extracted into ethyl acetate (3×20 mL). The combined organic layers were dried over sodium sulfate, filtered, and concentrated in vacuo to afford 2-(3-chloro-4-methanesulfonyl-phenyl)-3-cyclopentyl-propionic acid (4.54 g, 99.1%) as a white solid: mp 123.9–126.2° C.; FAB-HRMS m/e calcd for $C_{15}H_{19}ClO_4S$ (M+H)$^+$ 331.0771, found 331.0776.

A solution of 2-(3-chloro-4-methanesulfonyl-phenyl)-3-cyclopentyl-propionic acid (1.00 g, 3.023 mmol) in methylene chloride (16 mL) was cooled to 0° C. The reaction mixture was then treated with oxalyl chloride (1.15 mL, 13.18 mmol) followed by N,N-dimethylformamide (2 drops). The reaction mixture was stirred at 0° C. for 20 min and then at 25° C. for 2 h. The solution was then concentrated in vacuo. The residue was dissolved in methylene chloride (16 mL) and cooled to 0° C. To this solution was added a solution of 2-amino-5-bromopyrazine (530.0 mg, 3.046 mmol) and 2,6-lutidine (420 µL, 3.606 mmol) in tetrahydrofuran (16 mL) over 1 min. The reaction mixture was stirred at 0° C. for 30 min and then at 25° C. for 3 h. The reaction material was then diluted with ethyl acetate and washed with a 1N aqueous hydrochloric acid solution. The aqueous layer was back-extracted with a 1N aqueous hydrochloric acid solution. The combined organic layers were washed with a saturated aqueous sodium bicarbonate solution, dried over sodium sulfate, filtered, and concentrated in vacuo. Biotage chromatography (FLASH 40L, Silica, 1/3 ethyl acetate/hexanes) afforded N-(5-bromo-pyrazin-2-yl)-2-(3-chloro-4-methanesulfonyl-phenyl)-3-cyclopentyl-propionamide (1.00 g, 68%) as a white foam: (ES)$^+$-HRMS m/e calcd for $C_{19}H_{21}BrClN_3O_3S$ (M+H)$^+$ 486.0249, found 486.0254.

A solution of N-(5-bromo-pyrazin-2-yl)-2-(3-chloro-4-methanesulfonyl-phenyl)-3-cyclopentyl-propionamide (616.0 mg, 1.266 mmol), potassium cyanide (210.0 mg, 3.225 mmol), tetrakis(triphenylphosphine)palladium(0) (30.0 mg, 0.026 mmol), copper(I) iodide (605.0 mg, 3.177 mmol), and 18-crown-6 (33.0 mg, 0.125 mmol) in anhydrous N,N-dimethylformamide (6 mL) was heated at 150° C. under nitrogen. After 2.75 h, the mixture was allowed to cool to 25° C. The mixture was then concentrated to remove solvent. The residue was diluted with methylene chloride and ethyl acetate and then filtered through a pad of celite. The celite pad was then washed well with ethyl acetate and methylene chloride. The filtrate was then concentrated in vacuo and absorbed onto silica gel (Merck Silica gel 60, 230–400 mesh). Biotage chromatography (FLASH 40L, Silica, 1/3 to 1/1 ethyl acetate/hexanes) afforded 2-(3-chloro-4-methanesulfonyl-phenyl)-N-(5-cyano-pyrazin-2-yl)-3-cyclopentyl-propionamide (402.3 mg, 73.4%) as an off-white foam: (ES)$^+$-HRMS m/e calcd for $C_{20}H_{21}ClN_4O_3S$ (M+H)$^+$ 433.1096, found 433.1101.

A solution of 2-(3-chloro-4-methanesulfonyl-phenyl)-N-(5-cyano-pyrazin-2-yl)-3-cyclopentyl-propionamide (400.0 mg, 0.924 mmol) in dimethyl sulfoxide (6 mL) at 25° C. was treated with hydroxylamine hydrochloride (330.0 mg, 4.749 mmol). The reaction mixture was then treated with piperidine (500 µL, 5.056 mmol) and then was stirred at 25° C. for 1 h. The reaction mixture was then diluted with water and then extracted with ethyl acetate. The organic layer was dried over sodium sulfate, filtered, and concentrated in vacuo. Biotage chromatography (FLASH 40L, Silica, 1/1 to 2/1 ethyl acetate/hexanes) afforded the 2-(3-chloro-4-methanesulfonyl-phenyl)-3-cyclopentyl-N-[5-(N-hydroxy-carbamimidoyl)-pyrazin-2-yl]-propionamide (274.5 mg, 63.8%) as a white solid: (ES)$^+$-HRMS m/e calcd for $C_{20}H_{24}ClN_5O_4S$ (M+H)$^+$ 466.1311, found 466.1315.

A mixture of 2-(3-chloro-4-methanesulfonyl-phenyl)-3-cyclopentyl-N-[5-(N-hydroxycarbamimidoyl)-pyrazin-2-yl]-propionamide (197.0 mg, 0.423 mmol) and acetic anhydride (970 µL, 10.281 mmol) was placed into a one-dram glass vial. The vial was tightly sealed, and the reaction was stirred at 120° C. for 3.5 h. The reaction was diluted with ethyl acetate (75 mL) and washed with a saturated aqueous sodium bicarbonate solution (50 mL) and a saturated aqueous sodium chloride solution (50 mL). The combined aqueous layers were back-extracted with ethyl acetate (50 mL). The resulting combined organic layers were dried over sodium sulfate, filtered, and concentrated in vacuo. Biotage chromatography (FLASH 40L, Silica, 1/1 ethyl acetate/hexanes) afforded 2-(3-chloro-4-methanesulfonyl-phenyl)-3-cyclopentyl-N-[5-(5-methyl-[1,2,4]oxadiazol-3-yl)-pyrazin-2-yl]-propionamide (43.8 mg, 21%) as a white foam; mp 101.9–104.8° C. (foam to gel); (ES)$^+$-HRMS m/e calcd for $C_{22}H_{24}ClN_5O_4S$ (M+H)$^+$ 490.1311, found 490.1315.

EXAMPLE 34

3-Cyclopentyl-N-[5-(1-hydroxyimino-ethyl)-pyrazin-2-yl]-2(R)-(4-methanesulfonyl-phenyl)-propionamide

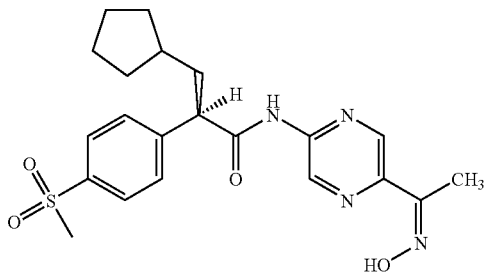

A solution of 3-cyclopentyl-2(R)-(4-methanesulfonylphenyl)-propionic acid (prepared as in Example 3, 500.0 mg, 1.687 mmol) in methylene chloride (4.2 mL) was cooled to 0° C. The reaction mixture was treated with N,N-dimethylformamide (1 drop) and oxalyl chloride (294 μL, 3.374 mmol). The reaction mixture was stirred at 0° C. for 15 min and then slowly allowed to warm to 25° C. where it was stirred for 3 h. The solution was then concentrated in vacuo. The resulting residue was dissolved in methylene chloride (8.4 mL) and then cooled to 0° C. This cooled solution was then treated dropwise with a solution of 1-(5-amino-pyrazin-2-yl)-ethanone O-tert-butyl-oxime (prepared as in Example 28, 351.4 mg, 1.687 mmol) and 2,6-lutidine (246 μL, 2.109) in tetrahydrofuran (8.4 mL). The reaction mixture was stirred at 0° C. for 30 min and then was allowed to warm to 25° C. where it was stirred overnight. The reaction mixture was then concentrated in vacuo, diluted with ethyl acetate (250 mL), and washed with a 1N aqueous hydrochloric acid solution (3×100 mL) and a saturated aqueous sodium chloride solution (1×300 mL). The organic layer was then dried over sodium sulfate, filtered, and concentrated in vacuo. Biotage chromatography (FLASH 40L, Silica, 1/4 ethyl acetate/hexanes) afforded the N-[5-(1-tert-butoxyimino-ethyl)-pyrazin-2-yl]-3-cyclopentyl-2(R)-(4-methanesulfonyl-phenyl)-propionamide (451.1 mg, 55%) as a yellow foam. This material was re-purified via Biotage chromatography (FLASH 40L, Silica, 5% ethyl acetate/methylene chloride) to afford N-[5-(1-tert-butoxyimino-ethyl)-pyrazin-2-yl]-3-cyclopentyl-2(R)-(4-methanesulfonyl-phenyl)-propionamide (380.4 mg, 46%) as a white foam: mp 81–83° C. (foam to gel); (ES)$^+$-HRMS m/e calcd for $C_{25}H_{34}N_4O_4S$ (M+H)$^+$ 487.2374, found 487.2377.

A solution of N-[5-(1-tert-butoxyimino-ethyl)-pyrazin-2-yl]-3-cyclopentyl-2(R)-(4-methanesulfonyl-phenyl)-propionamide (342.6 mg, 0.704 mmol) in methylene chloride (1.4 mL) was cooled to 0° C. and then was treated with a 1.0M solution of titanium tetrachloride in methylene chloride (2.10 mL, 2.10 mmol). The resulting reaction solution was stirred at 0° C. for 2 h and then was stirred at 25° C. for 1 h 50 min. The reaction solution was concentrated in vacuo and then partitioned between ethyl acetate (210 mL) and water (150 mL). The organic layer was washed with a saturated aqueous sodium chloride solution (150 mL), dried over sodium sulfate, filtered, and concentrated in vacuo. Biotage chromatography (FLASH 40L, Silica, 3/2 ethyl acetate/hexanes) afforded the 3-cyclopentyl-N-[5-(1-hydroxyimino-ethyl)-pyrazin-2-yl]-2(R)-(4-methanesulfonyl-phenyl)-propionamide (276.3 mg, 91%) as a white foam: mp 118.8–122.4° C. (foam to gel); (ES)$^+$-HRMS m/e calcd for $C_{21}H_{26}N_4O_4S$ (M+H)$^+$ 431.1748, found 431.1752.

EXAMPLE 35

2(R)-(3-Chloro-4-methanesulfonyl-phenyl)-3-cyclopentyl-N-[5-(3-methyl-[1,2,4]oxadiazol-5-yl)-pyrazin-2-yl]-propionamide

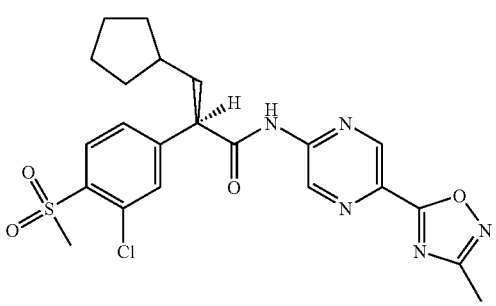

A solution of 5-[2(R)-(3-chloro-4-methanesulfonyl-phenyl)-3-cyclopentyl-propionylamino]-pyrazine-2-carboxylic acid (prepared as in Example 29, 149.5 mg, 0.331 mmol) in methylene chloride (1.8 mL) was cooled to 0° C. The reaction mixture was then treated with oxalyl chloride (61 μL, 0.699 mmol) and N,N-dimethylformamide (1 drop). The reaction mixture was stirred at 0° C. for 30 min and then slowly warmed to 25° C. for 3 h. The solution was then concentrated in vacuo. The residue was dissolved in methylene chloride (1.8 mL) and cooled to 0° C. The resulting solution was then treated with a mixture of acetamide oxime (27.4 mg, 0.370 mmol) and 2,6-lutidine (46 μL, 0.395 mmol) in methylene chloride (1.0 mL) followed by a methylene chloride rinse (0.8 mL). The pH of the reaction was roughly 3, and a second aliquot of 2,6-lutidine (23 μL, 0.198 mmol) was added to bring the pH to roughly 5. The reaction mixture was stirred at 0° C. for 30 min and then stirred at 25° C. overnight. The reaction was then quenched with water (3 mL) and partitioned between ethyl acetate (50 mL) and water (25 mL). The organic layer was washed with a saturated aqueous sodium chloride solution (100 mL), dried over sodium sulfate, filtered, and concentrated in vacuo to afford the (Z)-N-[[[5-[[2(R)-(3-chloro-4-methylsulfonyl-phenyl)-3-cyclopentyl-1-oxopropyl]amino]-2-pyrazinyl]carbonyl]oxy]ethanimidamide as an orange oil which was used without further purification.

A solution of crude (Z)-N-[[[5-[[2(R)-(3-chloro-4-methylsulfonyl-phenyl)-3-cyclopentyl-1-oxopropyl]amino]-2-pyrazinyl]carbonyl]oxy]ethanimidamide (0.331 mmol) in toluene (3.6 mL) was treated with 4 Å molecular sieves and warmed to 80° C. where it stirred for 48 h. The reaction was then partitioned between ethyl acetate (25 mL) and water (50 mL). The organic layer was washed with a 1N aqueous hydrochloric acid solution (50 mL). The combined aqueous layers were then back-extracted with ethyl acetate (50 mL). The combined organic layers were washed with a saturated aqueous sodium chloride solution (50 mL), dried over sodium sulfate, filtered, and concentrated in vacuo. Biotage chromatography (FLASH 40S, Silica, 2/3 ethyl acetate/hexanes) afforded impure 2(R)-(3-chloro-4-methanesulfonyl-phenyl)-3-cyclopentyl-N-[5-(3-methyl-[1,2,4]oxadiazol-5-yl)-pyrazin-2-yl]-propionamide as a light yellow foam (22.5 mg, 13%). The impure product was re-purified by reverse phase high-performance liquid chromatography (Waters symmetry packing, acetonitrile/water with 0.05% trifluoroacetic acid, 2% to 45% acetonitrile gradient). The fractions containing product were concentrated in vacuo and lyophilized to afford 2(R)-(3-chloro-4-methanesulfonyl-phenyl)-3-cyclopentyl-N-[5-(3-methyl-[1,2,4]oxadiazol-5-yl)-pyrazin-2-yl]-propionamide (12 mg, 7%) as a white lyophilized solid: mp 101–105° C. (foam to gel); (ES)$^+$-HRMS m/e calcd for $C_{22}H_{24}ClN_5O_4S$ (M+H)$^+$ 490.1311, found 490.1315.

EXAMPLE 36

2(R)-(3-Chloro-4-methanesulfonyl-phenyl)-3-cyclopentyl-N-(5-methylsulfanylmethyl-pyrazin-2-yl)-propionamide

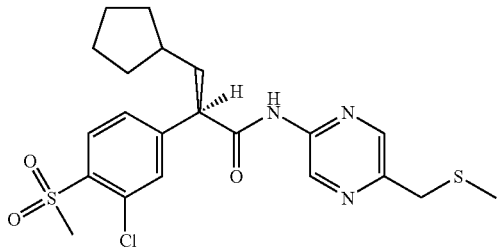

A solution of (5-bromomethyl-pyrazin-2-yl)-carbamic acid tert-butyl ester (prepared according to WO 02/070494, 1.03 g, 3.575 mmol) in acetone (11.6 mL) was treated with sodium thiomethoxide (0.33 g, 4.473 mmol). The reaction mixture was stirred at 25° C. for 5 h 15 min. The reaction was then concentrated in vacuo, and the residue was partitioned between ethyl acetate (200 mL) and water (200 mL). The aqueous layer was back-extracted with ethyl acetate (100 mL). The combined organic layers were dried over magnesium sulfate, filtered, and concentrated in vacuo. Biotage chromatography (FLASH 40L, Silica, 5% ethyl acetate/methylene chloride) afforded (5-methylsulfanylmethyl-pyrazin-2-yl)-carbamic acid tert-butyl ester as a crude white solid (0.45 g, 49%) which was used without further purification.

A solution of (5-methylsulfanylmethyl-pyrazin-2-yl)-carbamic acid tert-butyl ester (0.45 g, 1.762 mmol) in methylene chloride (18 mL) was treated with trifluoroacetic acid (1.4 mL, 18.172 mmol) and then was stirred at 25° C. for 2 h 15 min. The reaction solution was then treated with a second aliquot of trifluoroacetic acid (0.7 mL, 9.086 mmol) and was stirred at 25° C. for 5 h. At this time, the reaction mixture was concentrated in vacuo. Biotage chromatography (FLASH 40S, Silica, 1/9 methanol/methylene chloride with 0.1% ammonium hydroxide) afforded 5-methylsulfanylmethyl-pyrazin-2-ylamine (276.1 mg, quant.) as a white solid: mp 102.0–102.7° C.; EI-HRMS m/e calcd for $C_6H_9N_3S$ (M$^+$) 155.0517, found 155.0516.

A solution of 2(R)-(3-chloro-4-methanesulfonyl-phenyl)-3-cyclopentyl-propionic acid (prepared as in Example 1, 581.7 mg, 1.758 mmol) in methylene chloride (8.6 mL) was cooled to 0° C. The reaction mixture was then treated with oxalyl chloride (310 mg, 3.554 mmol) and N,N-dimethylformamide (2 drops). The reaction mixture was stirred at 0° C. for 45 min and then slowly warmed to 25° C. over 6 h. The solution was then concentrated in vacuo. The resulting yellow slurry was dissolved in methylene chloride (7 mL) and then cooled to 0° C. To this solution was added a solution of 5-methylsulfanylmethyl-pyrazin-2-ylamine (267.2 mg, 1.721 mmol) and pyridine (174 μL, 2.151 mmol) in methylene chloride (8.6 mL), followed by a methylene chloride rinse (1.7 mL). The pH of the reaction was roughly 3–4, and a second aliquot of pyridine (50 μL, 0.618 mmol) was added to adjust the pH to roughly 5. The reaction mixture was stirred at 0° C. and slowly warmed to 25° C. overnight. The reaction was then quenched with water (10 mL), stirred at 25° C. for 10 min, and concentrated in vacuo. The reaction slurry was partitioned between ethyl acetate (250 mL) and a 1N aqueous hydrochloric acid solution (250 mL). The organic layer was washed with a 1N aqueous hydrochloric acid solution (250 mL), a saturated aqueous sodium bicarbonate solution (250 mL), water (250 mL), and a saturated aqueous sodium chloride solution (250 mL), dried over magnesium sulfate, filtered, and concentrated in vacuo. Biotage chromatography (FLASH 40L, Silica, 1/2 ethyl acetate/hexanes) afforded the desired chiral 2(R)-(3-chloro-4-methanesulfonyl-phenyl)-3-cyclopentyl-N-(5-methylsulfanylmethyl-pyrazin-2-yl)-propionamide (679.0 mg, 84%) as a white foam: mp 75.0–76.7° C. (foam to gel); (ES)$^+$-HRMS m/e calcd for $C_{21}H_{26}ClN_3O_3S_2$ (M+H)$^+$ 468.1177, found 468.1180.

EXAMPLE 37

2-(3-Chloro-4-methanesulfonyl-phenyl)-N-[5-(cyano-hydroxyimino-methyl)-pyrazin-2-yl]-3-cyclopentyl-propionamide

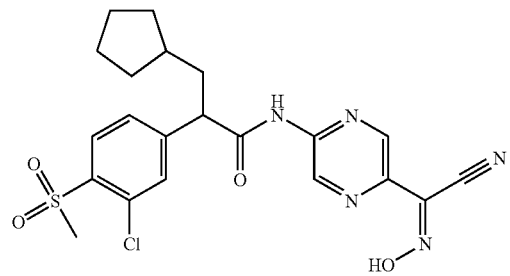

A solution of (5-bromomethyl-pyrazin-2-yl)-carbamic acid tert-butyl ester (prepared according to WO 02/070494, 1.00 g, 3.470 mmol) in N,N-dimethylformamide (6.9 mL) was treated with sodium cyanide (350.7 mg, 6.940 mmol). The reaction mixture was stirred at 40° C. for 1 h. The reaction was diluted with a saturated aqueous sodium chloride solution (100 mL) and then extracted with ethyl acetate (100 mL). The organic layer was dried over magnesium sulfate, filtered, and concentrated in vacuo. Biotage chromatography (FLASH 40L, Silica, 3/7 ethyl acetate/hexanes) afforded (5-cyanomethyl-pyrazin-2-yl)-carbamic acid tert-butyl ester (807.6 mg, 99%) as a light yellow solid: mp 162–164° C.; EI-HRMS m/e calcd for $C_{11}H_{14}N_4O_2$ (M$^+$) 234.1117, found 234.1120.

A solution of (5-cyanomethyl-pyrazin-2-yl)-carbamic acid tert-butyl ester (807.6 mg, 3.447 mol) in methylene chloride (4.3 mL) was treated with trifluoroacetic acid (2.7 mL, 34.470 mmol). The reaction mixture was stirred at 25° C. for 2 h and then concentrated in vacuo. Biotage chromatography (FLASH 40S, Silica, 1/9 methanol/methylene chloride with 0.1% ammonium hydroxide) afforded impure (5-amino-pyrazin-2-yl)-acetonitrile. Re-purification by Biotage chromatography (FLASH 40M, Silica, 99/1 ethyl acetate/methanol) afforded pure (5-amino-pyrazin-2-yl)-acetonitrile (281.4 mg, 60.8%) as an orange solid: mp 132–134° C.; EI-HRMS m/e calcd for $C_6H_6N_4$ (M+) 134.0592, found 134.0593.

A solution of 2-(3-chloro-4-methanesulfonyl-phenyl)-3-cyclopentyl-propionic acid (prepared as in Example 33, 663.1 mg, 2.004 mmol) in methylene chloride (10 mL) was treated with N,N-dimethylformamide (2 drops) and then cooled to 0° C. The reaction mixture was then treated with oxalyl chloride (357 μL, 4.009 mmol). The reaction mixture was stirred at 0° C. and then warmed to 25° C. where it was stirred for 1.5 h. At this time, the reaction mixture was concentrated in vacuo. The yellow slurry was dissolved in methylene chloride (10 mL) and then cooled to 0° C. To this solution was added a mixture of (5-amino-pyrazin-2-yl)-acetonitrile (268.9 mg, 2.004 mmol) and pyridine (324 μL, 4.009 mmol) in methylene chloride (10 mL). The reaction mixture was stirred at 0° C. for 30 min and then warmed to 25° C. where it was stirred for 16 h. The reaction mixture was then diluted with methylene chloride (100 mL) and water (50 mL). The organic layer was washed with a 1N aqueous hydrochloric acid solution (50 mL), a saturated aqueous sodium bicarbonate solution (50 mL), and a saturated aqueous sodium chloride solution (50 mL), dried over magnesium sulfate, filtered, and concentrated in vacuo. Biotage chromatography (FLASH 40L, Silica, 1/9 ethyl acetate/methylene chloride) afforded 2-(3-chloro-4-methanesulfonyl-phenyl)-N-(5-cyanomethyl-pyrazin-2-yl)-3-cyclopentyl-propionamide (523.4 mg, 58%) as a white foam: mp 79–82° C. (foam to gel); (ES)+-HRMS m/e calcd for $C_{21}H_{23}ClN_4O_3S$ (M+H)+ 447.1252, found 447.1255.

A solution of 2-(3-chloro-4-methanesulfonyl-phenyl)-N-(5-cyanomethyl-pyrazin-2-yl)-3-cyclopentyl-propionamide (300.0 mg, 0.671 mmol) in methanol (671 μL) was cooled to 0° C. and then was treated with sodium hydroxide (26.8 mg, 0.671 mmol) followed by tert-butyl nitrile (92.3 mg, 0.805 mmol). The reaction was stirred at 0° C. for 30 min and then warmed to 25° C. where it was stirred for 16 h. At this time, the reaction was acidified to a pH=7 with a 1N aqueous hydrochloric acid solution and was diluted with ethyl acetate (100 mL). The organic layer was washed with a saturated aqueous sodium chloride solution (50 mL), dried over magnesium sulfate, filtered, and concentrated in vacuo. Biotage chromatography (FLASH 40S, Silica, 1/1 ethyl acetate/hexanes) afforded the 2-(3-chloro-4-methanesulfonyl-phenyl)-N-[5-(cyano-hydroxyimino-methyl)-pyrazin-2-yl]-3-cyclopentyl-propionamide as a yellow oil. This material was re-purified by high-performance liquid chromatography (Metachem diol column, 10 Å, 10–50% ethyl acetate/hexanes) to afford 2-(3-chloro-4-methanesulfonyl-phenyl)-N-[5-(cyano-hydroxyimino-methyl)-pyrazin-2-yl]-3-cyclopentyl-propionamide as a white lyophilized powder (35.5 mg, 11%): mp 130–133° C. (foam to gel); (ES)+-HRMS m/e calcd for $C_{21}H_{22}ClN_5O_4S$ (M+H)+ 476.1154, found 476.1158.

EXAMPLE 38

2(R)-(3-Chloro-4-methanesulfonyl-phenyl)-3-cyclopentyl-N-(5-methanesulfinylmethyl-pyrazin-2-yl)-propionamide

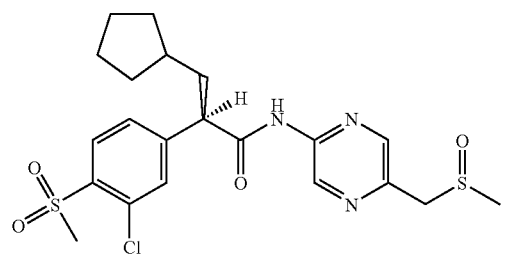

A solution of 2(R)-(3-chloro-4-methanesulfonyl-phenyl)-3-cyclopentyl-N-(5-methylsulfanylmethyl-pyrazin-2-yl)-propionamide (prepared as in Example 36, 514.3 mg, 1.099 mmol) in formic acid (11 mL) was treated with a 30% aqueous hydrogen peroxide solution (113 μL, 1.106 mmol). The reaction was stirred at 25° C. for 4 d. The reaction was then partitioned between ethyl acetate (250 mL) and water (250 mL). The organic layer was washed with a saturated aqueous sodium bicarbonate solution (250 mL) and a saturated aqueous sodium chloride solution (150 mL), dried over magnesium sulfate, filtered, and concentrated in vacuo. Biotage chromatography (FLASH 40S, Silica, 5% methanol/methylene chloride) afforded 2(R)-(3-chloro-4-methanesulfonyl-phenyl)-3-cyclopentyl-N-(5-methanesulfinylmethyl-pyrazin-2-yl)-propionamide (269.9 mg, 51%) as a light yellow foam: mp 102–106° C. (foam to gel); (ES)+-HRMS m/e calcd for $C_{21}H_{26}ClN_3O_4S_2$ (M+H)+ 484.1126, found 484.1134.

EXAMPLE 39

N-(5-Acetyl-pyrazin-2-yl)-2(R)-(3-chloro-4-methanesulfonyl-phenyl)-3-cyclopentyl-propionamide

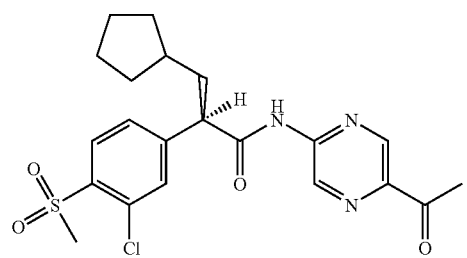

A suspension of N-(5-acetyl-pyrazin-2-yl)-2,2-dimethyl-propionamide (prepared as in Example 28, 2.00 g, 9.038 mmol) in trimethyl orthoformate (13.5 mL) and methanol (36 mL) was treated with p-toluenesulfonic acid monohydrate (174.5 mg, 0.904 mmol). The resulting reaction mixture was heated under reflux for 2.5 h and then concentrated in vacuo. The residue was diluted with ethyl acetate (200 mL). The organic layer was washed with a saturated aqueous sodium bicarbonate solution (100 mL) and a saturated aqueous sodium chloride solution (100 mL), dried over magnesium sulfate, filtered, and concentrated in vacuo.

Biotage chromatography (FLASH 40L, Silica, 1/4 ethyl acetate/hexanes) afforded N-[5-(1,1-dimethoxy-ethyl)-pyrazin-2-yl]-2,2-dimethyl-propionamide as a white solid (1.74 g, 72%): mp 108–109° C.; EI-HRMS m/e calcd for $C_{13}H_{21}N_3O_3$ (M$^+$) 267.1583, found 267.1486.

A solution of N-[5-(1,1-dimethoxy-ethyl)-pyrazin-2-yl]-2,2-dimethyl-propionamide (1.73 g, 6.47 mmol) in ethanol (13 mL) was treated with a 2N aqueous sodium hydroxide solution (11 mL, 22 mmol). The reaction was stirred at 25° C. for 63 h and then was heated at 65° C. for 1.5 h. The reaction mixture was then diluted with ethyl acetate (200 mL) and washed with a saturated aqueous sodium chloride solution (75 mL). The aqueous layer was back-extracted with ethyl acetate (100 mL). The combined organic layers were dried over magnesium sulfate, filtered, and concentrated in vacuo. Biotage chromatography (FLASH 40M, Silica, 4% methanol/methylene chloride) afforded impure 5-(1,1-dimethoxy-ethyl)-pyrazin-2-ylamine as a yellow solid. This material was re-purified via Biotage chromatography (FLASH 40L, Silica, 7/3 ethyl acetate/hexanes) to afford still impure 5-(1,1-dimethoxy-ethyl)-pyrazin-2-ylamine as a light yellow solid (880.4 mg, 74%) which used without further purification and characterization.

A solution of 2(R)-(3-chloro-4-methanesulfonyl-phenyl)-3-cyclopentyl-propionic acid (prepared as in Example 1, 1.59 g, 4.805 mmol) in methylene chloride (24 mL) and N,N-dimethylformamide (2 drops) was cooled to 0° C. The reaction mixture was then treated with oxalyl chloride (855 μL, 9.609 mmol). The reaction mixture was stirred at 0° C. for 30 min and then warmed to 25° C. where it was stirred for 2 h. The solution was then concentrated in vacuo. The yellow slurry was dissolved in methylene chloride (24 mL) and then cooled to 0° C. To this solution was added a solution of 5-(1,1-dimethoxy-ethyl)-pyrazin-2-ylamine (880.4 mg, 4.805 mmol) and pyridine (466 μL, 5.766 mmol) in methylene chloride (24 mL). The reaction mixture was stirred at 0° C. for 1 h. The reaction was then quenched with a saturated aqueous sodium chloride solution (50 mL), and the layers were separated. The aqueous layer was back-extracted with methylene chloride (50 mL). The combined organic layers were washed with a saturated aqueous sodium bicarbonate solution (75 mL), an aqueous copper(II) sulfate solution (2×50 mL), and a saturated aqueous sodium chloride solution (75 mL), dried over magnesium sulfate, filtered, and concentrated in vacuo. Biotage chromatography (FLASH 40L, Silica, 3/7 ethyl acetate/hexanes) afforded 2(R)-(3-chloro-4-methanesulfonyl-phenyl)-3-cyclopentyl-N-[5-(1,1-dimethoxy-ethyl)-pyrazin-2-yl]-propionamide (1.25 g, 52%) as a white foam: mp 85–88° C. (foam to gel); (ES)$^+$-HRMS m/e calcd for $C_{23}H_{30}ClN_3O_5S$ (M+Na)$^+$ 518.1487, found 518.1488.

A solution of 2(R)-(3-chloro-4-methanesulfonyl-phenyl)-3-cyclopentyl-N-[5-(1,1-dimethoxy-ethyl)-pyrazin-2-yl]-propionamide (1.22 g, 2.459 mmol) in acetone (28 mL) and water (3 mL) was treated with p-toluenesulfonic acid monohydrate (142.5 mg, 0.738 mmol). The reaction mixture was heated to 60° C. for 30 min and then was diluted with ethyl acetate (100 mL). The organic layer was washed with a saturated aqueous sodium bicarbonate solution (100 mL), water (100 mL), and a saturated aqueous sodium chloride solution (100 mL), dried over magnesium sulfate, filtered, and concentrated in vacuo. Biotage chromatography (FLASH 40M, Silica, 1/3 ethyl acetate/hexanes) afforded the N-(5-acetyl-pyrazin-2-yl)-2(R)-(3-chloro-4-methanesulfonyl-phenyl)-3-cyclopentyl-propionamide as a white foam (1.07 g, 96%): mp 77–80° C. (foam to gel); (ES)$^+$-HRMS m/e calcd for $C_{21}H_{24}ClN_3O_4S$ (M+H)$^+$ 450.1249, found 450.1253.

EXAMPLE 40

2(R)-(3-Chloro-4-methanesulfonyl-phenyl)-3-cyclopentyl-N-[5-(2-hydroxy-1-hydroxymethyl-ethyl)-pyrazin-2-yl]-propionamide

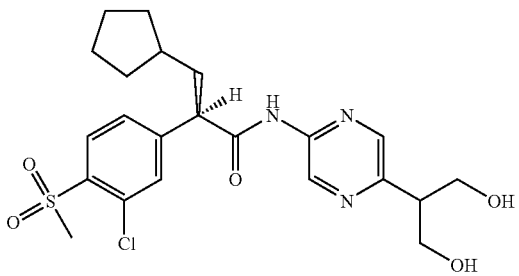

A solution of 2-bromo-5-nitropyrazine (3.0 g, 14.7 mmol) in tetrahydrofuran (24.5 mL) was treated with diethylmalonate (3.35 mL, 22.0 mmol) and potassium carbonate (5.08 g, 36.7 mmol). The mixture was then stirred at 90–95° C. overnight. At this time, the reaction was cooled to 25° C. and then poured onto a 1N aqueous hydrochloric acid solution (60 mL). This solution was diluted with a saturated aqueous sodium chloride solution (50 mL) and then was extracted with ethyl acetate (3×75 mL). The combined organic layers were dried over sodium sulfate, filtered, and concentrated in vacuo. Biotage chromatography (FLASH 40M, Silica 1/3 ethyl acetate/hexanes) afforded 2-(5-nitro-pyrazin-2-yl)-malonic acid diethyl ester (3.28 g, 78%) as a pale yellow oil: EI-HRMS m/e calcd for $C_{11}H_{13}N_3O_6$ (M$^+$) 283.0804, found 283.0801.

A solution of 2-(5-nitro-pyrazin-2-yl)-malonic acid diethyl ester (425 mg, 1.5 mmol) in ethanol (10 mL) at 25° C. was treated with ammonium formate (510 mg, 8.1 mmol) and 10% palladium on activated carbon (51 mg). The mixture was heated to 95–100° C. for 4 h and then was stirred at 25° C. overnight. At this time, the catalyst was removed by filtration through a pad of celite (ethanol wash). The filtrate was concentrated in vacuo. Biotage chromatography (FLASH 40M, Silica, 1/1 ethyl acetate/hexanes) afforded 2-(5-amino-pyrazin-2-yl)-malonic acid diethyl ester (131.5 mg, 37%) as a light tan solid: EI-HRMS m/e calcd for $C_{11}H_{15}N_3O_4$ (M$^+$) 253.1063, found 253.1065.

A solution of 2(R)-(3-chloro-4-methanesulfonyl-phenyl)-3-cyclopentyl-propionic acid (prepared as in Example 1, 170 mg, 0.51 mmol) in methylene chloride (10 mL) cooled to 0° C. was treated with a 2.0M solution of oxalyl chloride in methylene chloride (385 μL, 0.77 mmol) and catalytic N,N-dimethylformamide. The reaction mixture was stirred at 0° C. for 30 min and at 25° C. for 2 h. The solution was then concentrated in vacuo. The residue was dissolved in methylene chloride (10 mL), cooled to 0° C., and then treated with a solution of 2-(5-amino-pyrazin-2-yl)-malonic acid diethyl ester (130 mg, 0.51 mmol) and 2,6-lutidine (120 μL, 1.03 mmol) in tetrahydrofuran (10 mL). The reaction mixture was then stirred at 0° C. for 15 min and at 25° C. for 16 h. The reaction was then concentrated in vacuo. Biotage chromatography (FLASH 40M, Silica, 1/1 ethyl acetate/hexanes) afforded the 2(R)-{5-[2-(3-chloro-4-methanesulfonyl-phenyl)-3-cyclopentyl-propionylamino]-pyrazin-2-yl}-malonic acid diethyl ester (76.9 mg, 26%) as a pale yellow oil. This material was further purified by dissolving it in methylene chloride and washing with a 1N aqueous hydrochloric acid solution (25 mL). The organic layer was then dried over magnesium sulfate, filtered, and concentrated in vacuo to afford the 2(R)-{5-[2-(3-chloro-4-methanesulfonyl-phenyl)-3-cyclopentyl-propionylamino]-pyrazin-2-yl}-malonic acid diethyl ester (51.3 mg, 18%) as a pale yellow oil: (ES)$^+$-HRMS m/e calcd for $C_{26}H_{32}ClN_3O_7S$ (M+H)$^+$ 566.1722, found 566.1726.

A solution of 2(R)-{5-[2-(3-chloro-4-methanesulfonyl-phenyl)-3-cyclopentyl-propionylamino]-pyrazin-2-yl}-malonic acid diethyl ester (189 mg, 0.33 mmol) in tetrahydrofuran (5.0 mL) cooled to 0° C. was treated with a 1.0M solution of diisobutylaluminum hydride in hexanes (1.84 mL, 1.84 mmol). The reaction mixture was stirred at 0° C. for 1.25 h and then at 25° C. for 2 h. At this time, the reaction was re-cooled to 0° C. and was treated with an additional amount of a 1.0M solution of diisobutylaluminum hydride in hexanes (0.92 mL, 0.92 mmol). The reaction was stirred at 0° C. for 15 min and then at 25° C. for 1 h. At this time, the reaction mixture was poured onto a mixture of ice, water, and ethyl acetate. The aqueous layer was extracted with ethyl acetate and diethyl ether. The combined organic layers were washed with a 1N aqueous citric acid solution, a cold saturated aqueous sodium bicarbonate solution, a saturated aqueous sodium chloride solution, dried over magnesium sulfate and sodium sulfate, treated with charcoal, filtered, and concentrated in vacuo. Biotage chromatography (FLASH 40M, Silica, 9/1 ethyl acetate/acetonitrile) afforded 2(R)-(3-chloro-4-methanesulfonyl-phenyl)-3-cyclopentyl-N-[5-(2-hydroxy-1-hydroxymethyl-ethyl)-pyrazin-2-yl]-propionamide (17.9 mg, 11%) as a pale yellow foam: mp 110–120° C.; (ES)$^+$-HRMS m/e calcd for $C_{22}H_{28}N_3O_5$ (M+H)$^+$ 482.1511, found 482.1512.

EXAMPLE 41

2(R)-(3-Chloro-4-methanesulfonyl-phenyl)-3-cyclopentyl-N-(5-[1,3]dioxolan-2-yl-pyrazin-2-yl)-propionamide

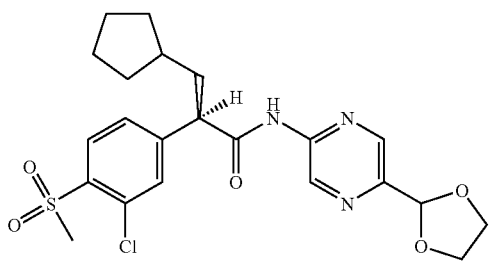

A solution of 5-methylpyrazine-2-carboxylic acid (5.0 g, 36.2 mmol), N,N-dimethylformamide dimethyl acetal (15 mL, 113 mmol) and N,N-dimethylformamide (15 mL) was heated with stirring in an oil-bath at 90° C. under argon for 60 min. The temperature of the oil-bath was raised to 120° C., and the heating and stirring continued for an additional 120 min. The reaction mixture was then cooled to 25° C. and concentrated in vacuo to a volume of about 10 mL. The oily residue was partitioned with water (50 mL) and ethyl acetate (50 mL). The aqueous phase was further extracted with ethyl acetate (2×50 mL), and each organic extract was washed with a portion of a saturated aqueous sodium chloride solution (25 mL). The combined organic extracts were dried over sodium sulfate, filtered, and concentrated in vacuo to a dark oil. The residue was treated with a solution of diethyl ether/hexanes (50 mL, 3:2) to produce an orange solid. The solid was collected by filtration and washed with a mixture of diethyl ether/hexanes (25 mL, 1:1) to afford 5-(2-dimethylamino-vinyl)-pyrazine-2-carboxylic acid methyl ester (4.94 g, 66%) as a bright orange solid.

A solution of the 5-(2-dimethylamino-vinyl)-pyrazine-2-carboxylic acid methyl ester (415 mg, 2.0 mmol) in tetrahydrofuran and water (10 mL, 1:1) was treated with powdered sodium periodate (1.3 g, 6.07 mmol). The mixture was stirred at 25° C. for 30 min, at which time, thin layer chromatography suggested complete conversion to a product less polar than starting material. The reaction mixture was concentrated in vacuo nearly to dryness, and the residue was partitioned with ethyl acetate (50 mL) and a saturated aqueous sodium bicarbonate solution (25 mL). The aqueous phase was extracted with ethyl acetate (2×50 mL). Each of the organic extracts was washed with a saturated aqueous sodium chloride solution (25 mL). The combined organic extracts were dried over sodium sulfate, filtered, and concentrated in vacuo to afford the crude aldehyde, 5-formyl-pyrazine-2-carboxylic acid methyl ester (180 mg), as an orange oil which was used without further characterization or purification.

A mixture of 5-formyl-pyrazine-2-carboxylic acid methyl ester (325 mg, 1.56 mmol), ethylene glycol (100 μL, 1.79 mmol), and p-toluenesulfonic acid monohydrate (30 mg, 0.157 mmol) in benzene (10 mL) was heated under reflux with a Dean-Stark condenser for 17 h. The mixture was cooled and diluted with benzene (25 mL). The organic layer was washed with a saturated aqueous sodium bicarbonate solution (25 mL) and a saturated aqueous sodium chloride solution (25 mL). Each aqueous wash was back-extracted with a small portion of benzene. The combined organic layers were dried over sodium sulfate, filtered, and concentrated in vacuo to afford 5-[1,3]dioxolan-2-yl-pyrazine-2-carboxylic acid methyl ester as an orange-red oil (250 mg).

A solution of 5-[1,3]dioxolan-2-yl-pyrazine-2-carboxylic acid methyl ester (250 mg, 1.19 mmol) in tetrahydrofuran (5 mL) was treated with potassium hydroxide (150 mg, 2.27 mmol) followed by methanol (2 mL) and water (1 mL). The mixture was stirred at 25° C. for 30 min then concentrated in vacuo to dryness. The residue was concentrated in vacuo to dryness from a 20 mL portion of benzene to afford the potassium salt (~280 mg, 1.19 mmol) as a brown solid. The salt was suspended in N,N-dimethylformamide (10 mL) and treated while stirring with diphenylphosphoryl azide (0.35 mL, 1.62 mmol). The mixture was stirred at 25° C. for 18 h. The solution was then concentrated in vacuo, and the residue was partitioned with ethyl acetate (50 mL) and water (25 mL). The aqueous phase was extracted with ethyl acetate (2×25 mL). Each organic extract was washed with a small portion of a saturated aqueous sodium chloride solution. The combined organic extracts were dried over sodium sulfate, filtered, and concentrated in vacuo to afford the acid azide (~240 mg) as an orange oil. The acid azide was treated with benzyl alcohol (185 μL, 1.78 mmol), and the mixture was heated with stirring at 85° C. for 30 min. The reaction mixture was cooled and stirred with diethyl ether (10 mL). The resulting solid was filtered to afford the carbamate (153 mg, 43%) as a light brown solid: mp 95–99° C. The filtrate was concentrated in vacuo to dryness, and the residue was purified by flash chromatography (Merck Silica gel 60, 230–400 mesh, elution with various concentrations of ethyl acetate/hexanes) to afford an additional amount of the carbamate (60 mg, 16%).

A solution of the carbamate (200 mg, 0.66 mmol) in methanol (5 mL) was treated with 10% palladium on activated carbon (40 mg). The reaction mixture was then hydrogenated under a hydrogen atmosphere at 25° C. and atmospheric pressure for 60 min, at which time, thin layer chromatography (1/1 ethyl acetate/hexanes) suggested complete conversion to a polar product. The mixture was filtered through celite, and the filtrate was concentrated in vacuo to afford the desired aminopyrazine derivative (110 mg, 100%) as an off-white solid.

A solution of 2(R)-(3-chloro-4-methanesulfonyl-phenyl)-3-cyclopentyl-propionic acid (prepared as in Example 1, 200 mg, 0.604 mmol) in methylene chloride (5 mL) and N,N-dimethylformamide (2 drops) was cooled to 5° C. and then treated with oxalyl chloride (105 µL, 1.2 mmol). The solution was stirred at 5° C. for 5 min, the cooling bath was removed, and the stirring was continued for 10 min. At this time, the reaction mixture was concentrated in vacuo, the residue was dissolved in benzene (10 mL), and the solvent was concentrated in vacuo again. The resulting acid chloride was dissolved in methylene chloride (5 mL), cooled to 5° C., and then treated with a solution of 5-[1,3]dioxolan-2-yl-pyrazin-2-ylamine (105 µL, 0.628 mmol), pyridine (100 µL, 1.23 mmol) in methylene chloride (5 mL). After 5 min, the cooling bath was removed, and the stirring was continued for 18 h. The reaction mixture was then diluted with methylene chloride (50 mL), and the solution was washed with a saturated aqueous sodium bicarbonate solution (25 mL), a 0.5M aqueous hydrochloric acid solution (25 mL), and a saturated aqueous sodium chloride solution (25 mL). Each aqueous wash was extracted with a small portion of methylene chloride. The combined organic layers were dried over sodium sulfate, filtered, and concentrated in vacuo to afford a yellow oil. Flash chromatography (Merck Silica gel 60, 230–400 mesh, various concentrations of ethyl acetate/hexanes) afforded the 2(R)-(3-chloro-4-methanesulfonyl-phenyl)-3-cyclopentyl-N-(5-[1,3]dioxolan-2-yl-pyrazin-2-yl)-propionamide (148 mg, 51%) as a colorless foam: (ES)$^+$-HRMS m/e calcd for $C_{22}H_{26}ClN_3O_5S$ (M+H)$^+$ 480.1355, found 480.1357.

EXAMPLE 42

2(R)-(3-Chloro-4-methanesulfonyl-phenyl)-3-cyclopentyl-N-(5-[1,3]dioxolan-2-ylmethyl-pyrazin-2-yl)-propionamide

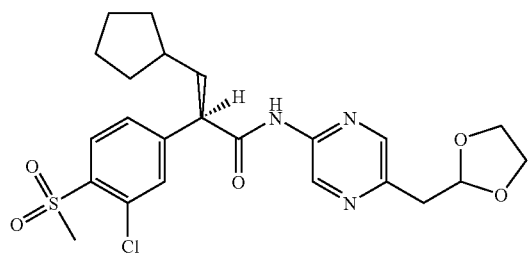

A solution of 5-(2-dimethylamino-vinyl)-pyrazine-2-carboxylic acid methyl ester (prepared as in Example 41, 600 mg, 2.9 mmol) in benzene (5 mL) was treated with a solution of a 1M aqueous hydrochloric acid solution (5 mL) and water (5 mL) and then stirred vigorously at 50° C. for 60 min. The mixture was cooled and then treated with sodium chloride (2 g). The mixture was extracted with benzene (3×25 mL). Each extract was washed with a saturated aqueous sodium chloride solution (2×20 mL). The combined organic extracts were dried over sodium sulfate, filtered, and concentrated in vacuo to afford 5-(2-oxo-ethyl)-pyrazine-2-carboxylic acid methyl ester (295 mg, 56%) as yellow crystals.

A solution of 5-(2-oxo-ethyl)-pyrazine-2-carboxylic acid methyl ester (295 mg, 1.42 mmol) and ethylene glycol (100 µL, 1.79 mmol) in benzene (10 mL) was treated with p-toluenesulfonic acid monohydrate (27 mg, 0.142 mmol), and the mixture was heated under reflux with a Dean-Stark condenser for 20 h. The mixture was cooled, diluted with benzene (15 mL), and then washed with a saturated aqueous sodium bicarbonate solution (10 mL) followed by a saturated aqueous sodium chloride solution (10 mL). Each aqueous phase was extracted with a small portion of benzene. The combined organic extracts were dried over sodium sulfate, filtered, and concentrated in vacuo to dryness to afford 5-[1,3]dioxolan-2-ylmethyl-pyrazine-2-carboxylic acid methyl ester as an orange oil (273 mg, 86%).

A solution of 5-[1,3]dioxolan-2-ylmethyl-pyrazine-2-carboxylic acid methyl ester (273 mg, 1.22 mmol) in methanol (1.5 mL) and tetrahydrofuran (1.5 mL) was treated with potassium hydroxide (150 mg, 2.3 mmol). Water (0.2 mL) was added dropwise to the reaction mixture until the potassium hydroxide dissolved. After 90 min, thin layer chromatography indicated that the starting material was completely converted to a polar product. The reaction was concentrated in vacuo. The residue was suspended in toluene (10 mL) and further concentrated in vacuo to dryness to give the potassium salt as a tan solid (300 mg, 100%). The salt was used without further purification or characterization. This salt (300 mg, 1.2 mmol) was combined with diphenylphosphoryl azide (0.4 mL, 1.85 mmol) in N,N-dimethylformamide (10 mL), and the reaction mixture was stirred at 25° C. for 18 h. The solution was concentrated in vacuo, and the residue was partitioned with ethyl acetate (25 mL) and water (25 mL). The aqueous phase was back-extracted with ethyl acetate (25 mL), and each organic extract was washed with a small portion of a saturated aqueous sodium chloride solution. The combined organic layers were combined, dried over sodium sulfate, filtered, and concentrated in vacuo to afford the acid azide as a pale yellow oil (263 mg). This oil was treated with benzyl alcohol (160 µL, 1.55 mmol) and heated with stirring at 85° C. for 35 min. The residue was stirred with diethyl ether (10 mL) and filtered to give the carbamate as an off-white solid (138 mg, 36%). The filtrate was purified by flash chromatography (Merck Silica gel 60, 230–400 mesh, gradient mixtures of ethyl acetate/hexanes) to afford an additional amount of the 5-[1,3]dioxolan-2-ylmethyl-pyrazin-2-yl-carbamic acid benzyl ester (21 mg, 5.5%).

A solution of 5-[1,3]dioxolan-2-ylmethyl-pyrazin-2-yl-carbamic acid benzyl ester (240 mg, 0.49 mmol) in methanol (5 mL) was treated with 10% palladium on activated carbon (40 mg). The reaction mixture was then hydrogenated under a hydrogen atmosphere at 25° C. and atmospheric pressure for 60 min, at which time, thin layer chromatography (ethyl acetate) suggested complete conversion to a polar product. The reaction was filtered through celite, and the filtrate was concentrated in vacuo to afford 5-[1,3]dioxolan-2-ylmethyl-pyrazin-2-ylamine (140 mg, 100%) as an oil which crystallized.

A solution of 2(R)-(3-chloro-4-methanesulfonyl-phenyl)-3-cyclopentyl-propionic acid (prepared as in Example 1, 160 mg, 0.48 mmol) in methylene chloride (5 mL) and N,N-dimethylformamide (2 drops) was cooled to 5° C. and then treated with oxalyl chloride (90 μL, 1.03 mmol). After 5 min, the cooling bath was removed, and the stirring was continued for 15 min. The mixture was concentrated in vacuo to dryness, and the residue was further concentrated in vacuo to dryness from benzene (15 mL). The resulting acid chloride was dissolved in methylene chloride (10 mL), cooled to 5° C., and then treated with a solution of the 5-[1,3]dioxolan-2-ylmethylpyrazin-2yl-amine (0.49 mmol) and pyridine (100 μL, 1.23 mmol) in methylene chloride (5 mL). The mixture was stirred at 5° C. for 30 min then at 25° C. for 18 h. The mixture was diluted with methylene chloride (25 mL) and washed with a saturated aqueous sodium bicarbonate solution (20 mL), a 0.5M aqueous hydrochloric acid solution (20 mL), and a saturated aqueous sodium chloride solution (20 mL). Each aqueous layer was back-extracted with a small portion of ethyl acetate. The combined organic extracts were dried over sodium sulfate, filtered, and concentrated in vacuo. Flash chromatography (Merck Silica gel 60, 230–400 mesh, gradient elution with ethyl acetate/hexanes) afforded 2(R)-(3-chloro-4-methanesulfonyl-phenyl)-3-cyclopentyl-N-(5-[1,3]dioxolan-2-ylmethyl-pyrazin-2-yl)-propionamide (112 mg, 47%) as a colorless foam: (ES)$^+$-HRMS m/e calcd for $C_{23}H_{28}ClN_3O_5S$ (M+H)$^+$ 494.1511, found 494.1517.

EXAMPLE 43

2(R)-(3-Chloro-4-methanesulfonyl-phenyl)-3-cyclopentyl-N-5-(2-methoxyethoxy-pyrazin-2-yl)-propionamide

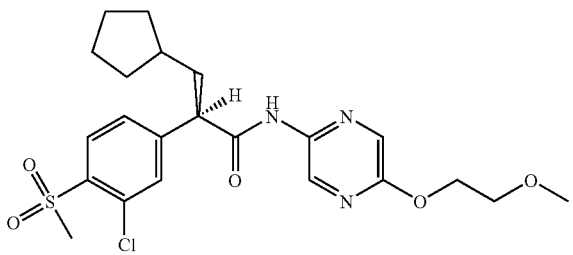

A solution of methyl 5-chloropyrazine-2-carboxylate (2.0 g, 11.63 mmol) in 2-methoxyethanol (20 mL) was treated with solid potassium carbonate (4.8 g, 34.8 mmol). The mixture was heated at 95° C. and was stirred at this temperature for 4.5 h. The mixture was dissolved in water (20 mL) and extracted with diethyl ether. The aqueous layer was neutralized with a 1N aqueous hydrochloric acid solution and extracted with ethyl acetate. The organic layer was washed with a saturated aqueous sodium chloride solution, dried over sodium sulfate, filtered, and concentrated in vacuo to afford 5-methoxyethoxypyrazine-2-carboxylic acid as a pale yellow solid powder: (1.89 g, 82.2%).

A mixture of 5-methoxyethoxypyrazine-2-carboxylic acid (1.0 g, 5.05 mmol) in tert-butyl alcohol (20 mL) was treated with diphenylphosphoryl azide (1.14 mL, 5.30 mmol) and triethylamine (1.40 mL, 10.10 mmol). The mixture was heated under reflux for 4 h. The solvents were concentrated in vacuo, and the residue was extracted with ethyl acetate and a saturated aqueous sodium bicarbonate solution. The organic layer was washed with a saturated aqueous sodium chloride solution, dried over sodium sulfate, filtered, and concentrated in vacuo. Biotage chromatography (FLASH 40S, Silica, 3/1 hexanes/ethyl acetate) afforded 2-N-tert-butyloxycarbonylamino-5-methoxyethoxypyrazine (259.4 mg, 19.1%) as a white solid.

A solution of 2-N-tert-butyloxycarbonylamino-5-methoxyethoxypyrazine (254 mg, 0.944 mmol) in methylene chloride (3 mL) was treated with trifluoroacetic acid (1 mL). The mixture was stirred at 25° C. for 5 h. The mixture was concentrated in vacuo to dryness and then dried in vacuo. The red oily residue was extracted with ethyl acetate and a saturated aqueous sodium bicarbonate solution. The organic layer was washed with a saturated aqueous sodium chloride solution, dried over sodium sulfate, filtered, and concentrated in vacuo to afford 2-amino-5-methoxyethoxypyrazine (148 mg, 87.6%) as an oily residue.

A solution of 2(R)-(3-chloro-4-methylsulfonyl-phenyl)-3-cyclopentyl-propionic acid (prepared as in Example 1, 288.9 mg, 0.8757 mmol) in methylene chloride (6 mL) was treated with oxalyl chloride (153 μL, 1.7514 mmol) and of N,N-dimethylformamide (1 drop). The mixture was stirred at 25° C. for 2 h, at which time, the solvents were concentrated in vacuo, and the residue was dried in vacuo overnight. The residue was then dissolved in benzene, the solvents were concentrated in vacuo, and the residue was dried in vacuo. This material was dissolved in methylene chloride (4 mL), cooled to 0° C., and then treated with a solution of the 2-amino-5-methoxyethoxypyrazine (148 mg, 0.8757 mmol) and pyridine (180 μL) in methylene chloride (5 mL). The ice bath was removed, and the solution was stirred at 25° C. overnight. The solvents were then concentrated in vacuo. Flash chromatography (1.5/1 hexanes/ethyl acetate) afforded the 2(R)-(3-chloro-4-methanesulfonyl-phenyl)-3-cyclopentyl-N-5-(2-methoxyethoxy-pyrazin-2-yl)-propionamide (363 mg, 86.2%) as a fluffy solid: (ES)$^+$-HRMS m/e calcd for $C_{22}H_{28}ClN_3O_5S$ (M+H)$^+$ 482.1511, observed 482.1518.

EXAMPLE 44

2(R)-(3-Chloro-4-methanesulfonyl-phenyl)-3-cyclopentyl-N-[5-2(R),3-dihydroxy-propoxy)-pyrazin-2-yl]-propionamide

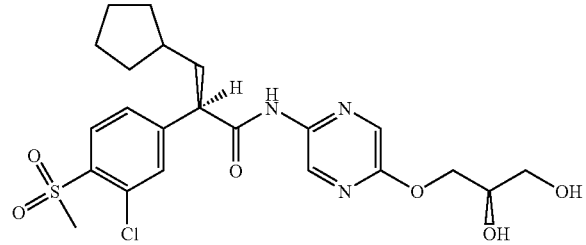

A mixture of methyl 5-chloropyrazine-2-carboxylate (1.7 g, 10 mmol) and allyl alcohol (10 mL, 147 mmol) was heated with stirring to 95° C. and then treated with pulverized potassium hydroxide (1.3 g, 23 mmol). Within 10 min, a thick paste developed. The heating was continued for 2 h. The reaction mixture was concentrated in vacuo to dryness, and the residue was further concentrated in vacuo to dryness from toluene (2×50 mL). The 5-allyloxy-pyrazine-2-carboxylic acid potassium salt (2.2 g) that was isolated was used without further purification and characterization.

The 5-allyloxy-pyrazine-2-carboxylic acid potassium salt (2.2 g, 10 mmol) was combined with diphenylphosphoryl azide (2.8 mL, 12.99 mmol) in N,N-dimethylformamide (75 mL), and the suspension was stirred at 25° C. for 18 h. The reaction mixture, which had clarified on stirring, was concentrated in vacuo, and the residue was diluted with ethyl acetate (50 mL) and water (35 mL). The aqueous phase was back-extracted with ethyl acetate (2×50 mL). The combined organic extracts were dried over sodium sulfate, filtered, and concentrated in vacuo. The residue was suspended in tert-butyl alcohol (25 mL), and the mixture was heated under reflux until no gas was observed. The solvents were then concentrated in vacuo. Flash chromatography (Merck Silica gel 60, 230–400 mesh, eluting with mixtures of ethyl acetate/hexanes) afforded 5-allyloxy-pyrazin-2-yl-carbamic acid tert-butyl ester (480 mg, 19%).

A solution of 5-allyloxy-pyrazin-2-yl-carbamic acid tert-butyl ester (400 mg, 1.59 mmol) in methylene chloride (2 mL) was treated with a 25% solution of trifluoroacetic acid in methylene chloride (5 mL). The mixture was stirred at 25° C. for 90 min, poured with stirring into a saturated aqueous sodium bicarbonate solution (50 mL) and then sodium chloride (3 g) was added. The resulting mixture was extracted with methylene chloride (3×25 mL), and each of the organic extracts was washed with a small portion of a saturated aqueous sodium chloride solution. The combined organic extracts were dried over potassium carbonate, filtered, and concentrated in vacuo to afford 5-allyloxy-pyrazin-2-ylamine (240 mg, 100%) as pale yellow crystals.

A solution of 2(R)-(3-chloro-4-methanesulfonyl-phenyl)-3-cyclopentyl-propionic acid (prepared as in Example 1, 510 mg, 1.54 mmol) in methylene chloride (15 mL) and N,N-dimethylformamide (2 drops) was cooled to 5° C. and then treated with oxalyl chloride (0.27 mL, 3.09 mmol). After stirring for 5 min, the cooling bath was removed, and the stirring continued at 25° C. for 10 min. The solvents were concentrated in vacuo, the residue was dissolved in benzene (25 mL), and the solvent was concentrated in vacuo again. The resulting acid chloride was dissolved in methylene chloride (10 mL), cooled to 5° C. and then treated with a solution of 5-allyloxy-pyrazin-2-ylamine (238 mg, 1.57 mmol) and pyridine (0.32 mL, 3.96 mmol) in methylene chloride (15 mL). The mixture was further stirred at 25° C. for 16 h. The reaction mixture was then diluted with methylene chloride (25 mL) and washed with a saturated aqueous sodium bicarbonate solution (25 mL), a 0.5M aqueous hydrochloric acid solution (25 mL), and a saturated aqueous sodium chloride solution (25 mL). Each aqueous layer was back-extracted with another portion of methylene chloride (25 mL). The combined organic phases were dried over sodium sulfate, filtered, and concentrated in vacuo. Flash chromatography (Merck Silica gel 60, 230–400 mesh, eluted with increasing concentrations of ethyl acetate/hexanes) afforded N-(5-allyloxy-pyrazin-2-yl)-2(R)-(3-chloro-4-methanesulfonyl-phenyl)-3-cyclopentyl-propionamide as a white foam (574 mg, 80%).

A mixture of potassium ferricyanide (430 mg, 1.3 mmol), potassium carbonate (180 mg, 1.3 mmol), and (DHQ)$_2$PHAL (8 mg, 0.010 mmol) was treated with a solution of water/tert-butyl alcohol (10 mL, 1:1), and the reaction mixture was stirred at 25° C. for 5 min. The reaction mixture was cooled to 0° C. and then treated with a 0.2M solution of osmium tetroxide in toluene (20 μL, 0.004 mmol) followed by a mixture of N-(5-allyloxy-pyrazin-2-yl)-2(R)(3-chloro-4-methanesulfonyl-phenyl)-3-cyclopentyl-propionamide (210 mg, 0.452 mmol) in water/tert-butyl alcohol (3 mL, 1:1). The heterogeneous mixture was stirred for 5 min, the cooling bath was removed, and the stirring continued for 2 h. The mixture was then treated while stirring with ethyl acetate (20 mL) and sodium metabisulfite (150 mg, 0.79 mmol), and the stirring continued for 30 min. The color of the reaction mixture changed from yellow to colorless, and a defined aqueous phase developed. The phases were separated, and the aqueous layer was diluted with water (25 mL) and extracted with ethyl acetate (3×50 mL). The extracts were washed with a saturated aqueous sodium chloride solution (20 mL). The combined organic phases were dried over sodium sulfate, filtered, and concentrated in vacuo. Flash chromatography (Merck Silica gel 60, 230–400 mesh, eluted with increasing concentrations of ethyl acetate/hexanes) afforded 2(R)-(3-chloro-4-methanesulfonyl-phenyl)-3-cyclopentyl-N-[5-2(R),3-dihydroxy-propoxy)-pyrazin-2-yl]-propionamide (110 mg, 49%) as a white foam: (ES)$^+$-HRMS m/e calcd for $C_{22}H_{28}ClN_3O_6S$ (M+H)$^+$ 498.1460, found 498.1462. Slightly less pure material (75 mg, 33%) was also obtained.

EXAMPLE 45

2(R)-(3-Chloro-4-methanesulfonyl-phenyl)-3-cyclopentyl-N-[5-(2,2-dimethoxy-ethyl)-pyrazin-2-yl]-propionamide

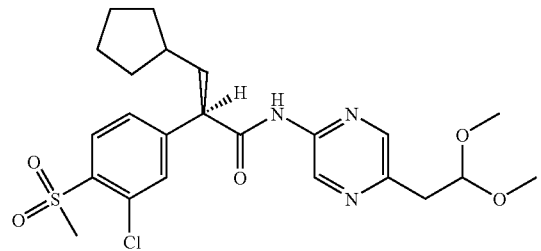

A mixture of 5-(2-oxo-ethyl)-pyrazine-2-carboxylic acid methyl ester (prepared as in Example 42, 330 mg, 1.83 mmol), p-toluenesulfonic acid monohydrate (35 mg, 0.184 mmol), trimethyl orthoformate (3 mL, 137 mmol), and methanol (10 mL) was heated under reflux for 90 min. The mixture was concentrated in vacuo to dryness, and the residue was further concentrated in vacuo to dryness from toluene (10 mL). The resulting residue was shaken with methylene chloride (25 mL) and a saturated aqueous sodium bicarbonate solution (10 mL). The aqueous phase was back-extracted with methylene chloride (10 mL). Each extract was washed with a saturated aqueous sodium chloride solution (5 mL). The combined organic layers were dried over sodium sulfate, filtered, and concentrated in vacuo to afford 5-(2,2-dimethoxy-ethyl)-pyrazine-2-carboxylic acid methyl ester (325 mg, 78%) as a yellow oil.

A mixture of 5-(2,2-dimethoxy-ethyl)-pyrazine-2-carboxylic acid methyl ester (320 mg, 1.4 mmol) in a mixture of methanol/tetrahydrofuran/water (5 mL, 3:3:1) was treated with potassium hydroxide (160 mg, 2.4 mmol). After 60 min, the solvents were concentrated in vacuo, and the residue was further concentrated to dryness from toluene (2×20 mL) to afford the salt (380 mg) as a brownish solid which was used without further purification or characterization.

A suspension of N,N-dimethylformamide (10 mL), diphenylphosphoryl azide (0.45 mL, 2.08 mmol), and 5-(2,2-dimethoxy-ethyl)-pyrazine-2-carboxylic acid potassium salt (380 mg, 1.4 mmol) was stirred at 25° C. for 18 h. The reaction mixture was concentrated in vacuo to dryness, and the residue was partitioned with ethyl acetate (50 mL) and water (25 mL). The organic layer was washed with water (25 mL), and each aqueous phase was back-extracted with another portion of ethyl acetate (25 mL). The combined organic extracts were dried over sodium sulfate, filtered, and concentrated in vacuo to afford the acyl azide as an orange oil (209 mg). The acid azide was treated with benzyl alcohol (160 μL, 1.54 mmol) and heated at 90° C. for 45 min. The reaction mixture was left on a vacuum pump (25° C., 1 mmHg) for 17 h. Flash chromatography (Merck Silica gel 60, 230–400 mesh, elution with gradient mixtures of ethyl acetate/hexanes) afforded 5-(2,2-dimethoxy-ethyl)-pyrazin-2-yl-carbamic acid benzyl ester (132 mg, 42%) as a white solid.

A solution of 5-(2,2-dimethoxy-ethyl)-pyrazin-2-yl-carbamic acid benzyl ester (130 mg, 0.4096 mmol) in methanol (5 mL) was treated with 10% palladium on activated carbon (30 mg). The reaction mixture was then hydrogenated under a hydrogen atmosphere at 25° C. and atmospheric pressure for 60 min, The mixture was filtered through celite, and the filtrate was concentrated in vacuo to afford 5-(2,2-dimethoxy-ethyl)-pyrazin-2-ylamine (75 mg, 100%) as a pale yellow oil.

A solution of 2(R)-(3-chloro-4-methanesulfonyl-phenyl)-propionic acid (prepared as in Example 1, 136 mg, 0.41 mmol) in methylene chloride (5 mL) and N,N-dimethylformamide (2 drops) was cooled to 5° C. and then treated with oxalyl chloride (75 μL, 0.86 mmol). The mixture was stirred at 5° C. for 5 min, the cooling bath was removed, and the mixture stirred an additional 10 min. The solvent was concentrated in vacuo. The residue was dissolved in benzene (10 mL), and the solvent again concentrated in vacuo. The resulting acid chloride was dissolved in methylene chloride (5 mL), cooled to 0° C., and then treated with a solution of 5-(2,2-dimethoxy-ethyl)-pyrazin-2-ylamine (75 mg, 0.41 mmol) and pyridine (85 μL, 1.05 mmol) methylene chloride (5 mL). The reaction mixture was stirred at 0° C. for 5 min, the cooling bath was removed, and the stirring was continued for 18 h. The mixture was diluted with methylene chloride (25 mL), and the solution was washed consecutively with a saturated aqueous sodium bicarbonate solution (25 mL), a 0.5M aqueous hydrochloric acid solution, and a saturated aqueous sodium chloride solution (25 mL). Each aqueous wash was back-extracted with another small portion of methylene chloride. The combined organic layers were dried over sodium sulfate, filtered, and concentrated in vacuo. Flash chromatography (Merck Silica gel 60, 230–400 mesh, eluted with 1/3 to 1/1 ethyl acetate/hexanes) afforded 2(R)-(3-chloro-4-methanesulfonyl-phenyl)-3-cyclopentyl-N-[5-(2,2-dimethoxy-ethyl)-pyrazin-2-yl]-propionamide (120 mg, 59%): (ES)⁺-HRMS m/e calcd for C₂₃H₃₀ClN₃O₅S (M+H)⁺ 496.1668, found 496.1672.

EXAMPLE 46

3-Cyclopentyl-N-5-[(4-hydroxy-tetrahydropyran-4-yl-ethynyl)pyrazin-2-yl]-2(R)-(4-methanesulfonyl-phenyl)-propionamide

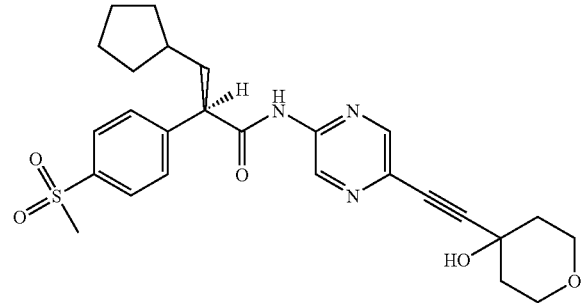

A solution of tetrahydro-4H-pyran-4-one (1.25 g, 12.5 mmol) in tetrahydrofuran (10 mL) was cooled to 0° C. and then treated with a 0.5M solution of ethylene magnesium bromide in tetrahydrofuran (40 mL, 20 mmol). The mixture was stirred at 0° C. for 2 h and at 25° C. for 4 h. The resulting mixture was cooled to 0° C. and then diluted with methanol (10 ml). The solvents were concentrated in vacuo, and the residue was extracted with a saturated aqueous ammonium chloride solution and ethyl acetate. The organic layer was washed with a saturated aqueous sodium chloride solution, dried over sodium sulfate, filtered, and concentrated in vacuo. The residue was dried in vacuo to afford solid 4-ethynyl-tetrahydro-pyran-4-ol (1.2 g, 95.2%).

A suspension of 2(R)-(4-methanesulfonyl-phenyl)-3-cyclopentyl-5-bromo-pyrazin-2-yl-propionamide (prepared as in Example 3, 452 mg, 1.0 mmol) in toluene (8 mL) was treated with N,N-diisopropylethylamine (2 mL), 4-ethynyl-tetrahydro-pyran-4-ol (252 mg, 2.0 mmol), dichlorobis(triphenylphosphine)palladium(II) (40 mg), and copper(I) iodide (20 mg). The mixture was stirred at 25° C. overnight and an oily black precipitate was obtained. The top clear solution was decanted, and the oily precipitate was first rinsed with toluene (8 ml) and then rinsed with hexanes/ethyl acetate (2×8 mL, 4:1). The residue was dissolved in methylene chloride and extracted with methylene chloride and a 0.2N aqueous hydrochloric acid solution. The organic layer was washed with a saturated aqueous sodium chloride solution, dried over sodium sulfate, filtered, and concentrated in vacuo. Flash chromatography (ethyl acetate) afforded 3-cyclopentyl-N-5-[(4-hydroxy-tetrahydropyran-4-yl-ethynyl)pyrazin-2-yl]-2(R)-(4-methanesulfonyl-phenyl)-propionamide (390 mg, 78.5%) as a fluffy solid: (ES)⁺-HRMS m/e calcd for C₂₆H₃₁N₃O₅S (M+H)⁺ 498.2057, found 498.2063.

EXAMPLE 47

2(R)-(3-Chloro-4-methanesulfonyl-phenyl)-3-cyclopentyl-N-[5-(3-methoxy-prop-1-ynyl)-pyrazin-2-yl]-propionamide

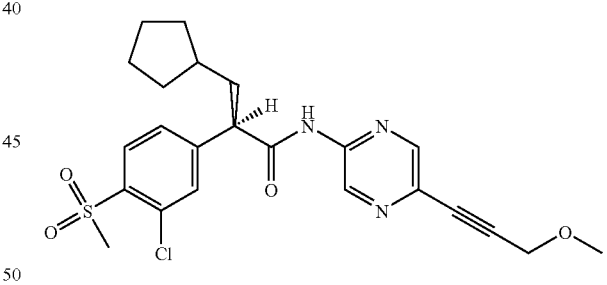

A suspension of N-(5-bromo-pyrazin-2-yl)-2(R)-(3-chloro-4-methanesulfonyl-phenyl)-3-cyclopentyl-propionamide (prepared as in Example 6, 486 mg, 1.0 mmol) in toluene (8 mL) was treated with N,N-diisopropylethylamine (2 mL), 3-methoxypropyne (350 mg, 10.0 mmol), dichlorobis(triphenylphosphine)palladium(II) (40 mg), and copper (I) iodide (20 mg). The mixture was stirred at 25° C. overnight, and an oily black precipitate was obtained. The top clear solution was decanted, and the oily precipitate was rinsed with toluene (5 mL). The residue was dissolved in methylene chloride and extracted with methylene chloride and a 0.2N aqueous hydrochloric acid solution. The organic layer was washed with a saturated aqueous sodium chloride solution, dried over sodium sulfate, filtered, and concentrated in vacuo. Flash chromatography (1/3 to 1/2 ethyl acetate/hexane) afforded 2(R)-(3-chloro-4-methanesulfonyl-phenyl)-3-cyclopentyl-N-[5-(3-methoxy-prop-1-ynyl)- pyrazin-2-yl]-propionamide (330 mg, 69.5%) as a fluffy solid: (ES)⁺-HRMS m/e calcd for $C_{23}H_{26}ClN_3O_4S$ (M+H)⁺ 476.1406, found 476.1405.

EXAMPLE 48

3-Cyclopentyl-2(R)-(4-methanesulfonyl-phenyl)-N-[5-(3-methoxyprop-1-ynyl)-pyrazin-2-yl]-propionamide

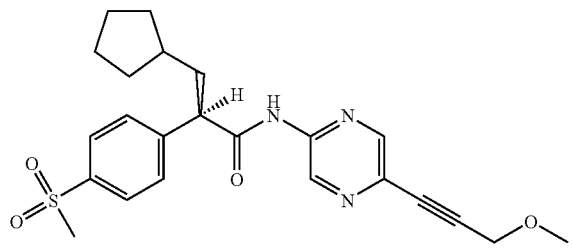

A suspension of 2(R)-(4-methanesulfonyl-phenyl)-3-cyclopentyl-5-bromo-pyrazin-2-yl-propionamide (prepared as in Example 3, 452 mg, 1.0 mmol) in toluene (8 mL) was treated with N,N-diisopropylethylamine (2 mL), 3-methoxypropyne (700 mg, 10.0 mmol), dichlorobis(triphenylphosphine)palladium(II) (40 mg), and copper(I) iodide (20 mg). The mixture was stirred at 25° C. overnight, and an oily black precipitate was obtained. The top clear solution was decanted, and the oily precipitate was first rinsed with toluene (8 mL) and then with hexanes/ethyl acetate (2×8 ml, 8:1). The residue was dissolved in methylene chloride and extracted with methylene chloride and a 0.2N aqueous hydrochloric acid solution. The organic layer was washed with a saturated aqueous sodium chloride solution, dried over sodium sulfate, filtered, and concentrated in vacuo. Flash chromatography (1/2 ethyl acetate/hexanes) afforded 3-cyclopentyl-2(R)-(4-methanesulfonyl-phenyl)-N-[5-(3-methoxyprop-1-ynyl)-pyrazin-2-yl]-propionamide (217 mg, 49.2%) as a fluffy solid: (ES)⁺-HRMS m/e calcd for $C_{23}H_{27}N_3O_4S$ (M+H)⁺ 442.1795, found 442.1800.

EXAMPLE 49

2(R)-(3-Chloro-4-methanesulfonyl-phenyl)-3-cyclopentyl-N-[5-(2(S),3-dihydroxy-propoxy)-pyrazin-2-yl]-propionamide

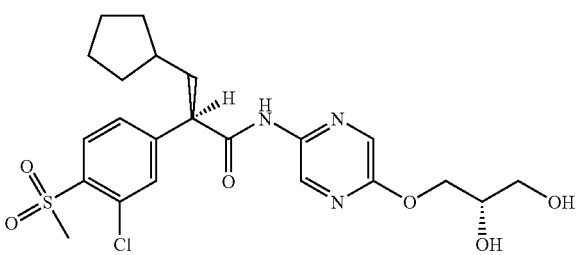

A mixture of potassium ferricyanide (430 mg, 1.3 mmol), potassium carbonate (180 mg, 1.3 mmol), and (DHQD)₂PHAL (8 mg, 0.010 mmol) was treated with a solution of water/tert-butyl alcohol (10 mL, 1:1), and the reaction mixture was stirred at 25° C. for 5 min. The reaction mixture was cooled to 0° C. and then treated with a 0.2M solution of osmium tetroxide in toluene (20 μL, 0.004 mmol) followed by a mixture of N-(5-allyloxy-pyrazin-2-yl)-2(R)(3-chloro-4-methanesulfonyl-phenyl)-3-cyclopentyl-propionamide (prepared as in Example 44, 210 mg, 0.452 mmol) in water/tert-butyl alcohol (3 mL, 1:1). The heterogeneous mixture was stirred for 5 min, the cooling bath was removed, and the stirring continued for 2 h. The mixture was then treated while stirring with ethyl acetate (20 mL) and sodium metabisulfite (150 mg, 0.79 mmol), and the stirring continued for 30 min. The color of the reaction mixture changed from yellow to colorless, and a defined aqueous phase developed. The phases were separated, and the aqueous layer was diluted with water (25 mL) and extracted with ethyl acetate (3×50 mL). The extracts were washed with a saturated aqueous sodium chloride solution (20 mL). The combined organic phases were dried over sodium sulfate, filtered, and concentrated in vacuo. Flash chromatography (Merck Silica gel 60, 230–400 mesh, eluted with increasing concentrations of ethyl acetate/hexanes) afforded impure 2(R)-(3-chloro-4-methanesulfonyl-phenyl)-3-cyclopentyl-N-[5-2(S),3-dihydroxy-propoxy)-pyrazin-2-yl]-propionamide (80 mg) as a white foam. Re-purification under the same conditions afforded pure 2(R)-(3-chloro-4-methanesulfonyl-phenyl)-3-cyclopentyl-N-[5-2(S),3-dihydroxy-propoxy)-pyrazin-2-yl]-propionamide (40 mg, 18.6%) as a colorless foam: (ES)⁺-HRMS m/e calcd for $C_{22}H_{28}ClN_3O_6S$ (M+H)⁺ 498.1460, found 498.1468.

EXAMPLE 50

2(R)-(3-Chloro-4-methanesulfonyl-phenyl)-3-cyclopentyl-N-[5-(4-hydroxy-tetrahydropyran-4-yl-ethynyl)-pyrazin-2-yl]-propionamide

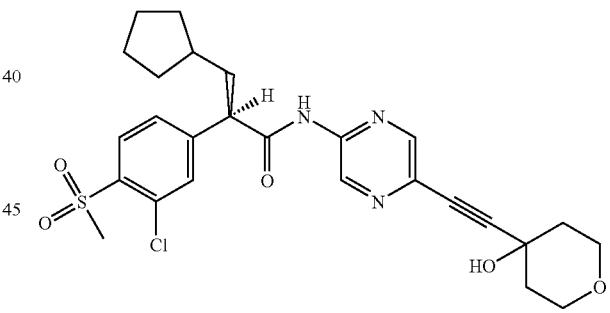

A suspension of N-(5-bromo-pyrazin-2-yl)-2(R)-(3-chloro-4-methanesulfonyl-phenyl)-3-cyclopentyl-propionamide (prepared as in Example 6, 486 mg, 1.0 mmol) in toluene (8 mL) was treated with N,N-diisopropylethylamine (2 mL), 4-ethynyl-tetrahydropyran-4-ol (prepared as in Example 46, 252 mg, 2.0 mmol), copper(I) iodide (20 mg), and dichlorobis(triphenylphosphine)palladium(II) (40 mg). The mixture was stirred at 25° C. overnight, and an oily black precipitate was obtained. The top clear solution was decanted, and the oily precipitate was rinsed first with toluene (5 mL) and then with hexanes (5 mL). The residue was dissolved in methylene chloride and extracted with methylene chloride and a 0.2N aqueous hydrochloric acid solution. The organic layer was washed with a saturated aqueous sodium chloride solution, dried over sodium sulfate, filtered, and concentrated in vacuo. Flash chromatography (Merck Silica gel 60, 230–400 mesh, 2/1 ethyl acetate/ hexanes) afforded 2(R)-(3-chloro-4-methanesulfonyl-phenyl)-3-cyclopentyl-N-[5-(4-hydroxy-tetrahydropyran-4-yl-ethynyl)-pyrazin-2-yl]-propionamide (474 mg, 89.30%) as a fluffy solid: (ES)$^+$-HRMS m/e calcd for $C_{23}H_{30}ClN_3O_4S$ (M+H)$^+$ 532.1668, found 532.1675.

EXAMPLE 51

2(R)-(3-Chloro-4-methanesulfonyl-phenyl)-3-cyclopentyl-N-[5-(4-hydroxy-tetrahydropyran-4-yl-ethyl)-pyrazin-2-yl]-propionamide

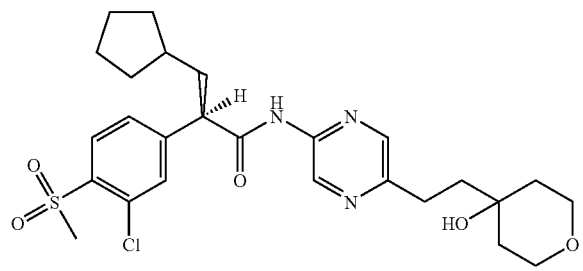

A solution of 2(R)-(3-chloro-4-methanesulfonyl-phenyl)-3-cyclopentyl-N-[5-(4-hydroxy-tetrahydropyran-4-yl-ethynyl)-pyrazin-2-yl]-propionamide (prepared as in Example 50, 200 mg, 0.376 mmol) in methanol (30 mL) was treated with 10% palladium on activated carbon (39 mg). The reaction mixture was then placed on a Parr shaker under a hydrogen atomsphere of 50 psi for 4 h. The mixture was filtered, and solvents were concentrated in vacuo. Flash chromatography (Merck Silica gel 60, 230–400 mesh, ethyl acetate) afforded 2(R)-(3-chloro-4-methanesulfonyl-phenyl)-3-cyclopentyl-N-[5-(4-hydroxy-tetrahydropyran-4-yl-ethyl)-pyrazin-2-yl]-propionamide (169 mg, 84%) as a fluffy solid: (ES)$^+$-HRMS m/e calcd for $C_{26}H_{34}ClN_3O_5S$ (M+H)$^+$ 536.1981, found 536.1988.

EXAMPLE 52

2(R)-(3-Chloro-4-methanesulfonyl-phenyl)-3-cyclopentyl-N-[5-(3-hydroxy-3-methyl-but-1-ynyl)-pyrazin-2-yl]-propionamide

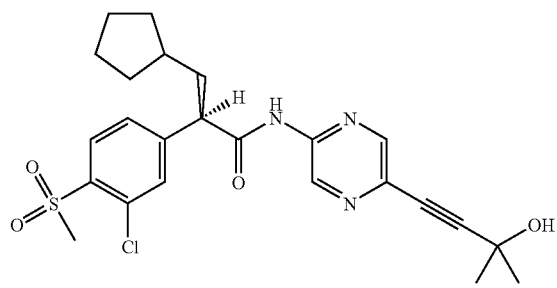

A suspension of N-(5-bromo-pyrazin-2-yl)-2(R)-(3-chloro-4-methanesulfonyl-phenyl)-3-cyclopentyl-propionamide (prepared as in Example 6, 486 mg, 1.0 mmol) in toluene (8 mL) was treated with N,N-diisopropylethylamine (2 mL), 3-hydroxy-3-methylbutyne (168 mg, 2.0 mmol), dichlorobis(triphenylphosphine)palladium(II) (40 mg), and copper(I) iodide (20 mg). The mixture was stirred at 25° C. overnight, and an oily black precipitate was obtained. The top clear solution was decanted, and the oily precipitate was rinsed first with toluene (5 mL) and then with hexanes (5 mL). The residue was dissolved in methylene chloride and extracted with methylene chloride and a 0.2N aqueous hydrochloric acid solution. The organic layer was washed with a saturated aqueous sodium chloride solution, dried over sodium sulfate, filtered, and concentrated in vacuo. Flash chromatography (Merck Silica gel 60, 230–400 mesh, elution with 1/1 ethyl acetate/hexanes) afforded 2(R)-(3-chloro-4-methanesulfonyl-phenyl)-3-cyclopentyl-N-[5-(3-hydroxy-3-methyl-but-1-ynyl)-pyrazin-2-yl]-propionamide (412 mg, 84%) as a fluffy solid: (ES)$^+$-HRMS m/e calcd for $C_{24}H_{28}ClN_3O_4S$ (M+H)$^+$ 490.1562, found 490.1553.

EXAMPLE 53

2(R)-(3-Chloro-4-methanesulfonyl-phenyl)-3-cyclopentyl-N-[5-(4-hydroxy-but-1-ynyl)-pyrazin-2-yl]-propionamide

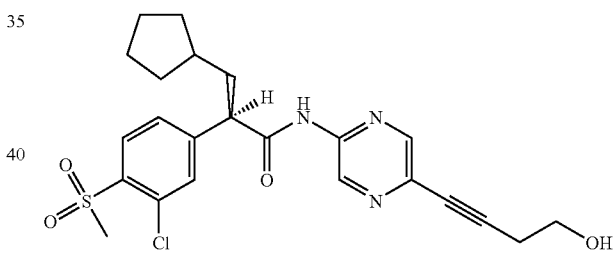

A suspension of N-(5-bromo-pyrazin-2-yl)-2(R)-(3-chloro-4-methanesulfonyl-phenyl)-3-cyclopentyl-propionamide (prepared as in Example 6, 729 mg, 1.5 mmol) in toluene (8 mL) was treated with N,N-diisopropylethylamine (2 mL), 4-hydroxybutyne (210 mg, 3.0 mmol), dichlorobis(triphenylphosphine)palladium(II) (60 mg), and copper(I) iodide (30 mg). The mixture was stirred at 25° C. overnight, and an oily black precipitate was obtained. The top clear solution was decanted, and the oily precipitate was rinsed first with toluene (5 mL) and then with hexanes (5 mL). The residue was dissolved in methylene chloride and extracted with methylene chloride and a 0.2N aqueous hydrochloric acid solution. The organic layer was washed with a saturated aqueous sodium chloride solution, dried over sodium sulfate, filtered, and concentrated in vacuo. Flash chromatography (Merck Silica gel 60, 230–400 mesh, elution with 1/1 ethyl acetate/hexanes) afforded 2(R)-(3-chloro-4-methanesulfonyl-phenyl)-3-cyclopentyl-N-[5-(4-hydroxy-but-1-ynyl)-pyrazin-2-yl]-propionamide (650 mg, 88.4%) as a fluffy solid: (ES)$^+$-HRMS m/e calcd for $C_{23}H_{26}ClN_3O_4S$ (M+H)$^+$ 476.1406, found 476.1395.

EXAMPLE 54

2(R)-(3-Chloro-4-methanesulfonyl-phenyl)-3-cyclopentyl-N-[5-(1(S),2-dihydroxy-ethyl)-pyrazin-2-yl]-propionamide

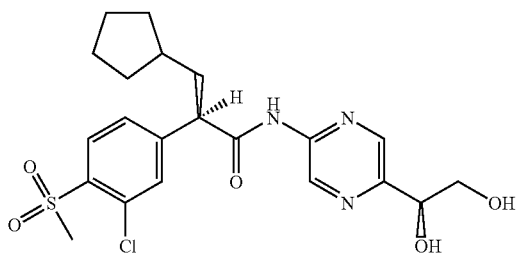

This compound was prepared through a linear synthesis (Method A) and a convergent synthesis (Method B).

Method A:

A solution of 2-amino-5-bromopyrazine (500 mg, 2.87 mmol) in N,N-dimethylformamide (15 mL) was treated with tetrakis(triphenylphosphine)palladium(0) (66 mg, 0.06 mmol), N,N-diisopropylethylamine (1.25 mL, 7.18 mmol), lithium chloride (426 mg, 0.06 mmol), and vinyltri-n-butyltin (840 µL, 2.87 mmol), and the reaction was heated at 120° C. for 4 h. After such time, the reaction was cooled to 25° C., treated with a saturated aqueous potassium fluoride solution (10 mL), and stirred at 25° C. overnight for 16 h. The solution was then diluted with methylene chloride (25 mL) and extracted with methylene chloride (3×15 mL). The combined organic layers were dried over sodium sulfate, filtered, and concentrated in vacuo. Biotage chromatography (FLASH 40S, Silica, 2/3 to 1/4 hexanes/ethyl acetate) afforded 2-amino-5-vinylpyrazine (211 mg, 61%) as a light yellow solid: EI-HRMS m/e calcd for $C_6H_7N_3$ $(M^+)$ 121.0640, found 121.0642.

A solution of 2(R)-(3-chloro-4-methanesulfonyl-phenyl)-3-cyclopentyl-propionic acid (prepared as in Example 1, 470 mg, 1.42 mmol) in methylene chloride (7 mL) was cooled to 0° C. and then was treated with a 2.0M solution of oxalyl chloride in methylene chloride (817 µL, 1.63 mmol) and N,N-dimethylformamide (1 mL). The reaction mixture was stirred at 0° C. for 30 min, concentrated in vacuo, and azeotroped with methylene chloride (3×2 mL). The resulting oil was then dissolved in tetrahydrofuran (10 mL) at 25° C. and then treated dropwise with a solution of 2-amino-5-vinylpyrazine (207 mg, 1.71 mmol) and 2,6-lutidine (198 µL, 1.71 mmol) in tetrahydrofuran (8 mL) via an addition funnel. The resulting cloudy solution was then stirred 25° C. overnight for 16 h. After this time, the reaction was diluted with water (10 mL) and then extracted with methylene chloride (3×25 mL). The combined organic layers were dried over sodium sulfate, filtered, and concentrated in vacuo. Biotage chromatography (FLASH 40S, Silica, 65/35 to 20/80 hexanes/ethyl acetate) afforded the 2(R)-(3-chloro-4-methanesulfonyl-phenyl)-3-cyclopentyl-N-(5-vinyl-pyrazin-2-yl)-propionamide (472 mg, 77%) as a light yellow solid: $(ES)^+$-HRMS m/e calcd for $C_{21}H_{24}ClN_3O_3S$ $(M+H)^+$ 434.1300, found 434.1301.

A mixture of potassium ferricyanide (375 mg, 1.14 mmol), potassium carbonate (160 mg, 1.16 mmol), and $(DHQ)_2PHAL$ (7 mg, 0.00898 mmol) was treated with a solution of water/tert-butyl alcohol (10 mL, 1:1) and stirred at 25° C. for 5 min. The reaction mixture was cooled to 0° C. and then treated with a 0.2M solution of osmium tetroxide in toluene (17 µL, 0.0034 mmol) followed by a mixture of 2(R)-(3-chloro-4-methanesulfonyl-phenyl)-3-cyclopentyl-N-(5-vinyl-pyrazin-2-yl)-propionamide (175 mg, 0.374 mmol) in water/tert-butyl alcohol (2 mL, 1:1). The heterogeneous mixture was stirred for 10 min, and the cooling bath was removed. After 30 min, there was still undissolved vinyl substrate and an additional amount of tert-butyl alcohol (2 mL) was added to the reaction mixture. The stirring was continued for 18 h. The mixture was then treated while stirring with ethyl acetate (20 mL) and sodium metabisulfite (150 mg, 0.79 mmol), and the stirring continued for 15 min. The phases were separated, and the organic layer was washed with a saturated aqueous sodium chloride solution (2×25 mL). Each aqueous phase was back-extracted with ethyl acetate (25 mL). The combined organic layers were dried over sodium sulfate, filtered, and concentrated in vacuo. Flash chromatography (Merck Silica gel 60, 230–400 mesh, 1/3 to 1/1 ethyl acetate/hexanes) afforded the 2(R)-(3-chloro-4-methanesulfonyl-phenyl)-3-cyclopentyl-N-[5-(1(S),2-dihydroxy-ethyl)-pyrazin-2-yl]-propionamide (50 mg) as a colorless foam: $(ES)^+$-HRMS m/e calcd for $C_{21}H_{26}ClN_3O_5S$ $(M+H)^+$ 468.1355, found 468.1360.

Method B:

A solution of 2-amino-5-bromopyrazine (10.00 g, 57.47 mmol) and pyridine (5.6 mL, 68.96 mmol) in methylene chloride (144 mL) was cooled to 0° C. and then was treated slowly with trimethylacetyl chloride (8.6 mL, 68.96 mmol). The resulting reaction mixture was stirred at 0° C. for 30 min and then was allowed to warm to 25° C. where it was stirred for 18 h. At this time, the reaction mixture still contained the starting material 2-amino-5-bromopyrazine. The reaction mixture was treated with an additional amount of trimethylacetyl chloride (4.3 mL, 34.48 mmol) and then stirred at 25° C. for 4 h. The reaction mixture was then concentrated in vacuo to remove methylene chloride. The resulting residue was diluted with ethyl acetate (700 mL). The organic layer was washed with a 1N aqueous hydrochloric acid solution (2×200 mL) and a saturated aqueous sodium chloride solution (1×200 mL), dried over sodium sulfate, filtered, and concentrated in vacuo. Biotage chromatography (FLASH 65M, Silica, 1/9 ethyl acetate/hexanes) afforded N-(5-bromo-pyrazin-2-yl)-2,2-dimethyl-propionamide (12.19 g, 82%) as a white solid: mp 122–124° C.; $(ES)^+$-HRMS m/e calcd for $C_9H_{12}BrN_3O$ $(M+H)^+$ 258.0237, found 258.0240.

A mixture of N-(5-bromo-pyrazin-2-yl)-2,2-dimethyl-propionamide (29.67 g, 114.9421 mmol), dichloro[1,1'-bis(diphenylphosphino)ferro-cene]palladium(II) dichloromethane adduct (0.95 g, 1.1633 mmol), triethylamine (17.6 mL, 126.2733 mmol), and potassium vinyltrifluoroborate (19.25 g, 143.7103 mmol) in ethanol (245 mL) was heated at 100° C. for 90 min. At this time, the reaction mixture was allowed to cool to 25° C. and then was concentrated in vacuo. The resulting orange slurry was diluted with methylene chloride (200 mL). The organic layer was washed with a 1N aqueous hydrochloric acid solution (2×200 mL), a saturated aqueous sodium bicarbonate solution (1×200 mL), and a saturated aqueous sodium chloride solution (1×200 mL). The combined aqueous layers were back-extrated with methylene chloride (1×200 mL). The combined organic layers were dried over magnesium chloride and decolorizing carbon, filtered, and concentrated in vacuo. Biotage chromatography (FLASH 75S, Silica, 100% hexanes to 10% ethyl acetate/hexanes) afforded 2,2-dimethyl-N-(5-vinyl-pyrazin-2-yl)-propionamide (21.64 g, 92%) as an off-white solid: mp 80.4–81.8° C.; EI-HRMS m/e calcd for $C_{11}H_{15}N_3O$ (M$^+$) 205.1215, found 205.1214.

A mixture of potassium ferricyanide (148.74 g, 450 mmol), potassium carbonate (62.25 g, 450 mmol), and (DHQ)$_2$PHAL (2.6 g, 3.34 mmol) was treated with a solution of water/tert-butyl alcohol (2 L, 1:1), and the reaction mixture was stirred at 25° C. for 15 min. The reaction mixture was cooled to 5° C., treated with a 0.2M solution of osmium tetroxide in toluene (7.5 mL, 1.5 mmol), and then treated with 2,2-dimethyl-N-(5-vinyl-pyrazin-2-yl)-propionamide (30.8 g, 150 mmol) which was partially dissolved in water/tert-butyl alcohol (150 mL, 1:1). The mixture was stirred at 4–5° C. for 18 h using a Neslab Endocal cooling system to control the temperature. While stirring at 4–5° C., the mixture was then slowly treated with sodium metabisulfite (35 g, 184 mmol) which resulted in effervescence. The cooling bath was removed, and the stirring continued for 15 min. The layers were separated, and the aqueous layer was extracted with ethyl acetate (600 mL). Each organic layer was washed with a saturated aqueous sodium chloride solution (500 mL). The combined organic layers were dried over sodium sulfate, filtered, and concentrated in vacuo to afford N-[5-(1(S),2-dihydroxy-ethyl)-pyrazin-2-yl]-2,2-dimethyl-propionamide (46 g, 100%) as a red oil which was used without further purification.

A solution of N-[5-(1(S),2-dihydroxy-ethyl)-pyrazin-2-yl]-2,2-dimethyl-propionamide (46 g slightly wet with solvent, ~170 mmol) in tetrahydrofuran (275 mL) was treated with 2,2-dimethoxypropane (225 mL, 1.88 mol) and p-toluenesulfonic acid monohydrate (3.4 g, 17.9 mmol). The reaction mixture was stirred at 25° C. for 16.5 h, at which time, thin layer chromatography showed that the reaction was complete to form a less polar product. The reaction mixture was concentrated in vacuo, and the residue was dissolved in methylene chloride (600 mL). The organic layer was washed with a saturated aqueous sodium chloride solution (250 mL) and a saturated aqueous sodium bicarbonate solution (250 mL). Each aqueous layer was back-extracted with methylene chloride (250 mL). The combined organic layers were stirred with sodium sulfate (35 mg) and Norit A Charcoal (8 g) and then filtered through a pad of celite. The filtrate was concentrated in vacuo to a weight of about 250 g. The material was treated with diethyl ether (300 mL), and the mixture again was concentrated in vacuo to a weight of about 350 g, at which time, crystallization began. The mixture was stored in a refrigerator (4° C.) for 4 h and filtered. The solids were dried in a vacuum oven at 30° C. for 16 h to afford white crystals (32.3 g, 68%), mp 144–144.5° C. Collection of an additional crop from the mother liquor afforded white crystals (9.5 g, 20%) which were comparable in purity to the first crop. High-performance liquid chromatography analysis with a chiral column indicated both crops were 100% ee as compared to an authentic racemate sample. The two crops were combined to afford the desired N-[5-((S)-2,2-dimethyl-[1,3]dioxolan-4-yl)-pyrazin-2-yl]-2,2-dimethyl-propionamide.

A mixture of N-[5-((S)-2,2-dimethyl-[1,3]dioxolan-4-yl)-pyrazin-2-yl]-2,2-dimethyl-propionamide (8.4 g, 30.7 mmol) and potassium carbonate (4.32 g, 31.2 mmol) in methanol (150 mL) was stirred at 25° C. for 16.5 h, at which time, thin layer chromatography suggested partial conversion to a more polar product. In an effort to avoid epimerization at the stereogenic center, the reaction was discontinued before completion. Therefore, the solvent was removed under reduced pressure at 25° C. The resulting residue was again concentrated in vacuo from ethyl acetate (50 mL). The material was purified using Biotage chromatography (FLASH 40L, Silica, ethyl acetate). The early fractions collected allowed for the recovery of unreacted starting pivaloylamide as a white solid (2.0 g, 24%). The later fractions were concentrated in vacuo to provide 5-((S)-2,2-dimethyl-[1,3]dioxolan-4-yl)-pyrazin-2-ylamine (3.7 g, 63%) as a pale yellow oil. High-performance liquid chromatography analysis with a chiral column indicated 100% ee.

A solution of 2(R)-(3-chloro-4-methanesulfonyl-phenyl)-3-cyclopentyl-propionic acid (prepared as in Example 1, 6.29 g, 19.01 mmol) and N,N-dimethylformamide (2 drops) in methylene chloride (70 mL) was stirred at 2° C. and then treated with oxalyl chloride (4.15 mL, 45.7 mmol). The mixture was stirred at 2° C. for 5 min and at 25° C. for 15 min. The reaction mixture was then concentrated in vacuo. The residue was dissolved in benzene (25 mL), and the evaporation was repeated. The resulting acid chloride was dissolved in methylene chloride (40 mL), cooled to 0° C., and then treated with a solution composed of 5-((S)-2,2-dimethyl-[1,3]dioxolan-4-yl)-pyrazin-2-ylamine (3.65 g, 18.95 mmol), pyridine (4.6 mL, 56.9 mmol) and methylene chloride (40 mL). The mixture was stirred for 16 h without replenishing the cooling bath. The reaction mixture was then treated with a 1N aqueous hydrochloric acid solution (100 mL). The layers were separated, and the aqueous layer was extracted with methylene chloride (75 mL). The organic layers were washed with a saturated aqueous sodium bicarbonate solution (100 mL) and a saturated aqueous sodium chloride solution. The combined organic layers were dried over sodium sulfate, filtered, and concentrated in vacuo. Biotage chromatography (FLASH 40L, Silica, 1/1 ethyl acetate/hexanes) afforded 2(R)-(3-chloro-4-methanesulfonyl-phenyl)-3-cyclopentyl-N-[5-((S)-2,2-dimethyl-[1,3]dioxolan-4-yl)-pyrazin-2-yl]-propionamide (8.9 g, 92%) as a white foam: (ES)$^+$-HRMS m/e calcd for $C_{24}H_{30}ClN_3O_5S$ (M+H)$^+$ 508.1668, found 508.1671.

A solution of 2(R)-(3-chloro-4-methanesulfonyl-phenyl)-3-cyclopentyl-N-[5-((S)-2,2-dimethyl-[1,3]dioxolan-4-yl)-pyrazin-2-yl]-propionamide (8.85 g, 17.4 mmol) in tetrahydrofuran (50 mL) was treated with a 1N aqueous hydrochloric acid solution (50 mL). The resulting milky reaction mixture was stirred at 25° C., and within 15 min, the milky reaction mixture became clear. The stirring was continued at 25° C. for 16 h. The reaction was concentrated in vacuo, and the residue was extracted with methylene chloride (1×100 mL then 2×50 mL). Each organic extract was washed with a saturated aqueous sodium bicarbonate solution (50 mL) and a saturated aqueous sodium chloride solution (50 mL). The combined organic layers were dried over sodium sulfate, filtered, and concentrated in vacuo. Biotage chromatography (FLASH 40L, Silica, 1/1 ethyl acetate/hexanes then 100% ethyl acetate) afforded 2(R)-(3-chloro-4-methanesulfonyl-phenyl)-3-cyclopentyl-N-[5-(1(S),2-dihydroxy-ethyl)-pyrazin-2-yl]-propionamide (7.15 g, 88%) as a colorless foam: (ES)$^+$-HRMS m/e calcd for $C_{21}H_{26}ClN_3O_5S$ (M+H)$^+$ 468.1355, found 468.1360.

EXAMPLE 55

2(R)-(3-Chloro-4-methanesulfonyl-phenyl)-3-cyclopentyl-N-[5-1(R),2-dihydroxy-ethyl)-pyrazin-2-yl]-propionamide

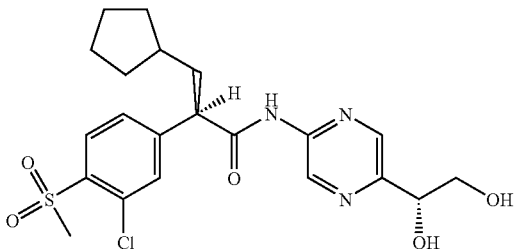

A mixture of potassium ferricyanide (365 mg, 1.10 mmol), potassium carbonate (155 mg, 1.12 mmol), and (DHQD)$_2$PHAL (7 mg, 0.00898 mmol) was treated with a solution of water/tert-butyl alcohol (10 mL, 1:1), and the reaction mixture was stirred at 25° C. for 5 min. The reaction mixture was cooled to 0° C. and then treated with a 0.2M solution of osmium tetroxide in toluene (17 μL, 0.0034 mmol) followed by a mixture of 2(R)-(3-chloro-4-methanesulfonyl-phenyl)-3-cyclopentyl-N-(5-vinyl-pyrazin-2-yl)-propionamide (prepared as in Example 54, 175 mg, 0.374 mmol) in water/tert-butyl alcohol (2 mL, 1:1). The heterogeneous mixture was stirred for 10 min, the cooling bath was removed, and the stirring was continued for 18 h. The mixture was then treated while stirring with ethyl acetate (20 mL) and sodium metabisulfite (150 mg, 0.79 mmol), and the stirring continued for 15 min. The phases were separated, and the organic layer was washed with a saturated aqueous sodium chloride solution (2×25 mL). Each aqueous phase was back-extracted with ethyl acetate (25 mL). The combined organic layers were dried over sodium sulfate, filtered, and concentrated in vacuo. Flash chromatography (Merck Silica gel 60, 230–400 mesh, 1/3 ethyl acetate/hexanes to 100% ethyl acetate) afforded the 2(R)-(3-chloro-4-methanesulfonyl-phenyl)-3-cyclopentyl-N-[5-(1(S),2-dihydroxy-ethyl)-pyrazin-2-yl]-propionamide (65 mg) as a colorless foam: (ES)$^+$-HRMS m/e calcd for $C_{21}H_{26}ClN_3O_5S$ (M+H)$^+$ 468.1355, found 468.1359.

EXAMPLE 56

2(R)-(3-Chloro-4-methanesulfonyl-phenyl)-3-cyclopentyl-N-[5-(2-hydroxy-1-hydroxymethyl-ethoxy)-pyrazin-2-yl]-propionamide

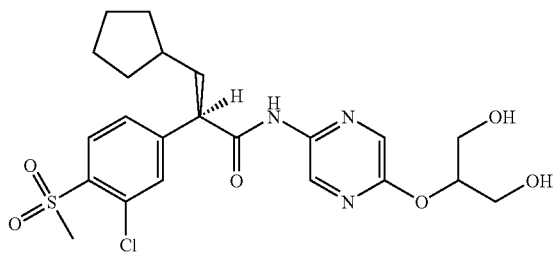

A suspension of 5-chloro-pyrazine-2-carboxylic acid (prepared as in Example 29, 1.00 g, 6.33 mmol) in methylene chloride (30 mL) was treated with 1,3-dibenzyloxy-2-propanol (2.06 g, 7.57 mmol), bis(2-oxo-3-oxazolidinyl)phosphinic chloride (1.61 g, 6.34 mmol), and triethylamine (1.83 mL, 12.66 mmol). The mixture was stirred at 25° C. overnight. The solution was extracted with methylene chloride and a saturated aqueous sodium bicarbonate solution. The organic layer was washed with water, a saturated aqueous sodium chloride solution, a 1N aqueous hydrochloric acid solution, and a saturated aqueous sodium chloride solution. The organic layer was dried over sodium sulfate, filtered, and concentrated in vacuo. Biotage chromatography (FLASH 40L, Silica, 3/1 hexanes/ethyl acetate) afforded the 5-chloropyrazine-2-carboxylic acid 2-benzyloxy-1-benzyloxymethyl-ethyl ester (1.45 g, 55.7%) as a colorless oil.

A solution of 1,3-dibenzyloxy-2-propanol (2.815 g, 10.35 mmol) in dry tetrahydrofuran (30 mL) was treated with sodium hydride (60% dispersion in mineral oil, 0.345 g, 8.62 mmol). The solution was stirred at 0° C. for 10 min and then at 25° C. for 2 h. The reaction mixture was then treated with a solution of 5-chloropyrazine-2-carboxylic acid 2-benzyloxy-1-benzyloxymethyl-ethyl ester (1.43 g, 3.45 mmol) in dry tetrahydrofuran (10 mL). The mixture was stirred at 25° C. for 1 h and then heated under reflux for 2 h. The reaction mixture was concentrated in vacuo, and the residue was suspended in water (30 mL) and a 1N aqueous sodium hydroxide solution (5 mL). This mixture was heated to 80° C. where it was stirred for 3 h, at which time, thin layer chromatography indicated incomplete hydrolysis so additional tetrahydrofuran (10 mL) and methanol (10 mL). The mixture was heated under reflux for 6 h until all the ester was hydrolyzed. The reaction mixture was concentrated in vacuo, and the residue was suspended in water (100 mL). The mixture was extracted with diethyl ether. The aqueous layer was acidified with a 1N aqueous hydrochloric acid solution and extracted with diethyl ether. The organic layer was concentrated in vacuo to afford 5-[(2-benzyloxy-1-benzyloxymethyl)-ethoxy-pyrazine]-2-carboxylic acid (440 mg, 32%) as as an oil.

A solution of 5-[(2-benzyloxy-1-benzyloxymethyl)-ethoxy-pyrazine]-2-carboxylic acid (0.44 g, 1.11 mmol) in tert-butyl alcohol (5 mL) was treated with diphenylphosphoryl azide (0.24 ml, 1.11 mmol) and triethylamine (0.16 ml, 1.11 mmol). The reaction mixture was stirred at 25° C. for 30 min and then under reflux for 5 h. The reaction mixture was then concentrated in vacuo, and the residue was extracted with methylene chloride and a 0.1N aqueous hydrochloric acid solution. The organic layer was washed with a saturated aqueous sodium chloride solution and a saturated aqueous sodium bicarbonate solution and then concentrated in vacuo. Biotage chromatography (FLASH 40S, Silica, 4/1 hexanes/ethyl acetate) afforded [5-(2-benzyloxy-1-benzyloxymethyl-ethoxy)-pyrazin-2-yl]-carbamic acid tert-butyl ester (163.2 mg, 31.4%) as a pale yellow oil.

A solution of [5-(2-benzyloxy-1-benzyloxymethyl-ethoxy)-pyrazin-2-yl]-carbamic acid tert-butyl ester (163 mg) in methylene chloride (4 mL) was treated with trifluoroacetic acid (1 mL). The mixture was stirred at 25° C. overnight and then concentrated in vacuo. The residue was extracted with methylene chloride and a saturated aqueous sodium bicarbonate solution. The organic layer was dried over sodium sulfate, filtered, and concentrated in vacuo to afford 2-amino-5-[(2-benzyloxy-1-benzyloxymethyl)-ethoxy]-pyrazine as an oil (111 mg).

A solution of 2(R)-(3-chloro-4-methanesulfonyl-phenyl)-3-cyclopentyl-propionic acid (prepared as in Example 1, 101 mg, 0.3061 mmol) in methylene chloride (3 mL) was treated with oxalyl chloride (55 µL, 0.6122 mmol) and N,N-dimethylformamide (1 drop). The mixture was stirred at 25° C. for 2 h and then concentrated in vacuo. The residue was dried in vacuo overnight. The residue was then dissolved in benzene, and the solvents were concentrated in vacuo. The resulting residue was dried in vacuo. This material was dissolved in methylene chloride (4 mL), cooled to 0° C., and then treated with a solution of 2-amino-5-[(2-benzyloxy-1-benzyloxymethyl)-ethoxy]-pyrazine (111 mg, 0.3041 mmol) and pyridine (50 µL) in methylene chloride (2 mL). The ice bath was removed, and the solution was stirred at 25° C. overnight. The mixture was extracted with methylene chloride and a 0.2N aqueous hydrochloric acid solution. The organic layer was washed with a saturated aqueous sodium chloride solution, dried over sodium sulfate, filtered, and concentrated in vacuo. Biotage chromatography (FLASH, 40S, Silica, 2/1 hexanes/ethyl acetate) afforded N-[5-(2-benzyloxy-1-benzyloxymethyl)ethoxy-pyrazin-2-yl]-2(R)-(3-chloro-4-methanesulfonyl-phenyl)-3-cyclopentyl-propionamide (179.3 mg, 87%) as an oil.

A solution of N-[5-(2-benzyloxy-1-benzyloxymethyl)ethoxy-pyrazin-2-yl]-2(R)-(3-chloro-4-methanesulfonyl-phenyl)-3-cyclopentyl-propionamide (179 mg) in methanol (30 mL) and tetrahydrofuran (2 mL) was treated with 10% palladium on activated carbon (105 mg). The reaction mixture was then placed on a Parr shaker under a hydrogen atomsphere of 50 psi for 5 h until all the starting material was consumed. LC-MS indicated the desired product and the dechlorinated side product (5:1 ratio). The best condition for thin layer chromatography separation of the two compounds was ethyl acetate/hexanes/isopropanol (20:5:1) with Rf values of 0.27 and 0.21. The crude material was purified using high-performance liquid chromatography (diol column using a linear gradient of 40% to 90% of ethyl acetate in hexanes within 20 min). The first compound eluted afforded 2(R)-(3-chloro-4-methanesulfonyl-phenyl)-3-cyclopentyl-N-[5-(2-hydroxy-1-hydroxymethyl-ethoxy)-pyrazin-2-yl]-propionamide (45 mg) as a colorless foam: (ES)$^+$-HRMS m/e calcd for $C_{22}H_{28}ClN_3O_6S$ $(M+H)^+$ 498.1460, found 498.1451.

EXAMPLE 57

3-Cyclopentyl-N-[5-(3-hydroxy-3-methyl-but-1-ynyl)-pyrazin-2-yl]-2(R)-(4-methanesulfonyl-3-methyl-phenyl)-propionamide

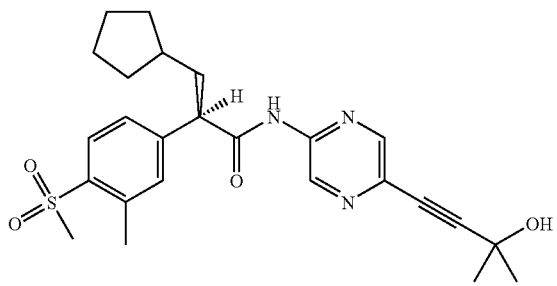

A solution of o-thiocresol (5 g, 40 mmol) in acetone (50 mL) was treated with potassium carbonate (22 g, 159 mmol) followed by iodomethane (16 mL, 257 mmol). An exotherm ensued that raised the temperature (~38–40° C.). The resulting reaction mixture was stirred at 25° C. for 17 h. The reaction mixture was concentrated in vacuo, and the residue was shaken with methylene chloride (100 mL) and a saturated aqueous sodium chloride solution (50 mL). The aqueous phase was back-extracted with methylene chloride (50 mL). Each organic phase was washed again with a saturated aqueous sodium chloride solution (25 mL). The combined organic layers were dried over magnesium sulfate, filtered, and concentrated in vacuo to afford 1-methyl-2-thiomethyl-benzene (5.5 g, 100%) as a pale yellow oil.

A suspension of aluminum chloride (7 g, 52.5 mmol) in methylene chloride (25 mL) was cooled to 3° C. Separately, the neat liquid 1-methyl-2-thiomethyl-benzene (5.5 g, 40 mmol) was cooled to 5° C. and then treated dropwise with ethyl oxalyl chloride (4.7 mL, 42.06 mmol). When the addition was complete, this mixture thus formed was added via a syringe to the cooled aluminum chloride-methylene chloride suspension. A vigorous evolution of hydrogen chloride gas was observed. The reaction mixture was stirred at 5° C. for 5 min. The cooling bath was removed, and the stirring was continued for 18 h. The reaction was then cooled back down to 10° C. and treated dropwise with a 2N aqueous hydrochloric acid solution (40 mL). For the first 10 mL added, there was a rapid evolution of gas. The methylene chloride phase was separated, and the aqueous phase was extracted with methylene chloride (2×35 mL). The combined organic layers were concentrated in vacuo to afford (4-methanesulfanyl-3-methyl-phenyl)-oxo-acetic acid ethyl ester (~9.5 g) as a yellow oil which was used without further purification.

A mixture of (4-methanesulfanyl-3-methyl-phenyl)-oxo-acetic acid ethyl ester (9.5 g, 39.8 mmol) and a 6N aqueous hydrochloric acid solution (25 mL) was heated under reflux (104–105° C.) for 4 h. At this time, the reaction mixture was treated with water (25 mL), and the bath temperature was raised to 125° C. The heating and stirring continued for 8 h. The heating was then discontinued, and the reaction mixture was diluted with water (10 mL) and toluene (10 mL). A yellow solid precipitated. After sitting several hours, the solid was filtered, washed with water, and then air-dried to afford (4-methanesulfanyl-3-methyl-phenyl)-oxo-acetic acid (9.5 g, slightly wet) which was used without further purification.

A suspension of (4-methanesulfanyl-3-methyl-phenyl)-oxo-acetic acid (9.0 g, 38 mmol) in toluene (25 mL) was treated with 2-ethoxyethanol (5 mL, 51.6 mmol), and the mixture became clear. The reaction mixture was then treated dropwise with hydrazine monohydrate (2.3 mL, 48 mmol) over 5 min. The reaction mixture changed from a brown liquid to an orange liquid and finally to a deep orange suspension. The reaction mixture was placed in an oil-bath set at 105° C. The internal temperature of the reaction rose to 90° C. over 8 min. At this time, the reaction mixture was gradually treated with an aqueous potassium hydroxide solution (50% w/v, 62 mmol) over 10 min, maintaining the internal temperature above 90° C. The bath temperature was increased to 115° C., and a controlled evolution of ammonia gas was observed. The water was azeotropically distilled via a Dean-Stark condenser. After 90 min. the internal temperature of the reaction reached 106° C. The mixture was allowed to cool and then concentrated in vacuo to about one-half volume. The mixture was cooled to 80° C. and then treated slowly with a 6N aqueous hydrochloric acid solution (12.5 mL). The reaction mixture was cooled to 25° C. and extracted with diethyl ether (3×50 mL). Each organic extract was washed with a saturated aqueous sodium chloride solution (25 mL). The combined organic layers were dried over magnesium sulfate, filtered, and concentrated in vacuo to afford a yellow semi-solid (7 g). This solid was dissolved in diethyl ether (30 mL), treated with hexanes (40 mL), and allowed to crystallize. Filtration, in two crops, afforded (3-methyl-4-methylsulfanyl-phenyl)-acetic acid (4.27 g, 54%) as a yellow solid.

A mixture of (3-methyl-4-methylsulfanyl-phenyl)-acetic acid (1.55 g, 7.89 mmol) and potassium carbonate (2.75 g, 19.89 mmol) in tetrahydrofuran (10 mL) was stirred at 25° C. for 15 min. The suspension was cooled to −15° C. under argon and then treated dropwise via syringe with trimethylacetyl chloride (1.02 mL, 8.28 mmol) over 2 min. The stirring was continued for 20 min and then the reaction mixture was treated with (1R, 2R)-(−)-pseudoephedrine (1.7 g, 10.28 mmol) in a portionwise manner over 3 min. The reaction mixture was placed in a cooling bath at 0° C. and stirred for 90 min. The reaction mixture was then treated with water (10 mL) and toluene (25 mL). The layers were separated, and the aqueous layer was extracted with toluene (2×25 mL). Each organic extract was washed with 25 mL each of a 1N aqueous sulfuric acid solution, a saturated aqueous sodium chloride solution, a saturated aqueous sodium bicarbonate solution, and a saturated aqueous sodium chloride solution. The combined organic layers were dried over sodium sulfate, filtered, and concentrated in vacuo to afford the unpurified crude product (2.75 g) as amber oil which crystallized upon standing. The solid mass was digested in stirring diethyl ether (25 mL) and filtered. The solid product was washed with diethyl ether/hexanes (1:1) and dried to afford N-[2(R)-hydroxy-1(R)-methyl-2(R)-phenyl-ethyl]-N-methyl-2-(3-methyl-4-methylsulfanyl-phenyl)-acetamide (2.17 g, 80%) as off-white crystals: mp 104–105° C.

A solution of N-[2(R)-hydroxy-1(R)-methyl-2(R)-phenyl-ethyl]-N-methyl-2-(3-methyl-4-methylsulfanyl-phenyl)-acetamide (1.0 g, 2.91 mmol) in dry tetrahydrofuran (20 mL) was cooled to −25° C. under argon and then slowly treated with a 1.0M solution of lithium bis(trimethysilyl) amide in tetrahydrofuran (6.1 mL, 6.1 mmol) while maintaining the temperature below −15° C. The cooling bath was removed, and the reaction temperature was allowed to rise to 0° C. where it was maintained for 20 min. At this time, the reaction mixture was treated via syringe with a solution of iodomethylcyclopentane (prepared as in Example 1, 0.75 g, 3.57 mmol) in 1,3-dimethyl-3,4,5,6-tetrahydro-2(1H)-pyrimidinone (0.75 mL, 6.2 mmol) over 2 min. The mixture was stirred at 0° C. for 2.5 h, at which time, the reaction mixture was quenched with a saturated aqueous sodium chloride solution (30 mL) and extracted with toluene (50 mL). The organic phase was washed with a 1N aqueous hydrochloric acid solution (30 mL), a saturated aqueous sodium chloride solution (30 mL), a saturated aqueous sodium bicarbonate solution (50 mL), and a saturated aqueous sodium chloride solution (30 mL). Each aqueous wash was back-extracted with toluene (20 mL). The combined organic layers were dried over sodium sulfate, filtered, and concentrated in vacuo to afford a crude white solid. This material was dissolved in warm diethyl ether (20 mL), treated with hexanes (15 mL), and allowed to crystallize. The solid was filtered, washed with a cold solution of diethyl ether/hexanes (1:1), and air-dried to afford 3-cyclopentyl-N-[2(R)-hydroxy-1(R)-methyl-2(R)-phenyl-ethyl]-N-methyl-2(R)-(3-methyl-4-methylsulfanyl-phenyl)-propionamide (820 mg, 66%) as a crystalline solid A mixture of 3-cyclopentyl-N-[2(R)-hydroxy-1(R)-methyl-2(R)-phenyl-ethyl]-N-methyl-2(R)-(3-methyl-4-methylsulfanyl-phenyl)-propionamide (800 mg, 1.87 mmol) in dioxane (2 mL) was treated with a 9N aqueous sulfuric acid solution (2 mL). The resulting reaction mixture was heated at 108–110° C. for 16 h. The cooled reaction was partitioned with water (20 mL) and ethyl acetate (30 mL). The aqueous phase was extracted with ethyl acetate (2×30 mL). Each organic layer was washed with a small portion of a saturated aqueous sodium chloride solution. The combine organic layers were dried over sodium sulfate, filtered, and concentrated in vacuo to afford 3-cyclopentyl-2(R)-(3-methyl-4-methylsulfanyl-phenyl)-propionic acid (550 mg, 100%) as an amber solid.

A suspension of 3-cyclopentyl-2(R)-(3-methyl-4-methylsulfanyl-phenyl)-propionic acid (510 mg, 1.83 mmol) in 98% formic acid (4 mL) was treated with a 30% aqueous hydrogen peroxide solution (0.75 mL, 6.2 mmol). The mixture was stirred at 25° C. for 90 min. The solvent was concentrated in vacuo, and the residue was stirred with water (20 mL). The solid was filtered and washed with water. The resulting material was dissolved in methylene chloride, dried over magnesium sulfate, filtered and concentrated in vacuo. The dry residue was recrystallized from diethyl ether/hexanes to afford 3-cyclopentyl-2(R)-(4-methanesulfonyl-3-methyl-pheny)-propionic acid (406 mg, 71%) as white crystals: (ES)$^+$-HRMS m/e calcd for $C_{16}H_{22}O_4S$ (M+Na)$^+$ 333.1131, found 333.1134

A solution of 3-cyclopentyl-2(R)-(4-methanesulfonyl-3-methyl-pheny)-propionic acid (310 mg, 1.0 mmol) in methylene chloride (5 mL) was treated with oxalyl chloride (0.175 mL, 2.0 mmol) and N,N-dimethylformamide (1 drop). The solution was stirred at 25° C. for 45 min. The reaction mixture was concentrated in vacuo, and the residue was suspended in toluene. The toluene was further concentrated in vacuo. The resulting residue was dried in vacuo. The waxy material was dissolved in methylene chloride (5 mL), cooled to 0° C., and then treated with a solution of 2-amino-5-bromopyrazine (1.74 g, 1.0 mmol) and pyridine (0.121 mL, 1.5 mmol) in methylene chloride (5 mL). The mixture was stirred at 0° C. for 20 min and then stirred at 25° C. for 3 h. The solution was extracted with methylene chloride and water. The organic layer was washed with a 1N aqueous hydrochloric acid solution, a saturated aqueous sodium chloride solution, a saturated aqueous sodium bicarbonate solution, and a saturated aqueous sodium chloride solution. The organic layer was dried over sodium sulfate, filtered, and concentrated in vacuo. Flash chromatography (Merck Silica gel 60, 230–400 mesh, 1/2 ethyl acetate/hexanes) afforded the N-(5-bromo-pyrazin-2-yl)-3-cyclopentyl-2(R)-(4-methanesulfonyl-3-methyl-pheny)-propionamide (391 mg, 84%) as a fluffy solid.

A mixture of N-(5-bromo-pyrazin-2-yl)-3-cyclopentyl-2(R)-(4-methanesulfonyl-3-methyl-pheny)-propionamide (120 mg, 0.257 mmol), N,N-diisopropylethylamine (0.5 mL, 2.87 mmol), and 3-hydroxy-3-methylbutyne (90 mg, 1.07 mmol) in toluene (2 mL) was treated with dichlorobis (triphenylphosphine)palladium(II) (11 mg, 0.0157 mmol) and copper(I) iodide (5.5 mg, 0.0288 mmol). The mixture was stirred at 25° C. for 18 h. The reaction mixture was then concentrated in vacuo, and the residue was partitioned with methylene chloride (25 mL) and a 0.2M aqueous hydrochloric acid solution (20 mL). The organic layer was washed with a saturated aqueous sodium chloride solution (20 mL), and each aqueous phase was back-extracted with a small volume of methylene chloride. The combined organic layers were dried over sodium sulfate, filtered, concentrated in vacuo. Flash chromatography (Merck Silica gel 60, 230–400 mesh, gradient elution with increasing concentrations of ethyl acetate/hexanes) afforded the 3-cyclopentyl-N-[5-(3-hydroxy-3-methyl-but-1-ynyl)-pyrazin-2-yl]-2(R)-(4-methanesulfonyl-3-methyl-phenyl)-propionamide (93 mg, 77%) as a yellow foam: (ES)$^+$-HRMS m/e calcd for $C_{25}H_{31}N_3O_4S$ (M+H)$^+$ 470.2108, found 470.2113.

EXAMPLE 58

3-Cyclopentyl-N-[5-1(S),2-dihydroxy-ethyl]-2(R)-(4-methanesulfonyl-3-methyl)-propionamide

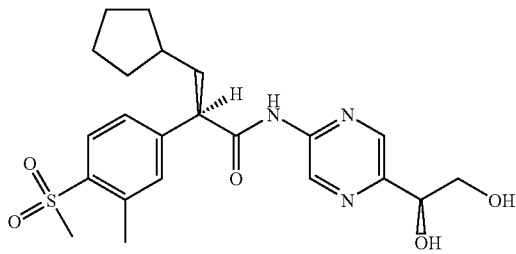

A solution of 3-cyclopentyl-2(R)-(4-methanesulfonyl-3-methyl-pheny)-propionic acid (prepared as in Example 57, 465 mg, 1.5 mmol) in methylene chloride (20 mL) was treated with oxalyl chloride (0.3 mL, 3.4 mmol) and N,N-dimethylformamide (1–2 drops). The solution was stirred at 0° C. for 5 min and then at 25° C. for 15 min. The reaction mixture was concentrated in vacuo. The residue was dissolved in methylene chloride (20 mL), cooled to 0° C., and then treated with a solution of 2-amino-5-vinylpyrazine (prepared as in Example 54, 182 mg, 1.5 mmol) and pyridine (0.37 mL, 4.6 mmol) in methylene chloride (5 mL). The mixture was stirred at 0° C. then stirred at 25° C. overnight. The solution was diluted with methylene chloride (25 mL). The organic layer was washed with a 1N aqueous sodium hydroxide solution (25 mL) and a 1N aqueous hydrochloric acid solution (25 mL). Each aqueous phase was back-extracted with a small volume of methylene chloride. The combined organic layers were dried over sodium sulfate, filtered, and concentrated in vacuo. Flash chromatography (Merck Silica gel 60, 230–400 mesh, 1/3 to 1/1 ethyl acetate/hexanes) afforded 3-cyclopentyl-2(R)-(4-methanesulfonyl-3-methyl-phenyl)-N-(5-vinyl-pyrazin-2-yl)-propionamide (385 mg, 63%) as a white foam: (ES)$^+$-HRMS m/e calcd for $C_{22}H_{27}N_3O_3S$ (M+H)$^+$ 414.1846, found 414.1849.

A mixture of potassium ferricyanide (442 mg, 1.34 mmol), potassium carbonate (190 mg, 1.37 mmol), and (DHQ)$_2$PHAL (8 mg, 0.010 mmol) was treated with a solution of water/tert-butyl alcohol (10 mL, 1:1) and stirred at 25° C. for 5 min. The reaction mixture was cooled to 0° C. and then treated with a 0.2M solution of osmium tetroxide in toluene (20 µL, 0.004 mmol) followed by a mixture of 3-cyclopentyl-2(R)-(4-methanesulfonyl-3-methyl-phenyl)-N-(5-vinyl-pyrazin-2-yl)-propionamide (185 mg, 0.447 mmol) in water/tert-butyl alcohol (5 mL, 1:1). The resulting reaction mixture was stirred at 0° C. for 5 min and then at 25° C. for 5 h. The mixture was then treated while stirring with ethyl acetate (25 mL) and sodium metabisulfite (150 mg, 0.79 mmol), and the stirring continued for 30 min. The phases were separated, and the organic layer was washed with a saturated aqueous sodium chloride solution (20 mL). Each aqueous phase was back-extracted with ethyl acetate (25 mL). The combined organic layers were dried over sodium sulfate, filtered, and concentrated in vacuo. Flash chromatography (Merck Silica gel 60, 230–400 mesh, 25% ethyl acetate/hexanes to 100% ethyl acetate) afforded 3-cyclopentyl-N-[5-1(S),2-dihydroxy-ethyl]-2(R)-(4-methanesulfonyl-3-methyl)-propionamide (135 mg, 67%) as a colorless foam: (ES)$^+$-HRMS m/e calcd for $C_{22}H_{29}N_3O_5S$ (M+H)$^+$ 448.1901, found 448.1904.

EXAMPLE 59

3-Cyclopentyl-N-[5-(4-hydroxy-tetrahydro-pyran-4-ylethynyl)-pyrazin-2-yl]-2(R)-(4-methanesulfonyl-3-methyl-phenyl)-propionamide

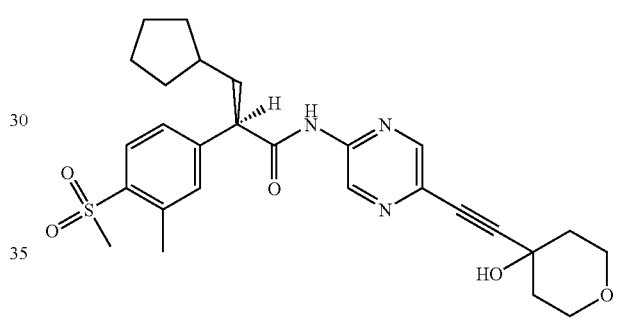

A mixture of N-(5-bromo-pyrazin-2-yl)-3-cyclopentyl-2 (R)-(4-methanesulfonyl-3-methyl-pheny)-propionamide (prepared as in Example 57, 154 mg, 0.33 mmol), N,N-diisopropylethylamine (0.6 mL, 3.44 mmol), and 4-ethynyl-tetrahydropyran-4-ol (prepared as in Example 46, 85 mg, 0.67 mmol) in toluene (2 mL) was treated with dichlorobis(triphenylphosphine)palladium(II) (14 mg, 0.02 mmol) and copper(I) iodide (7 mg, 0.0367 mmol). The mixture was stirred at 25° C. for 17 h. The reaction mixture was then concentrated in vacuo, and the residue was partitioned with methylene chloride (50 mL) and a 0.2M aqueous hydrochloric acid solution (25 mL) and the layers were separated. The aqueous phase was back-extracted with methylene chloride (25 mL). Each organic layer was washed with a saturated aqueous sodium chloride solution (1 mL). The combined organic layers were dried over sodium sulfate, filtered, concentrated in vacuo. Flash chromatography (Merck Silica gel 60, 230–400 mesh, gradient elution with mixtures of ethyl acetate/hexanes) afforded 3-cyclopentyl-N-[5-(4-hydroxy-tetrahydro-pyran-4-ylethynyl)-pyrazin-2-yl]-2(R)-(4-methanesulfonyl-3-methyl-phenyl)-propionamide (93 mg, 55%) as a yellow foam: (ES)$^+$-HRMS m/e calcd for $C_{27}H_{33}N_3O_5S$ (M+H)$^+$ 512.2214, found 512.2219.

EXAMPLE 60

3-Cyclopentyl-N-[5-1(R),2-dihydroxy-ethyl]-2(R)-(4-methanesulfonyl-3-methyl)-propionamide

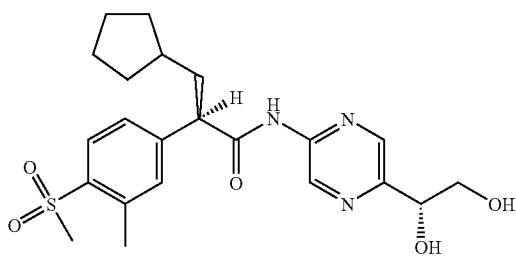

A mixture of potassium ferricyanide (410 mg, 1.24 mmol), potassium carbonate (175 mg, 1.26 mmol), and (DHQD)$_2$PHAL (8 mg, 0.010 mmol) was treated with a solution of water/tert-butyl alcohol (10 mL, 1:1) and stirred at 25° C. for 5 min. The reaction mixture was cooled to 0° C. and then treated with a 0.2M solution of osmium tetroxide in toluene (20 μL, 0.004 mmol) followed by a mixture of 3-cyclopentyl-2(R)-(4-methanesulfonyl-3-methyl-phenyl)-N-(5-vinyl-pyrazin-2-yl)-propionamide (prepared as in Example 58, 170 mg, 0.411 mmol) in water/tert-butyl alcohol (5 mL, 1:1). The resulting reaction mixture was stirred at 0° C. for 5 min and then at 25° C. for 5 h. The mixture was then treated while stirring with ethyl acetate (25 mL) and sodium metabisulfite (150 mg, 0.79 mmol), and the stirring continued for 30 min. The phases were separated. The aqueous phase was diluted with a saturated aqueous sodium chloride solution (20 mL) and extracted with ethyl acetate (2×25 mL). Each organic layer was washed with a saturated aqueous sodium chloride solution. The combined organic layers were dried over sodium sulfate, filtered, and concentrated in vacuo. Flash chromatography (Merck Silica gel 60, 230–400 mesh, elution with ethyl acetate/hexanes) afforded 3-cyclopentyl-N-[5-1(R),2-dihydroxy-ethyl]-2(R)-(4-methanesulfonyl-3-methyl)-propionamide (99 mg, 54%) as a colorless foam: (ES)$^+$-HRMS m/e calcd for C$_{22}$H$_{29}$N$_3$O$_5$S (M+H)$^+$ 448.1901, found 448.1900.

EXAMPLE 61

3-Cyclopentyl-2(R)-(4-methanesulfonyl-phenyl)-N-[5-(3-hydroxy-3-methyl-but-1-ynyl)-pyrazin-2-yl]-propionamide

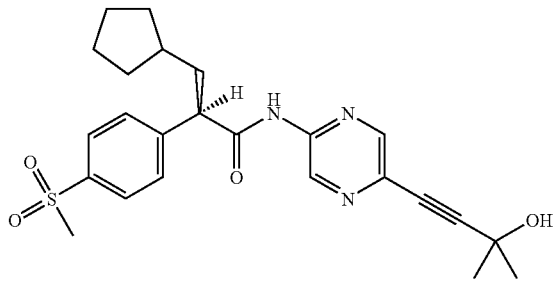

A mixture of 2(R)-(4-methanesulfonyl-phenyl)-3-cyclopentyl-5-bromo-pyrazin-2-yl-propionamide (prepared as in Example 3, 226 mg, 0.5 mmol) in toluene (6 mL) was treated with N,N-diisopropylethylamine (2 mL), 3-hydroxy-3-methylbutyne (84 mg, 1.0 mmol), dichlorobis(triphenylphosphine)palladium(II) (19 mg), and copper(I) iodide (9 mg). The mixture was stirred at 25° C. overnight, and an oily black precipitate was obtained. The top clear solution was decanted, and the oily precipitate was first rinsed with toluene (8 mL) and then with hexanes/ethyl acetate (2×8 ml, 8:1). The residue was dissolved in methylene chloride and extracted with methylene chloride and a 0.2N aqueous hydrochloric acid solution. The organic layer was washed with a saturated aqueous sodium chloride solution, dried over sodium sulfate, filtered, and concentrated in vacuo. Flash chromatography (Merck Silica gel 60, 230–400 mesh, 1/1 ethyl acetate/hexanes) afforded 3-cyclopentyl-2(R)-(4-methanesulfonyl-phenyl)-N-[5-(3-hydroxy-3-methyl-but-1-ynyl)-pyrazin-2-yl]-propionamide (100 mg, 44%) as a fluffy solid: (ES)$^+$-HRMS m/e calcd for C$_{24}$H$_{29}$N$_3$O$_4$S (M+H)$^+$ 456.1952, found 456.1943.

EXAMPLE 62

2(R)-(3-Chloro-4-methanesulfonyl-phenyl)-3-cyclopentyl-N-[5-(2-hydroxy-ethoxy)-pyrazin-2-yl]-propionamide

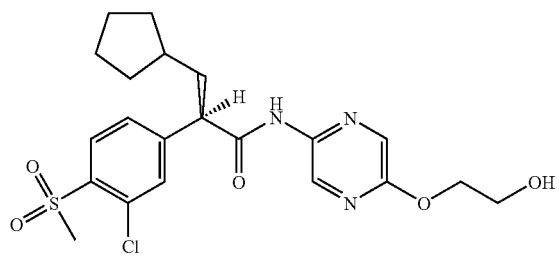

A solution of 5-chloro-pyrazine-2-carboxylic acid (prepared as in Example 29, 3.15 g, 19.94 mmol) in methylene chloride (50 mL) was treated with 2-(tetrahydropyran-2-yloxy)ethanol (2.91 g, 19.94 mmol). The solution was cooled to 0° C. and then was treated with triethylamine (5.60 mL, 39.88 mmol) and bis(2-oxo-3-oxazolidinyl)phosphinic chloride (5.07 g, 19.94 mmol). The mixture was stirred at 0° C. for 15 min and then at 25° C. for 24 h. The mixture was extracted with methylene chloride and water. The organic layer was washed with a saturated aqueous sodium chloride solution, dried over sodium sulfate, filtered, and concentrated in vacuo. Flash chromatography (Merck Silica gel 60, 230–400 mesh, 2/1 hexanes/ethyl acetate) afforded 5-chloro-pyrazine-2-carboxylic acid 2-(tetrahydro-pyran-2-yloxy)-ethyl ester as a colorless oil (3.41 g, 60%).

A solution of 2-(tetrahydropyran-2-yloxy)ethanol (5.22 g, 35.77 mmol) in dry tetrahydrofuran at 0° C. was treated with sodium hydride (1.43 g, 35.75 mmol, 60% dispersion in mineral oil that was prewashed with hexane). The mixture was stirred at 0° C. for 10 min and then at 25° C. for 2 h until all the sodium hydride was consumed. The reaction mixture was cooled to 0° C. and then treated with a solution of 5-chloro-pyrazine-2-carboxylic acid 2-(tetrahydro-pyran-2-yloxy)-ethyl ester (3.41 g, 11.92 mmol) in tetrahydrofuran (15 mL). The mixture was stirred at 0° C. for 20 min and at 25° C. overnight. The reaction mixture became deep colored, and thin layer chromatography indicated complete consumption of the starting material. The reaction mixture was concentrated in vacuo to dryness. The residue was diluted with water (30 mL) and a 1N aqueous sodium hydroxide solution (15 mL), and then the mixture was heated under reflux for 2 h. The resulting solution was diluted with water (30 mL) and then extracted with diethyl ether (3×30 mL). The aqueous layer was acidified with a 1N aqueous hydrochloric acid solution and then extracted with ethyl acetate. The organic layer was dried over sodium sulfate, filtered, and concentrated in vacuo to afford an oil (2.11 g). $^1$H-NMR indicated a mixture of 5-[2-(tetrahydro-pyran-2-yloxy)-ethoxy]-pyrazine-2-carboxylic acid and the unreacted 2-(tetrahydropyran-2-yloxy)ethanol (1.4/1 ratio). This oil was suspended in water (20 mL) and then a 1N aqueous sodium hydroxide solution (6.5 mL) was added to adjust the pH to a value of 8.0. The solution was concentrated in vacuo, and the residue was dried. The resulting material was suspended in diethyl ether and filtered to afford the sodium salt of 5-[2-(tetrahydro-pyran-2-yloxy)-ethoxy]-pyrazine-2-carboxylic acid (1.74 g, 50.3%) as a solid.

A suspension of the sodium salt of 5-[2-(tetrahydro-pyran-2-yloxy)-ethoxy]-pyrazine-2-carboxylic acid (1.72 g, 5.93 mmol) in N,N-dimethylformamide (20 mL) was treated with diphenylphosphoryl azide (1.40 ml, 6.50 mmol). The reaction mixture was stirred at 25° C. overnight and then was concentrated in vacuo. The residue was suspended in ethyl acetate, and the solid was removed by filtration. The organic filtrate was washed with water, dried over sodium sulfate, filtered, and concentrated in vacuo to afford the acyl azide (1.80 g) as an oil which was used without further purification. This acyl azide (1.80 g) was treated with benzyl alcohol (0.64 g) in toluene (15 mL). The mixture was heated at 90° C. for 1 h until gas evolution was completed. The reaction mixture was cooled to 25° C., and the reaction mixture solidified. Biotage chromatography (FLASH 40L, Silica, 2/1 hexanes/ethyl acetate) afforded {5-[2-(tetrahydro-pyran-2-yl)-ethoxy]-pyrazin-2-yl}-carbamic acid benzyl ester (1.12 g, 51%) as a solid.

A solution of {5-[2-(tetrahydro-pyran-2-yl)-ethoxy]-pyrazin-2-yl}-carbamic acid benzyl ester (560 mg, 1.5 mmol) in tetrahydrofuran (5 mL) and methanol (15 mL) was treated with 10% palladium on activated carbon (110 mg) in methanol (5 mL). The reaction mixture was stirred under a positive pressure of hydrogen gas (balloon) at 25° C. for 2 h, at which time, thin layer chromatography indicated complete removal of the protection group. The reaction mixture was filtered and concentrated in vacuo to afford 5-[2-(tetrahydro-pyran-2-yl)-ethoxy]-pyrazin-2-ylamine as an oil which was used without further purification.

A solution of 2(R)-(3-chloro-4-methanesulfonyl-phenyl)-3-cyclopentyl-propionic acid (prepared as in Example 1, 495 mg, 1.5 mmol) in methylene chloride (5 mL) was treated with oxalyl chloride (262 μL, 3.0 mmol) and N,N-dimethylformamide (1 drop). The mixture was stirred at 25° C. for 2 h. The reaction mixture was concentrated in vacuo, and the residue was dried in vacuo overnight. The residue was then dissolved in benzene, and the solvents were concentrated in vacuo. The residue was dried in vacuo. This material was dissolved in methylene chloride (5 mL), cooled to 0° C., and then treated with a mixture of 5-[2-(tetrahydro-pyran-2-yl)-ethoxy]-pyrazin-2-ylamine and pyridine (240 μL) in methylene chloride (7 mL). The ice bath was removed, and the solution was stirred at 25° C. for 2 h. The mixture was extracted with methylene chloride and a 0.1N aqueous hydrochloric acid solution. The organic layer was washed with a saturated aqueous sodium chloride solution, dried over sodium sulfate, filtered, and concentrated in vacuo. Flash chromatography (Merck Silica gel 60, 230–400 mesh, 1.5/1 hexanes/ethyl acetate) afforded 2(R)-(3-chloro-4-methanesulfonyl-phenyl)-3-cyclopentyl-N-[5-(2-tetrahydropyran-2-yloxy)ethoxy-pyrazin-2-yl]-propionamide (594 mg, 72%) as a white foam.

A solution of 2(R)-(3-chloro-4-methanesulfonyl-phenyl)-3-cyclopentyl-N-[5-(2-tetrahydropyran-2-yloxy)ethoxy-pyrazin-2-yl]-propionamide (300 mg) in methanol (8 mL) was treated with a 6N aqueous hydrochloric acid solution (0.2 mL). The mixture was stirred at 25° C. for 2 h until all the starting material was consumed. The solution was concentrated in vacuo, and the residue was extracted with ethyl acetate and a saturated aqueous sodium bicarbonate solution. The organic layer was dried over sodium sulfate, filtered, and concentrated in vacuo to afford 2(R)-(3-chloro-4-methanesulfonyl-phenyl)-3-cyclopentyl-N-[5-(2-hydroxy-ethoxy)-pyrazin-2-yl]-propionamide (254 mg, 100%) as a white foam: (ES)$^+$-HRMS m/e calcd for $C_{21}H_{26}ClN_3O_5S$ (M+H)$^+$ 468.1355, found 468.1339.

EXAMPLE 63

2(R)-(3-Chloro-4-methanesulfonyl-phenyl)-3-cyclopentyl-[5-(2-methoxyphenyl)-pyrazin-2-yl]-propionamide

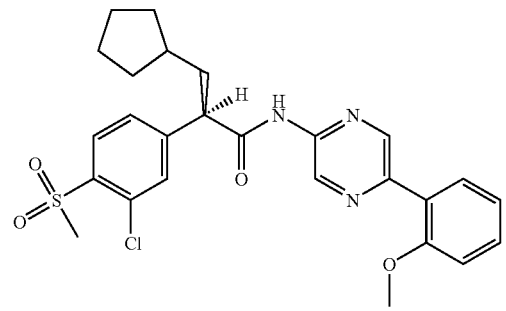

A solution of 2-amino-5-bromopyrazine (1.16 g, 6.67 mmol) and 2-methoxyphenylboronic acid (1.17 g, 7.70 mmol) in N,N-dimethylformamide (15 mL) was treated with tetrakis(triphenylphosphine)palladium(0) (193 mg, 0.17 mmol) and potassium carbonate (1.87 g, 13.34 mmol). The mixture was heated at 110° C. overnight. The reaction mixture was extracted with chloroform and water. The organic layer was washed with a saturated aqueous sodium chloride solution, dried over sodium sulfate, filtered, and concentrated in vacuo. Biotage chromatography (FLASH 40S, Silica, 2/1 ethyl acetate/hexanes (2/1 ratio) afforded 5-(2-methoxy-phenyl)-pyrazin-2-ylamine (210 mg, 16%).

A solution of 2(R)-(3-chloro-4-methanesulfonyl-phenyl)-3-cyclopentyl-propionic acid (prepared as in Example 1, 343 mg, 1.04 mmol) in methylene chloride (5 mL) was treated with oxalyl chloride (182 μL, 2.08 mmol) and N,N-dimethylformamide (1 drop). The mixture was stirred at 25° C. for 2 h. The reaction mixture was concentrated in vacuo, and the residue was dried in vacuo overnight. The residue was then dissolved in benzene, and the solvents were concentrated in vacuo. The residue was dried in vacuo. This material was dissolved in methylene chloride (5 mL), cooled to 0° C., and then treated with a mixture of 5-(2-methoxy-phenyl)-pyrazin-2-ylamine and pyridine (130 μL) in methylene chloride (10 mL). The ice bath was removed, and the solution was stirred at 25° C. overnight. The mixture was extracted with methylene chloride and a 0.3N aqueous hydrochloric acid solution. The organic layer was washed with a saturated aqueous sodium chloride solution, dried over sodium sulfate, filtered, and concentrated in vacuo. Flash chromatography (Merck Silica gel 60, 230–400 mesh, 2/1 hexanes/ethyl acetate) afforded 2(R)-(3-chloro-4-methanesulfonyl-phenyl)-3-cyclopentyl-N-[5-(2-methoxyphenyl)-pyrazin-2-yl]-propionamide (378 mg, 71%) as an off-white foam: (ES)$^+$-HRMS m/e calcd for $C_{26}H_{28}ClN_3O_4S$ (M+H)$^+$ 514.1562, found 514.1547.

EXAMPLE 64

2(R)-(3-Chloro-4-methanesulfonyl-phenyl)-3-cyclopentyl-N-[5-(2-hydoxyphenyl)-pyrazin-2-yl]-propionamide

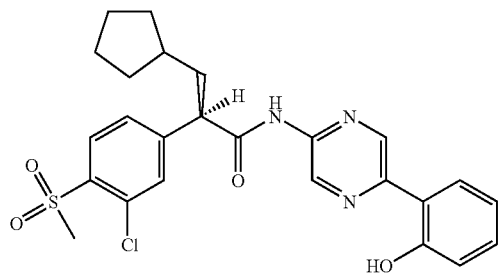

To each of 8 microwave tubes was added 2-amino-5-bromopyrazine (174 mg, 1.00 mmol), 2-hydroxyphenylboronic acid (151 mg, 1.10 mmol), acetonitrile (3 mL), dichlorobis(triphenylphosphine)palladium(II) (36 mg, 0.05 mmol), and a 1M aqueous sodium bicarbonate solution (1 mL). The 8 tubes were microwave-heated at 150° C. for 15 min. The reaction mixture was cooled and then poured into a solution of ethyl acetate and water. The organic layer was washed with a saturated aqueous sodium chloride solution, dried over sodium sulfate, filtered, and concentrated in vacuo. The residue was dissolved in hot methanol (100 mL). The methanol solution was concentrated in vacuo until a precipitate was observed. The precipitate was filtered. The filtrate was further concentrated and filtered to afford 5-(2-hydroxy-phenyl)-pyrazin-2-ylamine (478 mg, 32%) as a solid.

A solution of 2(R)-(3-chloro-4-methanesulfonyl-phenyl)-3-cyclopentyl-propionic acid (prepared as in Example 1, 330 mg, 1.0 mmol) in methylene chloride (5 mL) was treated with oxalyl chloride (175 μL, 2.0 mmol) and N,N-dimethylformamide (1 drop). The mixture was stirred at 25° C. for 2 h. The reaction mixture was concentrated in vacuo, and the residue was dried in vacuo. The residue was then dissolved in benzene, and the solvents were concentrated in vacuo. The residue was dried in vacuo. This material was dissolved in methylene chloride (5 mL), cooled to 0° C., and then treated with a mixture of 5-(2-hydroxy-phenyl)-pyrazin-2-ylamine and pyridine (125 μL) in methylene chloride (10 mL). The ice bath was removed, and the solution was stirred at 25° C. overnight. The mixture was extracted with methylene chloride and a 0.3N aqueous hydrochloric acid solution. The organic layer was washed with a saturated aqueous sodium chloride solution, dried over sodium sulfate, filtered, and concentrated in vacuo. Flash chromatography (Merck Silica gel 60, 230–400 mesh, 2/1 hexanes/ethyl acetate) afforded 2(R)-(3-chloro-4-methanesulfonyl-phenyl)-3-cyclopentyl-N-[5-(2-hydoxyphenyl)-pyrazin-2-yl]-propionamide (256 mg, 51%) as an off-white foam: (ES)$^+$-HRMS m/e calcd for $C_{25}H_{26}ClN_3O_4S$ (M+H)$^+$ 500.1406, found 500.1395.

EXAMPLE 65

2(R)-(3-Chloro-4-methanesulfonyl-phenyl)-3-cyclopentyl-N-[5-(1,2-dihydroxy-ethyl)-pyrazin-2-yl]-propionamide

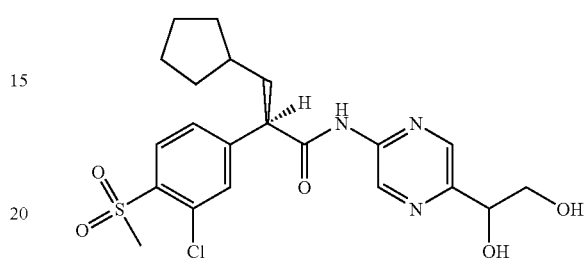

A solution of N-methyl morpholine oxide (27 mg, 0.23 mmol) and a 0.2M solution of osmium tetroxide in toluene (5 μL, 0.001 mmol) in acetone (0.5 mL) and water (0.5 mL) was treated with 2(R)-(3-chloro-4-methanesulfonyl-phenyl)-3-cyclopentyl-N-(5-vinyl-pyrazin-2-yl)-propionamide (prepared as in Example 54, 50 mg, 0.115 mmol). Two drops of tetrahydrofuran were added to fully dissolve the substrate, and the resulting mixture was stirred at 25° C. overnight. The reaction mixture was concentrated in vacuo, and the residue was treated with water (10 mL) and methylene chloride (25 mL). The organic phase was washed with a 1 N aqueous hydrochloric acid solution (10 mL), and each aqueous phase was extracted with a small portion of methylene chloride. The combined organic layers were dried over sodium sulfate, filtered, and concentrated in vacuo. Biotage chromatography (FLASH 12M, Silica, ethyl acetate) afforded 2(R)-(3-chloro-4-methanesulfonyl-phenyl)-3-cyclopentyl-N-[5-(1,2-dihydroxy-ethyl)-pyrazin-2-yl]-propionamide (48 mg) as a colorless foam: (ES)$^+$-HRMS m/e calcd for $C_{21}H_{26}N_3O_5S$ (M+H)$^+$ 468.1355, found 468.1357.

EXAMPLE 66

2(R)-(3-Chloro-4-methanesulfonyl-phenyl)-3-cyclopentyl-N [5-(1(S),2-dihydroxy-2-methyl-propyl)-pyrazin-2-yl]-propionamide

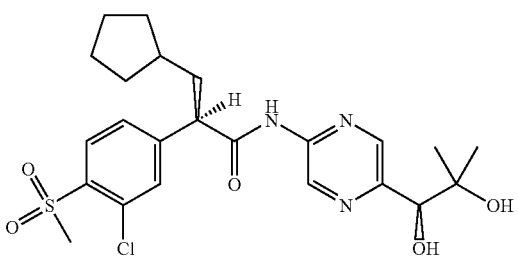

A suspension of magnesium (2.64 g, 110 mmol) in dry tetrahydrofuran (60 mL) was treated with a small amount of iodine and then 1-bromo-2-methylpropene (13.5 g, 100 mmol) in tetrahydrofuran (30 mL) was added in several portions. The mixture was heated under reflux for 3 min. The mixture was cooled to 25° C. and then treated with iodomethane (0.2 mL, 3.0 mmol). The reaction mixture was stirred at 25° C. for 30 min and then heated under reflux for 2 h until all the magnesium was consumed. The mixture was cooled to 25° C. then treated with a solution of tributyltin chloride (27 mL, 100 mmol) in tetrahydrofuran (30 mL). The mixture was heated under reflux for 19 h and then cooled to 25° C. The solution was extracted with diethyl ether and a saturated aqueous ammonium chloride solution. The organic layer was dried over sodium sulfate, filtered, and concentrated in vacuo to afford isobutenyltri-n-butyltin (31.95 g) as a crude oil. The $^1$H-NMR data of the crude oil indicated 58% purity of the desired isobutenyltri-n-butyltin.

A mixture of the crude isobutenyltri-n-butyltin (6.90 g, 58 purity), 2-amino-5-bromopyrazine (1.92 g, 11 mmol), and N,N-diisopropylethylamine (5 mL) in N,N-dimethylformamide (50 mL) was treated with lithium chloride (2.0 g) and tetrakis(triphenylphosphine)palladium(0) (381 mg, 0.33 mmol). The mixture was stirred at 130° C. for 4 h, at which time, thin layer chromatography indicated complete consumption of the starting material. The mixture was concentrated in vacuo. The residue was treated with a saturated aqueous potassium fluoride solution and then extracted with ethyl acetate. The organic layer was washed with a saturated aqueous sodium chloride solution, dried over sodium sulfate, filtered, and concentrated in vacuo. Flash chromatography (Merck Silica gel 60, 230–400 mesh, 1.5/1 hexanes/ethyl acetate) afforded 2-amino-5-(2,2-dimethylvinyl)-pyrazine (420 mg, 26%).

A solution of 2(R)-(3-chloro-4-methanesulfonyl-phenyl)-3-cyclopentyl-propionic acid (prepared as in Example 1, 930 mg, 2.82 mmol) in methylene chloride (10 mL) was treated with oxalyl chloride (490 µL, 5.64 mmol) and N,N-dimethylformamide (1 drop). The mixture was stirred at 25° C. for 2 h. The reaction mixture was concentrated in vacuo, and the residue was dried in vacuo. The residue was then dissolved in benzene, and the solvents were concentrated in vacuo. The residue was dried in vacuo. This material was dissolved in methylene chloride (10 mL), cooled to 0° C., and then treated with a mixture of 2-amino-5-(2,2-dimethylvinyl)-pyrazine (420 mg, 2.82 mmol) and pyridine (340 µL) in methylene chloride (10 mL). The ice bath was removed, and the solution was stirred at 25° C. overnight. The mixture was extracted with methylene chloride and a 0.1N aqueous hydrochloric acid solution. The organic layer was washed with a saturated aqueous sodium chloride solution, dried over sodium sulfate, filtered, and concentrated in vacuo. Flash chromatography (Merck Silica gel 60, 230–400 mesh, 2/1 hexanes/ethyl acetate) afforded the 2(R)-(3-chloro-4-methanesulfonyl-phenyl)-3-cyclopentyl-N-[5-(2-methyl-propenyl)-pyrazin-2-yl]-propionamide (1.10 g, 85%) as a light yellow foam.

A mixture of potassium ferricyanide (738 mg, 2.24 mmol), potassium carbonate (310 mg, 2.24 mmol), and (DHQ)$_2$PHAL (11.7 mg, 0.015 mmol) was treated with a solution of water/tert-butyl alcohol (15 mL, 1:1) and stirred at 25° C. to give a clear solution. The reaction mixture was then treated with a 0.2M solution of osmium tetroxide in toluene (37.4 µL). The reaction mixture was cooled to 0° C. and then was treated with 2(R)-(3-chloro-4-methanesulfonyl-phenyl)-3-cyclopentyl-N-[5-(2-methylpropenyl)-pyrazin-2-yl]-propionamide (345 mg, 0.748 mmol) followed by the addition of methane sulfonamide (71 mg, 0.747 mmol). The mixture was stirred at 0° C. for 18 h until all the olefin was reacted. The mixture was diluted with ethyl acetate (30 mL) and treated with sodium sulfite (1.0 g). The solution was extracted with ethyl acetate and water. The organic layer was dried over sodium sulfate, filtered, and concentrated in vacuo. Flash chromatography (Merck Silica gel 60, 230–400 mesh, 1/5 hexanes/ethyl acetate) afforded 2(R)-(3-chloro-4-methanesulfonyl-phenyl)-3-cyclopentyl-N-[5-(1(S),2-dihydroxy-2-methyl-propyl)-pyrazin-2-yl]-propionamide (255 mg, 69%) as an off-white foam: (ES)$^+$-HRMS m/e calcd for $C_{23}H_{30}ClN_3O_5S$ (M+H)$^+$ 496.1668, found 496.1657.

EXAMPLE 67

2(1R)-(3-Chloro-4-methanesulfonyl-phenyl)-3-cyclopentyl-N-[5-(1(R),2-dihydroxy-2-methyl-propyl)-pyrazin-2-yl]-propionamide

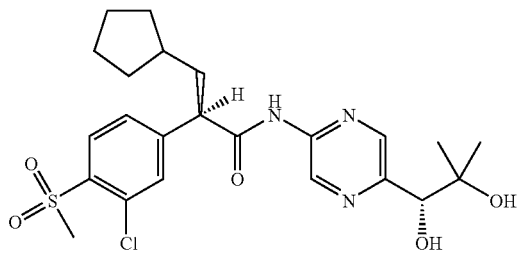

A mixture of potassium ferricyanide (738 mg, 2.24 mmol), potassium carbonate (310 mg, 2.24 mmol), and (DHQD)$_2$PHAL (11.7 mg, 0.015 mmol) was treated with a solution of water/tert-butyl alcohol (15 mL, 1:1) and stirred at 25° C. to give a clear solution. The reaction mixture was then treated with a 0.2M solution of osmium tetroxide in toluene (37.4 µL). The reaction mixture was cooled to 0° C. and then was treated with 2(R)-(3-chloro-4-methanesulfonyl-phenyl)-3-cyclopentyl-N-[5-(2-methylpropenyl)-pyrazin-2-yl]-propionamide (prepared as in Example 66, 345 mg, 0.748 mmol) followed by the addition of methane sulfonamide (71 mg, 0.747 mmol). The mixture was stirred at 0° C. for 18 h until all the olefin was reacted. The mixture was diluted with ethyl acetate (30 mL) and treated with sodium sulfite (1.0 g). The solution was extracted with ethyl acetate and water. The organic layer was dried over sodium sulfate, filtered, and concentrated in vacuo. Flash chromatography (Merck Silica gel 60, 230–400 mesh, 1/5 hexanes/ethyl acetate) afforded 2(R)-(3-chloro-4-methanesulfonyl-phenyl)-3-cyclopentyl-N-[5-(1(R),2-dihydroxy-2-methyl-propyl)-pyrazin-2-yl]-propionamide (328 mg, 89%) as an off-white foam: (ES)$^+$-HRMS m/e calcd for $C_{23}H_{30}ClN_3O_5S$ (M+H)$^+$ 496.1668, found 496.1654.

EXAMPLE 68

2(R)-(3-Chloro-4-methanesulfonyl-phenyl)-3-cyclopentyl-N-[5-(4-methyl-2,5-dioxo-imidazolidin-4-yl)-pyrazin-2-yl]-propionamide

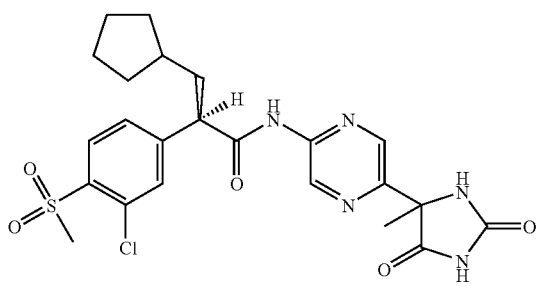

A suspension of N-(5-acetyl-pyrazin-2-yl)-2,2-dimethyl-propionamide (prepared as in Example 28, 884 mg, 4.0 mmol) in ethanol (32 mL) was heated to give a clear solution. The reaction mixture was then treated with sodium cyanide (294 mg, 6.0 mmol) and ammonium carbonate (1.54 g, 16 mmol) followed by the addition of water (32 mL). The mixture was stirred at 65° C. for 18 h. The reaction mixture was neutralized with a 1N aqueous hydrochloric acid solution to adjust the pH to about 3.0. The resulting mixture was extracted with ethyl acetate. The organic layer was washed with a saturated aqueous sodium chloride solution, dried over sodium sulfate, filtered, and concentrated in vacuo to afford 2,2-dimethyl-N-[5-(4-methyl-2,5-dioxo-imidazolidin-4-yl)-pyrazin-2-yl]-propionamide (1.16 g, 100%) as an off-white solid.

A suspension of 2,2-dimethyl-N-[5-(4-methyl-2,5-dioxo-imidazolidin-4-yl)-pyrazin-2-yl]-propionamide (1.16 g, 4.0 mmol) in methanol (30 mL) was treated with a 1N aqueous sodium hydroxide solution (15 mL). The mixture was heated at 65° C. for 4 h and at 25° C. overnight. The mixture was concentrated in vacuo, and the residue was dried in vacuo overnight to give a crude solid. This solid material was suspended in a mixture of ethyl acetate and methanol (100 mL, 1:1) and gently heated. The mixture was filtered, and the filtrate was concentrated in vacuo. Biotage chromatography (FLASH 40L, Silica, 1/9 to 3/7 methanol/ethyl acetate) afforded 5-(5-amino-pyrazin-2-yl)-5-methyl-imidazolidine-2,4-dione (841 mg, 100%) as a solid.

A solution of 2(R)-(3-chloro-4-methanesulfonyl-phenyl)-3-cyclopentyl-propionic acid (prepared as in Example 1, 200 mg, 0.606 mmol) in methylene chloride (5 mL) was treated with oxalyl chloride (116 µL, 1.212 mmol) and N,N-dimethylformamide (1 drop). The mixture was stirred at 25° C. for 1 h. The reaction mixture was concentrated in vacuo, and the residue was dried in vacuo. The residue was then dissolved in benzene, and the solvents were concentrated in vacuo. The residue was dried in vacuo. This material was dissolved in methylene chloride (5 mL), cooled to 0° C., and then treated with a mixture of 5-(5-amino-pyrazin-2-yl)-5-methyl-imidazolidine-2,4-dione (150 mg, 0.727 mmol) and pyridine (98 µL) in methylene chloride (1 mL) and dimethyl sulfoxide (1 mL). The ice bath was removed, and the solution was stirred at 25° C. overnight. The reaction mixture was concentrated in vacuo and then extracted with ethyl acetate and a 0.1N aqueous hydrochloric acid solution. The organic layer was washed with a saturated aqueous sodium chloride solution, dried over sodium sulfate, filtered, and concentrated in vacuo. Flash chromatography (Merck Silica gel 60, 230–400 mesh, 1/4 hexanes/ethyl acetate) afforded 2(R)-(3-chloro-4-methanesulfonyl-phenyl)-3-cyclopentyl-N-[5-(4-methyl-2,5-dioxo-imidazolidin-4-yl)-pyrazin-2-yl]-propionamide (82 mg, 26%) as a light yellow solid: (ES)$^+$-HRMS m/e calcd for $C_{23}H_{26}ClN_5O_5S$ (M+H)$^+$ 520.1416, found 520.1403.

EXAMPLE 69

2(R)-(3-Chloro-4-methanesulfonyl-phenyl)-3-cyclopentyl-N-[5-(tetrahydro-furan-2-yl)-pyridin-2-yl]-propionamide

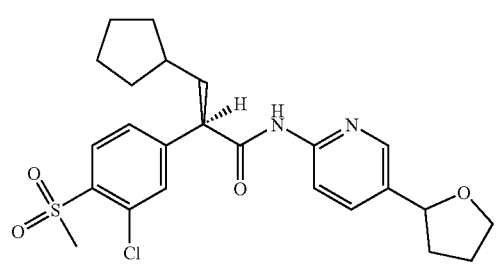

A solution of 2-amino-5-bromopyridine (5.00 g, 28.90 mmol) was dissolved in tetrahydrofuran (80 mL), cooled to −78° C., and then treated with a 2.5M solution of n-butyl-lithium in hexanes (11.68 mL, 29.20 mmol). The resulting reaction mixture was stirred for 1 h, at which time, a solution of 1,2-bis(chlorodimethylsilyl)ethane (6.22 g, 28.90 mmol) in tetrahydrofuran (15 mL) was added dropwise to the reaction. The reaction mixture was stirred for another 90 min at −78° C. and then was treated with another portion of a 2.5M solution of n-butyllithium in hexanes (11.68 mL, 29.20 mmol). The reaction was slowly warmed to 25° C. where it was stirred for 2 h. The reaction was then quenched by the addition of a saturated aqueous sodium chloride solution (50 mL) and then extracted with diethyl ether (2×200 mL). The combined organic layers were dried over magnesium sulfate, filtered, and concentrated in vacuo. Kugelrohr distillation at 125–135° C. at 0.5 mmHg afforded 5-bromo-2-(2,2,5,5-tetramethyl-[1,2,5]azadisilolidin-1-yl)-pyridine (5.38 g, 59%) as a white solid: mp 50.4–55.8° C.

A mixture of 2,3-dihydrofuran (1.40 g, 19.97 mmol) and benzene sulfinic acid (3.12 g, 21.97 mmol) in methylene chloride (80 mL) was stirred at 25° C. for 2 h. The reaction was then transferred to a separatory funnel and washed with a saturated aqueous sodium carbonate solution (15 mL). The organic layer was dried over sodium sulfate, filtered, and concentrated in vacuo. The resulting solid was then recrystallized using diethyl ether/petroleum ether to afford 2-benzenesulfonyl-tetrahydro-furan as a white solid: mp 55.9–56.8° C.

A solution of 5-bromo-2-(2,2,5,5-tetramethyl-[1,2,5]azadisilolidin-1-yl)-pyridine (1.26 g, 3.99 mmol) in tetrahydrofuran (6 mL) at −78° C. was treated dropwise with a 1.7M solution of tert-butyllithium in pentane (4.93 mL, 8.38 mmol) and then was stirred for 10 min. The reaction mixture was then treated with zinc bromide (539 mg, 2.39 mmol) and magnesium bromide diethyl etherate (1.03 g, 3.99 mmol), and the reaction mixture was allowed to warm to 25° C. where it was stirred for 30 min. This solution was then treated with the 2-benzenesulfonyl-tetrahydro-furan (424 mg, 1.99 mmol) in tetrahydrofuran (10 mL), and the reaction was stirred at 25° C. for 20 h. The reaction was then quenched with a saturate aqueous ammonium chloride solution (10 mL) and then extracted with ethyl acetate (3×15 mL). The combined organic layers were dried over sodium sulfate, filtered, and concentrated in vacuo. Biotage chromatography (FLASH 40S, Silica, 95/5 methylene chloride/methanol) afforded an inseparable mixture of 5-(tetrahydro-furan-2-yl)-pyridin-2-ylamine and 2-aminopyridine (227 mg) as a waxy solid.

A solution of 2(R)-(3-chloro-4-methanesulfonyl-phenyl)-3-cyclopentyl-propionic acid (prepared as in Example 1, 250 mg, 0.76 mmol) in methylene chloride (5 mL) was cooled to 0° C. and then was treated with a 2.0M solution of oxalyl chloride in methylene chloride (435 μL, 0.87 mmol) and N,N-dimethylformamide (1 drop). The reaction mixture was stirred at 0° C. for 30 min and then concentrated in vacuo. The resulting oil was dissolved in tetrahydrofuran (2 mL) at 25° C. and then was treated dropwise with a solution of the inseparable mixture of 5-(tetrahydro-furan-2-yl)-pyridin-2-ylamine and 2-aminopyridine (224 mg, 1.36 mmol) and 2,6-lutidine (263 μL, 2.27 mmol) in tetrahydrofuran (3 mL) via an addition funnel. The resulting cloudy solution was then stirred overnight for 16 h at 25° C. After this time, the reaction was diluted with water (10 mL) and then extracted with methylene chloride (3×25 mL). The combined organic layers were dried over sodium sulfate, filtered and concentrated in vacuo. Biotage chromatography (FLASH 12M, Silica, 65/35 to 50/50 hexanes/ethyl acetate) afforded 2(R)-(3-chloro-4-methanesulfonyl-phenyl)-3-cyclopentyl-N-[5-(tetrahydro-furan-2-yl)-pyridin-2-yl]-propionamide (86 mg, 24%) as a white foam: (ES)$^+$-HRMS m/e calcd for $C_{24}H_{29}ClN_2O_4S$ (M+H)$^+$ 477.1610, found 477.1616.

EXAMPLE 70

2(R)-(3-Chloro-4-methanesulfonyl-phenyl)-3-cyclopentyl-N-(5-furan-2-yl-pyrazin-2-yl)-propionamide

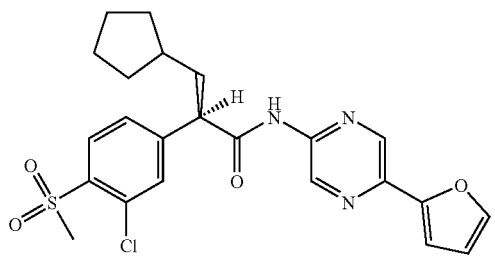

A solution of 2-amino-5-bromopyrazine (500 mg, 2.87 mmol) in N,N-dimethylformamide (15 mL) was treated with tetrakis(triphenylphosphine)palladium(0) (66 mg, 0.06 mmol), N,N-diisopropylethylamine (1.25 mL, 7.18 mmol), lithium chloride (426 mg, 10.06 mmol), and 2-(tributylstannyl)furan (905 μL, 2.87 mmol). The resulting reaction mixture was heated at 120° C. for 4 h. After such time, the reaction was cooled to 25° C., treated with a saturated aqueous potassium fluoride solution (10 mL), and then stirred at 25° C. overnight for 16 h. The solution was then diluted with methylene chloride (25 mL) and extracted with methylene chloride (3×15 mL). The combined organic layers were dried over sodium sulfate, filtered, and concentrated in vacuo. Biotage chromatography (FLASH 40S, Silica, 98/2 to 96/4 methylene chloride/methanol) afforded 5-furan-2-yl-pyrazin-2-ylamine (356 mg, 77%) as a brown solid: mp 80.2–83.8° C.

A solution of 2(R)-(3-chloro-4-methanesulfonyl-phenyl)-3-cyclopentyl-propionic acid (prepared as in Example 1, 125 mg, 0.38 mmol) in methylene chloride (2.5 mL) cooled to 0° C. was treated with a 2.0M solution of oxalyl chloride in methylene chloride (217 μL, 0.43 mmol) and N,N-dimethylformamide (1 drop). The reaction mixture was stirred at 0° C. for 30 min, concentrated in vacuo, and azeotroped with toluene (2 mL) two times. The resulting oil was then dissolved in tetrahydrofuran (1 mL) at 25° C. This solution was then treated dropwise with 5-furan-2-yl-pyrazin-2-ylamine (91 mg, 0.57 mmol) and 2,6-lutidine (66 μL, 0.57 mmol) in tetrahydrofuran (1.5 mL) via an addition funnel. The resulting cloudy solution was then stirred overnight for 16 h at 25° C. After this time, the reaction was diluted with water (10 mL) and then extracted with methylene chloride (3×25 mL). The combined organic layers were dried over sodium sulfate, filtered, and concentrated in vacuo. Biotage chromatography (FLASH 12M, Silica, 80/20 to 60/40 hexanes/ethyl acetate) afforded 2(R)-(3-chloro-4-methanesulfonyl-phenyl)-3-cyclopentyl-N-(5-furan-2-yl-pyrazin-2-yl)-propionamide (124 mg, 69%) as a yellow foam: (ES)$^+$-HRMS m/e calcd for $C_{23}H_{24}ClN_3O_4S$ (M+H)$^+$ 474.1249, found 474.1254.

EXAMPLE 71

2(R)-(3-Chloro-methanesulfonyl-phenyl)-3-cyclopentyl-N-[5-(3-methoxy-phenyl)-pyrazin-2-yl]-propionamide

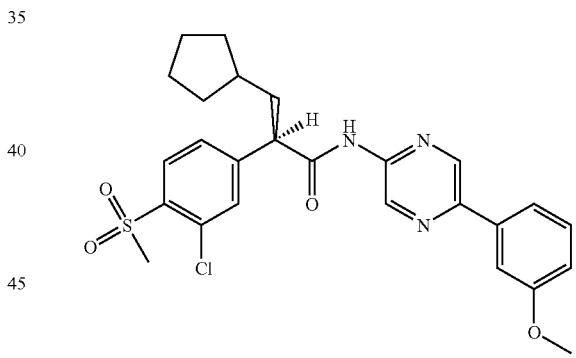

Nitrogen was bubbled through a solution of 3-methoxyphenyl boronic acid (393 mg, 2.59 mmol), 2-amino-5-bromopyrazine (300 mg, 1.72 mmol), sodium carbonate (603 mg, 5.69 mmol), dimethoxyethane (10 mL), and water (3 mL) for 15 min. After this time, the solution was treated with dichlorobis(triphenylphosphine)palladium(II) (121 mg, 0.17 mmol), and the resulting reaction mixture was heated at 90° C. for 2 d. The reaction was then poured into water (50 mL) and extracted with ethyl acetate (3×50 mL). The combined organic layers were dried over magnesium sulfate, filtered, and concentrated in vacuo. Biotage chromatography (FLASH 40S, Silica, 40/60 hexanes/ethyl acetate) afforded 5-(3-methoxy-phenyl)-pyrazin-2-ylamine (218 mg, 63%) as a light yellow solid: mp 113.2–115.5° C.; EI-HRMS m/e calcd for $C_{11}H_{11}N_3O$ (M$^+$) 201.0902, found 201.0905.

A solution of 2(R)-(3-chloro-4-methanesulfonyl-phenyl)-3-cyclopentyl-propionic acid (prepared as in Example 1, 300 mg, 0.91 mmol) in methylene chloride (15 mL) cooled to 0°

C. was treated with a 2.0M solution of oxalyl chloride in methylene chloride (522 µL, 1.04 mmol) and N,N-dimethylformamide (1 drop). The reaction mixture was stirred at 0° C. for 30 min, concentrated in vacuo, and azeotroped with methylene chloride (2 mL) two times. The resulting oil was dissolved in tetrahydrofuran (5 mL) at 25° C. and then treated dropwise with a solution of 5-(3-methoxy-phenyl)-pyrazin-2-ylamine (201 mg, 1.00 mmol) and 2,6-lutidine (126 µL, 1.09 mmol) in tetrahydrofuran (6 mL) via an addition funnel. The resulting cloudy solution was then stirred overnight for 16 h at 25° C. After this time, the reaction was diluted with water (10 mL) and then extracted with methylene chloride (3×25 mL). The combined organic layers were dried over sodium sulfate, filtered, and concentrated in vacuo. Biotage chromatography (FLASH 40S, Silica, 3/1 to 3/2 hexanes/ethyl acetate) afforded 2(R)-(3-chloro-methanesulfonyl-phenyl)-3-cyclopentyl-N-[5-(3-methoxy-phenyl)-pyrazin-2-yl]-propionamide (388 mg, 83%) as a light yellow foam: (ES)$^+$-HRMS m/e calcd for $C_{26}H_{28}ClN_3O_4S$ (M+H)$^+$ 514.1562, found 514.1567.

EXAMPLE 72

2(R)-(3-Chloro-4-methanesulfonyl-phenyl)-3-cyclopentyl-N-[5-(2-methoxy-ethylamino)-pyrazin-2-yl]-propionamide

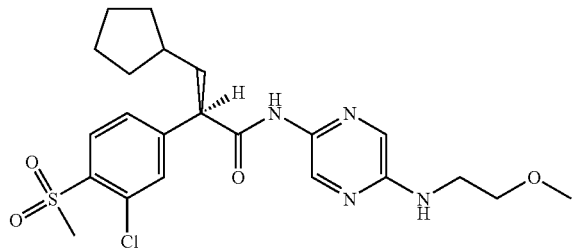

A mixture of 2-bromo-5-nitropyrazine (500 mg, 2.45 mmol) and 2-methoxyethylamine (276 mg, 3.67 mmol) in methanol (15 mL) was stirred at 25° C. for 5 h. After such time, the reaction was concentrated in vacuo. Biotage chromatography (FLASH 40S, Silica, 2/3 to 1/4 hexanes/ethyl acetate) afforded (2-methoxy-ethyl)-(5-nitro-pyrazin-2-yl)-amine (291 mg, 60%) as a yellow solid: mp 116.0–117.3° C.; EI-HRMS m/e calcd for $C_7H_{10}N_4O_3$ (M$^+$) 198.0753, found 198.0751.

A solution of (2-methoxy-ethyl)-(5-nitro-pyrazin-2-yl)-amine (290 mg, 1.46 mmol) in ethyl acetate (25 mL) was treated with 10% palladium on activated carbon (40 mg). The reaction mixture was then placed on a Parr shaker under a hydrogen atmosphere of 50 psi for 4 h. The catalyst was then filtered off through a pad of celite, and the celite pad was then washed well with ethyl acetate. The filtrate was then concentrated in vacuo. Biotage chromatography (FLASH 12M, Silica, 98/2 to 95/5 methylene chloride/methanol) afforded N-(2-methoxy-ethyl)-pyrazine-2,5-diamine (198 mg, 80%) as an orange solid: EI-HRMS m/e calcd for $C_7H_{12}N_4O$ (M$^+$) 168.1011, found 168.1018.

A solution of 2(R)-(3-chloro-4-methanesulfonyl-phenyl)-3-cyclopentyl-propionic acid (prepared as in Example 1, 325 mg, 0.33 mmol) in methylene chloride (15 mL) cooled to 0° C. was treated with a 2.0M solution of oxalyl chloride in methylene chloride (565 µL, 1.13 mmol) and N,N-dimethylformamide (1 drop). The reaction mixture was stirred at 0° C. for 30 min, concentrated in vacuo, and azeotroped with methylene chloride (2 mL) two times. The resulting oil was dissolved in tetrahydrofuran (5 mL) at 25° C. and then treated dropwise with a solution of N-(2-methoxy-ethyl)-pyrazine-2,5-diamine (182 mg, 1.08 mmol) and 2,6-lutidine (137 µL, 1.18 mmol) in tetrahydrofuran (6 mL) via an addition funnel. The resulting cloudy solution was then stirred overnight for 16 h at 25° C. After this time, the reaction was diluted with water (10 mL) and then extracted with methylene chloride (3×25 mL). The combined organic layers were dried over sodium sulfate, filtered, and concentrated in vacuo. Biotage chromatography (FLASH 40S, Silica, 2/3 to 1/4 hexanes/ethyl acetate) afforded 2(R)-(3-chloro-4-methanesulfonyl-phenyl)-3-cyclopentyl-N-[5-(2-methoxy-ethylamino)-pyrazin-2-yl]-propionamide (295 mg, 62%) as a white foam: (ES)$^+$-HRMS m/e calcd for $C_{22}H_{29}ClN_4O_4S$ (M+H)$^+$ 481.1671, found 481.1678.

EXAMPLE 73

2(R)-(3-Chloro-4-methanesulfonyl-phenyl)-3-cyclopentyl-N-[5-(2-hydroxy-ethylamino)-pyrazin-2-yl]-propionamide

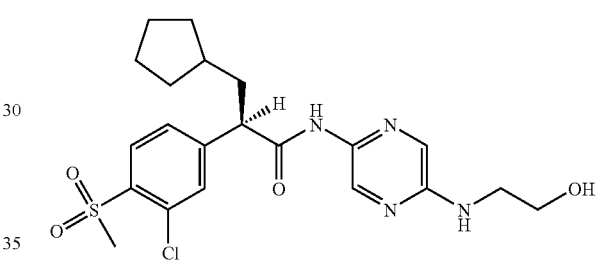

A mixture of 2-bromo-5-nitropyrazine (500 mg, 2.45 mmol) and ethanolamine (225 mg, 3.67 mmol) in methanol (15 mL) was stirred at 25° C. for 5 h. After such time, the reaction was concentrated in vacuo. Biotage chromatography (FLASH 40S, Silica, 20/80 hexanes/ethyl acetate to 97/3 ethyl acetate/methanol) afforded 2-(5-nitro-pyrazin-2-ylamino)-ethanol (375 mg, 83%) as a yellow solid: mp 157.5–159.8° C.; EI-HRMS m/e calcd for $C_6H_8N_4O_3$ (M$^+$) 184.0596, found 184.0603.

A solution of 2-(5-nitro-pyrazin-2-ylamino)-ethanol (370 mg, 2.01 mmol) in N,N-dimethylformamide (10 mL) at 0° C. was treated with chlorotriethylsilane (371 µL, 2.21 mmol) and imidazole (342 mg, 5.02 mmol). The reaction mixture was then allowed to warm up to 25° C. where it was stirred overnight for 16 h. After this time, the reaction was diluted with ethyl acetate (20 mL) and a saturated aqueous sodium chloride solution (10 mL) and then further extracted with ethyl acetate (2×10 mL). The combined organic layers were dried over sodium sulfate, filtered, and concentrated in vacuo. Biotage chromatography (FLASH 40S, Silica, 1/3 hexanes/ethyl acetate) afforded (5-nitro-pyrazin-2-yl)-(2-triethylsilanyloxy-ethyl)-amine (531 mg, 89%) as a light yellow solid: (ES)$^+$-HRMS m/e calcd for $C_{12}H_{22}N_4O_3Si$ (M+H)$^+$ 299.1534, found 299.1538.

A solution of (5-nitro-pyrazin-2-yl)-(2-triethylsilanyloxy-ethyl)-amine (530 mg, 1.78 mmol) in ethyl acetate (25 mL) was treated with 10% palladium on activated carbon (60 mg). The reaction mixture was then placed on a Parr shaker under a hydrogen atmosphere of 50 psi for 4 h. The catalyst was then filtered off through a pad of celite, and the celite pad was then washed well with ethyl acetate. The filtrate was then concentrated in vacuo. Biotage chromatography (FLASH 40S, Silica, ethyl acetate) afforded N-(2-triethylsilanyloxy-ethyl)-pyrazine-2,5-diamine (459 mg, 96%) as an orange-brown solid: (ES)$^+$-HRMS m/e calcd for $C_{12}H_{24}N_4O_2Si$ (M+H)$^+$ 269.1792, found 269.1794.

A solution of 2(R)-(3-chloro-4-methanesulfonyl-phenyl)-3-cyclopentyl-propionic acid (prepared as in Example 1, 500 mg, 1.51 mmol) in methylene chloride (20 mL) cooled to 0° C. was treated with a 2.0M solution of oxalyl chloride in methylene chloride (869 µL, 1.74 mmol) and N,N-dimethylformamide (1 drop). The reaction mixture was stirred at 0° C. for 30 min, concentrated in vacuo, and azeotroped with methylene chloride (2 mL) two times. The resulting oil was then dissolved in tetrahydrofuran (10 mL) at 25° C. and then treated dropwise with a solution of N-(2-triethylsilanyloxy-ethyl)-pyrazine-2,5-diamine (446 mg, 1.66 mmol) and 2,6-lutidine (211 µL, 1.81 mmol) in tetrahydrofuran (15 mL) via an addition funnel. The resulting cloudy solution was then stirred overnight for 16 h at 25° C. After this time, the reaction was diluted with water (10 mL) and then extracted with methylene chloride (3×25 mL). The combined organic layers were dried over sodium sulfate, filtered, and concentrated in vacuo. Biotage chromatography (FLASH 40M, Silica, 85/15 to 50/50 hexanes/ethyl acetate) afforded 2(R)-(3-chloro-4-methanesulfonyl-phenyl)-3-cyclopentyl-N-[5-(2-triethylsilanyloxy-ethylamino)-pyrazin-2-yl]-propionamide (606 mg, 69%) as a light yellow foam: (ES)$^+$-HRMS m/e calcd for $C_{27}H_{41}ClN_4O_4SSi$ (M+H)$^+$ 581.2379, found 581.2386.

A solution of 2(R)-(3-chloro-4-methanesulfonyl-phenyl)-3-cyclopentyl-N-[5-(2-triethylsilanyloxy-ethylamino)-pyrazin-2-yl]-propionamide (100 mg, 0.17 mmol) in tetrahydrofuran (2 mL), water (0.5 mL), and acetic acid (2 mL) was stirred at 25° C. for 6 h. The reaction mixture was then diluted with water (10 mL) and extracted with ethyl acetate (3×20 mL). The combined organic layers were washed with a saturated aqueous sodium bicarbonate solution (10 mL), dried over sodium sulfate, filtered, and concentrated in vacuo. Biotage chromatography (FLASH 12M, Silica, 2/3 hexanes/ethyl acetate to 100% ethyl acetate) afforded 2(R)-(3-chloro-4-methanesulfonyl-phenyl)-3-cyclopentyl-N-[5-(2-hydroxy-ethylamino)-pyrazin-2-yl]-propionamide (69 mg, 86%) as a white foam: (ES)$^+$-HRMS m/e calcd for $C_{21}H_{27}ClN_4O_4S$ (M+H)$^+$ 467.1515, found 467.1517.

EXAMPLE 74

2(R)-(3-Chloro-methanesulfonyl-phenyl)-3-cyclopentyl-N-[5-(1H-indo-5-yl)-pyrazin-2-yl]-propionamide

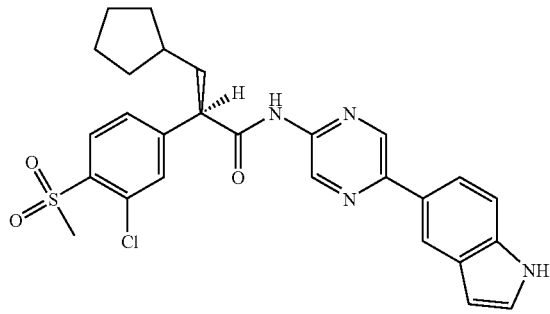

Nitrogen was bubbled through a solution of 5-indolylboronic acid (340 mg, 2.11 mmol), 2-amino-5-bromopyrazine (245 mg, 1.41 mmol), sodium carbonate (493 mg, 4.65 mmol), dimethoxyethane (12 mL), and water (4 mL) for 15 min. After this time, the solution was treated with dichlorobis(triphenylphosphine)palladium(II) (98 mg, 0.14 mmol), and the resulting reaction mixture was heated at 90° C. for 2 d. The reaction was then poured into water (50 mL) and extracted with ethyl acetate (3×50 mL). The combined organic layers were dried over magnesium sulfate, filtered, and concentrated in vacuo. Biotage chromatography (FLASH 40S, Silica, 35/65 hexanes/ethyl acetate) afforded 5-(1H-indol-5-yl)-pyrazin-2-ylamine (122 mg, 41%) as a brown solid: EI-HRMS m/e calcd for $C_2H_{10}N_4$ (M$^+$) 210.0905, found 210.0901.

A solution of 2(R)-(3-chloro-4-methanesulfonyl-phenyl)-3-cyclopentyl-propionic acid (prepared as in Example 1, 180 mg, 0.54 mmol) in methylene chloride (8 mL) cooled to 0° C. was treated with a 2.0M solution of oxalyl chloride in methylene chloride (313 µL, 0.63 mmol) and N,N-dimethylformamide (1 drop). The reaction mixture was stirred at 0° C. for 30 min, concentrated in vacuo, and azeotroped with methylene chloride (2 mL) two times. The resulting oil was dissolved in tetrahydrofuran (4 mL) at 25° C. and then treated dropwise with a solution of 5-(1H-indol-5-yl)-pyrazin-2-ylamine (126 mg, 0.60 mmol) and 2,6-lutidine (76 µL, 0.65 mmol) in tetrahydrofuran (6 mL) via an addition funnel. The resulting cloudy solution was then stirred at 25° C. overnight for 16 h. After this time, the reaction was diluted with water (10 mL) and then extracted with methylene chloride (3×25 mL). The combined organic layers were dried over sodium sulfate, filtered, and concentrated in vacuo. The material obtained from Biotage chromatography (FLASH 40S, Silica, 1/1 hexanes/ethyl acetate) was dissolved in methylene chloride (30 mL). This organic layer was washed with 1N aqueous citric acid solution (15 mL) and a saturated aqueous sodium bicarbonate solution (15 mL), dried over sodium sulfate, filtered, and concentrated in vacuo to afford 2(R)-(3-chloro-methanesulfonyl-phenyl)-3-cyclopentyl-N-[5-(1H-indol-5-yl)-pyrazin-2-yl]-propionamide (203 mg, 71%) as an off-white foam: (ES)$^+$-HRMS m/e calcd for $C_{27}H_{27}ClN_4O_3S$ (M+H)$^+$ 523.1565, found 523.1567.

EXAMPLE 75

2(1R)-(3-Chloro-4-methanesulfonyl-phenyl)-3-cyclopentyl-N-[5-(5,6-dihydro-4H-pyran-2-yl)-pyrazin-2-yl]-propionamide

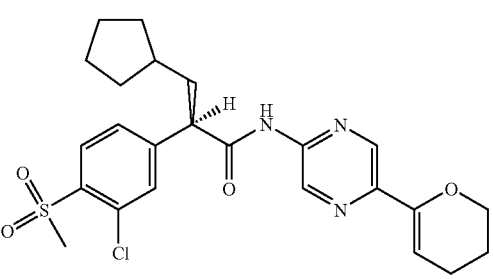

A solution of 2-amino-5-bromopyrazine (100 mg, 0.58 mmol) in N,N-dimethylformamide (6 mL) was treated with tetrakis(triphenylphosphine)palladium(0) (13 mg, 0.01 mmol), N,N-diisopropylethylamine (250 µL, 1.43 mmol), lithium chloride (85 mg, 2.01 mmol), and 5,6-dihydro-2-(tributylstannyl)-4H-pyran (214 mg, 0.58 mmol). The resulting reaction mixture was heated at 120° C. for 4 h. After such time, the reaction was cooled to 25° C., treated with a saturated aqueous potassium fluoride solution (10 mL), and stirred at 25° C. overnight for 16 h. The solution was then diluted with methylene chloride (25 mL) and extracted with methylene chloride (3×15 mL). The combined organic layers were dried over sodium sulfate, filtered, and concentrated in vacuo. Biotage chromatography (FLASH 12M, Silica, 1/1 to 1/3 hexanes/ethyl acetate) afforded 5-(5,6-dihydro-4H-pyran-2-yl)-pyrazin-2-ylamine (25 mg, 25%) as a foam: EI-HRMS m/e calcd for $C_9H_{11}N_3O$ $(M^+)$ 177.0902, found 177.0906.

A solution of 2(R)-(3-chloro-4-methanesulfonyl-phenyl)-3-cyclopentyl-propionic acid (prepared as in Example 1, 40 mg, 0.12 mmol) in methylene chloride (2 mL) cooled to 0° C. was treated with a 2.0M solution of oxalyl chloride in methylene chloride (70 μL, 1.40 mmol) and N,N-dimethylformamide (1 drop). The reaction mixture was stirred at 0° C. for 30 min, concentrated in vacuo, and azeotroped with methylene chloride (2 mL) three times. The resulting oil was dissolved in tetrahydrofuran (1 mL) at 25° C. and then treated dropwise with a solution of 5-(5,6-dihydro-4H-pyran-2-yl)-pyrazin-2-ylamine (24 mg, 0.13 mmol) and 2,6-lutidine (17 μL, 0.15 mmol) in tetrahydrofuran (1.5 mL) via an addition funnel. The resulting cloudy solution was then stirred overnight at 25° C. for 16 h. After this time, the reaction was diluted with water (10 mL) and then extracted with methylene chloride (3×25 mL). The combined organic layers were dried over sodium sulfate, filtered, and concentrated in vacuo. Biotage chromatography (FLASH 12M, Silica, 4/1 to 7/3 hexanes/ethyl acetate) afforded 2(R)-(3-chloro-4-methanesulfonyl-phenyl)-3-cyclopentyl-N-[5-(5,6-dihydro-4H-pyran-2-yl)-pyrazin-2-yl]-propionamide (25 mg, 42%) as a white foam: $(ES)^+$-HRMS m/e calcd for $C_{24}H_{28}ClN_3O_4S$ $(M+H)^+$ 490.1562, found 490.1562.

EXAMPLE 76

2(R)-(3-Chloro-4-methanesulfonyl-phenyl)-3-cyclopentyl-N-(5-thiophen-2-yl-pyrazin-2-yl)-propionamide

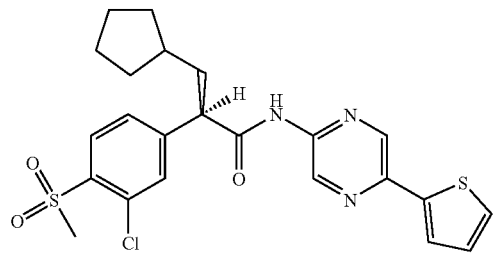

A mixture of 2-amino-5-bromopyrazine (500 mg, 2.874 mmol), dichlorobis(triphenylphosphine)palladium(II) (290 mg, 0.413 mmol), 2-thiopheneboronic acid (500 mg, 3.907 mmol), and a saturated aqueous sodium carbonate solution (4 mL) in ethylene glycol dimethyl ether (8 mL) and ethanol (8 mL) was heated under reflux overnight. The reaction mixture was cooled, diluted with ethyl acetate, water, and a saturated aqueous sodium chloride solution. After mixing, the layers were separated. The aqueous layer was extracted with ethyl acetate. The combined organic layers were dried over anhydrous sodium sulfate, filtered, and concentrated in vacuo. Biotage chromatography (FLASH 40M, Silica 1/1 hexanes/ethyl acetate) afforded 5-thiophen-2-yl-pyrazin-2-ylamine (267 mg, 52.4%) as a yellow solid: EI-HRMS m/e calcd for $C_8H_7N_3S$ $(M^+)$ 177.0361, found 177.0355.

A solution of triphenylphosphine (230.0 mg, 0.877 mmol) in methylene chloride (15 mL) cooled to 0° C. was treated with N-bromosuccinimide (160.0 mg, 0.899 mmol). The reaction mixture was stirred at 0° C. for 5 min and then treated with 2(R)-(3-chloro-4-methanesulfonyl-phenyl)-3-cyclopentyl-propionic acid (prepared as in Example 1, 232.0 mg, 0.701 mmol). The reaction mixture was allowed to warm to 25° C. over 15 min. The reaction mixture was then treated with 5-thiophen-2-yl-pyrazin-2-ylamine (260.0 mg, 1.467 mmol) followed by pyridine (0.24 mL, 2.967 mmol). The resulting reaction mixture was stirred at 25° C. for 1 h. The reaction mixture was then diluted with methylene chloride and washed with a dilute aqueous hydrochloric acid solution. The aqueous layer was back-extracted with methylene chloride. The combined organic layers were washed with a saturated aqueous sodium bicarbonate solution and water, dried over anhydrous sodium sulfate, filtered, and concentrated in vacuo. Biotage chromatography (FLASH 40M, Silica, 3/1 to 3/2 hexanes/ethyl acetate) afforded 2(R)-(3-chloro-4-methanesulfonyl-phenyl)-3-cyclopentyl-N-(5-thiophen-2-yl-pyrazin-2-yl)-propionamide (202.3 mg, 58.9%) as a yellow foam: mp 97–99° C. (foam to gel); $(ES)^+$-HRMS m/e calcd for $C_{23}H_{24}ClN_3O_3S_2$ $(M+H)^+$ 490.1021, found 490.1026.

EXAMPLE 77

2(R)-(3-Chloro-4-methanesulfonyl-phenyl)-3-cyclopentyl-N-(5-thiophen-3-yl-pyrazin-2-yl)-propionamide

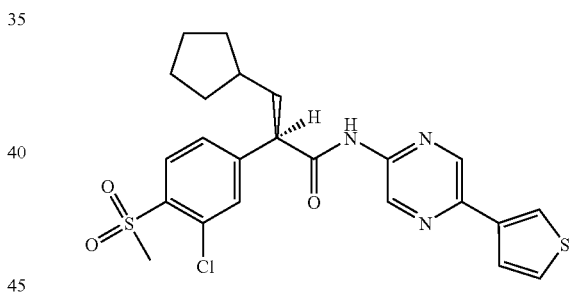

A mixture of 2-amino-5-bromopyrazine (500 mg, 2.874 mmol), dichlorobis(triphenylphosphine)palladium(II) (290 mg, 0.413 mmol), 3-thiopheneboronic acid (500 mg, 3.908 mmol), and a saturated aqueous sodium carbonate solution (4 mL) in ethylene glycol dimethyl ether (8 mL) and ethanol (8 mL) was heated under reflux for 45 min. The reaction mixture was then cooled, diluted with ethyl acetate, and washed with water and a saturated aqueous sodium chloride solution. The organic layer was dried over anhydrous sodium sulfate, filtered, and concentrated in vacuo. Biotage chromatography (FLASH 40M, Silica, 1/1 hexanes/ethyl acetate) afforded 5-thiophen-3-yl-pyrazin-2-ylamine (351.3 mg, 69%) as a light purple solid: EI-HRMS m/e calcd for $C_8H_7N_3S$ $(M^+)$ 177.0361, found 177.0358.

A solution of triphenylphosphine (149.0 mg, 0.568 mmol) in methylene chloride (8 mL) cooled to 0° C. was treated with N-bromosuccinimide (103.0 mg, 0.579 mmol). The reaction mixture was stirred at 0° C. for 5 min and then treated with 2(R)-(3-chloro-4-methanesulfonyl-phenyl)-3-cyclopentyl-propionic acid (prepared as in Example 1, 150.0 mg, 0.453 mmol). The reaction mixture was allowed to warm to 25° C. over 15 min. The reaction mixture was then treated with 5-thiophen-3-yl-pyrazin-2-ylamine (168.0 mg, 0.948 mmol) followed by pyridine (0.16 mL, 1.978 mmol). The resulting reaction mixture was stirred at 25° C. for 1.5 h. The reaction mixture was then diluted with methylene chloride and washed with a dilute aqueous hydrochloric acid solution. The aqueous layer was extracted with methylene chloride. The combined organic layers were washed with a saturated aqueous sodium bicarbonate solution, dried over anhydrous sodium sulfate, filtered, and concentrated in vacuo. Biotage chromatography (FLASH 40S, Silica, 3/1 to 2/1 hexanes/ethyl acetate) afforded 2(R)-(3-chloro-4-methanesulfonyl-phenyl)-3-cyclopentyl-N-(5-thiophen-3-yl-pyrazin-2-yl)-propionamide (105.6 mg, 47.5%) as a pale yellow foam: mp 96–102° C. (foam to gel); (ES)$^+$-HRMS m/e calcd for $C_{23}H_{24}ClN_3O_3S_2$ (M+H)$^+$ 490.1021, found 490.1023.

EXAMPLE 78

2(R)-(3-Chloro-4-methanesulfonyl-phenyl)-3-cyclopentyl-N-(5-furan-3-yl-pyrazin-2-yl)-propionamide

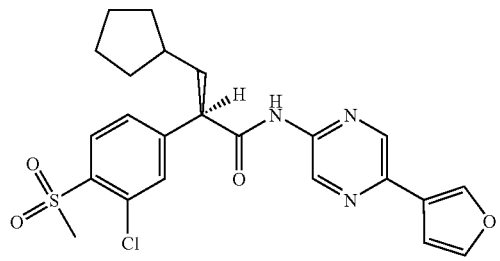

A mixture of 2-amino-5-bromopyrazine (300 mg, 1.724 mmol), tetrakis(triphenylphosphine)palladium(0) (340 mg, 0.294 mmol), furan-3-boronic acid acid (300 mg, 2.681 mmol), and a saturated aqueous sodium carbonate solution (2 mL) in ethylene glycol dimethyl ether (5 mL) and ethanol (5 mL) was heated under reflux for 45 min. The reaction mixture was cooled, diluted with ethyl acetate, and washed with water and a saturated aqueous sodium chloride solution. The organic layer was dried over anhydrous sodium sulfate, filtered, and concentrated in vacuo. Biotage chromatography (FLASH 40M, Silica, 2/3 hexanes/ethyl acetate to ethyl acetate) afforded 5-furan-3-yl-pyrazin-2-ylamine (256.9 mg, 92.5%) as a yellow solid: LRMS for $C_8H_7N_3O$ (M+H)$^+$ at m/z=162.

A solution of triphenylphosphine (230.0 mg, 0.877 mmol) in methylene chloride (14 mL) cooled to 0° C. was treated with N-bromosuccinimide (160.0 mg, 0.899 mmol). The reaction mixture was stirred at 0° C. for 5 min and then treated with 2(R)-(3-chloro-4-methanesulfonyl-phenyl)-3-cyclopentyl-propionic acid (prepared as in Example 1, 232.0 mg, 0.701 mmol). The reaction mixture was allowed to warm to 25° C. over 15 min. The reaction mixture was then treated with 5-furan-3-yl-pyrazin-2-ylamine (250.0 mg, 1.551 mmol) followed by pyridine (0.12 mL, 1.484 mmol). The resulting reaction mixture was stirred at 25° C. for 2.5 h. The reaction mixture was then diluted with methylene chloride and washed with a dilute aqueous hydrochloric acid solution. The aqueous layer was extracted with methylene chloride. The combined organic layers were washed with a saturated aqueous sodium bicarbonate solution and water, dried over anhydrous sodium sulfate, filtered, and concentrated in vacuo. Biotage chromatography (FLASH 40M, Silica, 3/2 to 45/55 hexanes/ethyl acetate) afforded 2(R)-(3-chloro-4-methanesulfonyl-phenyl)-3-cyclopentyl-N-(5-furan-3-yl-pyrazin-2-yl)-propionamide (161.1 mg, 48.5%) as a pale yellow foam: mp 97–101° C. (foam to gel); (ES)$^+$-HRMS m/e calcd for $C_{23}H_{24}ClN_3O_3S_2$ (M+H)$^+$ 474.1249, found 474.1252.

EXAMPLE 79

2(R)-(3-Chloro-4-methanesulfonyl-phenyl)-N-[5-(5-cyano-thiophen-2-yl)-pyrazin-2-yl]-3-cyclopentyl-propionamide

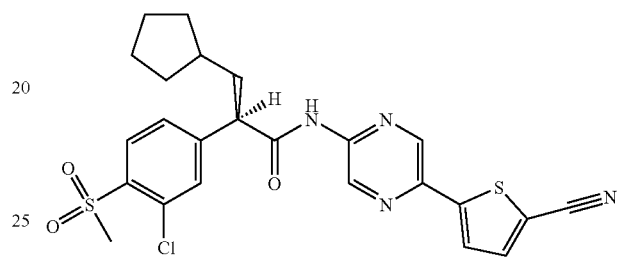

A mixture of 2-amino-5-bromopyrazine (300 mg, 1.724 mmol), dichlorobis(triphenylphosphine)palladium(II) (175 mg, 0.249 mmol), 5-cyanothiophene-2-boronic acid acid (540 mg, 3.53 mmol) and a saturated aqueous sodium carbonate solution (2 mL) in ethylene glycol dimethyl ether (5 mL) and ethanol (5 mL) was heated under reflux overnight. The reaction mixture was cooled, diluted with ethyl acetate, and washed with water and a saturated aqueous sodium chloride solution. The organic layer was dried over anhydrous sodium sulfate, filtered, and concentrated in vacuo. Biotage chromatography (FLASH 40S, Silica, 2/3 to 1/9 hexanes/ethyl acetate) afforded 5-(5-amino-pyrazin-2-yl)-thiophene-2-carbonitrile (49.1 mg, 14.1%) as a yellow solid: LRMS for $C_9H_6N_4S$ (M+H)$^+$ at m/z=203.

A solution of triphenylphosphine (50.0 mg, 0.191 mmol) in methylene chloride (2 mL) cooled to 0° C. was treated with N-bromosuccinimide (35.0 mg, 0.197 mmol). The reaction mixture was stirred at 0° C. for 5 min and then treated with 2(R)-(3-chloro-4-methanesulfonyl-phenyl)-3-cyclopentyl-propionic acid (prepared as in Example 1, 51.0 mg, 0.154 mmol). The reaction mixture was allowed to warm to 25° C. over 15 min. The reaction mixture was then treated with 5-(5-amino-pyrazin-2-yl)-thiophene-2-carbonitrile (47.0 mg, 0.232 mmol) followed by pyridine (30.0 uL, 0.371 mmol). The resulting reaction mixture was stirred at 25° C. for 2 h. The reaction mixture was then diluted with methylene chloride and washed with a dilute aqueous hydrochloric acid solution. The aqueous layer was extracted with methylene chloride. The combined organic layers were washed with a saturated aqueous sodium bicarbonate solution and water, dried over anhydrous sodium sulfate, filtered, and concentrated in vacuo. Biotage chromatography (FLASH, 40S, Silica, 1/1 hexanes/ethyl acetate) afforded 2(R)-(3-chloro-4-methanesulfonyl-phenyl)-N-[5-(5-cyano-thiophen-2-yl)-pyrazin-2-yl]-3-cyclopentyl-propionamide (44.4 mg, 55.9%) as a yellow foam: mp 101–107° C. (foam to gel); (ES)$^+$-HRMS m/e calcd for $C_{24}H_{23}ClN_4O_3S_2$ (M+H)$^+$515.0973, found 515.0974.

EXAMPLE 80

2(R)-(3-Chloro-4-methanesulfonyl-phenyl)-3-cyclo-pentyl-N-{5-(4,5-dihydro-1H-imidazol-2-yl)-pyrazin-2-yl}-propionamide trifluoro-acetic acid salt

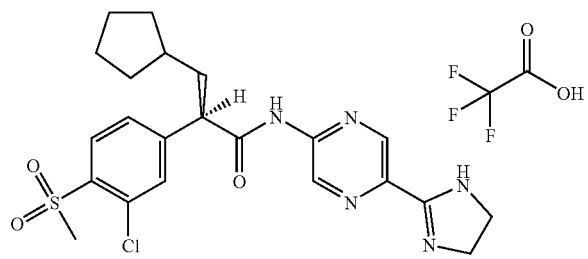

A mixture of 2-amino-5-cyanopyrazine (500.0 mg, 4.163 mmol), ethylenediamine (3.0 mL, 44.88 mmol), and phosphorous pentasulfide (185.1 mg, 0.416 mmol) was placed in a sealed tube and heated at 120° C. for 3 h. At this time, the reaction was poured onto ice. The resulting reaction mixture was diluted with chloroform (50 mL), water (10 mL), and a saturated aqueous sodium chloride solution (20 mL). The layers were separated. The organic layer was washed with a saturated aqueous sodium chloride solution, dried over anhydrous magnesium sulfate, filtered, and concentrated in vacuo to afford 5-(4,5-dihydro-1H-imidazol-2-yl)-pyrazin-2-ylamine (327.0 mg, 48.1%) as a white solid which was used without further purification.

A solution of 2(R)-(3-chloro-4-methanesulfonyl-phenyl)-3-cyclopentyl-propionic acid (prepared as in Example 1, 288.0 mg, 0.871 mmol) in methylene chloride (4 mL) cooled to 0° C. was treated with N,N-dimethylformamide (1 drop) followed by oxalyl chloride (0.16 mL, 1.834 mmol). The reaction mixture was stirred at 0° C. for 15 min and then stirred at 25° C. for 1 h. The reaction mixture was concentrated in vacuo to afford an oil. A solution of this oil in methylene chloride (4 mL) was cooled to 0° C. and then treated with a slurry of 5-(4,5-dihydro-1H-imidazol-2-yl)-pyrazin-2-ylamine (150.0 mg, 0.919 mmol) and pyridine (0.08 mL, 0.989 mmol) in tetrahydrofuran (4 mL), followed by a tetrahydrofuran (2 mL) rinse of the slurry into the reaction mixture. The resulting orange reaction mixture was treated with pyridine (0.08 mL, 0.989 mmol), stirred at 0° C. for 30 min and then at 25° C. overnight. The reaction mixture was then diluted with 90/10/1 methylene chloride/methanol/concentrated aqueous ammonium hydroxide solution and washed with water and a saturated aqueous sodium chloride solution. The aqueous layer was extracted with 90/10/1 methylene chloride/methanol/concentrated aqueous ammonium hydroxide solution. The combined organic layers were washed with a saturated aqueous sodium chloride solution, dried over anhydrous sodium sulfate, filtered, and concentrated in vacuo. The crude product was purified by reverse phase high-performance liquid chromatography to afford 2(R)-(3-chloro-4-methanesulfonyl-phenyl)-3-cyclopentyl-N-{5-(4,5-dihydro-1H-imidazol-2-yl)-pyrazin-2-yl}-propionamide; compound with trifluoro-acetic acid (1.1 mg, 0.21%) as a white solid: LRMS for $C_{22}H_{26}ClN_5O_3S$ $(M+H)^+$ at m/z=476.

EXAMPLE 81

2(R)-(3-Chloro-4-methanesulfonyl-phenyl)-3-cyclo-pentyl-N-[5-(2(S),3-dihydroxy-propyl)-pyrazin-2-yl]-propionamide

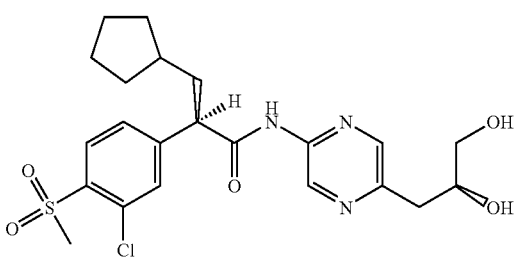

A mixture of 2-amino-5-bromopyrazine (1.00 g, 5.746 mmol), tetrakis(triphenylphosphine)palladium(0) (132 mg, 0.114 mmol), allyltri-n-butyltin (2.2 mL, 7.096 mmol), lithium chloride (875.0 mg, 20.64 mmol) and N,N-diisopropylethylamine (2.6 mL, 14.93 mmol) in N,N-dimethylformamide (29 mL) was stirred at 120° C. for 45 min. The reaction mixture was cooled to 25° C. and then treated with a saturated aqueous potassium fluoride solution (20 mL). The mixture was stirred for 3 h, treated with a solution of water and a saturated aqueous sodium chloride solution, and extracted with ethyl acetate. The combined organic layers were dried over anhydrous sodium sulfate, filtered, and concentrated in vacuo. Biotage chromatography (FLASH 40L, Silica, 1/1 hexanes/ethyl acetate) afforded 5-allyl-pyrazin-2-ylamine (378.2 mg, 48.7%) as a yellow solid: LRMS for $C_7H_9N_3$ $(M+H)^+$ at m/z=136.

A solution of 2(R)-(3-chloro-4-methanesulfonyl-phenyl)-3-cyclopentyl-propionic acid (prepared as in Example 1, 800.0 mg, 2.418 mmol) in methylene chloride (12 mL) cooled to 0° C. under nitrogen was treated with oxalyl chloride (0.64 mL, 7.336 mmol), followed by N,N-dimethylformamide (2 drops). The reaction mixture was stirred at 0° C. for 20 min and then stirred at 25° C. for 1.25 h. The reaction mixture was concentrated in vacuo. The residue was dissolved in methylene chloride (12 mL), cooled to 0° C. under nitrogen, and then treated with a solution of 5-allyl-pyrazin-2-ylamine (0.37 g, 2.737 mmol) and pyridine (0.59 mL, 7.295 mmol) in methylene chloride (12 mL) over 1 min. The resulting reaction mixture was stirred at 0° C. for 30 min and then at 25° C. for 1 h. The reaction mixture was then diluted with ethyl acetate and washed with a 1N aqueous hydrochloric acid solution. The aqueous layer was extracted with ethyl acetate. The combined organic layers were dried over anhydrous sodium sulfate, filtered, and concentrated in vacuo. Biotage chromatography (FLASH, 40L, Silica, 1/1 hexanes/ethyl acetate) afforded N-(5-allyl-pyrazin-2-yl)-2 (R)-(3-chloro-4-methanesulfonyl-phenyl)-3-cyclopentyl-propionamide (965 mg, 89.1%) as a white foam: LRMS for $C_{22}H_{26}ClN_3O_3S$ $(M-H)^+$ at m/z=446

A yellow solution of potassium ferricyanide (1.00 g, 3.037 mmol), potassium carbonate (430.0 mg, 3.111 mmol), and $(DHQ)_2PHAL$ (19.0 mg, 0.0244 mmol) in tert-butyl alcohol/water (16.0 mL, 1:1) was cooled to 0° C. and then treated with a 0.2M solution of osmium tetroxide in toluene (0.048 mL, 0.0096 mmol) followed by the N-(5-allyl-pyrazin-2-yl)-2(R)-(3-chloro-4-methanesulfonyl-phenyl)-3-cyclopentylpropionamide (446.0 mg, 0.996 mmol). The reaction mixture was stirred at 0° C. for 4 h. The reaction mixture was then diluted with ethyl acetate and sodium metabisulfite (0.45 g, 2.37 mmol) and allowed to warm to 25° C. where it was stirred for 15 min. The mixture was then diluted with a saturated aqueous sodium chloride solution and water and extracted with ethyl acetate. The combined organic layers were dried over anhydrous sodium sulfate, filtered, and concentrated in vacuo. Biotage chromatography (FLASH 40M, Silica, 2/3 hexanes/ethyl acetate to ethyl acetate) afforded 2(R)-(3-chloro-4-methanesulfonyl-phenyl)-3-cyclopentyl-N-[5-(2(S),3-dihydroxy-propyl)-pyrazin-2-yl]-propionamide (370.2 mg, 77.1%) as a white foam: mp 61–65° C. (foam to gel); (ES)$^+$-HRMS m/e calcd for $C_{22}H_{28}ClN_3O_5S$ (M+H)$^+$ 482.1511, found 482.1516.

EXAMPLE 82

2(R)-(3-chloro-4-methanesulfonyl-phenyl)-3-cyclopentyl-N-[5-(2(R),3-dihydroxy-propyl)-pyrazin-2-yl]-propionamide

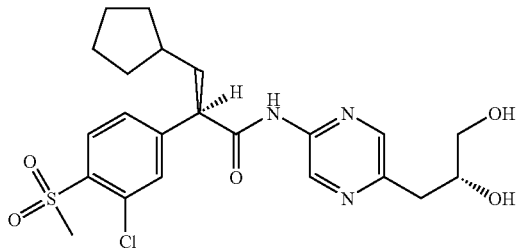

A yellow solution of potassium ferricyanide (1.00 g, 3.037 mmol), potassium carbonate (430.0 mg, 3.111 mmol), and (DHQD)$_2$PHAL (19.0 mg, 0.0244 mmol) in tert-butyl alcohol/water (16.0 mL, 1:1) was cooled to 0° C. and then treated with a 0.2M solution of osmium tetroxide in toluene (0.048 mL, 0.0096 mmol) followed by N-(5-allyl-pyrazin-2-yl)-2(R)-(3-chloro-4-methanesulfonyl-phenyl)-3-cyclopentylpropionamide (prepared as in Example 81, 446.0 mg, 0.996 mmol). The reaction mixture was stirred at 0° C. for 4 h. The reaction mixture was then diluted with ethyl acetate and sodium metabisulfite (0.45 g, 2.37 mmol) and allowed to warm to 25° C. where it was stirred for 15 min. The mixture was diluted with a saturated aqueous sodium chloride solution and water and extracted with ethyl acetate. The combined organic layers were dried over anhydrous sodium sulfate, filtered, and concentrated in vacuo. Biotage chromatography (FLASH 40M, Silica, 2/3 hexanes/ethyl acetate to ethyl acetate) afforded 2(R)-(3-chloro-4-methanesulfonyl-phenyl)-3-cyclopentyl-N-[5-(2(R),3-dihydroxy-propyl)-pyrazin-2-yl]-propionamide (469.2 mg, 89%) as a white foam: mp 64–69° C. (foam to gel); (ES)$^+$-HRMS m/e calcd for $C_{22}H_{28}ClN_3O_5S$ (M+H)$^+$ 482.1511, found 482.1511.

BIOLOGICAL ACTIVITY EXAMPLES

Example A

In Vitro Glucokinase Activity

Glucokinase In Vitro Assay Protocol: Glucokinase (GK) was assayed by coupling the production of glucose-6-phosphate to the generation of NADH with glucose-6-phosphate dehydrogenase (G6PDH, 0.75–1 kunits/mg; Boehringer Mannheim, Indianapolis, Ind.) from *Leuconostoc mesenteroides* as the coupling enzyme (Scheme 2).

Scheme 2

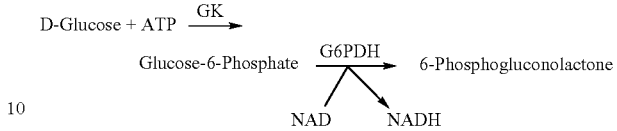

Recombinant human liver GK1 was expressed in *E. coli* as a glutathione S-transferase fusion protein (GST-GK) [Liang et al, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 25° C. in a flat bottom 96-well tissue culture plate from Costar (Cambridge, Mass.) with a final incubation volume of 120 μL. The incubation mixture contained the following: 25 mM Hepes buffer (pH 7.1), 25 mM KCl, 5 mM D-glucose, 1 mM ATP, 1.8 mM NAD, 2 mM MgCl$_2$, 1 μM sorbitol-6-phosphate, 1 mM dithiothreitol, test drug or 10% DMSO, 1.8 unit/ml G6PDH, and GK (see below). All organic reagents were >98% pure and were from Boehringer Mannheim with the exceptions of D-glucose and Hepes which were from Sigma Chemical Co, St Louis, Mo. Test compounds were dissolved in DMSO and were added to the incubation mixture minus GST-GK in a volume of 12 μL to yield a final DMSO concentration of 10%. This mix was pre-incubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 μL GST-GK.

After addition of enzyme, the increase in optical density (OD) at 340 nm was monitored over a 10 minute incubation period as a measure of GK activity. Sufficient GST-GK was added to produce an increase in $OD_{340}$ of 0.08 to 0.1 units over the 10 minute incubation period in wells containing 10% DMSO but no test compound. Preliminary experiments established that the GK reaction was linear over this period of time even in the presence of activators that produced a 5-fold increase in GK activity. The GK activity in control wells was compared with the activity in wells containing test GK activators, and the concentration of activator that produced a 50% increase in the activity of GK, i.e., the $SC_{1.5}$, was calculated. All of the compounds of formula I described in the Synthesis Examples had an $SC_{1.5}$ less than or equal to 100 μM.

References

Liang, Y., Kesavan, P., Wang, L., Niswender, K., Tanizawa, Y., Permut, M. A., Magnuson, M., and Matschinsky, F. M. Variable effects of maturity-onset-diabetes-of-youth (MODY)-associated glucokinase mutations on the substrate interactions and stability of the enzyme. *Biochem. J.* 309: 167–173, 1995.

Neet, K., Keenan, R. P., and Tippett, P. S. Observation of a kinetic slow transition in monomeric glucokinase. *Biochemistry* 29;770–777, 1990.

Example B

In Vivo Glucokinase Activity

Glucokinase Activator in vivo Screen Protocol: C57BL/6J mice are orally dosed via gavage with Glucokinase (GK) activator at 50 mg/kg body weight following a two hour fasting period. Blood glucose determinations are made five times during the six hour post-dose study period.

Mice (n=6) are weighed and fasted for a two hour period prior to oral treatment. GK activators are formulated at 6.76 mg/ml in Gelucire vehicle (Ethanol:Gelucire44/14:PEG400q.s. 4:66:30 v/w/v. Mice are dosed orally with 7.5 µL formulation per gram of body weight to equal a 50 mg/kg dose. Immediately prior to dosing, a pre dose (time zero) blood glucose reading is acquired by snipping off a small portion of the animal's tail (~1 mm) and collecting 15 µL blood into a heparinized capillary tube for analysis. Following GK activator administration, additional blood glucose readings are taken at 1, 2, 4 and 6 hours post dose from the same tail wound. Results are interpreted by comparing the mean blood glucose values of six vehicle treated mice with six GK activator treated mice over the six hour study duration. Preferred compounds are considered to be those that exhibit a statistically significant (p≦0.05) decrease in blood glucose compared to vehicle for two consecutive assay time points.

What is claimed is:

1. A compound according to formula I

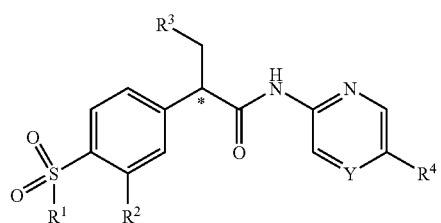

wherein $R^1$ is a lower alkyl having from 1 to 5 carbon atoms;
$R^2$ is hydrogen, halo, nitro, cyano, methyl, trifluoromethyl, hydroxy, or methoxy;
$R^3$ is cycloalkyl having from 4 to 6 carbons;
Y is independently selected from the group of CH and N to form a pyridine or pyrazine ring, respectively;
$R^4$ is a substituent in position 5 of the pyridine or pyrazine ring selected from the group consisting of:

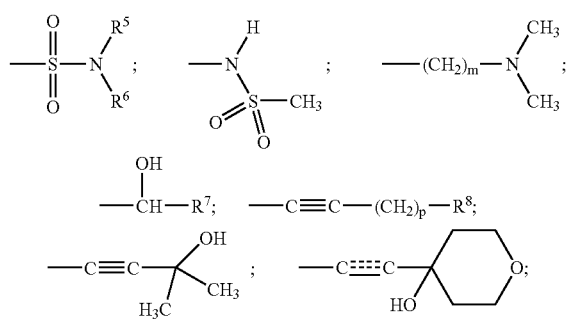

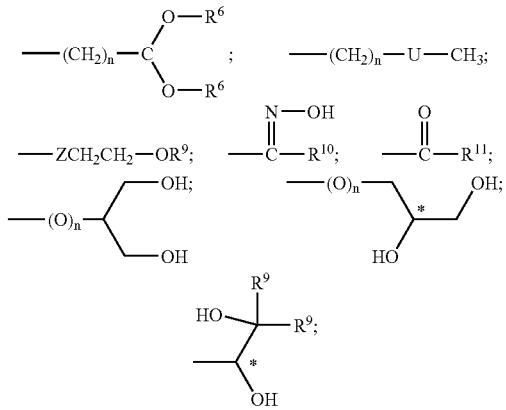

—$(CH_2)_n$-Q, wherein Q is a 5-membered saturated, substituted, heterocyclic ring connected by a ring carbon atom, said heterocyclic ring containing two heteroatoms selected from nitrogen, sulfur and oxygen, and substituted at each of two ring carbons with an oxo group, and optionally substituted at the connecting ring carbon with a substituent which is methyl or amino;

—$(CH_2)_n$—V, wherein V is an unsubstituted or mono-substituted five- or six-membered saturated or unsaturated heterocyclic ring connected by a ring carbon, which said heterocyclic ring containing from one to three hetero atoms selected from sulfur, oxygen or nitrogen; said mono-substituted heterocyclic ring being a heterocyclic ring which is mono-substituted with a substituent selected from the group consisting of cyano, halo, nitro, amino, methyl, methoxy and hydroxy;

a nine- or ten-membered bicyclic heterocyclic ring connected by a ring carbon atom, said bicyclic heterocyclic ring containing one hetero atom selected from the group consisting of oxygen, nitrogen or sulfur; and an unsubstituted or mono-substituted six-membered aryl ring connected by a ring carbon atom, said mono-substituted aryl ring being mono-substituted at a position on a ring carbon atom other than the connecting carbon atom with a substituent selected from the group consisting of cyano, halo, nitro, amino, methyl, methoxy, and hydroxy;

$R^5$ is hydrogen or lower alkyl;
$R^6$ is lower alkyl;
$R^7$ is lower alkyl, cyano, or —C(=O)NH$_2$;
$R^8$ is hydroxy, methoxy, or dimethylamine;
$R^9$ is hydrogen or methyl;
$R^{10}$ is lower alkyl, cyano, or —NH$_2$;
$R^{11}$ is hydrogen, lower alkyl, or NHOH;
m is 0, 1, 2, or 3;
n is 0 or 1;
p is 1 or 2;
U is S, SO, or SO$_2$;
Z is O, S, or NH;
---- denotes an optional bond;
* denotes an asymmetric carbon atom;
or a pharmaceutically acceptable salt thereof.

2. The compound according to claim 1, wherein $R^1$ is methyl.

3. The compound according to claim 1, wherein $R^2$ is hydrogen or halo.

4. The compound according to claim 3, wherein halo is chlorine.

5. The compound according to claim 1, wherein $R^3$ is cyclopentyl.

6. The compound according to claim 1, wherein $R^4$ is —$(CH_2)_n$—U—$CH_3$.

7. The compound according to claim 6, wherein U is S.

8. The compound according to claim 7, which is selected from the group consisting of:
- 2(R)-(3-Chloro-4-methanesulfonyl-phenyl)-3-cyclopentyl-N-(5-methylsulfanyl-pyrazin-2-yl)-propionamide;
- 3-Cyclopentyl-2(R)-(4-methanesulfonyl-phenyl)-N-(5-methylsulfanyl-pyrazin-2-yl)-propionamide;
- 2-(3-Chloro-4-methanesulfonyl-phenyl)-3-cyclopentyl-N-(5-methylsulfanylmethyl-pyrazin-2-yl)-propionamide; and
- 2(R)-(3-Chloro-4-methanesulfonyl-phenyl)-3-cyclopentyl-N-(5-methylsulfanylmethyl-pyrazin-2-yl)-propionamide.

9. The compound according to claim 6, wherein U is SO.

10. The compound according to claim 9, which is selected from the group consisting of:
- 2(R)-(3-Chloro-4-methanesulfonyl-phenyl)-3-cyclopentyl-N-(5-methanesulfinyl-pyrazin-2-yl)-propionamide; and
- 2(R)-(3-Chloro-4-methanesulfonyl-phenyl)-3-cyclopentyl-N-(5-methanesulfinylmethyl-pyrazin-2-yl)-propionamide.

11. The compound according to claim 6, wherein U is $SO_2$.

12. The compound according to claim 11, which is 2(R)-(3-Chloro-4-methanesulfonyl-phenyl)-3-cyclopentyl-N-(5-methanesulfonylmethyl-pyrazin-2-yl)-propionamide.

13. The compound according to claim 1, wherein $R^4$ is -$ZCH_2CH_2$—$OR^9$.

14. The compound according to claim 13, wherein Z is S.

15. The compound according to claim 14, which is 2(R)-(3-Chloro-4-methanesulfonyl-phenyl)-3-cyclopentyl-N-[5-(2-hydroxy-ethylsulfanyl)-pyrazin-2-yl]-propionamide.

16. The compound according to claim 13, wherein Z is O or NH.

17. The compound according to claim 16, which is
- 2(R)-(3-Chloro-4-methanesulfonyl-phenyl)-3-cyclopentyl-N-5-(2-methoxyethoxy-pyrazin-2-yl)-propionamide;
- 2(R)-(3-Chloro-4-methanesulfonyl-phenyl)-3-cyclopentyl-N-[5-(2-hydroxy-ethoxy)-pyrazin-2-yl]-propionamide;
- 2(R)-(3-Chloro-4-methanesulfonyl-phenyl)-3-cyclopentyl-N-[5-(2-methoxy-ethylamino)-pyrazin-2-yl]-propionamide; and
- 2(R)-(3-Chloro-4-methanesulfonyl-phenyl)-3-cyclopentyl-N-[5-(2-hydroxy-ethylamino)-pyrazin-2-yl]-propionamide.

18. The compound according to claim 17, which is 2(R)-(3-Chloro-4-methanesulfonyl-phenyl)-3-cyclopentyl-N-[5-(2-hydroxy-ethoxy)-pyrazin-2-yl]-propionamide.

19. The compound according to claim 1, wherein $R^4$ is —$NHSO_2CH_3$.

20. The compound according to claim 19, wherein the compound is selected from
- 2(R)-(3-Chloro-4-methanesulfonyl-phenyl)-3-cyclopentyl-N-(5-methanesulfonylamino-pyridin-2-yl)-propionamide; and
- 2(R)-(3-Chloro-4-methanesulfonyl-phenyl)-3-cyclopentyl-N-(5-methanesulfonylamino-pyrazin-2-yl)-propionamide.

21. The compound according to claim 1, wherein $R^4$ is —$(CH_2)_m$—$N(CH_3)CH_3$.

22. The compound according to claim 21, wherein m is zero.

23. The compound according to claim 22, which is 2(R)-(3-Chloro-4-methanesulfonyl-phenyl)-3-cyclopentyl-N-(5-dimethylamino-pyridin-2-yl)-propionamide.

24. The compound according to claim 22, which is 2(R)-(3-Chloro-4-methanesulfonyl-phenyl)-3-cyclopentyl-N-(5-dimethylamino-pyrazin-2-yl)-propionamide.

25. The compound according to claim 21, which is selected from the group consisting of:
- 2(R)-(3-Chloro-4-methanesulfonyl-phenyl)-3-cyclopentyl-N-[5-(3-dimethylamino-propyl)-pyrazin-2-yl]-propionamide; and
- 2(R)-(3-Chloro-4-methanesulfonyl-phenyl)-3-cyclopentyl-N-(5-dimethylaminomethyl-pyrazin-2-yl)-propionamide.

26. The compound according to claim 1, wherein $R^4$ is —C(=O)$R^{11}$.

27. The compound according to claim 26, which is 2-(3-Chloro-4-methanesulfonyl-phenyl)-3-cyclopentyl-N-(5-formyl-pyrazin-2-yl)-propionamide.

28. The compound according to claim 26, which is selected from the group consisting of:
- N-(5-Acetyl-pyrazin-2-yl)-2-(3-chloro-4-methanesulfonyl-phenyl)-3-cyclopentyl-propionamide; and
- N-(5-Acetyl-pyrazin-2-yl)-2(R)-(3-chloro-4-methanesulfonyl-phenyl)-3-cyclopentyl-propionamide.

29. The compound according to claim 26, which is selected from the group consisting of:
- 2-(3-Chloro-4-methanesulfonyl-phenyl)-3-cyclopentyl-N-(5-isobutyryl-pyrazin-2-yl)-propionamide; and
- 5-[2(R)-(3-Chloro-4-methanesulfonyl-phenyl)-3-cyclopentyl-propionylamino]-pyrazine-2-carboxylic acid hydroxyamide.

30. The compound according to claim 1, wherein $R^4$ is —$(CH_2)_n$—$C(OR^6)OR^6$ and $R^6$ is methyl or ethyl.

31. The compound according to claim 30, which is 2(R)-(3-Chloro-4-methanesulfonyl-phenyl)-3-cyclopentyl-N-(5-dimethoxymethyl-pyrazin-2-yl)-propionamide.

32. The compound according to claim 30, which is 2(R)-(3-Chloro-4-methanesulfonyl-phenyl)-3-cyclopentyl-N-[5-(2,2-dimethoxy-ethyl)-pyrazin-2-yl]-propionamide.

33. The compound according to claim 1, wherein $R^4$ is —C(OH)$R^7$.

34. The compound according to claim 33, which is selected from
- 2-(3-Chloro-4-methanesulfonyl-phenyl)-3-cyclopentyl-N-[5-(1-hydroxy-ethyl)-pyrazin-2-yl]-propionamide;
- 2-(3-Chloro-4-methanesulfonyl-phenyl)-3-cyclopentyl-N-[5-(1-hydroxy-2-methyl-propyl)-pyrazin-2-yl]-propionamide;
- 2(R)-(3-Chloro-4-methanesulfonyl-phenyl)-N-[5-(cyano-hydroxy-methyl)-pyrazin-2-yl]-3-cyclopentyl-propionamide; and
- N-[5-(Carbamoyl-hydroxy-methyl)-pyrazin-2-yl]-2(R)-(3-chloro-4-methanesulfonyl-phenyl)-3-cyclopentyl-propionamide.

35. The compound according to claim 1, wherein R⁴ is

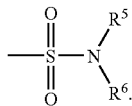

36. The compound according to claim 35, which is selected from the group consisting of:
   2(R)-(3-Chloro-4-methanesulfonyl-phenyl)-3-cyclopentyl-N-(5-methylsulfamoyl-pyrazin-2-yl)-propionamide; and
   2(R)-(3-Chloro-4-methanesulfonyl-phenyl)-3-cyclopentyl-N-(5-dimethylsulfamoyl-pyrazin-2-yl)-propionamide.

37. The compound of claim 1 according to formula II,

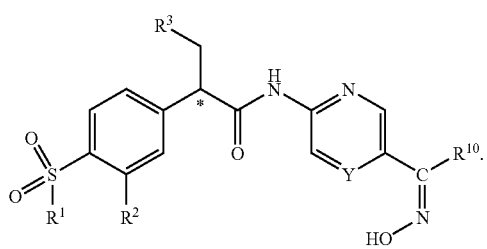

38. The compound according to claim 37, wherein R¹⁰ is —NH₂, cyano, or lower alkyl which is methyl or ethyl.

39. The compound according to claim 38, which is 2(R)-(3-Chloro-4-methanesulfonyl-phenyl)-3-cyclopentyl-N-[5-(N-hydroxycarbamimidoyl)-pyrazin-2-yl]-propionamide.

40. The compound according to claim 38, which is 2(R)-(3-Chloro-4-methanesulfonyl-phenyl)-3-cyclopentyl-N-[5-(N-hydroxycarbamimidoyl)-pyridin-2-yl]-propionamide.

41. The compound according to claim 38, which is 3-Cyclopentyl-2(R)-N-[5-(N-hydroxycarbamimidoyl)-pyrazin-2-yl]-2-(4-methanesulfonyl-phenyl)-propionamide.

42. The compound according to claim 38, which is 2(R)-(3-Chloro-4-methanesulfonyl-phenyl)-3-cyclopentyl-N-[5-(1-(Z)-hydroxyimino-ethyl)-pyrazin-2-yl]-propionamide.

43. The compound according to claim 38, which is selected from the group consisting of:
   3-Cyclopentyl-N-[5-(1-hydroxyimino-ethyl)-pyrazin-2-yl]-2(R)-(4-methanesulfonyl-phenyl)-propionamide; and
   2-(3-Chloro-4-methanesulfonyl-phenyl)-N-[5-(cyano-hydroxyimino-methyl)-pyrazin-2-yl]-3-cyclopentyl-propionamide.

44. The compound of claim 1, according to formula III,

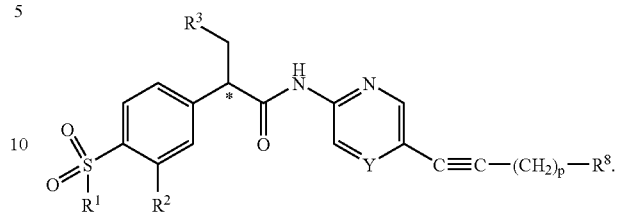

45. The compound according to claim 44, wherein p is 1.

46. The compound according to claim 44, wherein R⁸ is hydroxy or dimethylamine.

47. The compound according to claim 44, which is 2(R)-(3-Chloro-4-methanesulfonyl-phenyl)-3-cyclopentyl-N-[5-(3-hydroxy-prop-1-ynyl)-pyrazin-2-yl]-propionamide.

48. The compound according to claim 44, which is 2(R)-(3-Chloro-4-methanesulfonyl-phenyl)-3-cyclopentyl-N-[5-(3-dimethylamino-prop-1-ynyl)-pyrazin-2-yl]-propionamide.

49. The compound according to claim 44, which is selected from the group consisting of:
   2(R)-(3-Chloro-4-methanesulfonyl-phenyl)-3-cyclopentyl-N-[5-(3-methoxy-prop-1-ynyl)-pyrazin-2-yl]-propionamide;
   3-Cyclopentyl-2(R)-(4-methanesulfonyl-phenyl)-N-[5-(3-methoxyprop-1-ynyl)-pyrazin-2-yl]-propionamide; and
   2(R)-(3-Chloro-4-methanesulfonyl-phenyl)-3-cyclopentyl-N-[5-(4-hydroxy-but-1-ynyl)-pyrazin-2-yl]-propionamide.

50. The compound according to claim 1, wherein R⁴ is selected from the group consisting of:
   —(CH₂)ₙ-Q, wherein Q is a 5-membered saturated, substituted, heterocyclic ring connected by a ring carbon atom, said heterocyclic ring containing two heteroatoms selected from nitrogen, sulfur and oxygen, and substituted at each of two ring carbons with an oxo group, and optionally substituted at the connecting ring carbon with a substituent which is methyl or amino;
   —(CH₂)ₙ—V, wherein V is an unsubstituted or mono-substituted five- or six-membered saturated or unsaturated heterocyclic ring connected by a ring carbon, which said heterocyclic ring containing from one to three hetero atoms selected from sulfur, oxygen or nitrogen; said mono-substituted heterocyclic ring being a heterocyclic ring which is mono-substituted with a substituent selected from the group consisting of cyano, halo, nitro, amino, methyl, methoxy and hydroxy;
   a nine- or ten-membered bicyclic heterocyclic ring connected by a ring carbon atom, said bicyclic heterocyclic ring containing one hetero atom selected from the group consisting of oxygen, nitrogen or sulfur; and
   an unsubstituted or mono-substituted six-membered aryl ring connected by a ring carbon atom, said mono-substituted aryl ring being mono-substituted at a position on a ring carbon atom other than the connecting carbon atom with a substituent selected from the group consisting of cyano, halo, nitro, amino, methyl, methoxy, and hydroxy.

51. The compound according to claim 50, wherein R⁴ is selected from the group consisting of —(CH₂)ₙ—V; and an unsubstituted or mono-substituted 6-membered aryl ring connected by a ring carbon atom, said mono-substituted aryl ring being mono-substituted at a position on a ring carbon atom other than the connecting carbon atom with a substituent selected from the group consisting of chloro, bromo, nitro, amino, methyl, methoxy and hydroxy.

52. The compound according to claim 51, wherein $R^4$ is selected from the group consisting of —$(CH_2)_n$—V, wherein n is zero and V is an unsubstituted five- or six-membered heteroaromatic ring connected by a ring carbon atom, with said five- or six-membered heteroaromatic ring containing one heteroatom selected from sulfur, oxygen or nitrogen.

53. The compound according to claim 51, wherein $R^4$ is an unsubstituted or mono-substituted 6-membered aryl ring selected from the group consisting of unsubstituted aryl, aryl substituted with methoxy and aryl substituted with hydroxy.

54. The compound according to claim 53, which is selected from the group consisting of:
   2(R)-(3-Chloro-4-methanesulfonyl-phenyl)-3-cyclopentyl-N-[5-(2-methoxyphenyl)-pyrazin-2-yl]-propionamide;
   2(R)-(3-Chloro-4-methanesulfonyl-phenyl)-3-cyclopentyl-N-[5-(2-hydoxyphenyl)-pyrazin-2-yl]-propionamide; and
   2(R)-(3-Chloro-methanesulfonyl-phenyl)-3-cyclopentyl-N-[5-(3-methoxy-phenyl)-pyrazin-2-yl]-propionamide.

55. The compound according to claim 51, wherein $R^4$ is —$(CH_2)_n$—V which is selected from the group consisting of:

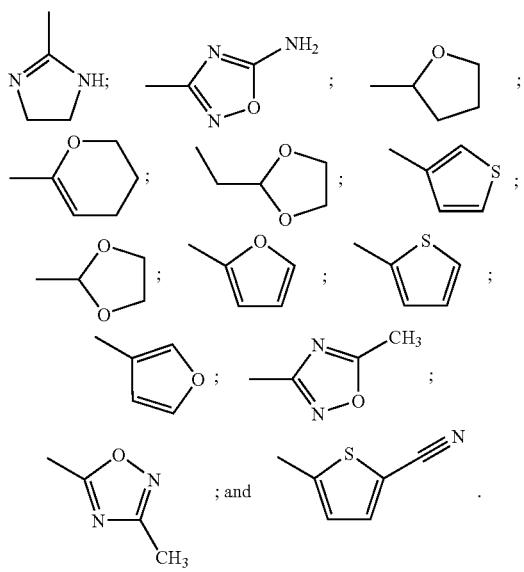

56. The compound according to claim 55, wherein $R^4$ is

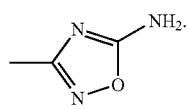

57. The compound according to claim 56, which is N-[5-(5-Amino-[1,2,4]oxadiazol-3-yl)-pyrazin-2-yl]-2 (R)-(3-chloro-4-methanesulfonyl-phenyl)-3-cyclopentyl-propionamide.

58. The compound according to claim 51, wherein $R^4$ is —$(CH_2)_n$—V which is selected from the group consisting of:
   2-(3-Chloro-4-methanesulfonyl-phenyl)-3-cyclopentyl-N-[5-(5-methyl-[1,2,4]oxadiazol-3-yl)-pyrazin-2-yl]-propionamide;
   2(R)-(3-Chloro-4-methanesulfonyl-phenyl)-3-cyclopentyl-N-[5-(3-methyl-[1,2,4]oxadiazol-5-yl)-pyrazin-2-yl]-propionamide;
   2(R)-(3-Chloro-4-methanesulfonyl-phenyl)-3-cyclopentyl-N-(5-[1,3]dioxolan-2-yl-pyrazin-2-yl)-propionamide;
   2(R)-(3-Chloro-4-methanesulfonyl-phenyl)-3-cyclopentyl-N-(5-[1,3]dioxolan-2-ylmethyl-pyrazin-2-yl)-propionamide;
   2(R)-(3-Chloro-4-methanesulfonyl-phenyl)-3-cyclopentyl-N-[5-(tetrahydro-furan-2-yl)-pyridin-2-yl]-propionamide;
   2(R)-(3-Chloro-4-methanesulfonyl-phenyl)-3-cyclopentyl-N-(5-furan-2-yl-pyrazin-2-yl)-propionamide;
   2(R)-(3-Chloro-4-methanesulfonyl-phenyl)-3-cyclopentyl-N-[5-(5,6-dihydro-4H-pyran-2-yl)-pyrazin-2-yl]-propionamide;
   2(R)-(3-Chloro-4-methanesulfonyl-phenyl)-3-cyclopentyl-N-(5-thiophen-2-yl-pyrazin-2-yl)-propionamide;
   2(R)-(3-Chloro-4-methanesulfonyl-phenyl)-3-cyclopentyl-N-(5-thiophen-3-yl-pyrazin-2-yl)-propionamide;
   2(R)-(3-Chloro-4-methanesulfonyl-phenyl)-3-cyclopentyl-N-(5-furan-3-yl-pyrazin-2-yl)-propionamide;
   2(R)-(3-Chloro-4-methanesulfonyl-phenyl)-N-[5-(5-cyano-thiophen-2-yl)-pyrazin-2-yl]-3-cyclopentyl-propionamide; and
   2(R)-(3-Chloro-4-methanesulfonyl-phenyl)-3-cyclopentyl-N-{5-(4,5-dihydro-1H-imidazol-2-yl)-pyrazin-2-yl}-propionamide trifluoro-acetic acid salt.

59. The compound according to claim 50, wherein $R^4$ is —$(CH_2)_n$-Q.

60. The compound according to claim 59, wherein $R^4$ is —$(CH_2)_n$-Q which is selected from the group consisting of:

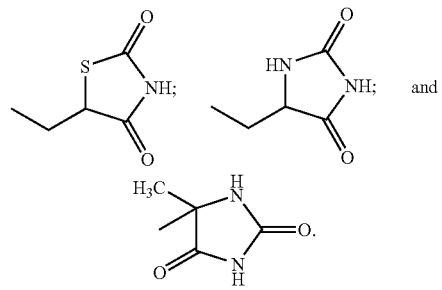

61. The compound according to claim 60, which is 2-(3-Choro-4-methanesulfonyl-phenyl)-3-cyclopentyl-N-[5-(2,4-dioxothiazolidin-5-ylmethyl)-pyrazin-2-yl]-propionamide.

62. The compound according to claim 60, which is selected from the group consisting of:
   2-(3-Chloro-4-methanesulfonyl-phenyl)-3-cyclopentyl-N-[5-(2,5-dioxo-imidazolidin-4-ylmethyl)-pyrazin-2-yl]-propionamide; and 2(R)-(3-Chloro-4-methanesulfonyl-phenyl)-3-cyclopentyl-N-[5-(4-methyl-2,5-dioxo-imidazolidin-4-yl)-pyrazin-2-yl]-propionamide.

63. The compound according to claim 50, wherein $R^4$ is a bicyclic heteroaromatic ring which is

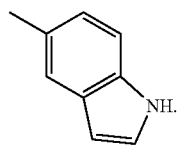

64. The compound according to claim 63, which is 2(R)-(3-Chloro-methanesulfonyl-phenyl)-3-cyclopentyl-N-[5-(1H-indol-5-yl)-pyrazin-2-yl]-propionamide.

65. The compound according to claim 54, wherein $R^4$ is —(CH$_2$)$_n$—V, and V is

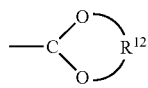

wherein $R^{12}$ is an unbranched alkyl chain of 2 or 3 carbon atoms wherein the chain, in combination with the oxygen atoms to which it is bonded, forms a five- or six membered-ring.

66. The compound according to claim 1, wherein $R^6$ is methyl or ethyl.

67. The compound according to claim 1, which is a racemic mixture at the chiral carbon upon which —CH$_2$R$^3$ is a substituent.

68. The compound according to claim 1, which is in the R configuration at the chiral carbon upon which —CH$_2$R$^3$ is a substituent.

69. The compound according to claim 1, wherein $R^4$ is

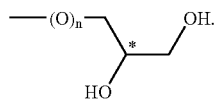

70. The compound according to claim 69, wherein the compound is a racemic mixture at the chiral carbon of $R^4$.

71. The compound according to claim 69, wherein when n is 1, the configuration is

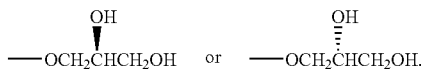

72. The compound according to claim 71, wherein $R^4$ is in the R configuration.

73. The compound according to claim 69, wherein when n is zero, the configuration is

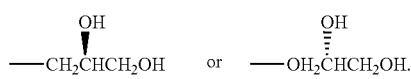

74. The compound according to claim 73, wherein $R^4$ is in the R configuration.

75. The compound according to claim 69, which is selected from the group cnsisting of:

2(R)-(3-Chloro-4-methanesulfonyl-phenyl)-3-cyclopentyl-N-[5-2(R),3-dihydroxy-propoxy)-pyrazin-2-yl]-propionamide;

2(R)-(3-Chloro-4-methanesulfonyl-phenyl)-3-cyclopentyl-N-[5-(2(S),3-dihydroxy-propoxy)-pyrazin-2-yl]-propionamide;

2(R)-(3-Chloro-4-methanesulfonyl-phenyl)-3-cyclopentyl-N-[5-(2(S),3-dihydroxy-propyl)-pyrazin-2-yl]-propionamide; and 2(R)-(3-chloro-4-methanesulfonyl-phenyl)-3-cyclopentyl-N-[5-(2(R),3-dihydroxy-propyl)-pyrazin-2-yl]-propionamide.

76. The compound according to claim 1, wherein $R^4$ is

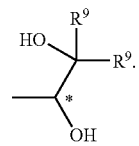

77. The compound according to claim 76, wherein the compound is a racemic mixture at the chiral carbon of $R^4$.

78. The compound according to claim 76, wherein the configuration is

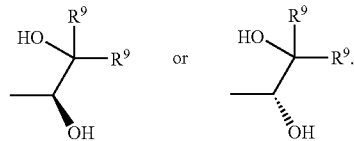

79. The compound according to claim 78, wherein $R^4$ is in the S configuration.

80. The compound according to claim 76, which is 2(R)-(3-Chloro-4-methanesulfonyl-phenyl)-3-cyclopentyl-N-[5-(1(S),2-dihydroxy-ethyl)-pyrazin-2-yl]-propionamide.

81. The compound according to claim 76, which is 2(R)-(3-Chloro-4-methanesulfonyl-phenyl)-3-cyclopentyl-N-[5-(1(S),2-dihydroxy-2-methyl-propyl)-pyrazin-2-yl]-propionamide.

82. The compound according to claim 76, which is selected from the group consisting of:

2(R)-(3-Chloro-4-methanesulfonyl-phenyl)-3-cyclopentyl-N-[5-1(R),2-dihydroxy-ethyl)-pyrazin-2-yl]-propionamide;

3-Cyclopentyl-N-[5-1(S),2-dihydroxy-ethyl]-2(R)-(4-methanesulfonyl-3-methyl)-propionamide;

3-Cyclopentyl-N-[5-1(R),2-dihydroxy-ethyl]-2(R)-(4-methanesulfonyl-3-methyl)-propionamide;

2(R)-(3-Chloro-4-methanesulfonyl-phenyl)-3-cyclopentyl-N-[5-(1,2-dihydroxy-ethyl)-pyrazin-2-yl]-propionamide; and 2(R)-(3-Chloro-4-methanesulfonyl-phenyl)-3-cyclopentyl-N-[5-(1(R),2-dihydroxy-2-methyl-propyl)-pyrazin-2-yl]-propionamide.

83. The compound according to claim 1, wherein R⁴ is

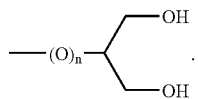

84. The compound according to claim 83, which is selected from the group consisting of:
    2(R)-(3-Chloro-4-methanesulfonyl-phenyl)-3-cyclopentyl-N-[5-(2-hydroxy-1-hydroxymethyl-ethyl)-pyrazin-2-yl]-propionamide; and
    2(R)-(3-Chloro-4-methanesulfonyl-phenyl)-3-cyclopentyl-N-[5-(2-hydroxy-1-hydroxymethyl-ethoxy)-pyrazin-2-yl]-propionamide.

85. The compound according to claim 1, wherein R⁴ is

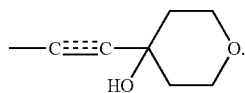

86. The compound according to claim 85, which is selected from the group consisting of:
    3-Cyclopentyl-N-5-[(4-hydroxy-tetrahydropyran-4-yl-ethynyl)pyrazin-2-yl]-2(R)-(4-methanesulfonyl-phenyl)-propionamide;
    2(R)-(3-Chloro-4-methanesulfonyl-phenyl)-3-cyclopentyl-N-[5-(4-hydroxy-tetrahydropyran-4-yl-ethynyl)-pyrazin-2-yl]-propionamide;
    2(R)-(3-Chloro-4-methanesulfonyl-phenyl)-3-cyclopentyl-N-[5-(4-hydroxy-tetrahydropyran-4-yl-ethyl)-pyrazin-2-yl]-propionamide; and
    3-Cyclopentyl-N-[5-(4-hydroxy-tetrahydro-pyran-4-yl-ethynyl)-pyrazin-2-yl]-2(R)-(4-methanesulfonyl-3-methyl-phenyl)-propionamide.

87. The compound according to claim 1, wherein R⁴ is

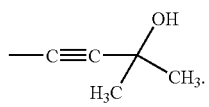

88. The compound according to claim 87, which is selected from the group consisting of:
    2(R)-(3-Chloro-4-methanesulfonyl-phenyl)-3-cyclopentyl-N-[5-(3-hydroxy-3-methyl-but-1-ynyl)-pyrazin-2-yl]-propionamide;
    3-Cyclopentyl-N-[5-(3-hydroxy-3-methyl-but-1-ynyl)-pyrazin-2-yl]-2(R)-(4-methanesulfonyl-3-methyl-phenyl)-propionamide; and
    3-Cyclopentyl-2(R)-(4-methanesulfonyl-phenyl)-N-[5-(3-hydroxy-3-methyl-but-1-ynyl)-pyrazin-2-yl]-propionamide.

89. A pharmaceutical composition comprising a compound according to claim 1 or a pharmaceutically acceptable salt thereof, and a pharmaceutically acceptable carrier.

90. The pharmaceutical composition according to claim 89, wherein the compound is selected from the group consisting of:
    2(R)-(3-Chloro-4-methanesulfonyl-phenyl)-3-cyclopentyl-N-[5-(N-hydroxycarbamimidoyl)-pyrazin-2-yl]-propionamide;
    3-Cyclopentyl-2(R)-N-[5-(N-hydroxycarbamimidoyl)-pyrazin-2-yl]-2-(4-methanesulfonyl-phenyl)-propionamide;
    2(R)-(3-Chloro-4-methanesulfonyl-phenyl)-3-cyclopentyl-N-(5-methylsulfanyl-pyrazin-2-yl)-propionamide;
    2(R)-(3-Chloro-4-methanesulfonyl-phenyl)-3-cyclopentyl-N-[5-(2-hydroxy-ethylsulfanyl)-pyrazin-2-yl]-propionamide;
    2(R)-(3-Chloro-4-methanesulfonyl-phenyl)-3-cyclopentyl-N-(5-methanesulfinyl-pyrazin-2-yl)-propionamide;
    2(R)-(3-Chloro-4-methanesulfonyl-phenyl)-3-cyclopentyl-N-[5-(3-hydroxy-prop-1-ynyl)-pyrazin-2-yl]-propionamide;
    2(R)-(3-Chloro-4-methanesulfonyl-phenyl)-3-cyclopentyl-N-[5-(3-dimethylamino-prop-1-ynyl)-pyrazin-2-yl]-propionamide;
    2(R)-(3-Chloro-4-methanesulfonyl-phenyl)-3-cyclopentyl-N-(5-methanesulfonylamino-pyridin-2-yl)-propionamide;
    2(R)-(3-Chloro-4-methanesulfonyl-phenyl)-3-cyclopentyl-N-(5-dimethylamino-pyridin-2-yl)-propionamide;
    2(R)-(3-Chloro-4-methanesulfonyl-phenyl)-3-cyclopentyl-N-(5-dimethylamino-pyrazin-2-yl)-propionamide;
    2(R)-(3-Chloro-4-methanesulfonyl-phenyl)-3-cyclopentyl-N-[5-(3-dimethylamino-propyl)-pyrazin-2-yl]-propionamide;
    N-[5-(5-Amino-[1,2,4]oxadiazol-3-yl)-pyrazin-2-yl]-2(R)-(3-chloro-4-methanesulfonyl-phenyl)-3-cyclopentyl-propionamide;
    2-(3-Chloro-4-methanesulfonyl-phenyl)-3-cyclopentyl-N-(5-formyl-pyrazin-2-yl)-propionamide;
    2-(3-Chloro-4-methanesulfonyl-phenyl)-3-cyclopentyl-N-[5-(2,4-dioxo-thiazolidin-5-ylmethyl)-pyrazin-2-yl]-propionamide;
    2(R)-(3-Chloro-4-methanesulfonyl-phenyl)-3-cyclopentyl-N-(5-dimethoxymethyl-pyrazin-2-yl)-propionamide;
    N-(5-Acetyl-pyrazin-2-yl)-2-(3-chloro-4-methanesulfonyl-phenyl)-3-cyclopentyl-propionamide;
    2(R)-(3-Chloro-4-methanesulfonyl-phenyl)-N-[5-(cyano-hydroxy-methyl)-pyrazin-2-yl]-3-cyclopentyl-propionamide;
    2(R)-(3-Chloro-4-methanesulfonyl-phenyl)-3-cyclopentyl-N-[5-(1-(Z)-hydroxyimino-ethyl)-pyrazin-2-yl]-propionamide; and
pharmaceutically acceptable salts thereof;
and a pharmaceutically acceptable carrier.

91. The pharmaceutical composition according to claim 90, wherein the compound is selected from the group consisting of:
    2(R)-(3-Chloro-4-methanesulfonyl-phenyl)-3-cyclopentyl-N-[5-(N-hydroxycarbamimidoyl)-pyrazin-2-yl]-propionamide;
    3-Cyclopentyl-2(R)-N-[5-(N-hydroxycarbamimidoyl)-pyrazin-2-yl]-2-(4-methanesulfonyl-phenyl)-propionamide;
    2(R)-(3-Chloro-4-methanesulfonyl-phenyl)-3-cyclopentyl-N-[5-(3-hydroxy-prop-1-ynyl)-pyrazin-2-yl]-propionamide;
    2(R)-(3-Chloro-4-methanesulfonyl-phenyl)-3-cyclopentyl-N-[5-(1-(Z)-hydroxyimino-ethyl)-pyrazin-2-yl]-propionamide, and
pharmaceutically acceptable salts thereof;
and a pharmaceutically acceptable carrier.

92. The pharmaceutical composition according to claim 89, wherein the compound is selected from the group consisting of:

5-[2(R)-(3-Chloro-4-methanesulfonyl-phenyl)-3-cyclopentyl-propionylamino]-pyrazine-2-carboxylic acid hydroxyamide;

2(R)-(3-Chloro-4-methanesulfonyl-phenyl)-3-cyclopentyl-N-(5-methanesulfonylmethyl-pyrazin-2-yl)-propionamide;

3-Cyclopentyl-N-[5-(1-hydroxyimino-ethyl)-pyrazin-2-yl]-2(R)-(4-methanesulfonyl-phenyl)-propionamide;

2(R)-(3-Chloro-4-methanesulfonyl-phenyl)-3-cyclopentyl-N-(5-[1,3]dioxolan-2-yl-pyrazin-2-yl)-propionamide;

2(R)-(3-Chloro-4-methanesulfonyl-phenyl)-3-cyclopentyl-N-5-(2-methoxyethoxy-pyrazin-2-yl)-propionamide;

2(R)-(3-Chloro-4-methanesulfonyl-phenyl)-3-cyclopentyl-N-[5-2(R),3-dihydroxy-propoxy)-pyrazin-2-yl]-propionamide;

3-Cyclopentyl-N-5-[(4-hydroxy-tetrahydropyran-4-yl-ethynyl)pyrazin-2-yl]-2(R)-(4-methanesulfonyl-phenyl)-propionamide;

2(R)-(3-Chloro-4-methanesulfonyl-phenyl)-3-cyclopentyl-N-[5-(3-methoxy-prop-1-ynyl)-pyrazin-2-yl]-propionamide;

2(R)-(3-Chloro-4-methanesulfonyl-phenyl)-3-cyclopentyl-N-[5-(2(S),3-dihydroxy-propoxy)-pyrazin-2-yl]-propionamide;

2(R)-(3-Chloro-4-methanesulfonyl-phenyl)-3-cyclopentyl-N-[5-(4-hydroxy-tetrahydropyran-4-yl-ethynyl)-pyrazin-2-yl]-propionamide;

2(R)-(3-Chloro-4-methanesulfonyl-phenyl)-3-cyclopentyl-N-[5-(4-hydroxy-tetrahydropyran-4-yl-ethyl)-pyrazin-2-yl]-propionamide;

2(R)-(3-Chloro-4-methanesulfonyl-phenyl)-3-cyclopentyl-N-[5-(3-hydroxy-3-methyl-but-1-ynyl)-pyrazin-2-yl]-propionamide;

2(R)-(3-Chloro-4-methanesulfonyl-phenyl)-3-cyclopentyl-N-[5-(4-hydroxy-but-1-ynyl)-pyrazin-2-yl]-propionamide;

2(R)-(3-Chloro-4-methanesulfonyl-phenyl)-3-cyclopentyl-N-[5-(1(S),2-dihydroxy-ethyl)-pyrazin-2-yl]-propionamide;

2(R)-(3-Chloro-4-methanesulfonyl-phenyl)-3-cyclopentyl-N-[5-1(R),2-dihydroxy-ethyl)-pyrazin-2-yl]-propionamide;

3-Cyclopentyl-N-[5-(3-hydroxy-3-methyl-but-1-ynyl)-pyrazin-2-yl]-2(R)-(4-methanesulfonyl-3-methyl-phenyl)-propionamide;

3-Cyclopentyl-N-[5-1(S),2-dihydroxy-ethyl]-2(R)-(4-methanesulfonyl-3-methyl)-propionamide;

3-Cyclopentyl-N-[5-(4-hydroxy-tetrahydro-pyran-4-yl-ethynyl)-pyrazin-2-yl]-2(R)-(4-methanesulfonyl-3-methyl-phenyl)-propionamide;

3-Cyclopentyl-2(R)-(4-methanesulfonyl-phenyl)-N-[5-(3-hydroxy-3-methyl-but-1-ynyl)-pyrazin-2-yl]-propionamide;

2(R)-(3-Chloro-4-methanesulfonyl-phenyl)-3-cyclopentyl-N-[5-(2-hydroxy-ethoxy)-pyrazin-2-yl]-propionamide;

2(R)-(3-Chloro-4-methanesulfonyl-phenyl)-3-cyclopentyl-N-[5-(1(S),2-dihydroxy-2-methyl-propyl)-pyrazin-2-yl]-propionamide;

2(R)-(3-Chloro-4-methanesulfonyl-phenyl)-3-cyclopentyl-N-[5-(tetrahydro-furan-2-yl)-pyridin-2-yl]-propionamide;

2(R)-(3-Chloro-4-methanesulfonyl-phenyl)-3-cyclopentyl-N-(5-furan-2-yl-pyrazin-2-yl)-propionamide;

2(R)-(3-Chloro-4-methanesulfonyl-phenyl)-3-cyclopentyl-N-[5-(2-hydroxy-ethylamino)-pyrazin-2-yl]-propionamide;

2(R)-(3-Chloro-4-methanesulfonyl-phenyl)-3-cyclopentyl-N-[5-(5,6-dihydro-4H-pyran-2-yl)-pyrazin-2-yl]-propionamide;

2(R)-(3-Chloro-4-methanesulfonyl-phenyl)-3-cyclopentyl-N-(5-thiophen-2-yl-pyrazin-2-yl)-propionamide;

2(R)-(3-Chloro-4-methanesulfonyl-phenyl)-3-cyclopentyl-N-(5-furan-3-yl-pyrazin-2-yl)-propionamide; and pharmaceutically acceptable salts thereof;

and a pharmaceutically acceptable carrier.

93. The pharmaceutical composition according to claim 92, wherein the compound is selected from the group consisting of:

2(R)-(3-Chloro-4-methanesulfonyl-phenyl)-3-cyclopentyl-N-[5-(1(S),2-dihydroxy-ethyl)-pyrazin-2-yl]-propionamide;

2(R)-(3-Chloro-4-methanesulfonyl-phenyl)-3-cyclopentyl-N-[5-(1(S),2-dihydroxy-2-methyl-propyl)-pyrazin-2-yl]-propionamide; and pharmaceutically acceptable salts thereof;

and a pharmaceutically acceptable carrier.

* * * * *

UNITED STATES PATENT AND TRADEMARK OFFICE
CERTIFICATE OF CORRECTION

PATENT NO. : 7,132,425 B2  Page 1 of 1
APPLICATION NO. : 10/732838
DATED : November 7, 2006
INVENTOR(S) : Chen et al.

It is certified that error appears in the above-identified patent and that said Letters Patent is hereby corrected as shown below:

In Claim 73, Col. 145, line 65, please delete the following

"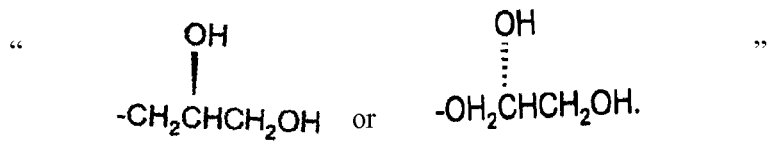"

and insert

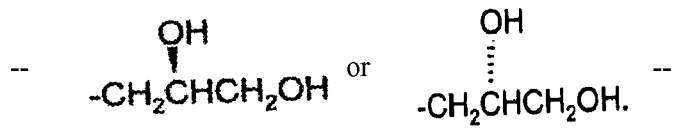

Signed and Sealed this

Twenty-ninth Day of April, 2008

JON W. DUDAS
*Director of the United States Patent and Trademark Office*